United States Patent [19]

Chen et al.

[11] Patent Number: 5,721,251
[45] Date of Patent: *Feb. 24, 1998

[54] PIPERIDINE, PYRROLIDINE AND HEXAHYDRO-1H-AZEPINES PROMOTE RELEASE OF GROWTH HORMONE

[75] Inventors: Meng H. Chen, Westfield; Ravi Nargund, East Brunswick; Arthur A. Patchett, Westfield; Lihu Yang, Edison, all of N.J.

[73] Assignee: Merck & Co., Inc., Rahway, N.J.

[*] Notice: The term of this patent shall not extend beyond the expiration date of Pat. No. 5,492,920.

[21] Appl. No.: 600,912

[22] Filed: Feb. 13, 1996

Related U.S. Application Data

[63] Continuation-in-part of Ser. No. 323,998, Oct. 17, 1994, Pat. No. 5,492,920, which is a continuation-in-part of Ser. No. 165,149, Dec. 10, 1993, abandoned.

[51] Int. Cl.$^6$ .................. A61K 31/445; C07D 401/02; C07D 401/14; C07D 409/02
[52] U.S. Cl. .................. 514/318; 514/323; 546/193; 546/201
[58] Field of Search .................. 546/193, 199, 546/201, 202, 205, 209, 210; 548/127, 128, 205, 214, 253, 306.1, 467, 468; 514/318, 319, 322, 323, 374, 326, 362, 363, 365, 372, 392, 414

[56] References Cited

U.S. PATENT DOCUMENTS

| | | | |
|---|---|---|---|
| 3,239,345 | 3/1966 | Hodge et al. | 514/450 |
| 4,036,979 | 7/1977 | Asato | 514/443 |
| 4,411,890 | 10/1983 | Momany | 514/17 |
| 4,782,139 | 11/1988 | Dimarchi et al. | 530/407 |
| 5,137,872 | 8/1992 | Seely et al. | 514/12 |
| 5,164,368 | 11/1992 | Recker | 514/12 |
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher et al. | 514/215 |
| 5,317,017 | 5/1994 | Ok et al. | 514/211 |
| 5,492,916 | 2/1996 | Morriello et al. | 514/318 |
| 5,492,920 | 2/1996 | Chen et al. | 514/323 |
| 5,494,919 | 2/1996 | Morriello et al. | 514/323 |
| 5,606,054 | 2/1997 | Fisher et al. | 540/521 |
| 5,614,364 | 3/1997 | Tuggle et al. | 435/6 |

FOREIGN PATENT DOCUMENTS

| | | |
|---|---|---|
| 0 144 230 A3 | 6/1985 | European Pat. Off. |
| 5-163224 | 6/1993 | Japan. |
| WO 94/07486 | 4/1994 | WIPO. |
| WO 94/08583 | 4/1994 | WIPO. |
| WO 94/13696 | 6/1994 | WIPO. |
| WO 94/19367 | 9/1994 | WIPO. |
| WO 95/13069 | 5/1995 | WIPO. |

OTHER PUBLICATIONS

R.G. Smith, et al., *Science*, Reprint Series, 11 Jun. 1993, vol. 260, pp. 1640-1643 "A Nonpeptidyl Growth Hormone Secretagogue".
Sakamoto, et al., *Chem. Abstracts*, 113 (9) 73,560u (1990).
Horwell, et al., *Chem. Abstracts*, 113(15) 132, 771p (1990).
Ammann, et al., *Am. J. Physiology*, vol. 265, pp. E770-776 (1993) "IGF-I and pamidronate increade bone mineral density in ovariectomized adult rats".

*Primary Examiner*—Ceila Chang
*Attorney, Agent, or Firm*—J. Eric Thies; David L. Rose

[57] ABSTRACT

The present invention is directed to certain novel compounds identified as substituted piperidines, pyrrolidines and hexahydro-1H-azepines of the general structural formula:

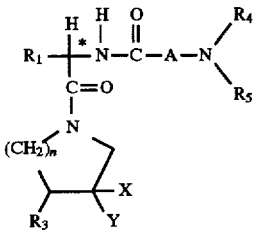

wherein $R_1$, $R_4$, $R_5$, A, X, Y and n are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by growth hormone. Growth hormone releasing compositions containing such compounds as the active ingredient thereof are also disclosed.

3 Claims, No Drawings

PIPERIDINE, PYRROLIDINE AND HEXAHYDRO-1H-AZEPINES PROMOTE RELEASE OF GROWTH HORMONE

CROSS REFERENCE TO RELATED APPLICATIONS

This application is a continuation-in-part of application Ser. No. 08/323,998, filed Oct. 17, 1994, issuing as U.S. Pat. No. 5,492,920 on Feb. 20, 1996, which is a continuation-in-part of application Ser. No. 08/165,149, filed Dec. 10, 1993, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues with a benzolactam structure are disclosed in e.g., U.S. Pat. Nos. 5,206,235, 5,283,241, 5,284,841, 5,310,737 and 5,317,017. Other growth hormone secretagogues are disclosed e.g., in PCT Pat. Publications WO 94/13696, WO 94/19367, and WO 95/09633. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain piperidine, pyrrolidine and hexahydro-1H-azepine compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the piperidine, pyrrolidine and hexahydro-1H-azepine compounds. It is a further object of this invention to describe procedures for the preparation of such compounds. A still further object is to describe the use of such compounds to increase the secretion of growth hormone in humans and animals. A still further object of this invention is to describe compositions containing the piperidine, pyrrolidine and hexahydro-1H-azepine compounds for the use of treating humans and animals so as to increase the level of growth hormone secretions. Further objects will become apparent from a reading of the following description.

DESCRIPTION OF THE INVENTION

The novel piperidine, pyrrolidine and hexahydro-1H-azepine compounds of the instant invention are best described in the following structural Formula I:

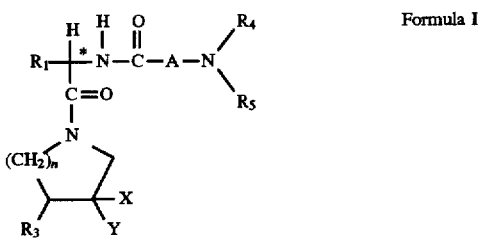

Formula I wherein:

$R_1$ is selected from the group consisting of:

$C_1$–$C_{10}$ alkyl, aryl, aryl($C_1$–$C_6$ alkyl), ($C_3$–$C_7$ cycloalkyl) ($C_1$–$C_6$ alkyl)-, ($C_1$–$C_5$ alkyl)-K—($C_1$–$C_5$ alkyl)-, aryl ($C_0$–$C_5$ alkyl)-K—($C_1$–$C_5$ alkyl)-, and ($C_3$–$C_7$ cycloalkyl)($C_0$–$C_5$ alkyl)-K—($C_1$–$C_5$ alkyl)-, where K is O, S(O)$_m$, N($R_2$)C(O), C(O)N($R_2$), OC(O), C(O)O, —$CR_2$=$CR_2$—, or —C≡C—, where aryl is selected from: phenyl, naphthyl, indolyl, azaindole, pyridyl, benzothienyl, benzofuranyl, thiazolyl, and benzimidazolyl, and $R_2$ and alkyl may be further substituted by 1 to 9 halogen, S(O)$_m$$R_{2a}$, 1 to 3 of OR$_{2a}$ or C(O)OR$_{2a}$, and aryl may be further substituted by 1 to 3 of $C_1$–$C_6$ alkyl, 1 to 3 of halogen, 1 to 2 of OR$_2$, methylenedioxy, —S(O)$_m$R$_2$, 1 to 2 of —CF$_3$, —OCF$_3$, nitro, —N(R$_2$)C(O)(R$_2$), —C(O)OR$_2$, —C(O)N(R$_2$) (R$_2$), -1H-tetrazol-5-yl, —SO$_2$N(R$_2$)(R$_2$), —N(R$_2$)SO$_2$ phenyl, or —N(R$_2$)SO$_2$R$_2$;

$R_2$ is selected from:

hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring, optionally including oxygen, sulfur or NR$_{3a}$, where R$_{3a}$ is hydrogen, or $C_1$–$C_6$ alkyl, optionally substituted by hydroxyl;

$R_3$ is selected from:

—(CH$_2$)$_r$phenyl, —(CH$_2$)$_r$naphthyl, —$C_1$–$C_{10}$ alkyl, —$C_3$–$C_7$ cycloalkyl, and the phenyl, naphthyl and $C_3$–$C_7$ cycloalkyl rings may be substituted by 1 to 3 substituents selected from the group consisting of: $C_1$–$C_6$ alkyl, halogen, —OR$_2$, —NHSO$_2$CF$_3$, —(CH$_2$)$_r$ OR$_6$, —(CH$_2$)$_r$N(R$_2$)(R$_6$), —(CH$_2$)$_r$(R$_6$), —(CH$_2$)$_r$C(O)OR$_2$, —(CH$_2$)—C(O)OR$_6$, —(CH$_2$)$_r$OC(O)R$_2$, —(CH2)rOC(O)R6, —(CH2)rC(O)R2, —(CH2)rC(O)R6, —(CH$_2$)$_r$C(O)N(R$_2$)(R$_2$), —(CH$_2$)$_r$C(O)N(R$_2$)(R$_6$), —(CH$_2$)$_r$N(R$_2$)C(O)R$_2$ —(CH$_2$)$_r$N(R$_2$)C(O)R$_6$, —(CH2)rN(R6)C(O)R2, —(CH2)rN(R$_6$)C(O)R$_6$, —(CH$_2$)$_r$N(R$_2$)C(O)OR$_2$, —(CH$_2$)$_r$N(R$_2$)C(O)OR$_6$, —(CH$_2$)$_r$N(R$_6$)C(O)OR$_2$, —(CH$_2$)$_r$N(R$_6$)C(O)OR$_6$, —(CH$_2$)$_r$N(R$_2$)C(O)N(R$_2$)(R$_6$), —(CH$_2$)$_r$N(R$_2$)C(O)N(R$_2$)(R$_2$), —(CH$_2$)$_r$N(R$_6$)C(O)N(R$_2$)(R$_6$), (CH$_2$)$_r$N(R$_2$)SO$_2$R$_6$, —(CH$_2$)$_r$N(R$_2$)SO$_2$R$_2$, —(CH$_2$)$_r$N(R$_6$)SO$_2$R$_2$, CH$_2$)$_r$N(R$_6$)SO$_2$R$_6$, —(CH$_2$)$_r$OC(O)N(R$_2$)(R$_6$), —(CH$_2$)$_r$OC(O)N(R$_2$)(R$_2$), —(CH$_2$)$_r$SO$_2$N(R$_2$)(R$_6$), —(CH$_2$)$_r$SO$_2$N(R$_2$)(R$_2$), (CH$_2$)$_r$SO$_2$NHC(O)R$_6$, —(CH$_2$)$_r$SO$_2$NHC(O)R$_2$, —(CH$_2$)$_r$SO$_2$NHC(O)OR$_6$, —(CH$_2$)$_r$SO$_2$NHC(O)OR$_2$, —(CH$_2$)$_r$C(O)NHC(O)NR$_2$, —(CH$_2$)$_r$C(O)NHC(O)NR$_6$, —(CH$_2$)$_r$C(O)NHC(O)R$_2$, —(CH$_2$)$_r$CONHC(O)R$_6$, —(CH$_2$)$_r$CONHSO$_2$R$_6$, —(CH$_2$)$_r$CONHSO$_2$R$_2$, —(CH$_2$)$_r$CONHSO$_2$N(R$_2$)R$_2$), —(CH$_2$)$_r$CONHSO$_2$N(R$_2$)R$_6$), —(CH$_2$)$_r$N(R$_2$)SO$_2$N(R$_2$)R$_6$), —(CH$_2$)$_r$N(R$_6$)SO$_2$N(R$_2$) R$_6$), —(CH$_2$)$_r$S(O)$_m$R$_6$, and —(CH$_2$)$_r$S(O)$_m$R$_2$;

X is selected from:

hydrogen, —C≡N, —(CH$_2$)$_q$N(R$_2$)C(O)R$_2$, —(CH$_2$)qN (R$_2$)C(O)(CH$_2$)$_r$aryl, —(CH$_2$)$_q$N(R$_2$)SO$_2$(CH$_2$)$_r$aryl, —(CH$_2$)$_q$N(R$_2$)SO$_2$R$_2$, —(CH$_2$)qN(R$_2$)C(O)N(R$_2$) (CH$_2$)$_r$aryl, —(CH$_2$)$_q$N(R$_2$)C(O)N(R$_2$)(R$_2$), —(CH$_2$)$_q$C(O)N(R$_2$)(R$_2$), —(CH$_2$)$_q$C(O)N(R$_2$)(CH$_2$)$_r$aryl, —(CH$_2$)$_q$C(O)OR$_2$, —(CH$_2$)$_q$C(O)O(CH$_2$)$_r$aryl, —(CH$_2$)$_q$OR$_2$, —(CH$_2$)$_q$OC(O)R$_2$, —(CH$_2$)$_q$OC(O) (CH$_2$)$_r$aryl, —(CH$_2$)$_q$OC(O)N(R$_2$)(CH$_2$)$_r$aryl, —(CH$_2$)$_q$ OC(O)N(R$_2$)(R$_2$), —(CH$_2$)qC(O)R$_2$, —(CH$_2$)qC(O)(CH$_2$)$_r$aryl, —(CH$_2$)qN(R$_2$)C(O)OR$_2$, —(CH$_2$)qN(R$_2$)SO$_2$N(R$_2$)(R$_2$), —(CH$_2$)$_q$S(O)$_m$R$_2$, and —(CH$_2$)$_q$S (O)$_m$(CH$_2$)$_r$aryl, where an R$_2$, (CH$_2$)$_q$ and (CH$_2$)$_r$ group may be optionally substituted by 1 to 2 C$_1$–C$_4$ alkyl, hydroxyl, C$_1$–C$_4$ lower alkoxy, carboxyl, CONH$_2$, S(O)$_m$CH$_3$, carboxylate C$_1$–C$_4$ alkyl esters, or 1H-tetrazol-5-yl, and aryl is phenyl, naphthyl, pyridyl, thiazolyl, or 1H-tetrazol-5-yl groups which may be optionally substituted by 1 to 3 halogen, 1 to 3 —OR$_2$, —CON(R$_2$)(R$_2$), —C(O)OR$_2$, 1 to 3 C$_1$–C$_4$ alkyl, —S(O)$_m$R$_2$, or 1H-tetrazol-5-yl;

Y is selected from:

hydrogen, C$_1$–C$_{10}$ alkyl, —(CH$_2$)$_q$aryl, —(CH$_2$)$_q$(C$_3$–C$_7$ cycloalkyl), —(CH$_2$)$_q$—K—(C$_1$–C$_6$ alkyl), —(CH$_2$)$_q$—K—(CH$_2$)$_r$aryl, —(CH$_2$)$_q$—K—(CH$_2$)$_r$ (C$_3$–C$_7$ cycloalkyl containing O, NR2, S), and —(CH$_2$)$_q$—K—(CH$_2$)$_r$(C$_3$–C$_7$ cycloalkyl), where K is O, S(O)$_m$, C(O)NR$_2$, CH=CH, C≡C, N(R$_2$)C(O), C(O)NR$_2$, C(O)O, or OC(O), and where the alkyl, R$_2$, (CH$_2$)$_q$ and (CH$_2$)$_r$ groups may be optionally substituted by C$_1$–C$_4$ alkyl, hydroxyl, C$_1$–C$_4$ lower alkoxy, carboxyl, —CONH$_2$ or carboxylate C$_1$–C$_4$ alkyl esters, and aryl is phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl which is optionally substituted by 1 to 3 halogen, 1 to 3 —OR$_2$, 1 to 2 —N(R$_2$)(R$_2$), —C(O)OR$_2$, —C(O)N (R$_2$)(R$_2$), nitro, —NHC(O)R$_2$, cyano, benzyl, 1 to 3 C$_1$–C$_4$ alkyl, —S(O)$_m$R$_2$, or 1H-tetrazol-5-yl;

R$_4$ and R$_5$ are independently hydrogen, C$_1$–C$_6$ alkyl, substituted C$_1$–C6 alkyl where the substituents may be 1 to 5 halo, 1 to 3 hydroxy, 1 to 3 C$_1$–C$_{10}$ alkanoyloxy, 1 to 3 C$_1$–C$_6$ alkoxy, phenyl, phenoxy, 2-furyl, C$_1$–C$_6$ alkoxycarbonyl, S(O)$_m$(C$_1$–C$_6$ alkyl); or R$_4$ and R$_5$ can be taken together to form —(CH$_2$)$_d$L$_a$(CH$_2$)e— where L$_a$ is C(R$_2$)$_2$, O, S(O)$_m$ or N(R$_2$), d and e are independently 1 to 3 and R$_2$ is as defined above;

A is:

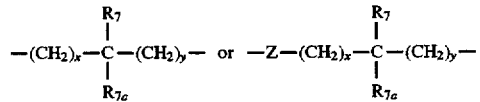

where x and y are independently 0, 1, 2 or 3;

Z is N—R$_{6a}$ or O, where R$_{6a}$ is hydrogen or C$_1$–C$_6$ alkyl;

R$_6$ is hydrogen, C$_1$–C$_6$ alkyl, or (CH$_2$)$_v$aryl, wherein the alkyl and (CH$_2$)$_v$ groups may be optionally substituted by 1-2O(R$_2$), S(O)$_m$R$_2$, 1H-tetrazol-5-yl, C(O)OR$_2$, C(O)N(R$_2$) (R$_2$) or SO$_2$N(R$_2$)(R$_2$), N(R$_2$)C(O)N(R$_2$)(R$_2$),and wherein aryl is phenyl, pyridyl, 1H-tetrazol-5-yl, triazolyl, imidazolyl, thiazolyl, pyrazolyl, thiadiazolyl, imidazolone-1-yl, oxadiazolyl, benzimidazol-2-yl, triazolinone-yl, optionally substituted with C$_1$–C$_6$ alkyl, C$_3$–C$_6$ cycloalkyl, amino, or hydroxyl;

R$_7$ and R$_{7a}$ are independently hydrogen, C$_1$–C$_6$ alkyl, trifluoromethyl, phenyl, substituted C$_1$–C$_6$ alkyl where the substituents are imidazolyl, phenyl, indolyl, p-hydroxyphenyl, OR$_2$, S(O)$_m$R$_2$, C(O)OR$_2$, C$_3$–C$_7$ cycloalkyl, N(R$_2$)(R$_2$), C(O)N(R$_2$)(R$_2$); or R$_7$ and R$_{7a}$ can independently be joined to one or both of R$_4$ and R$_5$ groups to form alkylene bridges between the terminal nitrogen and the alkyl portion of the R$_7$ or R$_{7a}$ groups, wherein the bridge contains 1 to 5 carbons atoms; or R$_7$ and R$_{7a}$ can be joined to one another to form a C$_3$–C$_7$ cycloalkyl; with the proviso that if R$_3$ is unsubstituted phenyl, X is H, and Y is H, R$_7$ and R$_{7a}$ are other than unsubstituted C$_1$–C$_6$ alkyl;

m is 0, 1, or 2;

n is 1, 2, or 3;

q is 0, 1, 2, 3 or 4;

r is 0, 1, 2, or 3;

t is 0, 1, 2, or 3;

v is 0, 1, or 2;

and pharmaceutically acceptable salts and individual diastereomers thereof.

When n is 1, a pyrrolidine ring is formed, when n is 2 a piperidine ring is formed, and when n is 3 the ring is designated as a hexahydro-1H-azepine.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, propinyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, propinyloxy, isobutenyloxy, hexenyloxy and the like.

The term "halogen" is intended to include the halogen atom fluorine, chlorine, bromine and iodine.

The term "aryl" within the present invention, unless otherwise specified, is intended to include aromatic rings, such as carbocyclic and heterocyclic aromatic rings selected the group consisting of: phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, thiopheneyl, quinolinyl, pyrrazinyl, or isothiazolyl, which may be optionally substituted by 1 to 3 of $C_1-C_6$ alkyl, 1 to 3 of halogen, 1 to 2 of $OR_2$, methylenedioxy, —$S(O)_mR_2$, 1 to 2 of —$CF_3$, —$OCF_3$, nitro, —$NCR_2)C(O)(R_2)$, —$C(O)OR_2$, —$C(O)N(R_2)(R_2)$, -1H-tetrazol-5-yl, —$SO_2N(R_2)(R_2)$, —$N(R_2)SO_2$ phenyl, or —$N(R_2)SO_2R_2$, wherein $R_2$ is as defined herein.

Certain of the above defined terms may occur more than once in the above formula and upon such occurrence each term shall be defined independently of the other.

Preferred compounds of the instant invention include those of Formula Ia:

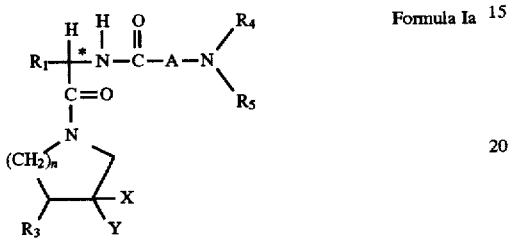

Formula Ia wherein:

$R_1$ is selected from the group consisting of:
$C_1-C_{10}$ alkyl, aryl ($C_1-C_4$ alkyl)-, $C_3-C_6$ cycloalkyl ($C_1-C_4$ alkyl)-, ($C_1-C_4$ alkyl)-K—($C_1-C_2$ alkyl)-, aryl ($C_0-C_2$ alkyl)-K—($C_1-C_2$ alkyl)-, and ($C_3-C_7$ cycloalkyl)($C_0-C_2$ alkyl)-K—($C_1-C_2$ alkyl)-, where K is O, $S(O)_m$, OC(O), or C(O)O, and the alkyl groups may be further substituted by 1 to 7 halogen, $S(O)_mR_2$, 1 to 3 $OR_2$ or $C(O)OR_2$, and aryl is phenyl, naphthyl, indolyl, pyridyl, benzimidazolyl, azaindoleyl, benzothienyl or benzofuranyl which may be further substituted by 1–2 $C_1-C_4$ alkyl, 1 to 2 halogen, 1 to 2 —$OR_2$, —$S(O)_mR_2$, or —$C(O)OR_2$;

$R_2$ is hydrogen, $C_1-C_6$ alkyl, $C_3-C_7$ cycloalkyl and where two $C_1-C_6$ alkyl groups are present on one atom they may be optionally joined to form a $C_4-C_7$ cyclic ring optionally including oxygen, sulfur or $NR_{3a}$;

$R_3$ is phenyl which is optionally substituted by 1 to 2 $C_1-C_6$ alkyl groups, 1 to 2 halogen, or 1 to 2 —$OR_2$, and which may be further substituted in the ortho position by a substitutent selected from the group consisting of:

—$NHSO_2CF_3$, —$(CH_2)_rOR_6$, —$(CH_2)_rN(R_2)(R_6)$, —$(CH_2)_r(R_6)$, —$(CH_2)_rC(O)OR_2$, —$(CH_2)_rC(O)OR_6$, —$(CH_2)_rOC(O)R2$, —$(CH_2)_rOC(O)R_6$, —$(CH_2)_rC(O)R_2$, —$(CH_2)_rC(O)R_6$, —$(CH_2)_rC(O)N(R_2)(R_2)$, —$(CH_2)_rC(O)N(R_2)(R_6)$, —$(CH_2)_rN(R_2)C(O)R_2$—$(CH_2)_rN(R_2)C(O)R_6$, —$(CH_2)_rN(R_6)C(O)R_2$, —$(CH_2)_rN(R_6)C(O)R_6$, —$(CH_2)_rN(R_2)C(O)OR_2$, —$(CH_2)_rN(R_2)C(O)OR_6$, —$(CH_2)_rN(R_6)C(O)OR_2$, —$(CH_2)_rN(R_6)C(O)OR_6$, —$(CH_2)_rN(R_2)C(O)N(R_2)(R_6)$, —$(CH_2)_rN(R_2)C(O)N(R_2)(R_2)$, —$(CH_2)_rN(R_6)C(O)N(R_2)(R_6)$, $(CH_2)_rN(R_2)SO_2R_6$, —$(CH_2)_rN(R_2)SO_2R_2$, —$(CH_2)_rN(R_6)SO_2R_2$, $(CH_2)_rN(R_6)SO_2R_6$, —$(CH_2)_rOC(O)N(R_2)(R_6)$, —$(CH_2)_rOC(O)N(R_2)(R_2)$, —$(CH_2)_r$ $SO_2N(R_2)(R_6)$, —$(CH_2)_rSO_2N(R_2)(R_2)$, $(CH_2)_r$ $SO_2NHC(O)R_6$, —$(CH_2)_rSO_2NHC(O)R_2$, —$(CH_2)_r$ $SO_2NHC(O)OR_6$, —$(CH_2)_rSO_2NHC(O)OR_2$, —$(CH_2)_rC(O)NHC(O)NR_2$, —$(CH_2)_rC(O)NHC(O)NR_6$, —$(CH_2)_rC(O)NHC(O)R_2$, —$(CH_2)_rCONHC(O)R_6$, —$(CH_2)_rCONHSO_2R_6$, —$(CH_2)_rCONHSO_2R_2$, —$(CH_2)_rCONHSO_2N(R_2)R_2)$, —$(CH_2)_r$ $CONHSO_2N(R_2)R_6)$, —$(CH_2)_rN(R_2)SO_2N(R_2)R_6)$, —$(CH_2)_rN(R_6)SO_2N(R_2)R_6)$, —$(CH_2)_rS(O)_mR_6$, and —$(CH_2)_rS(O)_mR_2$;

$R_{3a}$ is hydrogen, or $C_1-C_4$ alkyl;

X is selected from:

hydrogen, —$(CH_2)qN(R_2)C(O)R_2$, —$(CH_2)qN(R_2)C(O)(CH_2)_saryl$, (—$CH_2)qN(R_2)C(O)OR_2$, —$(CH_2)qN(R_2)SO_2(CH_2)_saryl$, —$(CH_2)qN(R_2)SO_2R_2$, —$(CH_2)qN(R_2)C(O)N(R_2)(CH_2)_saryl$, —$(CH_2)qN(R_2)C(O)N(R_2)(R_2)$, —$(CH_2)qC(O)N(R_2)(R_2)$, —$(CH_2)qC(O)N(R_2)(CH_2)_saryl$, —$(CH_2)qC(O)OR_2$, —$(CH_2)qC(O)O(CH_2)_saryl$, —$(CH_2)qOC(O)R_2$, —$(CH_2)qOC(O)(CH_2)_saryl$, —$(CH_2)qS(O)_mR_2$, and —$(CH_2)qS(O)m(CH_2)_saryl$, where an $R_2$ group may be optionally substituted by hydroxyl, carboxyl, $CONH_2$, $S(O)_mCH_3$, carboxylate $C1-C_4$ alkyl esters, or tetrazole and the aryl which is phenyl, naphthyl, pyridyl or 1-H-tetrazolyl may be optionally substituted by 1 to 2 halogen, 1 to 2 —$OR_2$, —$CONH_2$, —$C(O)OR_2$, 1 to 3 $C_1-C_4$ alkyl, —$S(O)_mR_2$, or 1H-tetrazole-5-yl;

Y is selected from:

hydrogen, $C_1-C_8$ alkyl, $(CH_2)_saryl$, —$(CH_2)q(C_5-C_6$ cycloalkyl), —$(CH_2)q$—K—$(C_1-C_6$ alkyl), —$(CH_2)q$—K—$(CH_2)_saryl$, —$(CH_2)_q$—K—$(CH_2)_s(C_3-C_7$ cycloalkyl containing O, $NR_2$, or S), and —$(CH_2)q$—K—$(CH_2)_s(C_5-C_6$ cycloalkyl), where K is O or S(O)m and where the alkyl groups may be optionally substituted by hydroxyl, carboxyl, $CONH_2$, carboxylate $C_1-C_4$ alkyl esters or 1H-tetrazole-5-yl and the aryl which is phenyl, naphthyl, pyridyl, 1-H-tetrazolyl, thiazolyl, imidazolyl, pyrimidinyl, thiadiazolyl, pyrazolyl, oxazolyl, isoxazolyl or thiopheneyl is optionally substituted by 1 to 3 halogen, 1 to 3 —$OR_2$, 1 to 2 —$N(R_2)(R_2)$, —$C(O)OR_2$, —$C(O)N(R_2)(R_2)$, cyano, 1 to 2 $C_1-C_4$ alkyl, benzyl, —$S(O)_mR_2$, or 1H-tetrazol-5-yl;

$R_4$ and $R_5$ are independently hydrogen, $C_1-C_6$ alkyl,or substituted $C_1-C_6$ alkyl where the substituents may be 1 to 5 halo, 1 to 3 hydroxyl, S(O)m $(C_1-C_6$ alkyl) or phenyl;

$R_6$ is H, $C_1-C_6$ alkyl, or $(CH_2)_varyl$, wherein the $(CH2)_v$ and alkyl groups may be optionally substituted by 1–2 $O(R_2)$, $S(O)_mR_2$, $C(O)OR_2$, $C(O)N(R_2)(R_2)$ or $SO_2N(R_2)(R_2)$, $N(R_2)C(O)N(R_2)(R_2)$, wherein the aryl group could be phenyl, pyridyl, 1H-tetrazol-5-yl, triazolyl, imidazolyl, thiazolyl, oxadiazolyl, pyrazolyl, thiadiazolyl, benzimidazol-2-yl, optionally substituted with $C_1-C_6$ alkyl, $C_3-C_6$ cycloalkyl, amino, or hydroxyl;

A is:

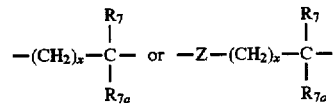

where x is 0 or 1;

Z is N—$R_{6a}$ or O, where $R_{6a}$ is hydrogen or $C_1-C_6$ alkyl;

$R_7$ and $R_{7a}$ are independently hydrogen $C_1-C_6$ alkyl, trifluoromethyl, phenyl, substituted $C_1-C_6$ alkyl where the substituents are imidazolyl, phenyl, indolyl, p-hydroxyphenyl, $OR_2$, S(O)m$R_2$, $C(O)OR_2$, $C_5-C_7$ cycloalkyl, $N(R_2)(R_2)$, $C(O)N(R_2)(R_2)$; or $R_7$ and $R_{7a}$ can independently be joined to one of $R_4$ or $R_5$ to form alkylene bridges between the terminal nitrogen and the alkyl portion of $R_7$ or $R_{7a}$ groups to form 5 or 6 membered rings; or $R_7$ and $R_{7a}$ can be joined to one another to form a $C_3$ cycloalkyl; with the proviso that if $R_3$ is unsubstituted phenyl, X is H, and Y is H, $R_7$ and $R_{7a}$ are other than unsubstituted $C_1-C_6$ alkyl;

n is 2;

m is 0, 1, or 2;

r is 0, 1, 2, or 3;
q is 0, 1, 2, or 3;
t is 0, 1, 2, or 3;
v is 0, 1, or 2,
and pharmaceutically acceptable salts and individual diastereomers thereof.

More preferred compounds of the instant invention include those of Formula Ib:

$$R_1-\underset{\underset{N}{\underset{|}{C=O}}}{\overset{H_*}{\underset{|}{C}}}-\overset{H}{\underset{|}{N}}-\underset{\overset{||}{O}}{\overset{|}{C}}-A-N\overset{R_4}{\underset{R_5}{\diagdown}}$$

Formula Ib (with piperidine ring bearing X, Y, $R_3$ substituents)

wherein:

$R_1$ is selected from the group consisting of:

$C_1$–$C_{10}$ alkyl, aryl ($C_1$–$C_3$ alkyl)-, ($C_3$–$C_7$ cycloalkyl) ($C_1$–$C_3$ alkyl)-, and aryl ($C_0$–$C_1$ alkyl)-K—($C_1$–$C_2$ alkyl)-, where K is O or S(O)$_m$ and aryl is specifically phenyl, pyridyl, naphthyl, indolyl, azaindolyl, or benzimidazolyl which is optionally substituted by 1–2 $C_1$–$C_4$ alkyl, 1 to 2 halogen, 1 to 2 OR$_2$, S(O)$_m$R$_2$, or C(O)OR$_2$;

$R_2$ is hydrogen, $C_1$–$C_6$ alkyl, $C_3$–$C_7$ cycloalkyl and where two $C_1$–$C_6$ alkyl groups are present on one atom they may be optionally joined to form a $C_5$–$C_7$ cyclic ring optionally including oxygen, sulfur or NR$_{3a}$;

$R_3$ is phenyl optionally substituted by 1 to 2 $C_1$–$C_6$ alkyl groups, 1 to 2 halogen or 1 to 2 OR$_2$, and which may be further substituted in the ortho position by a substitutent selected from the group consisting of: —NHSO$_2$CF$_3$, —(CH$_2$)$_r$OR$_6$, —(CH$_2$)$_r$N(R$_2$)(R$_6$), —(CH$_2$)$_r$(R$_6$), —(CH$_2$)$_r$C(O)OR$_6$, —(CH$_2$)$_r$OC(O)R$_2$, —(CH$_2$)$_r$OC(O)R$_6$, —(CH$_2$)$_r$C(O)R$_2$, —(CH$_2$)$_r$C(O)R$_6$, —(CH$_2$)$_r$C(O)N(R$_2$) (R$_2$), —(CH$_2$)$_r$C(O)N(R$_2$)(R$_6$), —(CH$_2$)$_r$N(R$_2$)C(O)R$_2$ —(CH$_2$)$_r$N(R$_2$)C(O)R$_6$, —(CH$_2$)$_r$N(R6)C(O)R2, —(CH$_2$)$_r$ N (R$_6$)C(O)R$_6$, —(CH$_2$)$_r$N (R$_2$)C(O)OR$_2$, —(CH$_2$)$_r$N(R$_2$)C (O)OR$_6$, —(CH$_2$)$_r$N(R$_6$)C(O)OR$_2$, —(CH$_2$)$_r$N(R$_6$)C(O) OR$_6$, —(CH$_2$)$_r$N(R$_2$)C(O)N(R$_2$)(R$_6$), —(CH$_2$)$_r$N(R$_2$)C(O) N(R$_2$)(R$_2$), —(CH$_2$)$_r$N(R$_6$)C(O)N(R$_2$)CR$_6$), (CH$_2$)$_r$N(R$_2$) SO$_2$R$_6$, —(CH$_2$)$_r$N(R$_2$)SO$_2$R$_2$, —(CH$_2$)N(R$_6$)SO$_2$R$_2$, CH$_2$)$_r$ N(R$_6$)SO$_2$R$_6$, —(CH$_2$)$_r$OC(O)N(R$_2$)(R$_6$), —(CH$_2$)$_r$ OC(O)N(R$_2$)(R$_2$), —(CH$_2$)$_r$SO$_2$N(R$_2$)(R$_6$), —(CH$_2$)$_r$SO$_2$N (R$_2$)(R$_2$), (CH$_2$)$_r$SO$_2$NHC(O)R$_6$, —(CH$_2$)$_r$SO$_2$NHC(O)R$_2$, —(CH$_2$)$_r$SO$_2$NHC(O)OR$_6$, —(CH$_2$)$_r$SO$_2$NHC(O)OR$_2$, —(CH$_2$)$_r$CONHSO$_2$R$_6$, —(CH$_2$)$_r$CONHSO$_2$R$_2$, —(CH$_2$)$_r$S (O)$_m$R$_6$, and —(CH$_2$)$_r$S(O)$_m$R$_2$;

$R_{3a}$ is hydrogen, or $C_1$–$C_4$ alkyl;

X is selected from:

hydrogen, —(CH$_2$)qN(R$_2$)C(O)R$_2$, —(CH$_2$)qN(R$_2$)C(O) (CH$_2$)$_t$aryl, —(CH$_2$)qN(R$_2$)SO$_2$(CH$_2$)$_t$aryl, —(CH$_2$) qN(R$_2$)SO$_2$R$_2$, —(CH$_2$)qN(R$_2$)C(O)N(R$_2$)(CH$_2$)$_t$aryl, —(CH$_2$)qN(R$_2$)C(O)N(R$_2$)(R$_2$), —(CH$_2$)qC(O)N(R$_2$) (R$_2$), —(CH$_2$)$_q$N(R$_2$)C(O)OR$_2$, —(CH$_2$)qC(O)N(R$_2$) (CH$_2$)$_t$aryl, —(CH$_2$)qC(O)OR$_2$, —(CH$_2$)qC(O)O (CH$_2$)$_t$aryl, —(CH$_2$)qOC(O)R$_2$, —(CH$_2$)qOC(O) (CH$_2$)$_t$aryl, —(CH$_2$)qS(O)$_m$R$_2$, and —(CH$_2$)qS(O)$_m$ (CH$_2$)$_t$aryl, where an R$_2$ group may be optionally substituted by hydroxyl, carboxyl, —CONH$_2$, —S(O)$_m$ CH$_3$, carboxylate $C_1$–$C_4$ alkyl esters or tetrazole and aryl is phenyl, napthyl or pyridyl which may be further substituted by 1–2 halogen, 1 to 2 OR$_2$, C(O)OR$_2$, 1 to 3 $C_1$–$C_4$ alkyl, S(O)$_m$R$_2$, or 1H-tetrazole-5-yl;

Y is selected from:

hydrogen, $C_1$–$C_8$ alkyl, (CH$_2$)$_t$aryl, —(CH$_2$)q $C_5$–$C_7$ cycloalkyl, —(CH$_2$)q—K—($C_1$–$C_6$ alkyl), —(CH$_2$) q—K—(CH$_2$)$_t$aryl, and —(CH$_2$)q—K—(CH$_2$)$_t$($C_5$–$C_6$ cycloalkyl), where K is S(O)$_m$ and where the alkyl groups may be optionally substituted by hydroxyl, carboxyl, CONH$_2$, carboxylate $C_1$–$C_4$ alkyl esters or 1H-tetrazole-5-yl and aryl is specifically phenyl, napthyl, pyridyl, thiazolyl, thiopheneyl, pyrazolyl, oxazolyl, isoxazolyl or imidazolyl which may be optionally substituted by 1 to 2 halogen, 1 to 2 OR$_2$, 1 to 2-N(R$_2$)(R$_2$), —CO(OR$_2$), 1 to 2 $C_1$–$C_4$ alkyl, S(O)$_m$ R$_2$, or 1H-tetrazol-5-yl;

$R_4$ and $R_5$ are independently hydrogen, $C_1$–$C_4$ alkyl, substituted $C_1$–$C_3$ alkyl where the substituents may be 1 to 2 hydroxyl;

$R_6$ is hydrogen, $C_1$–$C_6$ alkyl or (CH$_2$)$_v$aryl, wherein the $C_1$–$C_6$ alkyl and the (CH$_2$)$_v$aryl groups may be optionally substituted by 1–2O(R$_2$), S(O)$_m$R$_2$, C(O)OR$_2$, C(O)N(R$_2$) (R$_2$) or SO$_2$N(R$_2$)(R$_2$), N(R$_2$)C(O)N(R$_2$)(R$_2$), wherein aryl is specifically phenyl, pyridyl, 1H-tetrazol-5-yl, triazolyl, imidazolyl, thiazolyl, oxadiazolyl, pyrazolyl, thiadiazolyl, benzimidazol-2-yl, optionally substituted with $C_1$–$C_6$ alkyl, $C_3$–$C_6$ cycloalkyl, amino, or hydroxyl;

A is:

$$-(CH_2)_x-\underset{R_{7a}}{\overset{R_7}{\underset{|}{\overset{|}{C}}}}- \quad \text{or} \quad -Z-(CH_2)_x-\underset{R_{7a}}{\overset{R_7}{\underset{|}{\overset{|}{C}}}}-$$

where x is 0 or 1;

Z is N—$R_{6a}$ or O, where $R_{6a}$ is hydrogen or $C_1$–$C_6$ alkyl;

$R_7$ and $R_7$a are independently hydrogen, $C_1$–$C_2$ alkyl, phenyl, substituted $C_1$–$C_6$ alkyl wherein the substitutent is imidazolyl, phenyl, indolyl, p-hydroxyphenyl, OR$_2$, S(O)$_m$ R$_2$; or $R_7$ and $R_{7a}$ can be independently be joined to one another to form a $C_3$ cycloalkyl; with the proviso that if $R_3$ is unsubstituted phenyl, X is H, and Y is H, $R_7$ and $R_{7a}$ are other than unsubstituted $C_1$–$C_2$ alkyl;

m is 0, 1, or 2;

r is 0, 1, 2, or 3;

q is 0, 1, 2, or 3;

t is 0, 1, 2, or 3;

v is 0, 1, or 2;

and pharmaceutically acceptable salts and individual diastereomers thereof.

Still more preferred compounds of the instant invention are realized in Formula Ic:

$$R_1-\underset{\underset{N}{\underset{|}{C=O}}}{\overset{H}{\underset{|}{C}}}\blacktriangleleft\overset{H}{\underset{|}{N}}-\underset{\overset{||}{O}}{\overset{|}{C}}-A-N\overset{R_4}{\underset{R_5}{\diagdown}}$$

Formula Ic (with piperidine ring bearing X, Y, $R_3$ substituents)

wherein:

$R_1$ is selected from the group consisting of:

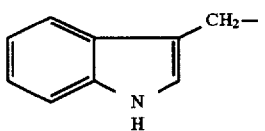
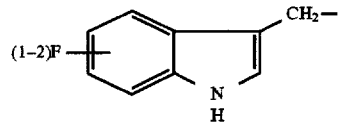
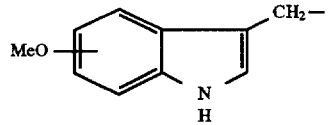
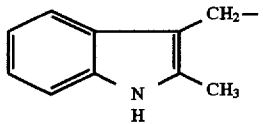
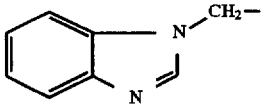
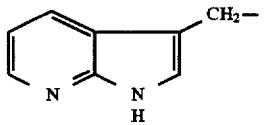
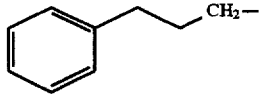
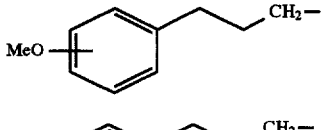
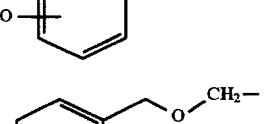
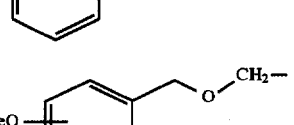
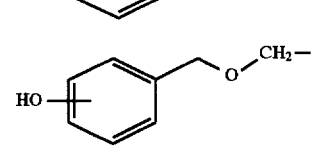
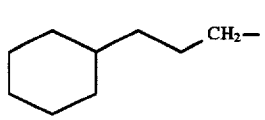

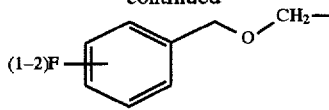
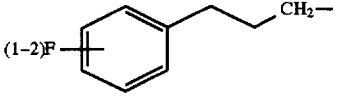
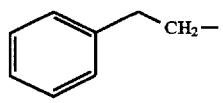
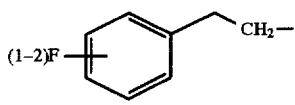
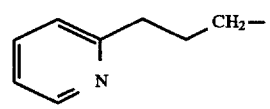

or their regioisomers where not specified;

$R_2$ is hydrogen, $C_1-C_6$ alkyl, or $C_3-C_7$ cycloalkyl and where two $C_1-C_6$ alkyl groups are present on one atom they may be optionally joined to form a $C_5-C_7$ cyclic ring optionally including oxygen, sulfur or $NR_{3a}$;

$R_3$ is phenyl optionally substituted in the ortho position with a substitutent selected from the group consisting of:

—$NHSO_2CF_3$, —$(CH_2)_rOR_6$, —$(CH_2)_r(R_6)$, —$(CH_2)_rC(O)OR_2$, —$(CH_2)_rC(O)OR_6$, —$(CH2)_rOC(O)R_2$, —$(CH2)_rOC(O)R_6$, —$(CH2)_rC(O)R2$, —$(CH2)_rC(O)R6$, —$(CH_2)_rC(O)N(R_2)(R_2)$, —$(CH_2)_rC(O)N(R_2)(R_6)$, —$(CH_2)_rN(R_2)C(O)R_2$ —$(CH_2)_rN(R_2)C(O)R_6$, —$(CH_2)_rN(R_6)C(O)R_2$, —$(CH_2)_rN(R_6)C(O)R_6$, —$(CH_2)_rN(R_2)C(O)OR_2$, —$(CH_2)_rN(R_2)C(O)OR_6$, —$(CH_2)_rN(R_6)C(O)OR_2$, —$(CH_2)_rN(R_6)C(O)OR_6$, —$(CH_2)_rN(R_2)C(O)N(R_2)(R_6)$, —$(CH_2)_rN(R_2)C(O)N(R_2)(R_2)$, —$(CH_2)_rN(R_6)C(O)N(R_2)(R_6)$, $(CH_2)_rN(R_2)SO_2R_6$, —$(CH_2)_rN(R_2)SO_2R_2$, —$(CH_2)_rN(R_6)SO_2R_2$, $CH_2)_rN(R_6)SO_2R_6$, —$(CH_2)_rOC(O)N(R_2)(R_6)$, —$(CH_2)_rOC(O)N(R_2)(R_2)$, —$(CH_2)_rSO_2N(R_2)(R_6)$, —$(CH_2)_rSO_2N(R_2)(R_2)$, $(CH_2)_rSO_2NHC(O)R_6$, —$(CH_2)_rSO_2NHC(O)R_2$, —$(CH_2)_rSO_2NHC(O)OR_6$, —$(CH_2)_rSO_2NHC(O)OR_2$, —$(CH_2)_rCONHSO_2R_6$, —$(CH_2)_rCONHSO_2R_2$, —$(CH_2)_rS(O)_mR_6$, and —$(CH_2)_rS(O)_mR_2$;

$R_{3a}$ is hydrogen, or $C_1-C_4$ alkyl;

X is selected from the group consisting of:

hydrogen,

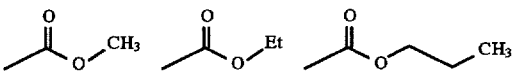
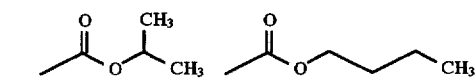
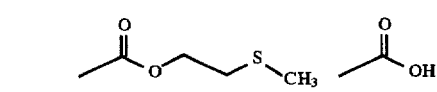

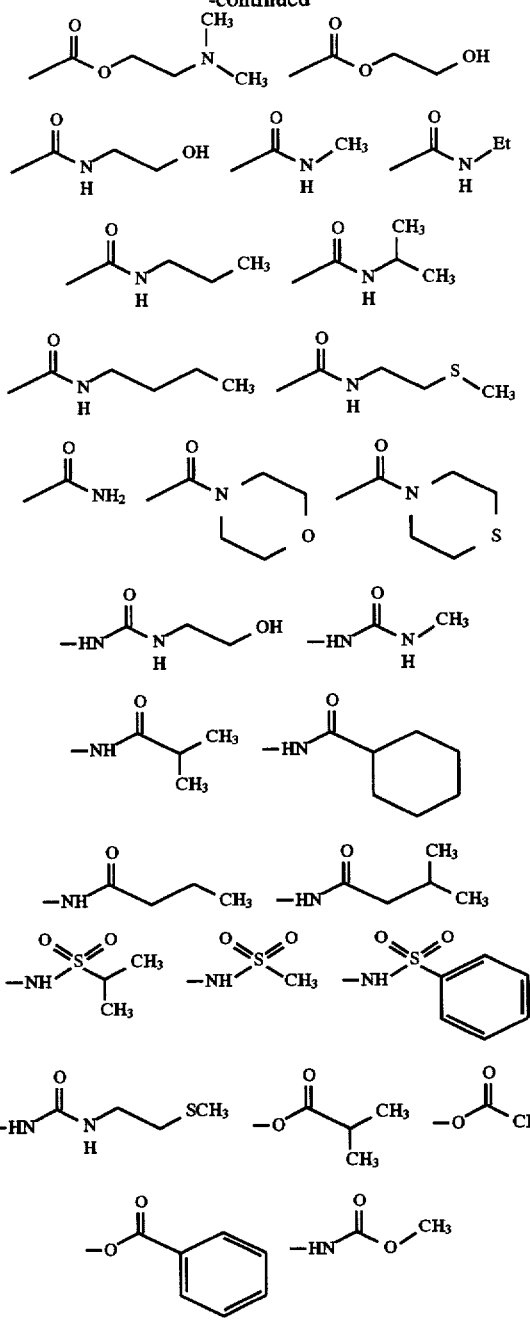

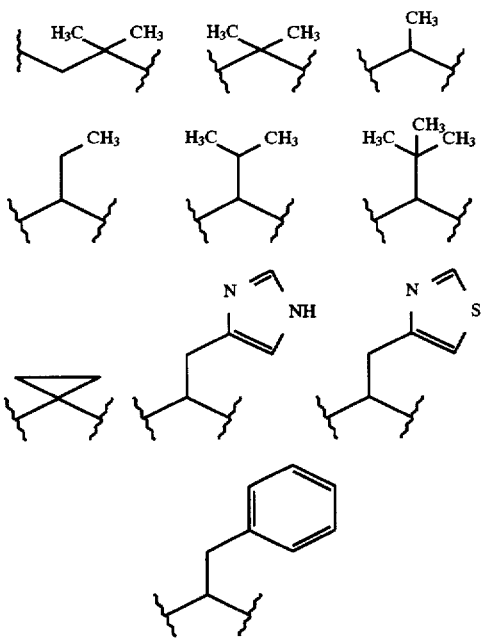

A is selected from the group consisting of:

$R_4$ and $R_5$ are independently selected from the group consisting of:

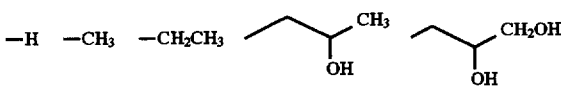

$R_6$ is hydrogen, $C_1$-$C_6$ alkyl or $(CH_2)_r$aryl wherein the alkyl and $(CH_2)_r$ groups may be optionally substituted by halogen, $OR_2$, $N(R_2)(R_2)$, $C_3$-$C_6$ cycloalkyl, 1H-tetrazol-5-yl, $C(O)OR_2$, $C(O)N(R_2)(R_2)$, $SO_2N(R_2)(R_2)$ or $N(R_2)C(O)N(R_2)(R_2)$, wherein aryl is selected from the following aromatic groups and their regioisomers:

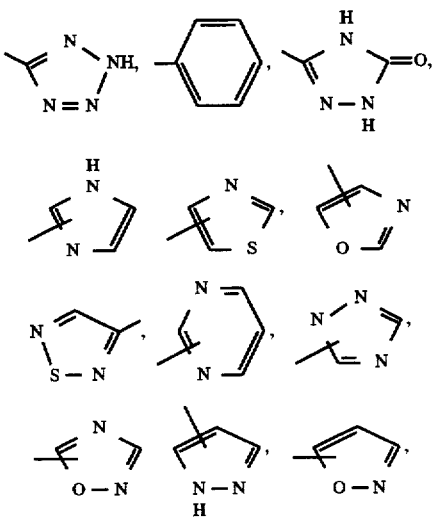

where the aromatic groups are optionally substituted with $C_1$-$C_2$ alkyl, $—N(R_2)(R_2)$, or hydroxy;

m is 0, 1, or 2;

r is 0, 1, 2, or 3;

q is 0 or 1;

Y is selected from the group consisting of:

hydrogen, $C_1$-$C_8$ alkyl, $(CH_2)_r$aryl, $—(CH_2)qC_5$-$C_7$ cycloalkyl, $—(CH_2)q—K—(C_1$-$C_6$ alkyl), $—(CH_2)q—K—(CH_2)_r$aryl, or $—(CH_2)q—K—(CH_2)_r(C_5$-$C_6$ cycloalkyl) where K is $S(O)_m$ and where the alkyl groups may be optionally substituted by hydroxyl, carboxyl, $CONH_2$, carboxylate $C_1$-$C_4$ alkyl esters or 1H-tetrazole-5-yl, and where aryl is specifically phenyl, naphthyl, pyridyl, thiazolyl, thiopheneyl, pyrazolyl, oxazolyl, isoxazolyl, thiadiazolyl, pyrimidinyl, or imidazolyl, which may be optionally substituted by 1 to 2 halogen, 1 to 2 $OR_2$, $CO(OR_2)$, 1 to 2 $C_1$-$C_4$ alkyl, $S(O)_mR_2$ or 1H-tetrazol-5-yl;

t is 0 or 1;

v is 0 or 1;

and pharmaceutically acceptable salts and individual diastereomers thereof.

All of the still more preferred compounds shown above have at least one asymmetric center. Additional asymmetric centers may be present on the molecule depending upon the nature of the substituents on the piperidine ring. Each such asymmetric center will produce two optical isomers and it is intended that all such optical isomers, as separated, pure or partially purified optical isomers, racemic mixtures or diastereomeric mixtures thereof, be included within the ambit of the present invention.

Specific compounds of the present invention include the following:

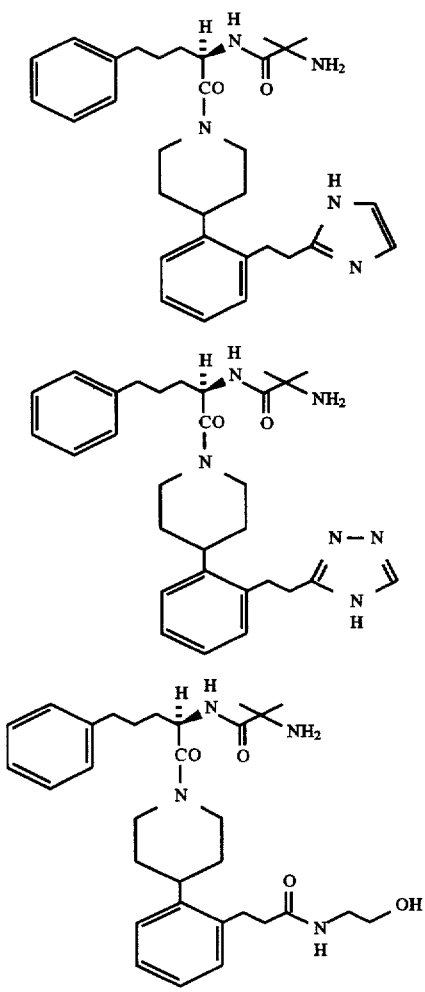

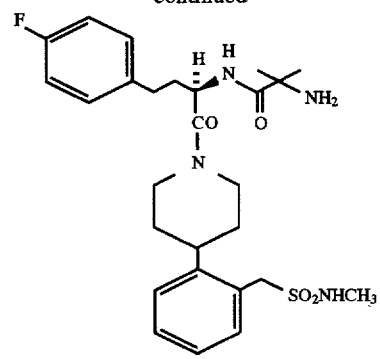

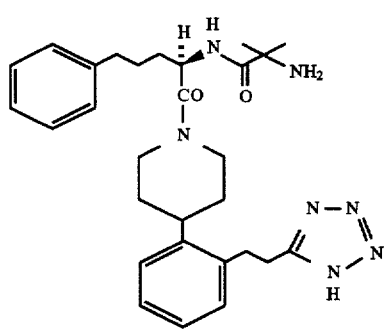

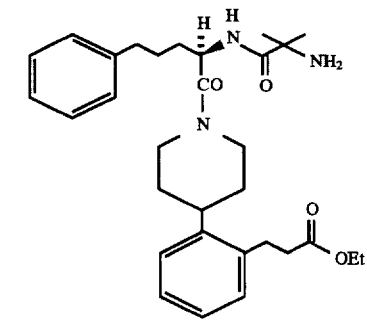

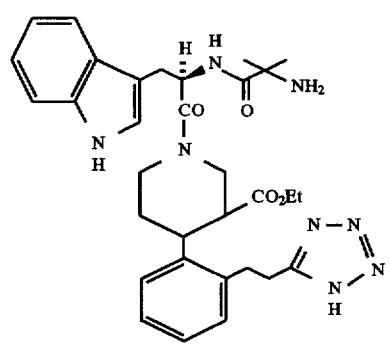

cis $d_1$, cis $d_2$, trans $d_1$, trans $d_2$

-continued
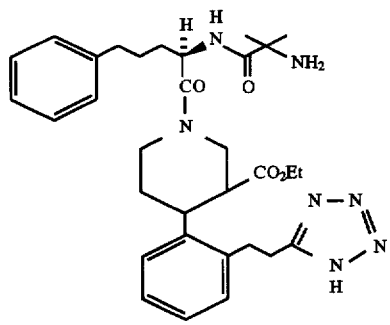
cis d₁, cis d₂, trans d₁, trans d₂
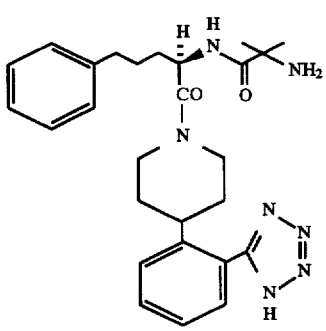
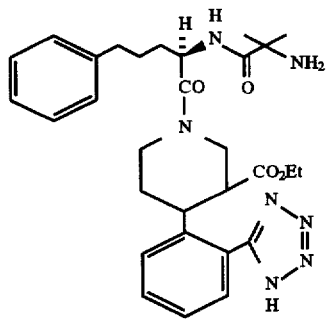
cis d₁, cis d₂, trans d₁, trans d₂
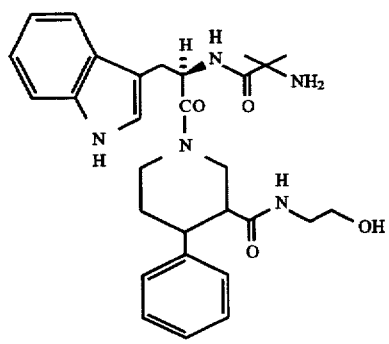
cis d₁, cis d₂, trans d₁, trans d₂
-continued
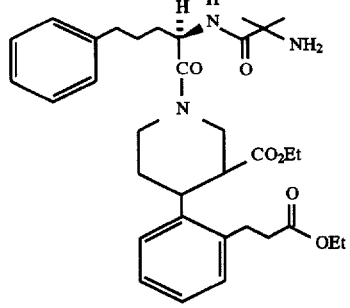
cis d₁, cis d₂, trans d₁, trans d₂
and their pharmaceutically acceptable salts and individual diasteromers thereof where not otherwise specified.
Additional specific compounds of the instant invention include the following:
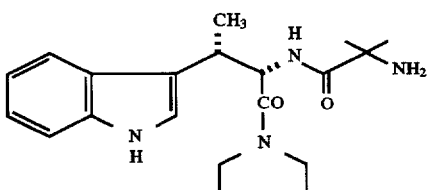
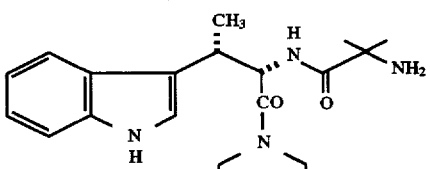
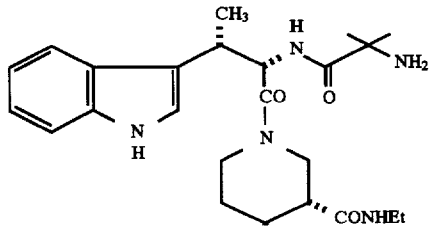

-continued
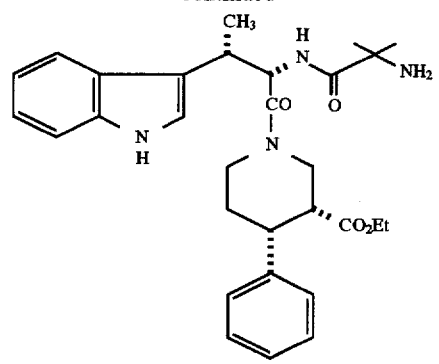
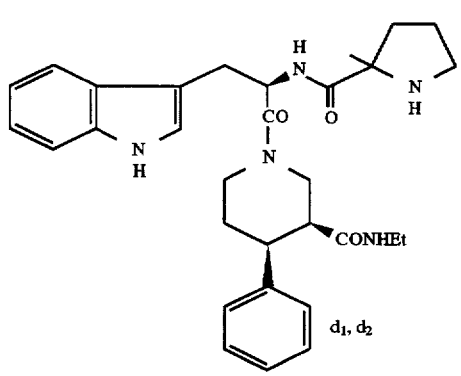
d₁, d₂
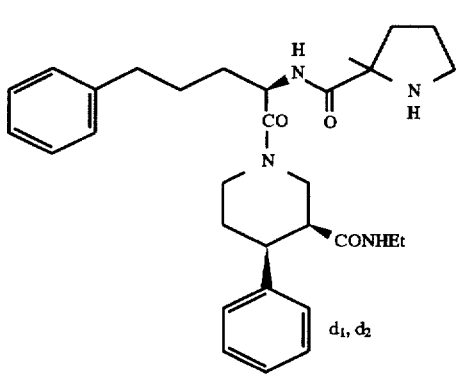
d₁, d₂
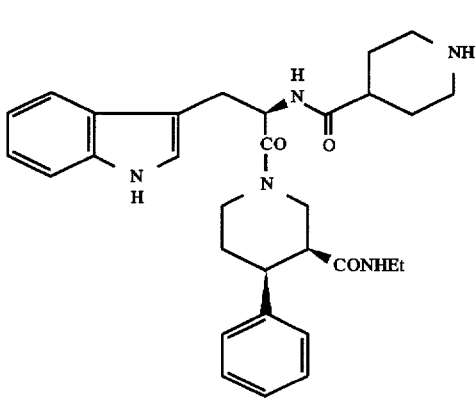
-continued
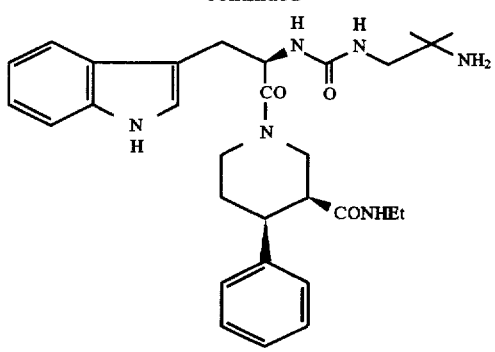
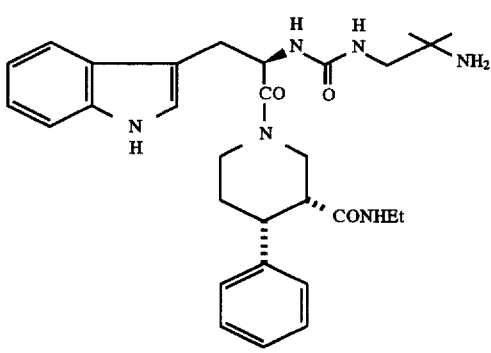
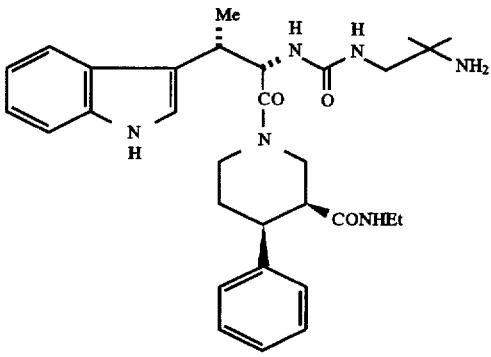
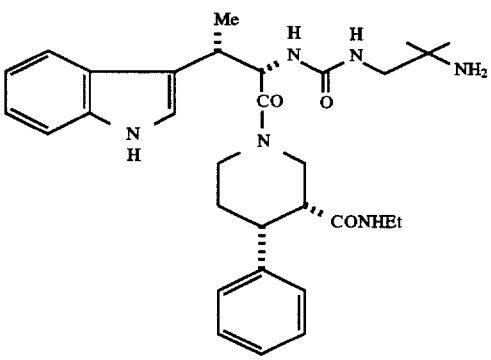

-continued
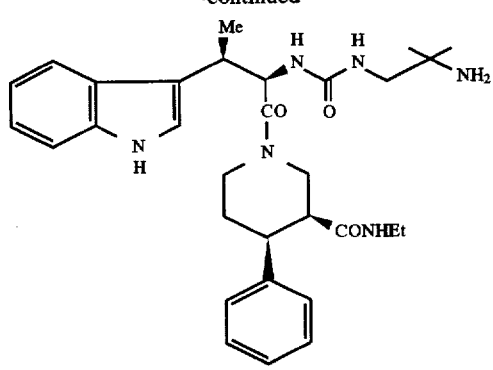
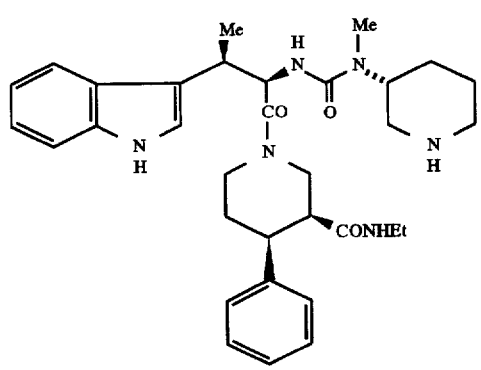
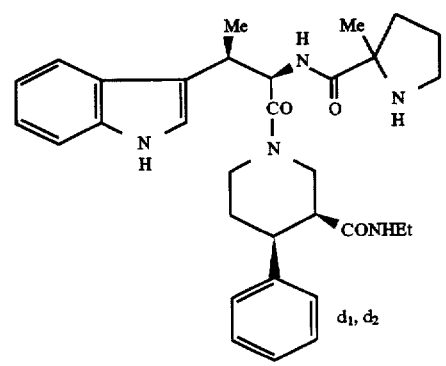
d₁, d₂
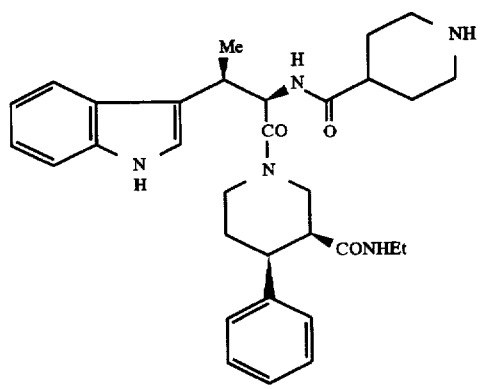
-continued
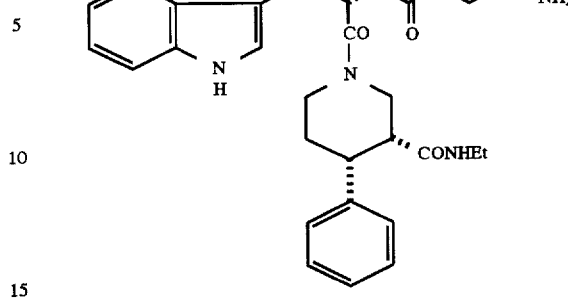
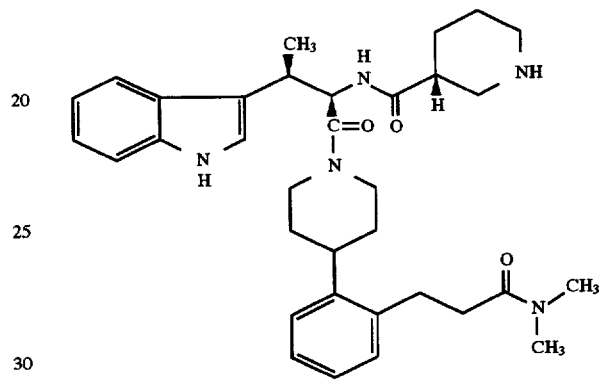
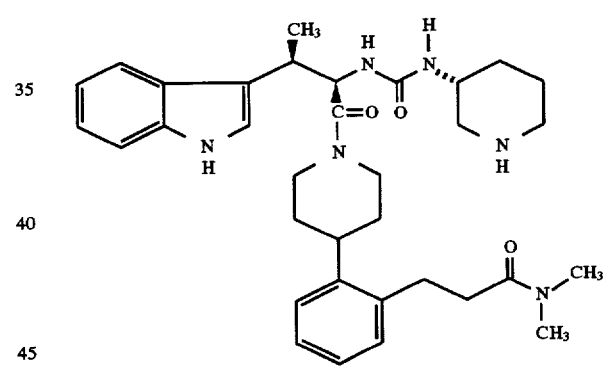
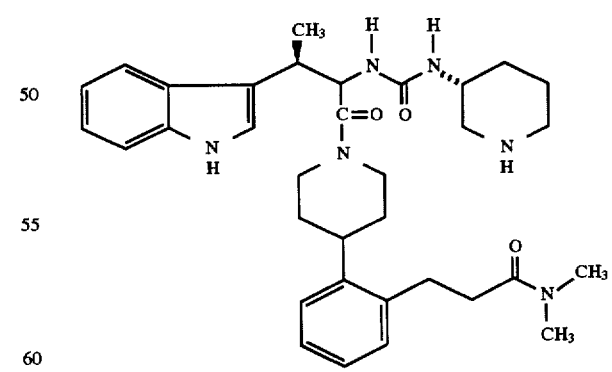

21
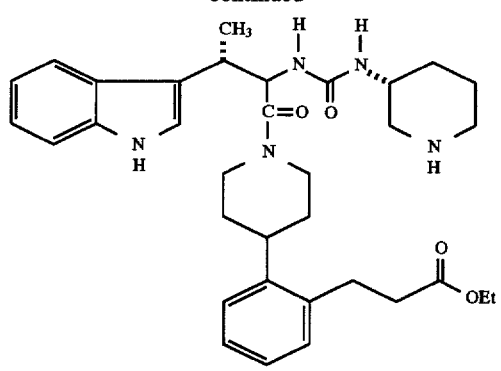
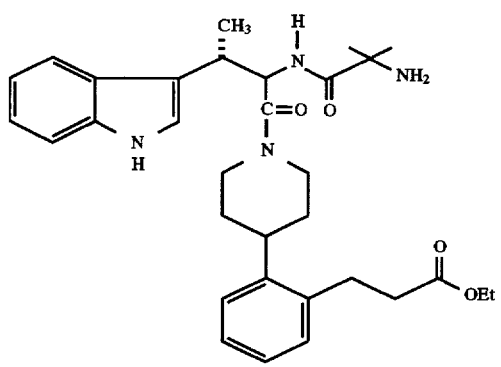
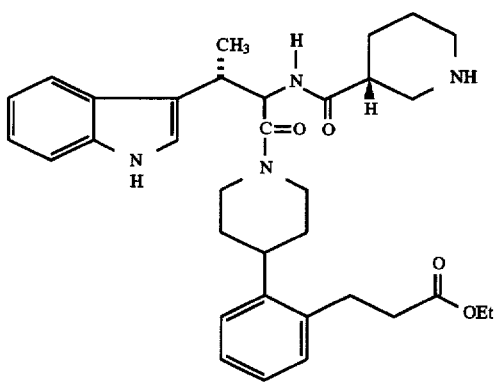
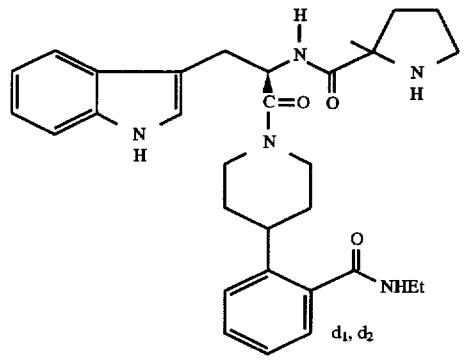
d₁, d₂
22
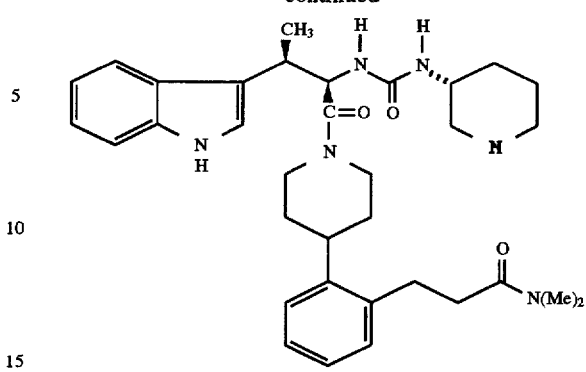
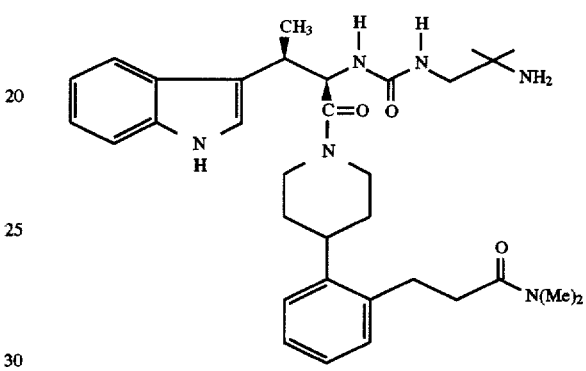
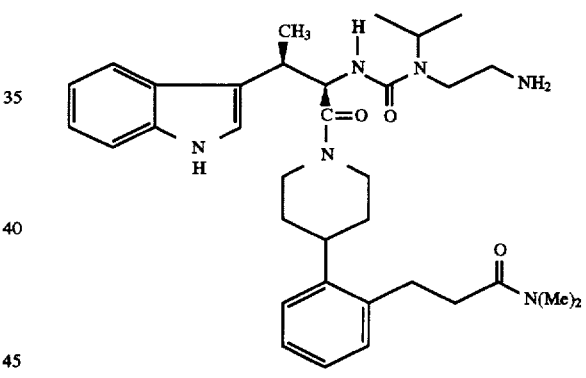
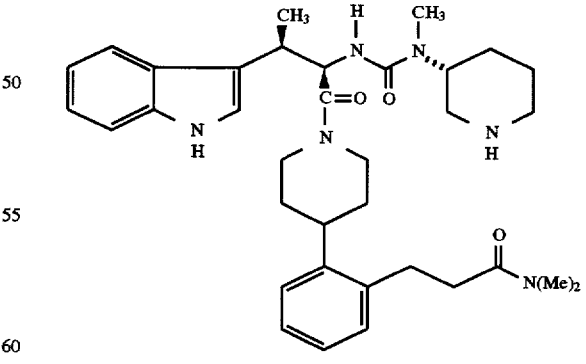

23
-continued
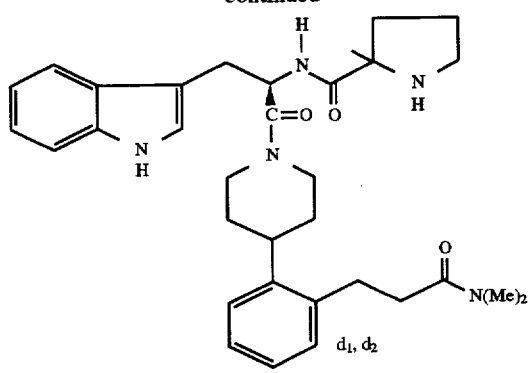
d₁, d₂
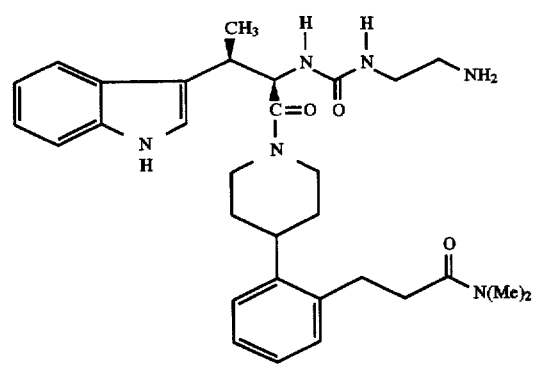
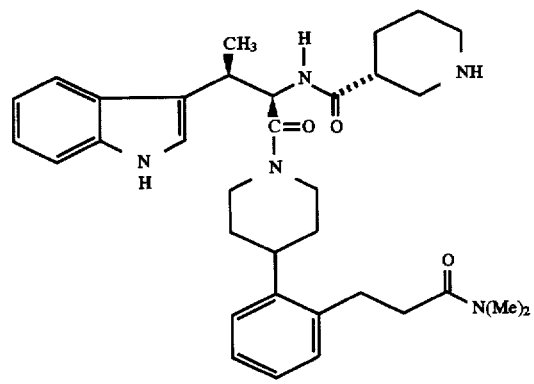
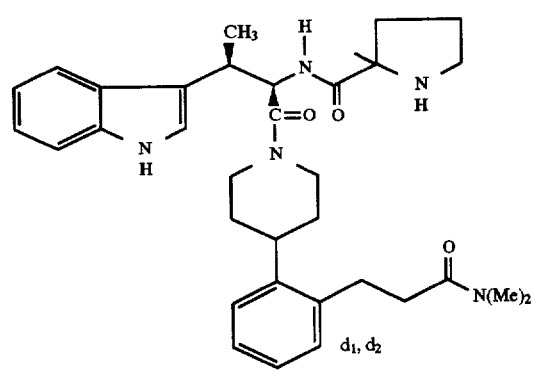
d₁, d₂
24
-continued
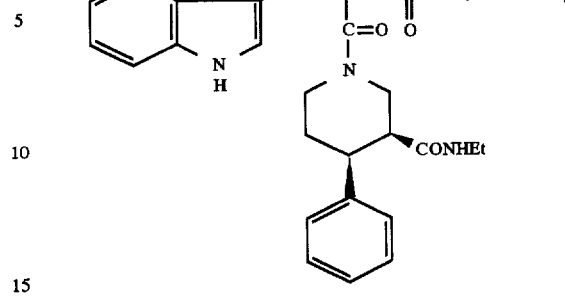
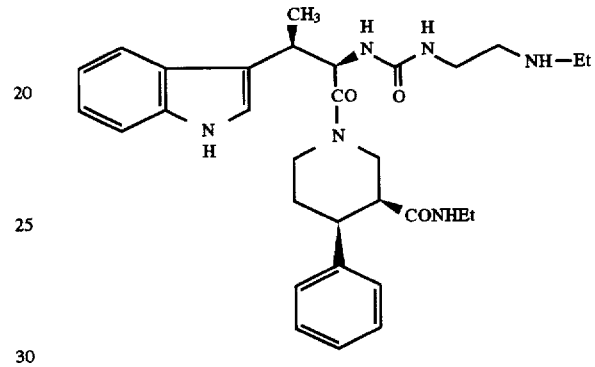
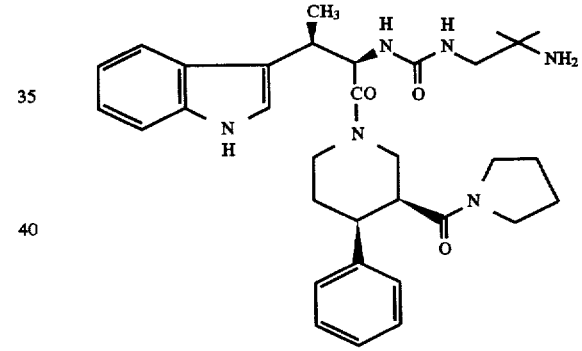
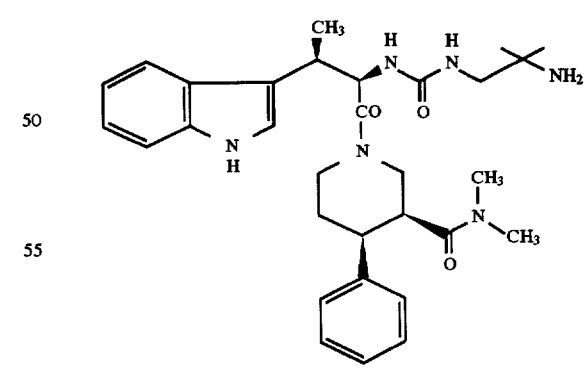

25
-continued
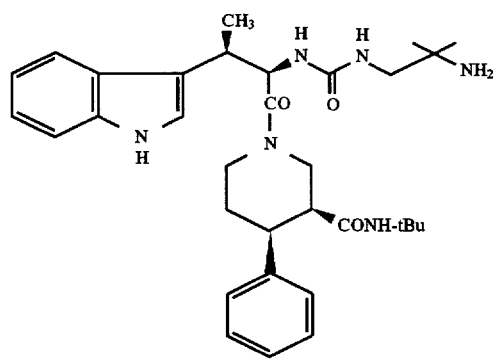
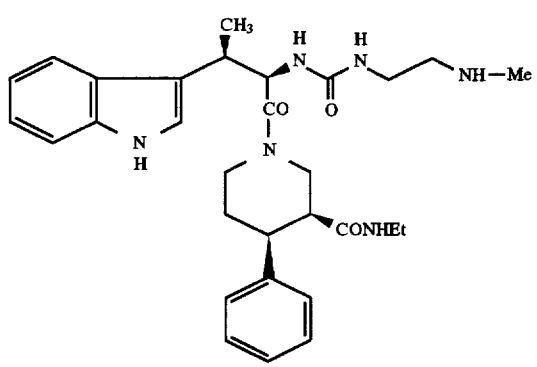
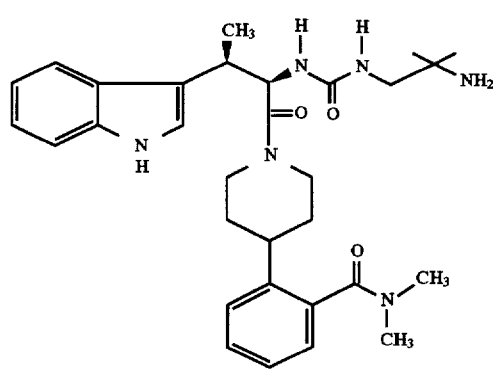
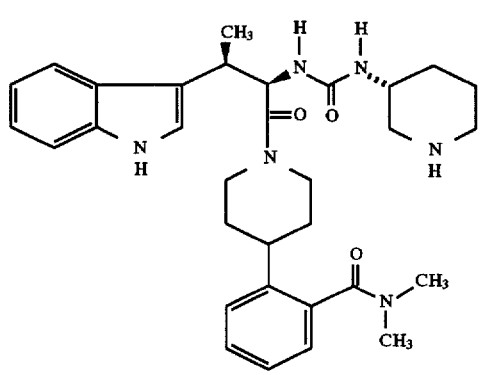
26
-continued
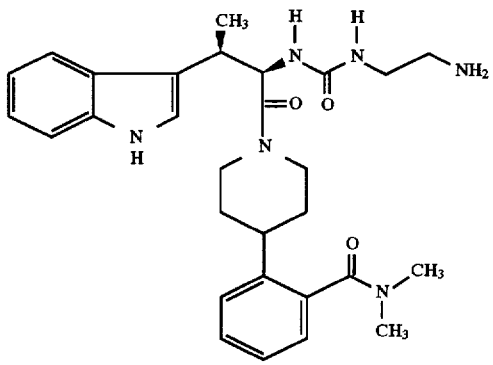
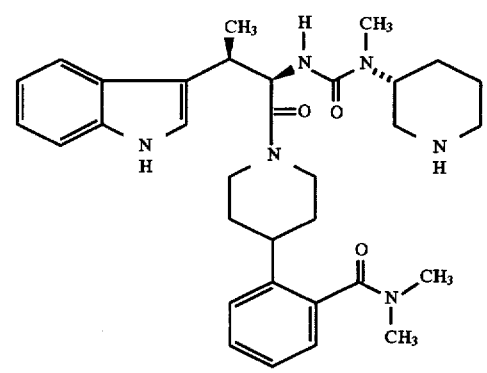
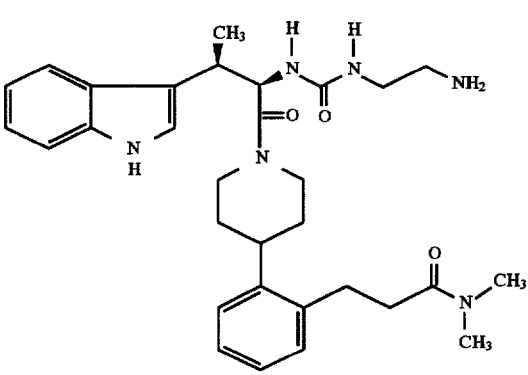
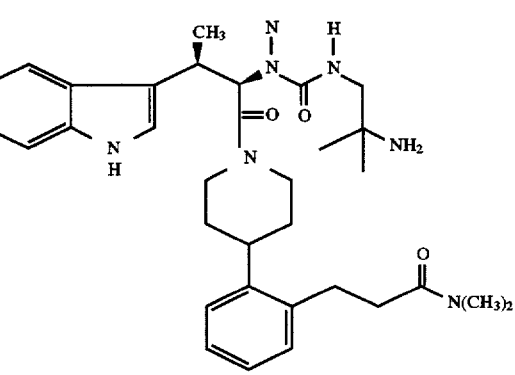

-continued

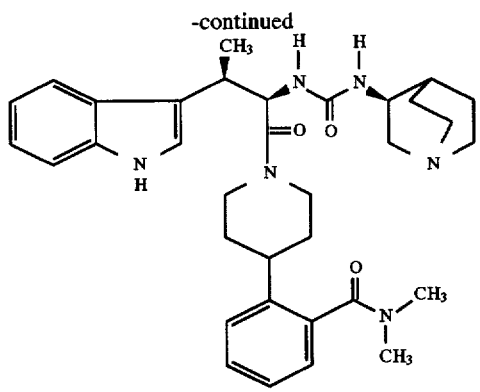

and pharmaceutically acceptable salts and individual diastereomers thereof where not otherwise specified.

All of the specific compounds shown above have at least one asymmetric center. Additional asymmetric centers may be present on the molecule depending upon the nature of the substituents on the piperidine ring. Each such asymmetric center will produce two optical isomers and it is intended that all such optical isomers, as separated, pure or partially purified optical isomers, racemic mixtures or diastereomeric mixtures thereof, be included within the ambit of the present invention.

Throughout the instant application, the following abbreviations are used with the following meanings:

| | |
|---|---|
| BOC | t-butyloxycarbonyl |
| BOP | Benzotriazol-1-yloxy tris(dimethylamino)-phosphonium hexafluorophosphate |
| CBZ | Benzyloxycarbonyl |
| DIBAL-H | diisobutylaluminum hydride |
| DMF | N,N-dimethylformamide |
| EDC | 1-(3-dimethylaminopropyl)-3-ethylcarbodiimide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| PLC | Preparative liquid chromatography |
| RPLC | Reverse phase liquid chromatography |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formula I:

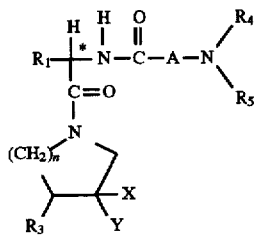

Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. Compounds are more active as growth hormone secretagogues and, therefore preferred, in which the nitrogen substituent is above and the hydrogen atom is below the plane of the structure as represented in Formula II. An equivalent representation places $R_1$ and the N-substituent in the plane of the structure with the C=O group above.

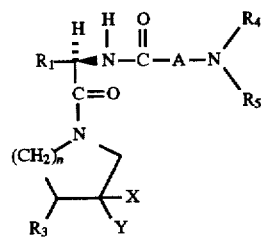

Formula II

This configuration corresponds to that present in a D-amino acid. In most cases, this is also designated as an R-configuration although this will vary according to the value of $R_1$ used in making the R- or S-stereochemical assignments. In the case of the asymmetric center which bears the X and Y groups, in most cases, both the R- and S-configurations are consistent with useful levels of growth hormone secretagogue activity. In addition configurations of many of the most preferred compounds of this invention are indicated. The X and Y groups may also be cis or trans- to the $R_3$ substituent. In some of the most preferred compounds a cis- or trans relationship is also specified in respect to the $R_3$ substituent. When the carbon atom in Formula I bearing an asterisk is of a defined and usually a D- configuration, diastereomers result according to the absolute configuration at the carbon atoms bearing the X, Y, and $R_3$ groups.

Surprisingly, certain compounds possessing both the L-configuration and a Beta-alkyl group, in particular, a Beta-methyl group, have also been found exhibit high activity as growth hormone secretagogues.

Diastereomers may arise from the presesence of asymmetric centers in any of the present compounds. They are designated as diastereomers $d_1$, $d_2$, $d_3$ or $d_4$ and if desired, their independent syntheses or chromatographic separations may be achieved by using standard means or as described herein. Their absolute stereochemistry may be determined by the X-ray crystallography of crystalline products or crystalline intermediates which are derivatized, if necessary, containing an asymmetric center of known configuration.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds of Formula I of the present invention can be carried out in sequential or convergent synthetic routes. Syntheses detailing the preparation of the compounds of Formula I in a sequential manner are presented in the following reaction schemes.

The "phrase standard peptide coupling reaction conditions" is used repeatedly here, and it means coupling a carboxylic acid with an amine using an acid activating agent such as EDC, DCC, and BOP in a inert solvent such as dichloromethane in the presence of a catalyst such as HOBT. The uses of protective groups for amine and carboxylic acid to facilitate the desired reaction and minimize undesired reactions are well documented. Conditions required to remove protecting groups which may be present are found in Greene, T; Wuts, P. G. M. *Protective Groups in Organic Synthesis*, John Wiley & Sons, Inc., New York, N.Y. (1991). CBZ and Boc were used extensively in the syntheses of this invention, and their removal conditions are known to those skilled in the art. Removal of CBZ groups can be achieved by a number of methods, for example, catalytic hydrogenation with hydrogen in the presence of palladium catalyst in a protic solvent such as ethanol. In cases where catalytic hydrogenation is contraindicated by the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol, with a strong acid, such as trifluoroacetic acid or hydrochloric acid.

The protected amino acid derivatives 1 are, in many cases, commercially available, where the protecting group L is, for example, BOC or CBZ groups. Other protected amino acid derivatives 1 can be prepared by literature methods (Williams, R. M. *Synthesis of Optically Active α-Amino Acids*, Pergamon Press: Oxford, 1989). Many of the piperidines, pyrrolidines and hexahydro-1H-azepines of formula 2 are either commercially available or known in the literature and others can be prepared following literature methods, some of which are described here. The skills required in carrying out the reaction and purification of the resulting reaction products are known to those skilled in the art. Purification procedures include crystallization, normal phase or reverse phase chromatography.

SCHEME 1

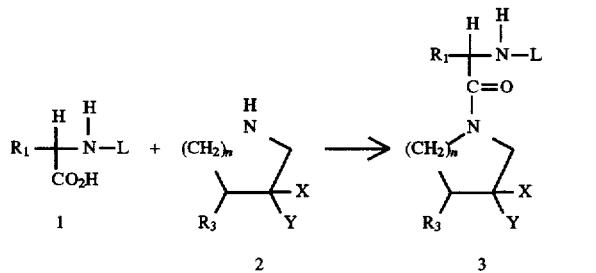

Intermediates of formula 3 can be synthesized as described in Scheme 1. Coupling of amine of formula 2, whose preparations are described later if they are not commercially available, to protected amino acids of formula 1, wherein L is a suitable protecting group, is conveniently carried out under standard peptide coupling conditions.

SCHEME 2

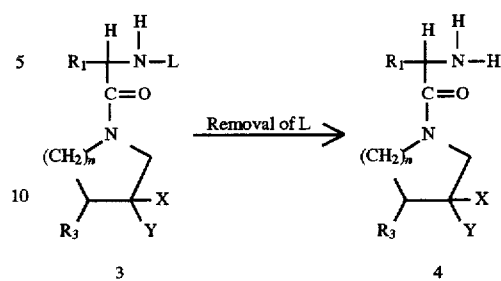

Conversion of 3 to intermediates 4 can be carried out as illustrated in Scheme 2 by removal of the protecting group L (CBZ, BOC, etc.)

SCHEME 3

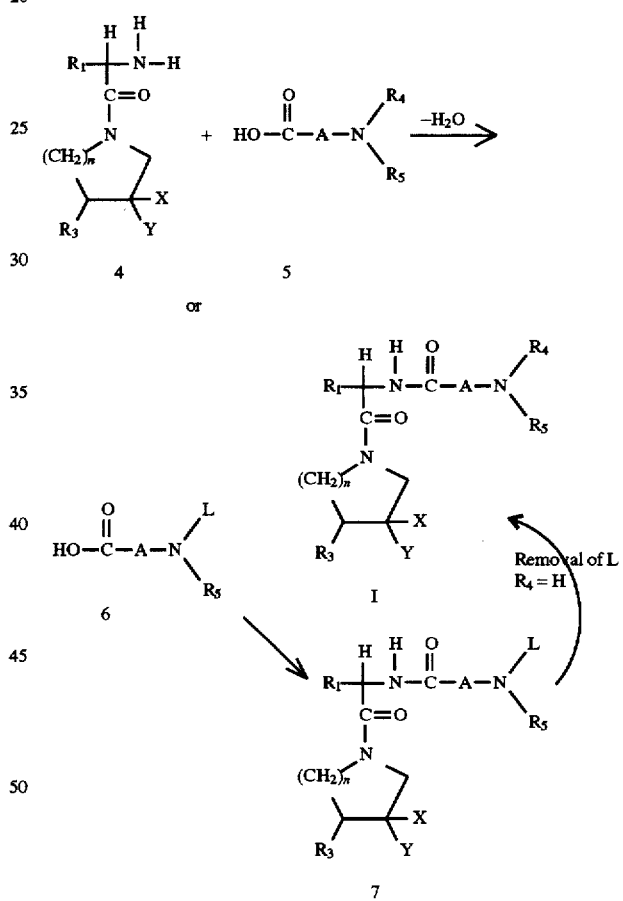

Intermediates of formula 5, wherein A is connected to the carbonyl by a carbon atom —$(CH_2)_xCR_7R_{7a}(CH_2)_y$— as shown in Scheme 3 can be coupled to intermediates of formula 4 under the standard peptide coupling reaction conditions. The amino acids 5, as amino acids 1, are either commercially available or may be synthesized. Also if $R_4$ or $R_5$ is a hydrogen then the protected amino acids 6 are employed in the coupling reaction, wherein L is a protecting group as defined above. Removal of L in 7 affords I, where $R_4$=H, can be carried out under conditions known in the art.

SCHEME 4

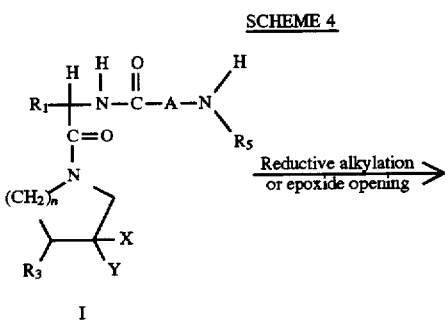

where R₄ is substituted/unsubstituted alkyl

Compounds of formula I wherein $R_4$ and/or $R_5$ is a hydrogen can be further elaborated to new compounds I (with most preferred side chains $R_4$=$CH_2$—$CH(OH)$—$CH_2X$, wherein X=H or OH) which are substituted on the amino group as depicted in Scheme 4. Reductive alkylation of I with an aldehyde is carried out under conditions known in the art; for example, by catalytic hydrogenation with hydrogen in the presence of platinum, palladium, or nickel catalysts or with chemical reducing agents such as sodium cyanoborohydride in an protic solvent such as methanol or ethanol in the present of catalytic amount of acid. Alternatively, a similar transformation can be accomplished via an epoxide opening reaction.

SCHEME 5

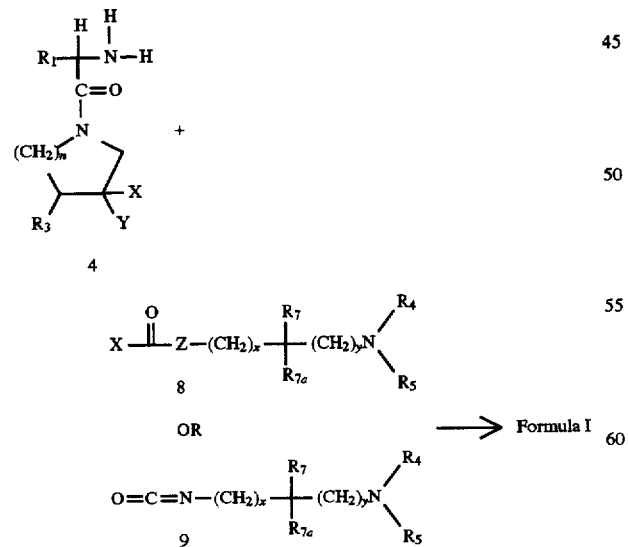

Compounds of formula I, wherein A is Z—$(CH_2)_x$—C$(R_7)(R_{7a})$—$(CH_2)_y$, and Z is N—R2 or O can be prepared as shown in Scheme 5 by reacting 4 with reagents 8, wherein X is a good leaving group such as Cl, Br, I, or imidazole. Alternatively, 4 can be reacted with an isocyanate of formula 9 in an inert solvent such as 1,2-dichloroethane which results in a compound of formula I where Z is NH.

The compounds of general formula I of the present invention can also be prepared in a convergent manner as described in reaction schemes 6, 7 and 8.

The carboxylic acid protected amino acid derivatives 10 are, in many cases, commercially available where M=methyl, ethyl, or benzyl esters. Other ester protected amino acids can be prepared by classical methods familiar to those skilled in the art. Some of these methods include the reaction of the amino acid with an alcohol in the presence of an acid such as hydrochloric acid or p-toluenesulfonic acid and azeotropic removal of water. Other reactions includes the reaction of a protected amino acid with a diazoalkane and removal of the protecting group L.

SCHEME 6

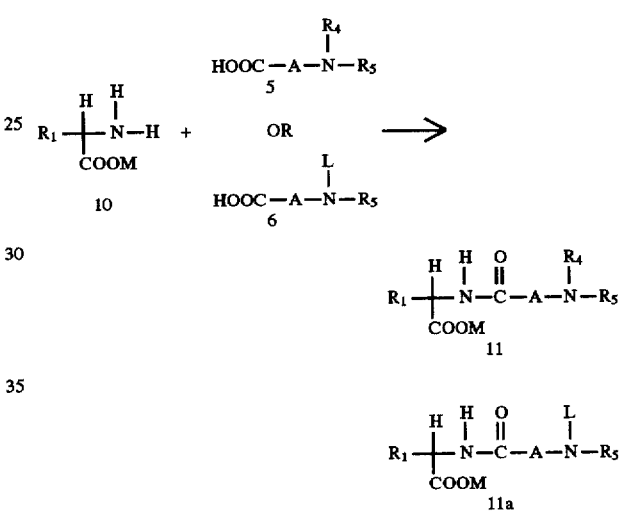

Intermediates of formula 11 or 11a, can be prepared as shown in Scheme 6 by coupling of amino acid esters 10 to amino acids of formula 5 or 6. When a urea linkage is present in 11 or 11a, it can be introduced as illustrated in Scheme 5.

SCHEME 7

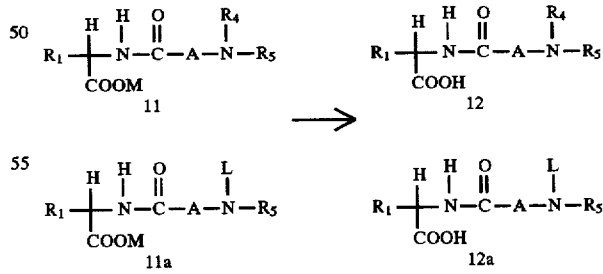

Conversion of the ester 11 or 11a to intermediate acids 12 or a can be achieved by a number of methods known in the art as described in Scheme 7. For example, methyl and ethyl esters can be hydrolyzed with lithium hydroxide in a protic solvent like aqueous methanol. In addition, removal of benzyl group can be accomplished by a number of reductive methods including hydrogenation in the presence of palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.* 1982, 42, 587).

SCHEME 8

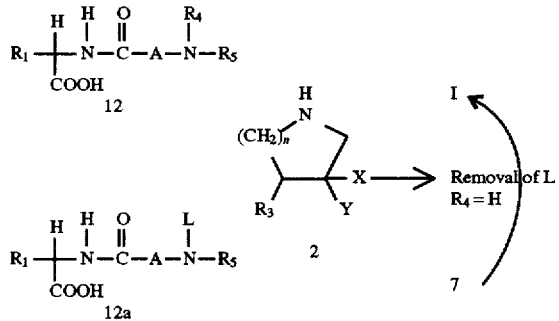

Acid 12 or 12a can then be elaborated to I or compound 7 as described in Scheme 8. Coupling of piperidines, pyrrolidines or hexahydro-1H-azepines of formula 2 to acids of formula 12 or 12a, wherein L is a suitable protecting group, is conveniently carried out under the standard peptide coupling reaction conditions. Transformation of 7 to I is achieved by removal of the protecting group L. When $R_4$ and/or $R_5$ is H, substituted alkyl groups may be optionally added to the nitrogen atom as described in Scheme 4.

The substituted piperidines, pyrrolidines or hexahydro-1H-azepines are either known compounds or can be prepared by literature procedures. Illustrated here are some, but by no means all the methods available for their preparation.

SCHEME 9

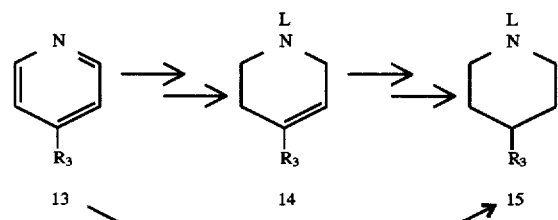

The synthesis of substituted piperidines of formula 2 (n=2) has been detailed in a number of research articles. For e.g., S. M. N. Efange et al. (*J. Med. Chem.* 1993, 36, 1278–1283) and M. S. Berridge et al. (*J. Med. Chem.* 1993, 36, 1284–1290) have used 4-substituted-pyridine intermediates 13 to synthesize 4-substituted tetrahydropiperidines of formula 14 (L=methyl) as detailed in Scheme 9. Removal of L from piperidines of formula 14 can be carried out by a number of methods familiar to those skilled in the art, including the cyanogen bromide protocol detailed by H. Ong et al. in *J. Med. Chem.* 1983, 23, 981–986 and ACE-$C_1$ method as described in R. Olofson et al. *J. Org. Chem.* 1984, 23, 2795. For intermediates of formula 14, wherein L=Bn, simultaneous removal of the benzyl group and hydrogenation of the olefin can be accomplished by use of platinum or palladium catalysts in a protic solvent like methanol. Alternatively, 13 can be directly transformed to piperidines of formula 15 (L=H) by carrying out the reduction with platinum oxide in a protic solvent like methanol with a catalytic amount of acid.

SCHEME 10

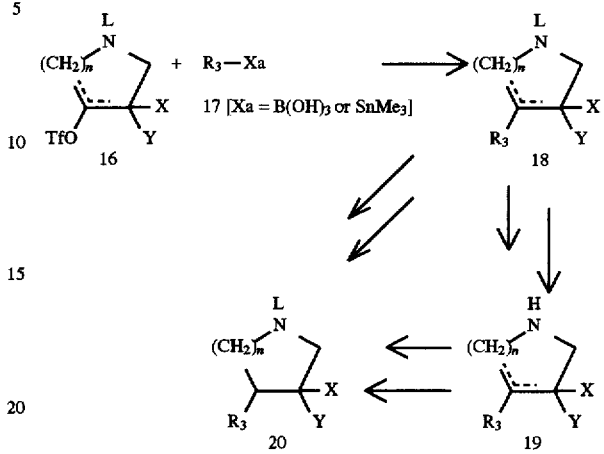

Other methods as shown in Scheme 10 can also be used to synthesize compounds of formula 2. For example, cross-coupling of enol triflates of formula 16 (L=protecting group) where X and Y are defined in formula I with aryl boronic acids of formula 17 (Xa=B(OH)$_3$) or aryl or phenyl or naphthyl tin reagents of formula 17 (Xa=SnMe$_3$) can be accomplished with palladium (II) or palladium (0) catalysts as detailed in the review article by W. J. Scott and J. E. McMurry *Acc. Chem. Res.* 1988, 21, 47 to give in their examples tetrahydropiperidines 18 (L=protecting group). Various methods exist for the synthesis of the enol triflate intermediates of formula 16, phenyl or naphthyl boronic acids, and phenyl or naphthyl tin reagents of formula 17 (X=B(OH)$_3$; SnMe$_3$) and are familiar to those skilled in the art. Removal of the protecting group L furnishes for example, piperidines of formula 19 (L=H). Hydrogenation of 18 followed by removal of the protection group L also gives saturated derivatives 20. Alternatively, 19 can be transformed to compounds of formula 20 by hydrogenating the olefin in the presence of platinum or palladium catalysts in a protic solvent like methanol.

SCHEME 11

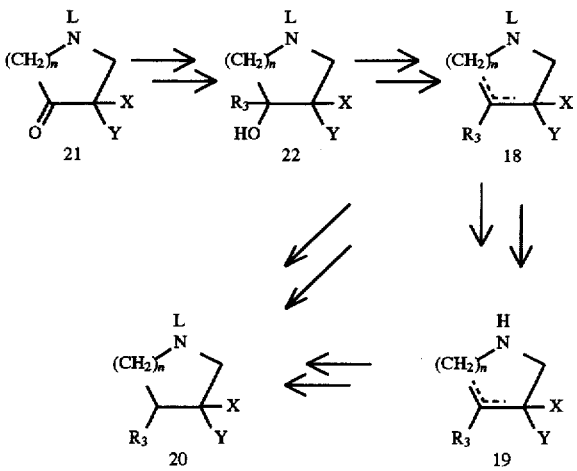

Methods for the synthesis of substituted pyrrolidines, piperidines, and hexahydro-1H-azepines also involve addition of substituted and/or unsubstituted alkyl, cycloalkyl, phenyl or naphthyl Grignard reagents or lithium reagents to oxo-piperidines, oxo-pyrrolidines, or oxo-hexahydro-1H-azepines of formula 21 (L=benzyl, methyl, etc.) to give compounds of formula 22 (L=benzyl, methyl, etc.). The dehydration of the hydroxyl group of 22 (L=benzyl, methyl, etc.) to yield 18 (L=benzyl, methyl, etc.) can be carried out by treating it with strong acid or via an elimination reaction of the corresponding mesylate derived from 22 (L=benzyl, methyl, etc.). Compounds 18 can be transformed to 19 or 20 as described above.

SCHEME 12

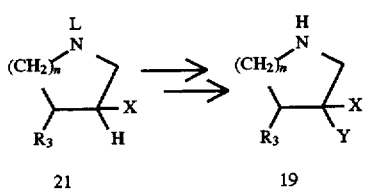

21    19

The 3,4-disubstituted piperidines, pyrrolidines and hexahydro-1H-azepines of formula 21 wherein X is an electron withdrawing group like an ester, ketone, nitrile, etc., can be further alkylated, hydroxylated, halogenated by using methods familiar to those skilled in the art. Once again, deprotection of the protecting group L can be carried out by methods familiar to those skilled in the art. Specifically, ortho-substituted phenyl piperidines of of formula 22a wherein X,Y=H can be prepared from the phenyl

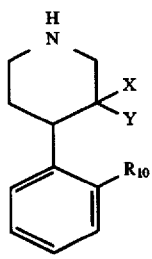

22a piperidine intermediate 23 (see S. M. N. Efange et al. *J. Med. Chem.* 1993, 26, 1278).

SCHEME 13

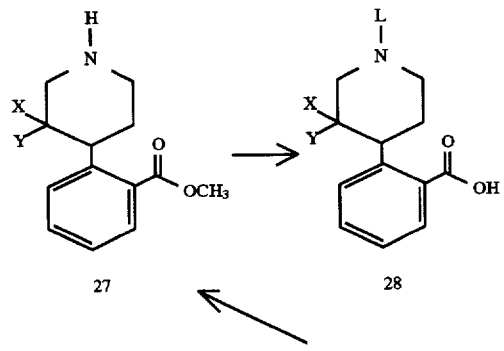

27    28

-continued
SCHEME 13

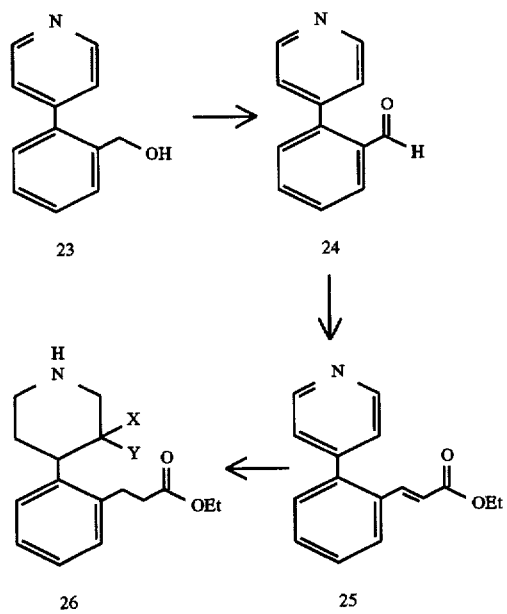

As shown in Scheme 13, the benzyl alcohol can be oxidized to aldehyde 24 by a variety of methods familiar to those skilled in the art. Commonly used methods are manganese dioxide in an inert solvent like chloroform or the Swern protocol. A variety of functional groups can now be elaborated from 24. For example, an Emmons reaction with triethylphosphonoacetate in the presence of base gives the α, β-unsaturated ester 25. Concurrent reduction of the pyridine unit and the olefin group with a platinum or palladium catalyst in an alcoholic solvent provides the piperidine of formula 26, wherein X, Y=H. The piperidine 26 may be derivatized to ester and acid bearing growth hormone secretagogues of formula I wherein X and Y=H by using chemistry detailed in Schemes 1–8. Alternatively, 24 can directly be transformed to a methyl ester 27, wherein X, Y=H, by oxidation of the aldehyde group to an ester with the Corey protocol (NaCN, acetic acid, $MnO_2$, in methanol) followed by reduction of the pyridine to a piperidine with platinum or palladium catalysts in a protic solvent like methanol. The piperidine 27 can be elaborated to growth hormone secretagogues of Formula I by using chemistry detailed in Schemes 1–8. The piperidine unit of 27 can be protected by a variety of protecting groups L familiar to those skilled in the an and the ester unit can be hydrolyzed by well documented methods to give the acid 28, wherein X, Y=H. The acid intermediate 28 can be used to prepare growth hormone secretagogues bearing a variety of highly functionalized piperidines that can be transformed to growth hormone secretagogues of formula I. For example, acid 28 can be coupled to primary and secondary amines under standard peptide-type coupling reaction conditions to give amides that can be elaborated to growth hormone secretagogues of formula I after removal of L.

Highly functionalized phenyl piperidines of formula 22, wherein X, Y=H, can be prepared by utilizing synthetic methods detailed below.

SCHEME 14

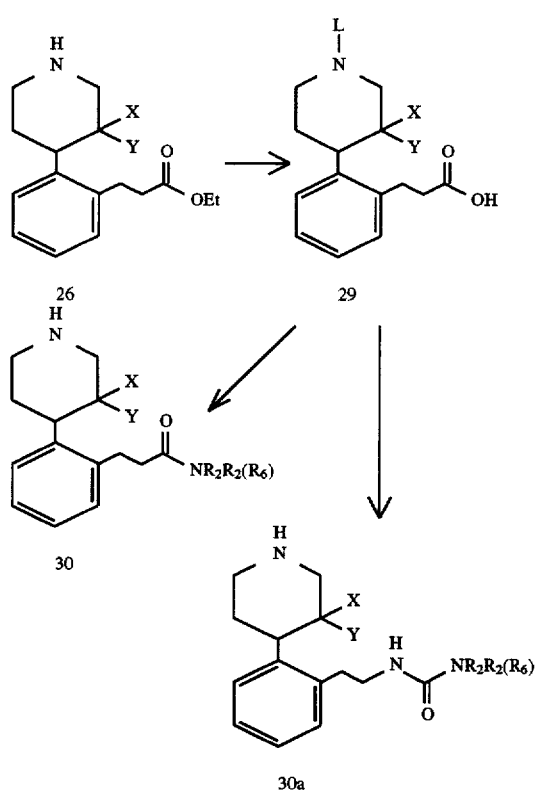

As depicted in Scheme 14 the piperidine 26 may also serve as a key intermediate for the synthesis of a variety of piperidines of formula 22a, wherein $R_{10}$ may be alkyl and aryl amides, alkyl and aryl acylsulfonamides, alkyl and aryl ureas, alkyl and aryl carbamates, etc. The piperidine nitrogen of 26 can be protected with a protecting group L (commonly used groups include BOC, CBZ, FMOC) by well documented methods and the ester unit can now be hydrolyzed with sodium or potassium hydroxide in aqueous or alcoholic media to give 29. Peptide type coupling of 29 with primary and secondary aliphatic amines, aryl amines, suitably protected amino acids, alkyl or aryl sulfonamides provides amides of formula 30, wherein X, Y=H, followed by removal of the protecting group L. Alternatively, the acid 29 can be activated with carbonyl diimidazole and subsequently reacted with primary and secondary aliphatic amines, aryl amines, suitably protected amino acids, alkyl or aryl sulfonamides in an inert solvent like tetrahydrofuran or dimethylformamide to give amides of formula 30, wherein X, Y=H, L is on the nitrogen, and $R_2$ and $R_6$ may be any of the groups described in the scope of this invention. Ureas of formula 30a, wherein X, Y=H, L is on the nitrogen and $R_2$ and $R_6$ may be any of the groups described in the scope of this invention, can be synthesized from 29 by carrying out a Curtius rearrangement and trapping the isocyanate intermediate with amines of formula $HNR_2R_2$ or $HNR_2R_6$. The protecting group L can be removed and elaborated to growth hormone secretagogues of Formula I using chemistry presented in Schemes 1–8.

SCHEME 15

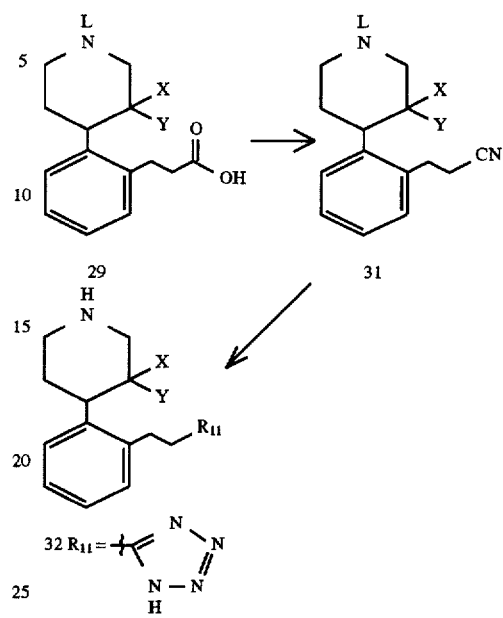

The acid intermediate 29 also serves as a key intermediate for the synthesis of heterocycle bearing growth hormone secretagogues of formula 32, wherein X, Y=H. As shown in Scheme 15, the acid 29 can be transformed to a nitrile of formula 31, wherein X, Y=H, by a 3-step sequence involving activation of the acid with ethylchloroformate in the presence of a base like triethylamine, addition of aqueous ammonia to yield a primary amide, and dehydration of the amide to a nitrile with phosphorous oxychloride in pyridine. The nitrile intermediate 31 can now be transformed to a piperidine of formula 32 wherein X, Y=H and $R_{11}$ is a 1H-tetrazole, by heating it with trimethyltin azide in an inert solvent like toluene or xylenes. The protecting group L can be removed and elaborated to growth hormone secretagogues of formula I by using chemistry detailed in Schemes 1–8.

SCHEME 16

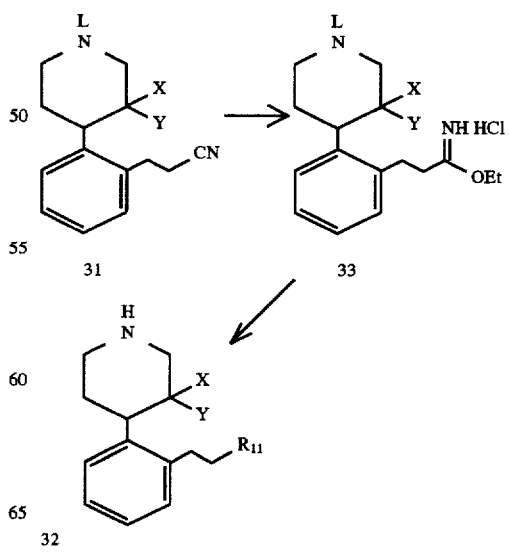

SCHEME 16 -continued

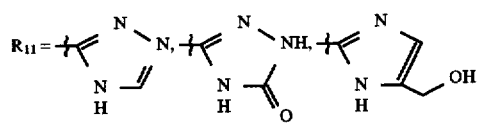

Other heterocycle bearing piperidines of formula 32 can also be prepared from intermediate 31 as shown in Scheme 16. Treatment of the nitrile 31 with anhydrous hydrochloric acid in dry ethanol gives imino-ether of formula 33. Addition of formyl hydrazine to 33 followed by heating of the intermediate in an inert solvent like toluene provides a piperidine of formula 32, wherein X, Y=H and $R_{11}$ is a 1,2,4-triazole. Alternatively, carbomethoxyhydrazine can be added to imino-ether 33 and cyclized to provide 32, wherein X, Y=H and $R_{11}$ is a triazolinone. Reaction of 33 with dihydroxyacetone in methanolic ammonia at high pressure gives 32, wherein X, Y=H and $R_{11}$ is a hydroxymethyl imidazole. The protecting group L can be removed by methods familiar to those skilled in the art and elaborated to compounds of formula I by using chemistry detailed in Schemes 1–8.

Furthermore, acids, acid chlorides, nitriles, and imino-ethers serve as key intermediates in the preparation of a number of other alkyl, phenyl, hydroxy, and amino-substituted heterocycles. Many of the methods are documented in A. R. Katrizky, *Handbook of Heterocyclic Chemistry*, Pergamon Press, 1985, New York, N.Y., and may be used to synthesize a variety of heterocycle bearing growth hormone secretagogues.

SCHEME 17

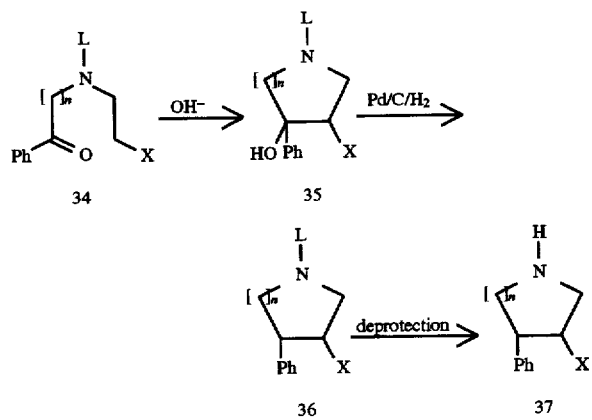

Other applicable routes for the synthesis of mono- and di-substituted pyrrolidines, piperidines, and hexahydro-1H-azepines of formula II (n=1 or 2) are known in the literature. For example, J. J. Plati and W. Wenner (*J. Org. Chem.* 1949, 14, 543) have demonstrated that the ketoamine intermediate 34 could be elaborated to 35 (n=1, 2, 3) under aldol condensation conditions. Dehydroxylation of 35 can be achieved by a number of methods including a catalytic hydrogenation method that utilizes palladium catalysts in a protic solvent like methanol. Removal of L from 36 can be carried out methods, including the ACE-Cl method as described in R. Olofson et al. (*J. Org. Chem.* 1984, 43, 2795).

SCHEME 18

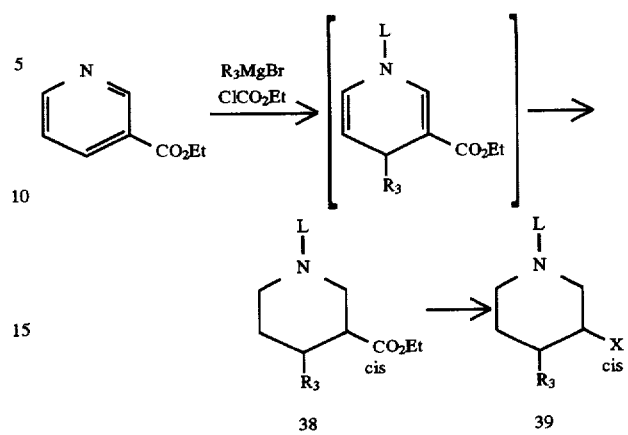

The synthesis of 3,4-disubstituted piperidines of formula 2 (n=2) can be conveniently prepared by literature procedures. Illustrated below is one of these general methods. G. T. Borrett has demonstrated the synthesis of cis 3,4-disubstituted piperidine 39 (U.S. Pat. No. 4,861,893) from the commercially available ethyl nicotinate and the Grignard reagent $R_3MgBr$ where $R_3$ is defined in formula I. The ester functionality of 38 can be further modified through conventional chemistry to provide other functional groups X as defined in the scope of the invention. Illustrated here are some, but by no means all, the methods available to prepare functional groups X. For example, the ester in 38 can be hydrolyzed to give the corresponding carboxylic acid 39 (X=$CO_2H$); 39 can now be converted to amides (X=$CONR_2R_2$) by a simple peptide-type coupling reaction, to ureas or carbamates (X= $NC(O)NR_2R_2$, $NC(O)OR_2$) by the Curtius rearrangement (Smith, *Org. React.* 1946, 3, 337) followed by trapping of the isocyanate intermediate with amines or alcohols or to an hydroxymethyl unit (X=$CH_2OR_2$) by borane reduction. The acid 39 can also be converted to a nitrile and then elaborated to heterocyclic compounds (X=tetrazolyl, triazolyl, triazolinolyl etc.) by the procedures described in Schemes 15 and 16. The carboxylic acid 39 (X=$CO_2H$) can also be converted into its higher homologue 39 (X=$CH_2CO_2H$) by an Arndt-Eisten reaction and further derivatized by methods which have been described above.

SCHEME 18A

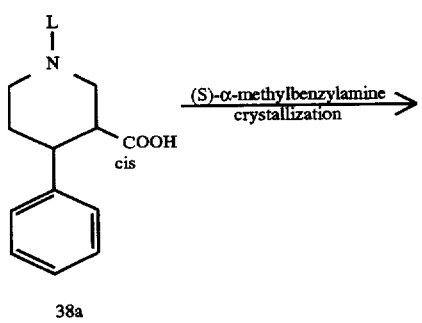

41
-continued
SCHEME 18A

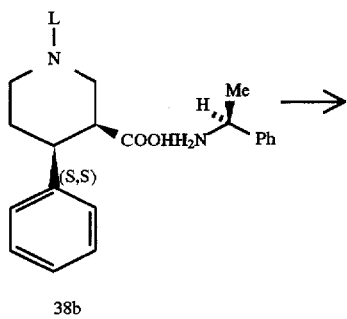

38b

38c

39a

The cis 3,4-disubstituted piperidines 38a generated by these synthetic protocols (Scheme 10 and 18) are racemic. Such compounds may be resolved by numerous methods including by the resolution of racemates as depicted in Scheme 18A. Resolution of compound 38a (wherein L=Boc, $R_3$=phenyl), for example, can be achieved by the formation of diastereomeric salts of 38a (L=Boc, $R_3$=phenyl) with (R) and (S)-α-methylbenzylamine. The absolute stereochemistry of 38b (L=Boc, R3=phenyl) is determinated by X-ray crystallographic analysis. The optically pure crystalline 38b can be obtained from crystallization of 38a (L=Boc, $R_3$=phenyl) and (S)-α-methylbenzylamine in methanol solution. The enantiomer of 38c (R,R stereochemistry) is crystallized out with (R)-α-methylbenzylamine. The chiral free carboxylic acid 38c can be obtained from its amine salt 38b by extraction in acid conditions. The carboxylic acid functionality of 38c may be further modified through conventional chemistry to provide other functional groups X as defined in the scope of the invention. For example, the carboxylic acid 38c can be converted to esters, amides, ureas, carbamates, and alcohols by methods which are well known in the art.

SCHEME 19

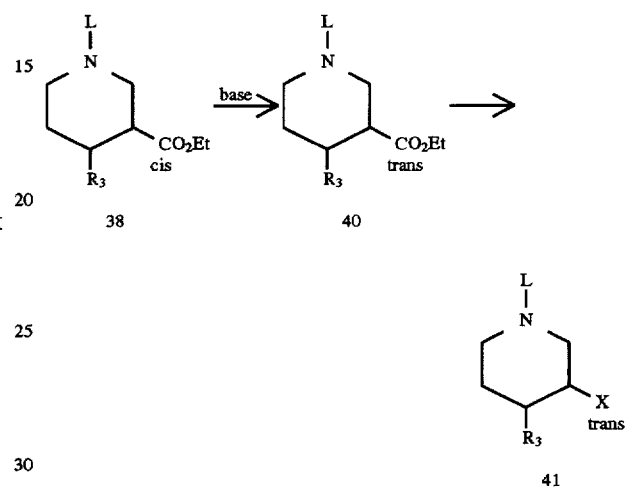

The cis 3,4-disubstituted piperidines 38 can be converted to trans 3,4-disubstituted piperidines 40 as shown in Scheme 19 by treating 38 with a catalytic amount of base such as sodium ethoxide in protic solvent. Once again, the ester functional group of 40 can be further modified by methods familiar to those skilled in the art, including the procedures described in Scheme 18. The protecting group L from compounds of formulas 39 and 41 can be removed through conventional chemistry and elaborated to growth hormone secretagogues of formula I by using chemistry described above.

SCHEME 20

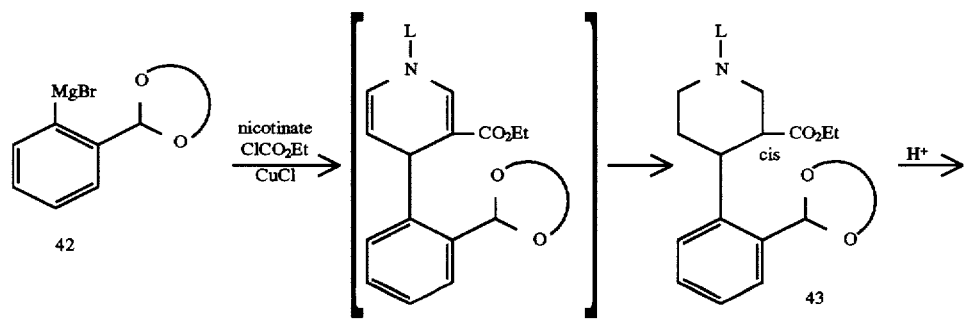

-continued
SCHEME 20

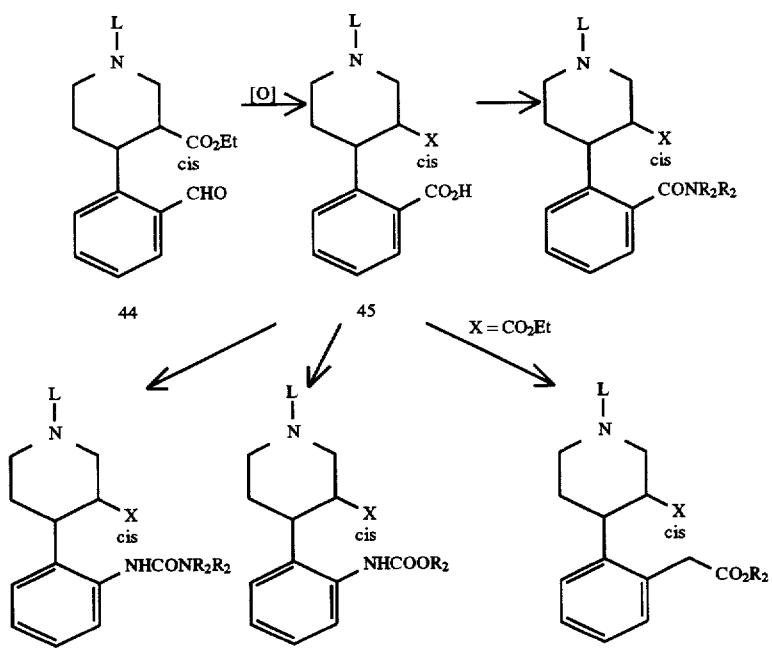

As described in Scheme 20, cis 3,4-disubstituted piperidines of formula 43 can be prepared by the addition of 42 to ethyl nicotinate by the procedure of G. T. Borrett (U.S. Pat. No. 4,861,893). The acetal protecting group can be removed by a number of methods familiar to those skilled in the art. The resulting aldehyde 44 serves as a key intermediate for the synthesis of highly functionalized 3,4-disubstituted piperidines. The aldehyde 44 can be oxidized to the corresponding carboxylic acid 45 and then further elaborated to a variety of functional groups such as amides, ureas, carbamates, acylsulfonamides and etc. Some examples of these transformations are discussed in connection with Scheme 14.

SCHEME 21

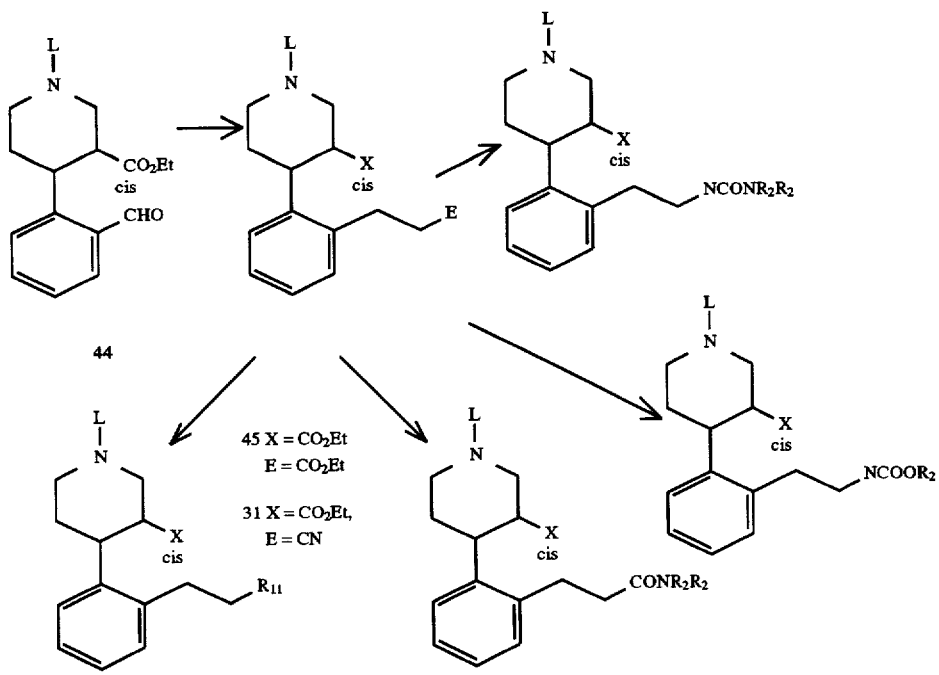

Compound 44 can also be converted to an α, β-unsaturated ester or nitrile by an Emmons reaction. The resulting unsaturated ester or nitrile can be hydrogenated using a catalytic amount of palladium or platinum under hydrogen atmosphere. The diester 45 (X=CO$_2$Et, E=CO$_2$Et) as shown in Scheme 21 can be selectively hydrolyzed to corresponding acid 45 (X=CO$_2$Et, E=CO$_2$H) which can be further elaborated to variety of functional groups by a number of methods. Compounds of formula 31 (X=CO$_2$Et, E=CN) can be transformed to compounds of formula 32 (X=CO$_2$Et, Y=H, R$_{11}$=1H-tetrazole) by heating 31 with trimethyl azide in toluene. Alternately, the nitrile intermediate 31 (for example, with X=CO$_2$Et, E=CN) may also serves as a synthetic precursor for the synthesis of heterocycle bearing growth hormone secretagogues of formula 32 (X=CO$_2$Et). Many of the synthetic methods as noted above in A. R. Katrizky, *Handbook of Heterocyclic Chemistry*, Pergamon Press, 1985, New York, N.Y. and are discussed in connection with Scheme 16.

The 3,4-disubstituted compounds 2 generated by these synthetic protocols are racemic. Mono and disubstituted pyrrolidines and hexahydro-1H-azepines 2 generated by these synthetic protocols are also racemic. Chiral intermediates of formula 2 are available by numerous methods including by the classical resolution of racemates. For example resolution can be achieved by the formation of diastereomeric salts of racemic amines with optically active acids such as D- and L- tartaric acid. The determination of the absolute stereochemistry can be accomplished in a number of ways including X-ray crystallography of a suitable crystalline derivative such as a D- or L- tartaric acid salt. Alternatively, asymmetric synthesis can be carried out to synthesize optically pure compounds.

Furthermore, the racemic intermediates of formula 2 can be derivatized with chiral reagents and these products may be separated by chromatography and chiral compounds of formula 2 may be regenerated from them by hydrolysis, or as stated earlier, racemic intermediates of formula 2 can be converted directly to growth hormone secretagogues, and the resulting diastereomeric mixtures can be separated by chromatography to yield the enantiomerically pure compounds.

The compounds of the present invention may also be prepared from a variety of substituted natural and unnatural amino acids of formulas 46. The preparation of many of these acids is described in U.S. Pat. No. 5,206,237. The preparation of these intermediates in racemic form is accomplished by classical methods familiar to those skilled in the art (Williams, R. M. "*Synthesis of Optically Active α-Amino Acids*" Pergamon Press: Oxford, 1989; Vol. 7). Several methods exist to resolve (DL)-

amino acids. One of the common methods is to resolve amino or carboxyl protected intermediates by crystallization of salts derived from optically active acids or amines. Alternatively, the amino group of carboxyl protected intermediates may be coupled to optically active acids by using chemistry described earlier. Separation of the individual diastereomers either by chromatographic techniques or by crystallization followed by hydrolysis of the chiral amide furnishes resolved amino acids. Similarly, amino protected intermediates may be converted to a mixture of chiral diastereomeric esters and amides. Separation of the mixture using methods described above and hydrolysis of the individual diastereomers provides (D) and (L) amino acids. Finally, an enzymatic method to resolve N-acetyl derivatives of (DL)-amino acids has been reported by Whitesides and coworkers in *J. Am. Chem. Soc.* 1989, 111, 6354–6364.

When it is desirable to synthesize these intermediates in optically pure form, established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenationof prochiral dehydroamino acid derivatives ("*Asymmetric Synthesis, Chiral Catalysis*; Morrison, J. D., Ed; Academic Press: Orlando, Fla., 1985; Vol 5), and (6) enzymatic syntheses (*Angew. Chem. Int. Ed. Engl.* 1978, 17, 176).

SCHEME 22

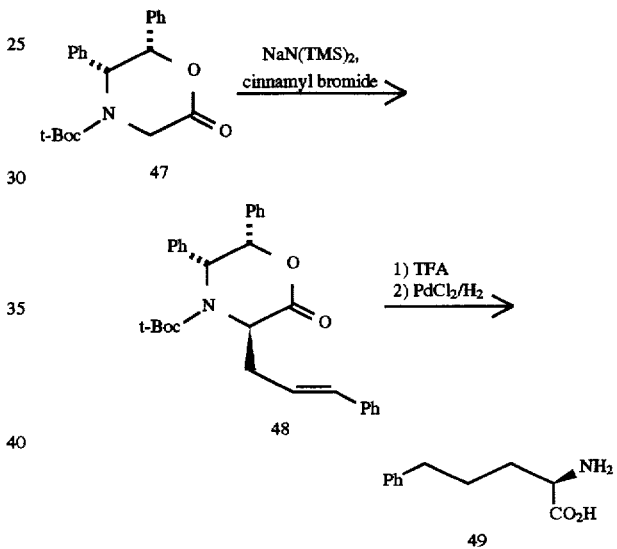

For example, alkylation of the enolate of diphenyloxazinone 47H (*J. Am. Chem. Soc.* 1991, 113, 9276) with cinnamyl bromide in the presence of sodium bis(trimethylsilyl) amide proceeds smoothly to afford 48H which is converted into the desired (D)-2-amino-5-phenylpentanoic acid 49 by removing the N-t-butyloxycarbonyl group with trifluoroacetic acid and hydrogenation over a PdCl$_2$ Catalyst (Scheme 22).

SCHEME 23

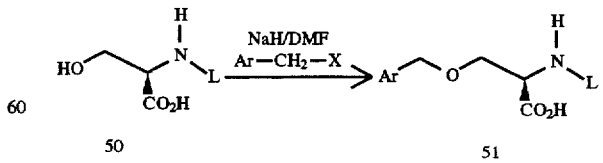

Intermediates of formula 46 which are O-benzyl-(D)-serine derivatives 51 are conveniently prepared from suitably substituted benzyl halides and N-protected-(D)-serine 50. The protecting group L is conveniently a BOC or a CBZ group. Benzylation of 50 can be achieved by a number of methods well known in the literature including deprotonation with two equivalents of sodium hydride in an inert solvent such as DMF followed by treatment with one equivalent of a variety of benzyl halides (*Synthesis* 1989, 36) as shown in Scheme 23.

The O-alkyl-(D)-serine derivatives may also be prepared using an alkylation protocol. Other methods that could be utilized to prepare (D)-serine derivatives of formula 51 include the acid catalyzed benzylation of carboxyl protected intermediates derived from 50 with reagents of formula $ArCH_2OC(=NH)CCl_3$(O. Yonemitsu et al., *Chem. Pharm. Bull.* 1988, 36, 4244). Alternatively, alkylation of the chiral glycine enolates (*J. Am. Chem. Soc.* 1991, 113, 9276; *J. Org. Chem.* 1989, 54, 3916) with $ArCH_2OCH_2X$ where X is a leaving group affords 51. In addition D,L-O-aryl(alkyl) serines may be prepared and resolved by methods described above.

It is noted that in some situations the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay described by Smith, et al., *Science*, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinepbxine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carder or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, amino acids, estrogens, β-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or α-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrodysplasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T. Role of Bisphosphonates in Metabolic Bone Diseases. *Trends in Endocrinol. Metab.*, 4, 19–25 (1993). Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

In the case of alendronate daily oral dosage levels of 0.1 mg to 50 mg are combined for effective osteoporosis therapy with 0.01 mg/kg to 20 mg/kg of the growth hormone secretagogues of this invention.

Osteoporosis and other bone disorders may also be treated with compounds of this invention in combination with calcitonin, estrogens, raloxifene and calcium supplements such as calcium citrate or calcium carbonate.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the scope or spirit of the disclosed invention.

INTERMEDIATE 1

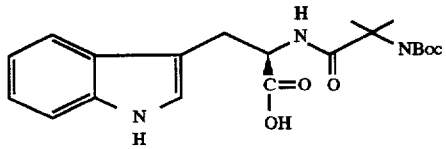

Step A:

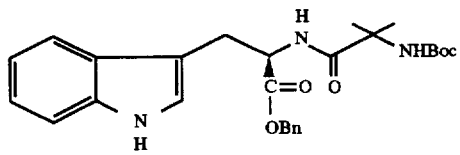

To 5.0 g (16.5 mmole) of the commercially available N-t-BOC-D-tryptophan in 100 ML of chloroform was added 1.80 mL (16.5 mmole) of benzyl alcohol, 0.20 g (1.65 mmole) of 4-N,N-dimethylamino pyridine (DMAP), and 3.20 g of EDC and stirred for 16 h. The reaction mixture was poured into 100 mL of water and the organic layer was separated. The aqueous was further extracted with 2×100 mL of chloroform. The combined organic solution was washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organic solution were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmole) of HOBT, 4.60 g (22.2 mmole) of N-BOC-α-methyl alanine, and 5.32 g (28.0 mmole) of EDC and stirred for 16 h. The reaction mixture was poured into 100 mL of water and the organic layer was separated. The aqueous was further extracted with 2×100 mL of chloroform. The combined organic solution were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam.

$^1$H NMR (CDCl$_3$, 200 MHz) d 8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H)

Step B:

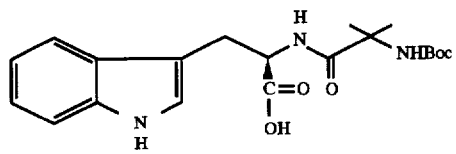

To a solution of 4.75 g of the material from Step A in 100 mL of ethanol was added 1.0 g of 10% Pd/C and stirred at RT under a H$_2$ balloon for 18 h. The catalyst was filtered off through a pad of celite and washed with ethyl acetate. The filtrate was concentrated to give 2.96 g of the acid as a colorless foam.

$^1$H NMR (CDCl$_3$, 200 MHz) d 8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H)

INTERMEDIATE 2

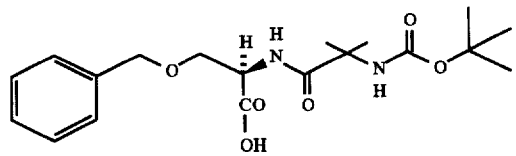

Step A

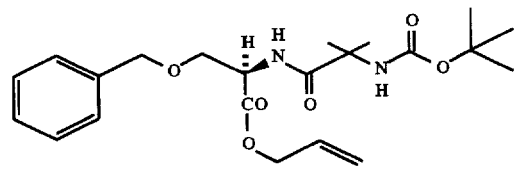

Prepared from N-tBOC-O-benzyl-D-serine and allyl alcohol by the procedure described in Intermediate 1, Step A and subsequent coupling to N-BOC-a-methylalanine to give the desired compound.

$^1$H NMR (400 MHz, CDCl$_3$) d 7.25 (s, 5H), 5.8 (m, 1H), 5.2 (dd, 2H), 5.0 (bs, 1H), 4.7 (m, 1H), 4.6 (m, 2H), 4.4 (dd, 2H), 3.9 (dd, 1H), 3.6 (dd, 1H), 1.45 (d, 6H), 1.39 (s, 9H).

Step B:

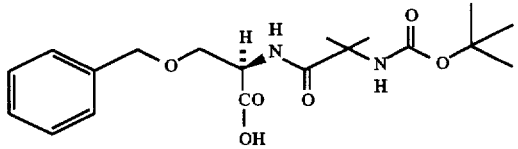

To a stirred solution of the crude intermediate obtained in Step A (6.7 g, 15.9 mmol), tetrakis (triphenylphosphine)-palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was separated and the aqueous fraction was acidified with citric acid (20%), then extracted with EtOAc. The EtOAc extracts were washed with brine, dried over magnesium sulfate, filtered and evaporated to give the title compound as a solid.

$^1$H NMR (400 Hz, CD$_3$OD) d 7.3 (s, 5H), 4.7 (m, 1H), 4.5 (s, 2H), 4.0 (m, 1H), 3.6 (m, 1H), 1.4 (d, 6H), 1.3 (s, 9H).

INTERMEDIATE 3

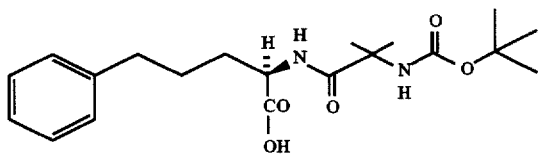

This intermediate was synthesized as described in Step A and B of Intermediate 1, but (2R)-N-t-BOC-5-phenylpentanoic acid (H. K. Chenault et al. *J. Am. Chem. Soc.*, 111, 6354–6364 (1989)) was used in place of N-t-BOC-(D)-Tryptophan.

$^1$H NMR (CDCl$_3$, 400 MHz) 7.24–7.20 (m, 2H), 7.15–7.04 (m, 3H), 4.60–4.55 (m, 1H), 2.62–2.55 (m, 2H), 2.00–1.86 (m, 1H), 1.78–1.60 (m, 3H), 1.50 (s, 6H), 1.30 (s, 9H).

INTERMEDIATE 4

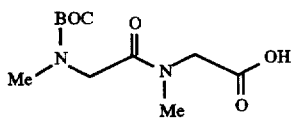

Step A:

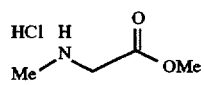

A solution of N-Boc Sarcosine (1.66 g) in methanol was cooled to 0° C. and thionyl chloride (0.67 ml) was added slowly. After stirring for 12 hours at room temperature the mixture was concentrated to give the desired product.

Step B:

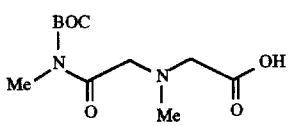

To a solution of the above intermediate in chloroform was added N-Boc Sarcosine (2.0 g), EDC (3.35 g), HOBt (1.42 g) and triethylamine (3.7 ml) and stirred for 12 hours at room temperature. The mixture was poured into 1N HCl and extracted with methylene chloride, dried over sodium sulfate, filtered and concentrated to give 3 g of coupled product. To this material in methanol was added 6N NaOH at room temperature and stirred for 5 hours. The mixture was concentrated to remove the methanol and the residue was extracted with methylene chloride. The organic layer was discarded. The aqueous layer was cooled to 0° C. and acidified with conc. HCl to pH=1.0 and extracted with ethyl acetate. The organic layer was dried over sodium sulfate and concentrated to give desired product (2.0 g).

EXAMPLE A1

N-acetyl-Threo-(2R,3S)-β-methyltryptophan R-(+)-α-methylbenzyl amine salt

Racemic N-methyl-β-methyltryptophan was prepared by the method of Snyder and Matteson (*J. Am. Chem. Soc.* 1957, 79, 2217). Isomer A (100 g) was suspended in 1.25 L of 90/10 acetone water at 20° C. and 50 mL of R-(+)-α-methylbenzylamine was added in one portion. The suspension cleared briefly before a thick white suspension formed which quickly turned to a solid mass. After aging overnight, an additional 500 mL of acetone was added to facilitate agitation and filtration. The suspension was filtered and the cake washed with 500 mL of acetone and sucked to a damp cake. The solid was suspended in 2.5 L of 90/10 acetone/water and heated to boiling on a steam bath. The white slurry was allowed to cool to 20° C. overnight. The product was collected by filtration, washed with acetone and dried yielding 39.1 g of the title compound. α=+9.1° (c=1, MeOH). Stereochemical assignments were made by comparison to published compounds: *J. Org. Chem.* 1994, 59, 4239 and *J. Org. Chem.* 1995, 60, 4978.

EXAMPLE A2

N-acetyl-Threo-(2S,3R)-β-methyltryptophan S-(−)-α-methylbenzyl amine salt

The mother liquors from Example A 1 were combined and concentrated to ca. 1 L and 400 mL of 1N HCl was added. The resulting suspension was stirred for 1 hr initially at 20° C. then at 0° C. The product was filtered and washed with water until the filtrate was neutral. The product was sucked to a damp cake weighing 79 g. The solid was suspended in 1 L of 95% acetone/water and 40 mL of S-(−)-α-methylbenzylamine was added followed by 1 L of 90% acetone/water. After a few minutes a solid mass formed. An additional 500 mL of acetone was added and the mixture heated on a stem bath for ca. 0.5 hr. This was then allowed to stand at 20° C. overnight. The product was collected by filtration, washed with 500 mL of acetone, and sucked to a damp cake. The product was suspended in 2 L of 95% acetone/water and heated on a steam bath to boiling. The white suspension was allowed to cool to 20° C. overnight.

The product was collected by filtration, washed with 500 mL of acetone and dried yielding 54 g. α=−9.0° (c=1, MeOH).

EXAMPLE A3

N-acetyl-Erythro(2R,3R)-β-methyltryptophan R-(+)-α-methylbenzyl amine salt 170 g of Isomer B (prepared as described by the reference in Example A1) which was a brittle foam containing ethyl acetate was dissolved in 2.5 L of ethyl acetate containing 100 mL of ethanol. To this was added 60 mL of R-(+)-α-methylbenzylamine. After 10 min, an additional 2 L of ethyl acetate was added and the resulting thick suspension was aged at 20° C. for 3 days. The product was collected by filtration, washed with ethyl acetate and and sucked to a damp cake. The salt was re-slurried four times with hot ethyl acetate containing 2% water (1×2.5 L, 2×6 L, and 1×8 L). The yield of dried product was 43.2 g of salt. α=−19.6° (c=1, MeOH).

EXAMPLE A4

N-acetyl-Erythro(2S,3S)-β-methyltryptophan S-(−)-α-methylbenzyl amine salt

The mother liquors from Example A3 were combined and concentrated to ca. 2 L and washed twice with 500 mL 1N HCl. The washes were back extracted once with ethyl acatate, and the combined ethyl acetate extracts washed twice with brine. The solution was diluted to 6 L with ethyl acetate and 60 mL of S-(−)-α-methylbenzylamine was added. After 10 min the resulting suspension was heated to boiling. The suspension was allowed to cool to ambient temperature with stirring overnight. The product was collected by filtration washed with ethyl acetate and and sucked to a damp cake. The salt was suspended in 6 L of ethyl acetate and suspension was heated to boiling. The suspension was allowed to cool to ambient temperature with stirring overnight. The product was collected by filtration washed with ethyl acetate and dried. The yield of dried product was 65.8 g of salt. α=+19.7° (c=1, MeOH).

EXAMPLE A5

N-acetyl-threo-(2S,3R)-β-methyltryptophan

The salt from Example A2 (53 g) was stirred with 400 mL 1N HCl at 20° C. for 20 min. The suspension was filtered and the cake washed with water until the filtrate was neutral. The wet cake was used directly for the next reaction. A sample was dried affording the title compound. α=−26.4° (c=1, MeOH).

EXAMPLE A6 threo-(2S,3R)-β-methyltryptophan

The wet cake from Example A5 was suspended in with 400 mL of 1N HCl and refluxed for 12 hours. The solution was cooled to 20° C., and half of the solution was used for Example A7. The title compound was isolated by adjusting the pH to 7.0 with sodium hydroxide, cooling the resulting suspension to 0° C., filtering, washing the cake with water and drying. α=−29.3° (c=0.9, H$_2$O).

EXAMPLE A7

N-t-BOC-threo-2(2S,3R)-β-methyltryptophan

The pH of the aqueous solution from Example A6 was adjusted to 7 with sodium hydroxide and cooled to 0° C. 20 g of potassium carbonate, 19 g of di-t-butyldicarbonate, and 150 mL of THF were added. The mixture was allowed to warm slowly to ambient temperature overnight. The reaction was extracted twice with ether, the aqueous acidified with 2N HCl and extracted twice with ethyl acetate. The combined ethyl acetate extracts were washed with brine, dried with MgSO$_4$, filtered and concentrated affording 21.2 g of the title compound.

EXAMPLE A8

N-acetyl-threo-(2R,3 S)-β-methyltryptophan

The title compound was prepared essentially following the proceedure of Example A5 using the salt from Example A1. α=+26.6° (c=1, MeOH).

EXAMPLE A9 threo-(2R,3S)-β-methyltryptophan

The title compound was prepared essentially following the proceedure of Example A6 using the salt from Example A8. α=+30.6° (c=0.9, H$_2$O).

EXAMPLE A10

N-t-BOC-threo-(2R,3R)-β-methyltryptophan

The title compound was prepared essentially following the proceedures of Examples A5, A6 and A7 using the salt from Example A3.

EXAMPLE A11

N-acetyl-Erythro(2S,3S)-β-methyltryptophan

The salt from Example A4 (65 g) was stirred with 250 mL 1N HCl and 1.5 L of ethyl acetate at ambient temperature for 5 min. The layers were partitioned and the ethyl acetate layer was washed with 1N HCl, H$_2$O and brine, dried with MgSO$_4$, filtered and concentrated to afford the title compound as a brittle foam.

EXAMPLE A12

Erythro(2S,3S)-β-methyltryptophan

The product from Example A11 was suspended in with 500 mL of 2N HCl and refluxed for 4 hours. The solution was cooled to 20° C., and half of the solution was used for Example A13. The title compound isolated as a foam by concentrating the solution in vacuo.

EXAMPLE A13

N-t-BOC-Erythro(2S,3S)-β-methyltryptophan

The pH of the aqueous solution from Example A12 was adjusted to 7 with sodium hydroxide and cooled to 0° C. 24 g of potassium carbonate, 22 g of di-t-butyldicarbonate, and 150 mL of THF were added. The mixture was allowed to warm slowly to ambient temperature overnight. The reaction was extracted twice with ether The aqueous acidified with 2N HCl, and extracted twice with ethyl acetate. The combined ethyl acetate extracts were washed with brine, dried with MgSO$_4$ filtered and concentrated. The solid was redissolved in ether, and the ether removed in vacuo while flushing with hexanes. The resulting slurry was filtered and dried affording 20.1 g of the title compound.

EXAMPLE A14

N-acetyl-erythro-(2R,3R)-β-methyltryptophan

The title compound was prepared essentially following the proceedure of Example A11 using the product from Example A3.

EXAMPLE A15

Erythro-(2R,3R)-β-methyltryptophan

The title compound was prepared essentially following the proceedure of Example A12.

EXAMPLE A16

N-t-BOC-erythro-(2R,3R)-β-methyltryptophan

The title compound was prepared essentially following the proceedure of Example A13.

EXAMPLE 1

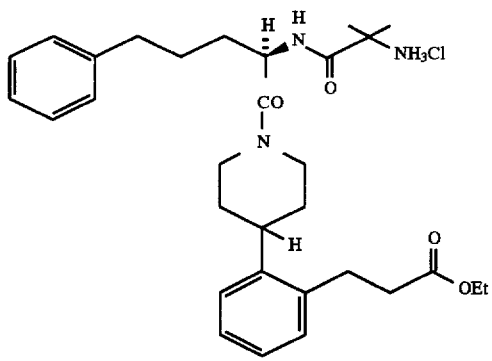

Step A:

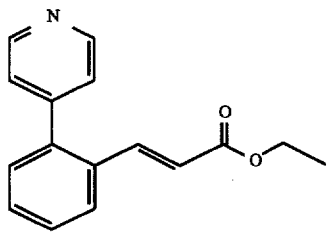

To 7.0 g of 2-bromobenzyl alcohol in 7.0 g of dihydropyran at room temperature was added 2 drops of concentrated hydrochloric acid and stirred at room temperature for 1 h. The reaction mixture was diluted with 150 mL of ether and washed with saturated NaHCO₃ (2×100 mL), brine (150 mL), dried over MgSO₄ and concentrated to give a thick oily material. The residue was purified by flash chromatography with hexane-EtOAc as eluent to give 10 g of the tetrahydropyranyl ether.

To 260 mL of dry ether at −78° C. was added 23.6 mL of 1.6M solution of nBuLi in hexanes. To this solution was added a solution of 7.5 g of the THP compound in 100 mL of ether and stirred at −78° C. for 30 min. and −40° C. for an additional 30 min. This solution was added in a dropwise manner to a mixture of 2.16 g of pyridine and 6.3 mL of t-butyldimethyl-silyl triflate in 200 mL of ether at −78° C. The reaction mixture was allowed to warm up to room temperature and stirred overnight. The reaction was quenched with 75 mL of water and oxygen gas was bubbled in for 3 h. The reaction mixture was diluted with ether and 3N HCl till the pH=1 and then the organic layer was separated. The aqueous layer was basified with 20% NaOH till the pH=8–9 and then extracted with chloroform (3×100 mL). The organic layer was washed with water, brine (200 mL), dried over Na₂SO₄, filtered, and evaporated.

To 3.42 g of the above compound in 100 mL of CHCl₃ was added 30 g of activated manganese dioxide and stirred overnight. The solids were filtered off through a pad of celite, and the filtrate was evaporated.

To 2.4 mL of triethylphosphonoacetate in 30 mL of dry THF at 0° C. was added 16.3 mL of a solution of sodium hexamethyldisilazide in THF and stirred for 30 min. A solution of the above aldehyde intermediate in 10 mL of THF was added and stirred for 30 min. The reaction was quenched with 25 mL of saturated NH₄Cl solution, and extracted with EtOAc(3×25 mL). The combined organics were washed with brine, dried over Na₂SO₄, and concentrated. Flash chromatography of the residue with hexane-EtOAc (4:1) as eluent gave 1.5 g of the desired product as a pale yellow solid.

¹H NMR (CDCl₃, 400 MHz) d 8.63 (d, 2H), 7.68 (dd, 1H), 7.60 (d, 1H), 7.45–7.35 (m, 2H), 7.30 (dd, 1H), 7.35 (d, 1H), 4.15 (q, 2H), 1.23 (t, 3H).

Step B:

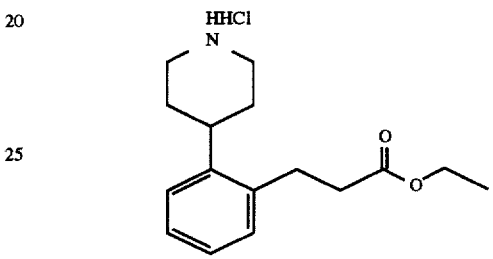

To 1.5 g of the above intermediate in 25 mL of methanol was added 5 mL of 4M HCl in EtOAc and evaporated to dryness. This solid was dissolved in 30 mL of methanol and 0.50 g of PtO₂ was added and hydrogenated at 50 psi for 5 h. The catalyst was filtered off through a pad of celite and the filtrate was concentrated to give the title compound.

¹H NMR indicated that this material contained about 5% of the cyclohexyl-piperidine.

¹H NMR (CD₃OD, 400 MHz) d 7.40–7.20 (m, 4H), 4.08 (q, 2H), 3.50 (m, 2H), 3.25–3.10 (m, 3H), 3.00 (t, 2H), 2.60 (t, 2H), 2.03–1.90 (m, 4H), 1.20 (t, 3H).

Step C:

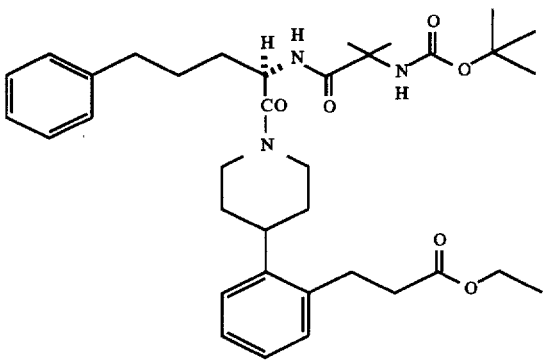

To a mixture of the above intermediate in 30 mL of CH₂Cl₂ was added 0.82 mL of triethylamine, 1.2 mL of NMM, 0.90 g of HOBT, 2.13 g of (2R)-N-tBOC-5-phenylpentanoic acid (prepared as described in H. K. Chenault et al. *J. Am. Chem. Soc.*, 111, 6354–6364 (1989)), and finally 1.7 g of EDC and stirred at room temperature for 18 h. The reaction mixture was poured into a saturated NaHCO₃ solution and extracted with CH₂Cl₂. The combined organics were washed with 0.1N HCl, brine, dried over Na₂SO₄, and concentrated.

The above crude material was dissolved in 30 mL of CH₂Cl₂ and 10 mL of TFA was added and stirred at RT for 1 h. The solvent was evaporated to dryness and the residue was neutralized with aqueous Na₂CO₃ solution, and extracted with CH₂Cl₂. The combined organics were washed with brine, dried over K₂CO₃, and concentrated. To a mixture of this intermediate in 30 mL of CH₂Cl₂ was added 1.04 g of HOBT, 1.56 g of N-tBOC-a-methylalanine, and finally 1.8 g of EDC and stirred at room temperature for 4 h. The reaction mixture was poured in saturated NaHCO₃ solution and extracted with CH₂Cl₂. The combined organics were washed with 0.1N HCl, brine, dried over MgSO₄, and concentrated. Flash chromatography of the oily residue with CH₂Cl₂-acetone-ether (6:1:1) as eluent gave the desired material.

¹H NMR (CDCl₃, 400 MHz) d 7.30–6.98 (m, 9H), 5.00–4.85 (m, 2H), 4.72–4.64 (m, 1H), 4.13 (2q, 2H), 4.00–3.82 (m, 1H), 3.14–2.85 (m, 4H), 2.7–2.50 (m, 5H), 1.83–1.50 (m, 5H), 1.50 (s, 3H), 1.46 (s, 1.5H), 1.44 (s, 1.5H), 1.40 (s, 9H), 1.40–1.28 (m, 1H), 1.23 (2t, 3H).

Step D:

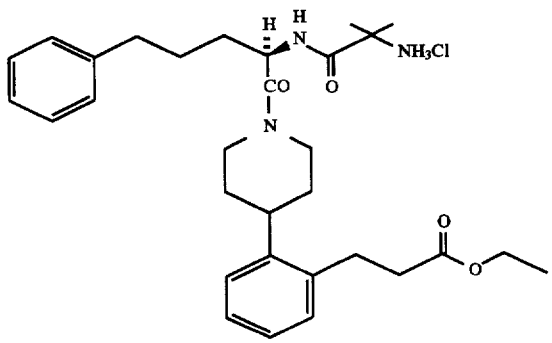

To 1.70 g of the intermediate in Step C in 30 mL of CH₂Cl₂ was added 10 mL of TFA and stirred at RT for 1 h. The reaction was evaporated to dryness, basified with aqueous Na₂CO₃, and extracted with CH₂Cl₂. The combined organics were washed with brine, dried over K₂CO₃, filtered, and evaporated to give free base as a thick oil. This material was dissolved in 5 mL of ether at 0° C. and 0.50 mL of 4M HCl in EtOAc was added. The precipitate was filtered under an N₂ atmosphere and dried to give the title compound.

¹H NMR (CD₃OD, 400 MHz) d 7.30–6.98 (m, 9H), 5.00–4.85 (m, 2H), 4.72–4.64 (m, 1H), 4.13 (2q, 2H), 4.00–3.82 (m, 1H), 3.14–2.85 (m, 4H), 2.7–2.50 (m, 5H), 1.83–1.50 (m, 5H), 1.50 (s, 3H), 1.46 (s, 1.5H), 1.44 (s, 1.5H), 1.40 (s, 9H), 1.40–1.28 (m, 1H), 1.23 (2t, 3H).

EXAMPLE 2

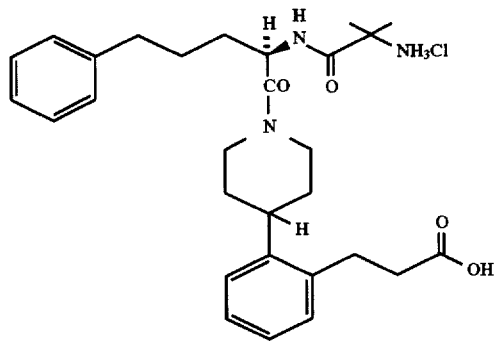

Step A:

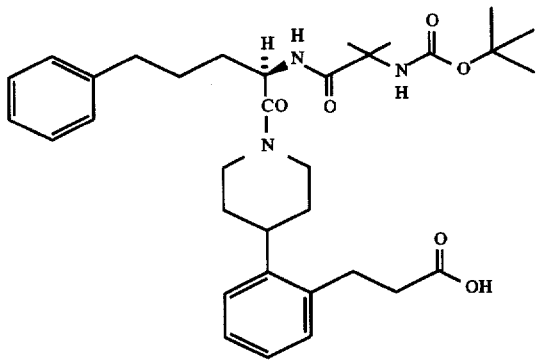

To a solution of 0.20 g of the intermediate from Example 1, Step C in 5 mL of anhydrous THF was added 46 mg of potassium trimethylsilanoate. After 2 h an additional 46 mg of potassium trimethylsilanoate and 2 mL of THF were added and stirred at RT overnight. The reaction was diluted with 10 ml of water and washed with ether (2×10 mL). The aqueous layer was acidified with 0.1N HCl to pH=2 and extracted with CH₂Cl₂ (2×15 mL). The combined organics were washed with brine, dried over Na₂SO₄, filtered and concentrated. Flash chromatography of the residue with CHCl₃—MeOH—NH₄OH (85:15:1) as the eluent gave 56 mg of the desired material.

¹H NMR (CDCl₃, 400 MHz) d 7.32–7.20 (m, 4H), 7.20–6.98 (m, 5H), 5.10 (bs, 1H), 5.00–4.90 (m, 1H), 4.65 (bt, 1H), 4.90 (dd, 1H), 3.10–2.85 (m, 4H), 2.70–2.50 (m, 5H), 1.80–1.50 (m, 5H), 1.50 (s, 4H), 1.46 (s, 1H), 1.42 (s, 1H), 1.38 (s, 9H), 1.35–1.20 (m, 1H).

Step B:

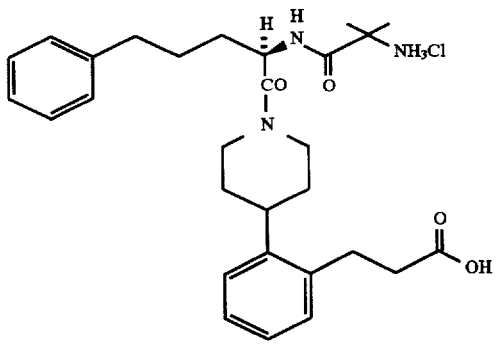

To the above intermediate at RT was added 2 mL of 4M HCl in EtOAc maintained at RT for 2 h. The reaction was evaporated to dryness and the residue was triturated with ether to give the title compound as a white solid.

$^1$H NMR (CD$_3$OD, 400 MHz) d 8.15 (t, 1H), 7.30–7.00 (m, 9H), 4.90 (m, 1H), 4.60 (bd, 1H), 4.05 (d, 1/2H), 3.95 (d, 1/2H), 3.25–3.05 (m, 2H), 3.00 (dt, 2H), 2.80–2.50 (m, 5H), 1.85–1.63 (m, 6H), 1.63 (s, 2H), 1.60 (s, 4H), 1.60–1.20 (m, 2H).

EXAMPLE 3

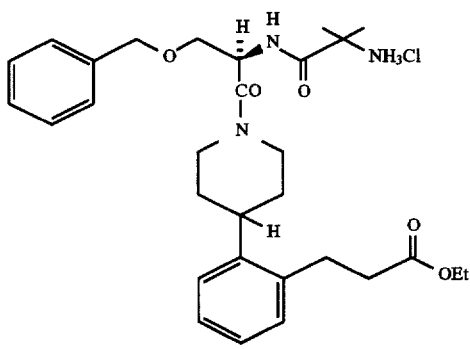

The title compound was prepared as described in Example 1 Steps C and D, but commercially available N-t-BOC-O-benzyl-D-serine was substituted for (R)-2-N-t-BOC-5-phenylpentanoic acid.

$^1$H NMR (CD$_3$OD, 400 MHz) d 8.30 (d, 1/2H), 8.23 (d, 1/2H), 7.40–7.25 (m, 5H), 7.20–7.05 (m, 3.5H), 6.88 (d, 1/2H), 5.20 (m, 1H), 4.70–4.50 (m, 3H), 4.20–4.05 (m, 3H), 3.84–3.65 (m, 2H), 3.28–2.95 9m, 4H), 2.75 (q, 1H), 2.58 (dt, 2H), 1.85–1.70 (m, 2H), 1.64 (s, 2H), 1.61 (s, 4H), 1.55–1.40 (m, 2H), 1.20 (2t, 3H).

EXAMPLE 4

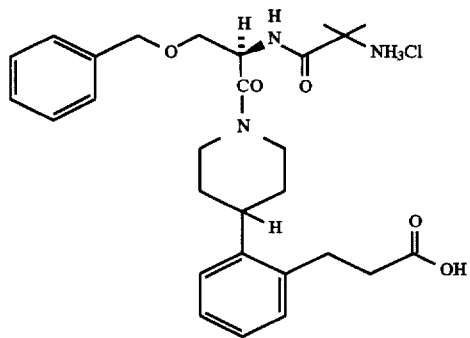

To 54 mg of the compound prepared in Example 3 was added 2 mL of 2N aqueous HCl and stirred at RT overnight. The solvents were removed under reduced pressure and the residue was dried under vacuum to give the title compound.

$^1$H NMR (CD$_3$OD, 400 MHz) d 8.30 (d, 1/2H), 8.23 (d, 1/2H), 7.40–7.25 (m, 5H), 7.20–7.05 (m, 3.5H), 6.88 (d, 1/2H), 5.20 (m, 1H), 4.70–4.50 (m, 3H), 4.20–4.05 (m, 1H), 3.84–3.65 (m, 2H), 3.28–2.95 (m, 4H), 2.75 (q, 1H), 2.58 (dt, 2H), 1.85–1.70 (m, 2H), 1.64 (s, 2H), 1.61 (s, 4H), 1.55–1.40 (m, 2H).

EXAMPLE 5

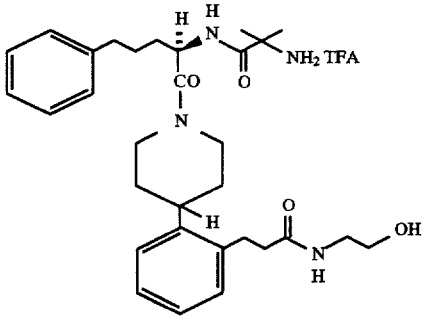

To a solution of 0.109 g of the intermediate obtained in Step A Example 2 in 3 mL of CH$_2$Cl$_2$ was added 0.017 mL of ethanolamine, 34 mg of HOBT, and 58 mg of EDC and stirred at RT overnight. The reaction mixture was diluted with 10 mL of CH$_2$Cl$_2$ and washed with 5 mL of 0.10N HCl, 5 mL of saturated aqueous NaHCO$_3$, dried over MgSO$_4$, and concentrated. Hash chromatograhy of the residue with CH$_2$Cl$_2$-acetone (3:2) as the eluent gave the coupled product.

As before, the above material was treated with CH$_2$Cl$_2$-TFA at RT for 30 min., evaporated to dryness, and triturated with ether to give the title compound as a pale yellow solid.

$^1$H NMR (CD$_3$OD, 400 MHz) d 8.15 (t, 1H), 7.30–7.00 (m, 9H), 4.95 (m, 1H), 4.60 (bd, 1H), 4.40 (bs, 1H), 4.00 (bdd, 1H), 3.60–3.50 (m, 2H), 3.40–3.10 (m, 4H), 3.05–2.90 (m, 2H), 2.85–2.60 (m, 5H), 2.52–2.40 (m, 4H), 1.90–1.65 (m, 6H), 1.63 (s, 2H), 1.60 (s, 4H), 1.60–1.20 (m, 2H).

EXAMPLE 6

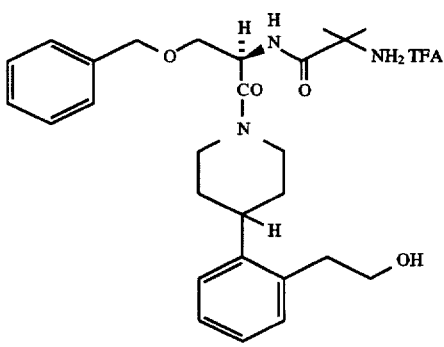

Step A:

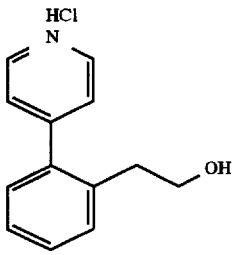

To 9.0 g of 2-bromophenethyl alcohol in 6.12 mL of dihydropyran at room temperature was added 2 drops of concentrated hydrochloric acid and stirred at room temperature for 1 h. The reaction mixture was diluted with 150 mL of ether and washed with saturated NaHCO$_3$ (2×100 mL), brine (150 mL), dried over MgSO$_4$ and concentrated to give a thick oily material. The residue was purified by flash chromatography with hexane-EtOAc as eluent to give 10 g of the ether.

To 200 mL of dry ether at −78° C. was added 17.7 mL of 1.6M solution of nBuLi in hexanes. To this solution was added a solution of 8.0 g of the ether intermediate in 100 mL of tetrahydropyranyl ether and stirred at −78° C. for 30 min. and −40° C. for an additional 30 min. This solution was added in dropwise manner to a mixture of 2.16 g of pyridine and 6.3 mL of t-butyldimethylsilyl triflate in 200 mL of ether at −78° C. The reaction mixture was allowed to warm up to room temperature and stirred overnight. The reaction was quenched with 75 mL of water and oxygen gas was bubbled in for 3 h. The reaction mixture was diluted with ether and 3N HCl till the pH=1 and then the organic layer was separated. The aqueous layer was basified with 20% NaOH till the pH=8–9 and then extracted with chloroform (3×100 mL). The organic layer was washed with water, brine (200 mL), dried over Na$_2$SO$_4$, filtered, and evaporated. Flash chromatography of the residue with hexane-ethylacetate (1:1) as the eluent gave the desired product.

Approximately 0.90 g of the phenyl-pyridine intermediate prepared as described above was converted to the hydrochloride salt by treating it with 4M HCl in EtOAc.

$^1$H NMR (CDCl$_3$, 400 MHz) d 8.90 (d, 2H), 8.20 (dd, 1H), 7.73–7.35 (m, 4H), 3.70 (t, 2H), 2.83 (t, 2H).

Step B:

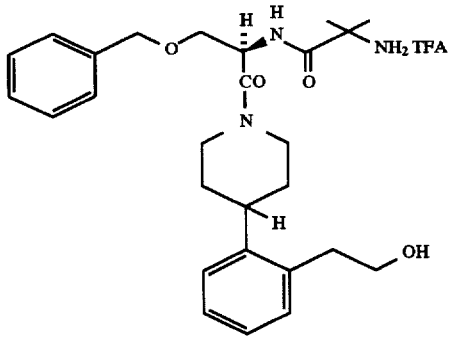

To 0.90 g of the above intermediate in 25 mL of methanol was added 0.10 g of PtO$_2$ and hydrogenated with pressurized hydrogen at 50 psi for 5 h. The catalyst was filtered off and the filtrate was concentrated. The residue was treated with 1.4 g of di-t-butylcarbonate in 3 mL of dioxane, 1 mL of water, and 1 mL of triethylamine for 18 h. The protected piperidine was separated by flash chromatography with CH$_2$Cl$_2$-acetone (10:1) as the eluent.

To 0.25 g of protected piperidine intermediate synthesized above was added 2 mL of CH$_2$Cl$_2$ and 0.50 mL of TFA and stirred at RT for 30 min. The reaction was evaporated to dryness and azeotroped with toluene.

To a solution of the above residue in 2 mL of CH$_2$Cl$_2$ was added 0.079 g of HOBT, 0.14 g of Intermediate 2, 0.070 mL of NMM, and 0.090 g of EDC and stirred at RT overnight. The reaction mixture was poured into saturated NaHCO$_3$ and extracted with CH$_2$Cl$_2$. The combined organics were washed with 0.5N HCl, brine, dried over MgSO$_4$, and concentrated. Flash chromatography of the residue with CH$_2$Cl$_2$-acetone (9:1) as the eluent gave the coupled product.

Deprotection of the N-t-butoxycarbonyl group was carried out by treating the above intermediate with 1 mL of TFA in 2 mL of CH$_2$Cl$_2$ for 2 h. Concentration of the reaction mixture, trituration with ether and drying under vacuum gave the title compound as a colorless solid.

$^1$H NMR (CD$_3$OD, 400 MHz) d 7.40–6.88 (m, 9H), 5.17 (bs, 1H), 4.77–4.50 (m, 3H), 4.18 (bd, 1H), 3.80–3.65 (m, 4H), 3.30–3.05 (m, 4H), 2.95–2.70 (m, 2H), 1.85–1.60 (m, 2H), 1.60 (s, 2H), 1.58 (s, 4H), 1.70–1.45 (m, 2H).

EXAMPLE 7

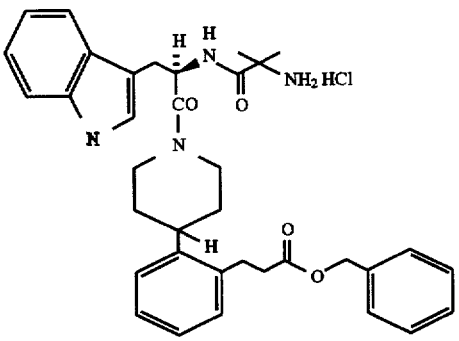

Step A:

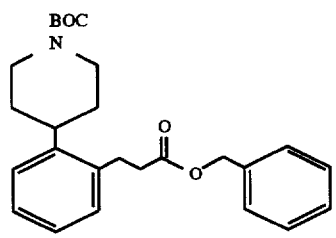

The PtO$_2$ reduction of the phenyl-piperidine intermediate prepared in Step A, Example 1 was attempted in different solvents like ethanol and methanol in the presence and absence of conc. HCl. Transesterification as well as unselective reduction of the pyridine was observed. Several of these reactions were combined and treated with excess di-t-butylcarbonate in CH$_2$Cl$_2$ and triethylamine. Approximately 5.0 g of the crude material thereby obtained after acid work-up was treated with 1.6 g of NaOH in 100 mL of methanol and 10 mL of water for 2 h. The reaction mixture was diluted with water and washed with ether. The aqueous layer was acidified with 0.50N HCl till acidic and extracted with CHCl$_3$. The combined organics were washed with brine, dried over Na$_2$SO$_4$, filtered, and concentrated. To about 4.0 g of this piperidine acid in 150 mL of CH$_2$Cl$_2$ at RT was added 1.86 mL of benzyl alcohol, 1.90 g of HOBT, 3.45 g of EDC and a catalytic amount of DMAP, and stirred at RT overnight. The reaction mixture was washed with saturated NaHCO$_3$, 0.50N HCl, brine, dried over Na$_2$SO$_4$, filtered and concentrated. The desired material was obtained after purification via flash chromatography.

$^1$H NMR (CDCl$_3$, 400 MHz) d 7.40–7.28 (m, 5H), 7.22–7.10 (m, 4H), 5.12 (s, 2H), 4.25 (bs, 2H), 3.04 (t, 2H), 2.94–2.70 (m, 3H), 2.67 9t, 2H), 1.75–1.60 (m, 3H), 1.53 (s, 9H), 1.33–1.20 (m, 1H).

Step B:

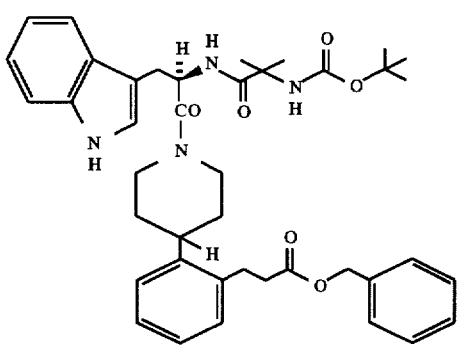

To a solution of 0.70 g of the above intermediate in 2.5 mL of CH$_2$Cl$_2$ was added 1 mL of TFA and the reaction mixture was stirred at RT for 1 h. The reaction mixture was evaporated to dryness, dissolved in saturated aqueous NaHCO$_3$, and extracted with CH$_2$Cl$_2$. The combined organics were washed with brine, dried over K$_2$CO$_3$, and concentrated. The residue was reacted with Intermediate 1 as described in Step B, Example 6. Flash chromatography of the residue with hexane-acetone-ether (6:1:1) as the eluent gave 0.47 g of the desired material.

Step C:

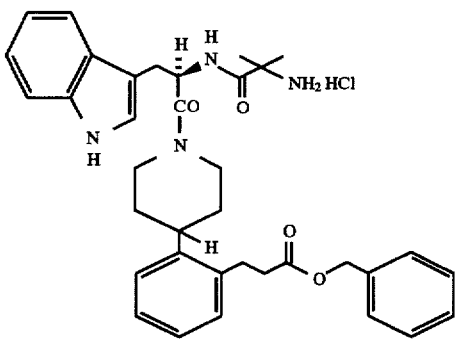

To a solution of 0.20 g of the above intermediate in EtOAc at 0° C. was bubbled in HCl gas for about 10 seconds. The reaction mixture was capped and stirred for 30 min. Ether was added and the precipitate was filtered under an N$_2$ atmosphere. This gave 0.195 g of the title compound as a white solid.

The NMR indicated a 2:1 mixture of rotamers. $^1$H NMR (CD$_3$OD, 400 MHz) d 8.30 and 8.20 (2d, 1H), 7.53 and 7.45 (2d, 1H), 7.40 and 7.35 (2d, 1H), 7.30–7.00 (m, 11 and 1/3), 6.54 (d, 2/3H), 5.30–5.18 (m, 1H), 5.09 and 5.05 (2s, 2H), 4.60 and 4.55 (2d, 1H), 3.90 (2d, 1H), 3.35 (dd, 1H), 3.20 (dd, 1H), 3.00–2.85 (m, 3H), 2.75–2.40 (4H), 1.64 (s, 6H), 1.40 (d, 2/3H), 1.06 (d, 2/3H), 0.73 (dt, 1/3H), −0.03 (dt, 1/3H).

EXAMPLE 8

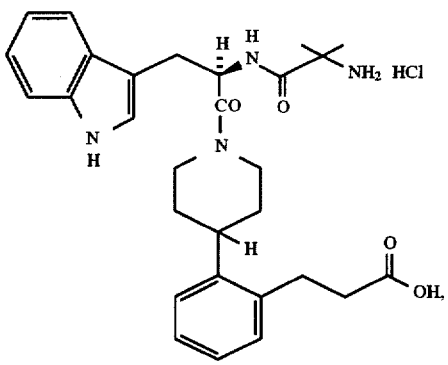

To a solution of 0.19 g of the intermediate from Step C, Example 7 in 3 mL of dioxane was added 50 mg of 10% Pd/C and hydrogenated under H$_2$ balloon for 3 h. The reaction was slow so about 50 mg of 20% Pd(OH)$_2$/C was added and hydrogenated overnight. The catalyst was filtered off through a pad of celite and washed with dioxane. Evaporation of the filtrate gave the title compound as a pink solid.

The NMR indicated a 2:1 mixture of rotamers. $^1$H NMR (CD$_3$OD, 400 MHz) d 8.30 and 8.20 (2d, 1H), 7.53 and 7.45 (2d, 1H), 7.40 and 7.35 (2d, 1H), 7.20–7.00 (m, 6 and 1/3), 6.54 (d, 2/3H), 5.30–5.18 (m, 1H), 4.60 and 4.55 (2d, 1H), 3.90 (2d, 1H), 3.35 (dd, 1H), 3.20 (dd, 1H), 3.00–2.85 (m, 3H), 2.75–2.40 (4H), 1.64 (s, 6H), 1.40 (d, 2/3H), 1.06 (d, 2/3H), 0.73 (dt, 1/3H), −0.03 (dt, 1/3H).

EXAMPLE 9

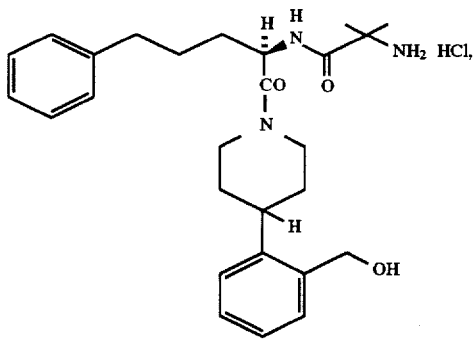

To 0.20 g of the benzyl alcohol-pyridine intermediate synthesized in Step A of Example 1 was added 2 mL of dry acetone and 0.10 mL of benzyl bromide and stirred at room temperature for 1 h. The volatiles were removed on the rotary evaporator and the residue was azeotroped with toluene. The residue was dissolved in methanol and treated with 0.10 g of sodium borohydride for 1 h. The reaction mixture was diluted with water and extracted with CH$_2$Cl$_2$. The combined organics were washed with brine, dried over magnesium sulfate, filtered, and evaporated. This gave a mixture of N-benzyl-tetrahydropyridines, which was hydrogenated in ethanol for 5 h with 10% Pd/C as the catalyst. The catalyst was filtered off and the filtrate was concentrated. Purification of the residue with CH$_2$Cl$_2$-methanol (90:10) as the eluent gave 70 mg of a mixture of tetrahydro- and hexahydropyridines. To a solution of 70 mg of the above mixture in 5 mL of CH$_2$Cl$_2$ was added 0.10 g of Intermediate 3, 0.040 g of HOBT and 0.070 g of EDC and stirred at RT overnight. The reaction mixture was poured into saturated aqueous NaHCO₃ and extracted with CH₂Cl₂. The combined organics were washed with brine, dried over Na₂SO₄, and concentrated. Purification of the residue by flash chromatography with hexane-EtOAc (4:1) as the eluent gave 0.090 g of the coupled product as a mixture of diastereomers.

The above coupled product was hydrogenated in ethanol with 10% Pd/C as the catalyst for 18 h. The catalyst was filtered off through a pad of celite and the filtrate was concentrated. Hash chromatography of the residue with CH₂Cl₂-ether (6:1) as the eluent gave 90 mg of the desired product.

A final deprotection of the above intermediate was carried out in methanol (2 mL) in the presence of 1 mL of concentrated HCl for 5h. The reaction mixture was evaporated to dryness and the residue was triturated with ether to give a solid. Purification of this material by MPLC on an LH₂₀ column with methanol as the eluent gave 34 mg of the title compound as a white solid.

¹H NMR (CD₃OD, 400 MHz) d 7.35–7.04 (m, 9H), 4.95 (m, 1H), 4.69 (d, 2H), 4.60 (d, 1H), 3.97 (dd, 1H), 3.30–3.10 9m, 3H), 2.82–2.60 9m, 4H), 1.90–1.70 (m, 5H), 1.63 9s, 2H), 1.60 (s, 4H), 1.55–1.40 (m, 1H).

EXAMPLE 10

(cis, d1+d2)

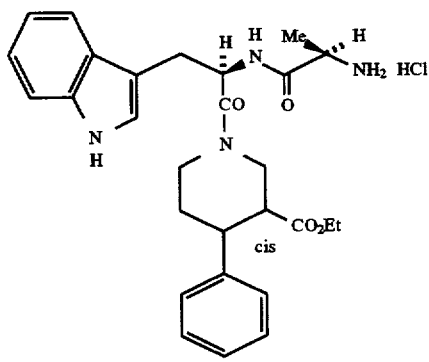

The intermediate prepared from Example 12, Step B (930 mg, mixture of two diastereomers) was dissolved in methanol and hydrogenated over Pd(OH)₂ at one atmosphere for 12 hours. The mixture was filtered through Celite and the filtrate concentrated under vacuum to give 700 mg of deprotected product. To the residue (5.5 mg) in 0.5 ml of methylene chloride was added N-BOC-(D)-alanine (4.9 mg). EDC (5.0 mg) and HOBt (3.5 mg). After stirring overnight, the mixture was poured into water, exacted with methylene chloride and washed with brine. The organic layer was dried over sodium sulfate, filtered and concentrated. The residue was purified by PLC (hexanes/ethyl acetate=1/1) to give coupling product. A final deprotection of the coupled intermediate was carried out by following the procedure described in Example 19, Step B to give 7.8 mg of desired compound.

¹H NMR (400 MHz, CD₃OD, mixture of diastereomers and rotamers): 7.59 (m, 1H), 7.39–7.01 (m, 9H), 5.37 (m, 1/2H), 5.18 (m, 1/2H), 4.61 (m, 1H), 4.30 (m, 1/2H), 4.02–3.61 (m, 3H), 3.35–2.35 (m, 7 1/2H), 1.60 (m, 1H), 1.56 (d, 7 Hz 3/2H), 1.50 (m, 3/2H), 0.95 (m, 3/2H), 0.88 (m, 3/2H). FAB-MS: 491.0 (M+1).

EXAMPLE 11

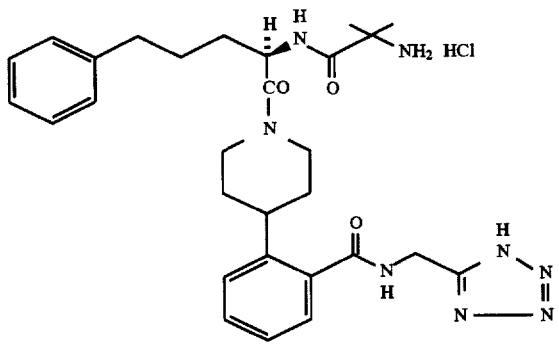

To a solution of 0.10 g of the compound prepared in Step A of Example 15 in 2 mL of chloroform at 0° C. was added 0.018 g of 5-aminomethyltetrazole, 0.027 g of HOBT, 0.65 mL of triethylamine and 0.048 g of EDC and stirred for 10 min. at 0° C. 1 mL of DMF was added to the suspension and stirred overnight. The reaction mixture was concentrated and the residue was separated by prep TLC (1 mm plate) with CHCl₃—MeOH—NH₄OH (90:10:1) as the eluent to give the desired material. FAB MS m/e calcd. for C₃₄H₄₆N₈O₅ 646.36; found 647.2 (m+1).

To a cooled solution of 0.025 g of the above product in 1 mL of ethyl acetate was bubbled in HCl(gas) till it was saturated and allowed to stand at rt for 30 min. The reaction was concentrated to give the title compound.

¹H NMR (200 MHz; CD₃OD) indicated a mixture of rotamers; 7.91 (d, J=8 Hz); 7.35–7.06 (m); 5.14 (bs); 4.65–4.48 (m); 3.92 (bt, J=13); 3.72–3.04 (m); 2.76–2.58 (m); 1.95–1.68 (m); 1.61 (s); 1.28 (s). FAB MS Calc. for C₃₄H₄₆N₈O₅: MW=546.31; found m/e=(m+1) 547.1.

EXAMPLE 12

(cis, d1)

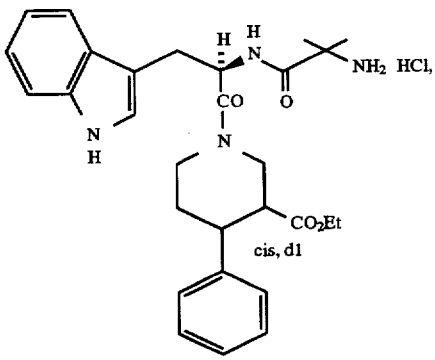

Step A-1:

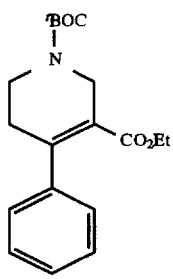

To a solution of 3-ethoxycarbonyl-4-piperidone hydrochloride (11.4 g, 54.9 mmole) in 82 ml of 1N aqueous sodium hydroxide was added di-t-butyl-dicarbonate (12.2 g, 56.0 mmole) in 82 ml of dioxane at room temperature. After 12 hours, the mixture was diluted with ethyl acetate and washed with 0.5N hydrochloric acid and brine. The organic layer was dried over magnesium sulfate, filtered and concentrated. To the crude residue in 200 ml of methylene chloride there was added diisopropylethylamine (14.3 ml, 82.3 mmole) and triflic anhydride (10.1 ml, 60.4 mmole) at −78° C. After ½ hour, the mixture was poured into saturated sodium bicarbonate solution and extracted with methylene chloride. The organic layer was washed with 1N hydrochloride, brine and dried over magnesium sulfate. The organic layer was concentrated to give the vinyl triflate (21.0 g, 95%). To a solution of the vinyl triflate (4.67 g, 11.6 mmole) in 100 ml of methylene chloride and 100 ml of 1-methyl-2-pyrrolidinone was added phenyltrimethyltin (2.1 ml, 11.6 mmole), and palladium acetate (0.13 g, 0.58 mmole) at room temperature. After a couple of hours, the reaction was poured into water and extracted with ether (3×). The organic layers were washed with water (3×), brine and dried over magnesium sulfate. After concentration and purification (MPLC, hexanes/ethyl acetate=10/1), the desired compound was isolated in 83% yield (3.2 g).

Step A:

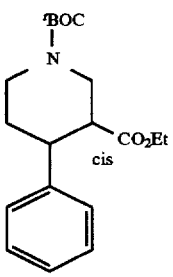

Prepared from the intermediate obtained from Step A-1 (3.2 g, 9.66 mole) which was dissolved in 100 ml of methanol, hydrogenated over PtO₂ at one atmosphere for a couple of hours (very slow reaction) and then a portion of Pd/C was added under hydrogen. The mixture was stirred for 72 hours and then filtered through Celite. The filtrate was concentrated under vacuum. The residue was purified by MPLC (hexanes/ethyl acetate=10/1) to give the cis compound (1.9 g).

Step B:

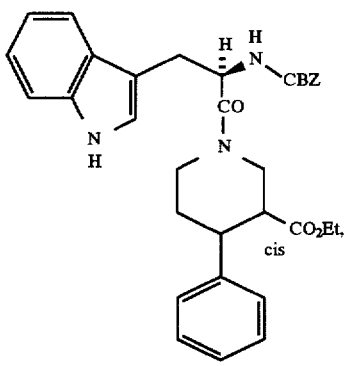

To intermediate prepared from Step A (200 mg, 0.6 mmole) there was added 2 ml of TFA. After 10 minutes, the mixture was concentrated and azeotroped with toluene (3×). The residue was dissolved in ethyl acetate and washed with sodium bicarbonate. The organic layer was concentrated. To the residue in 10 ml of methylene chloride there was added N-CBZ-D-tryptophan (223 mg, 0.66 mmole), EDC (138 mg, 0.72 mmole), and HOBt (89 mg, 0.66 mmole). After a couple of hours, the reaction was poured into water and extracted with methylene chloride, dried over sodium sulfate, filtered and concentrated. The residue was purified by MPLC (hexanes/ethyl acetate=2/1) to give two diastereomers in total 66% yield (the less polar diastereomer d1, 82 mg; and the more polar diastereomer d2, 138 mg).

Step C:

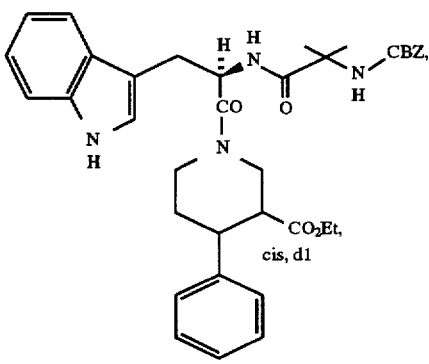

The less polar diastereomer from Step B (82 mg) was dissolved in 5 ml of methanol and hydrogenated over Pd/C at one atmosphere for a couple of hours (monitored by TLC). The mixture was filtered through Celite and the filtrate concentrated under vacuum. To the residue in 5 ml of chloroform was added N-CBZ-a-methylalanine (38 mg), EDC (31 mg) and HOBt (21 mg). After 3 hours stirring at room temperature, the mixture was poured into water, extracted with methylene chloride, and washed with brine. The organic layer was dried over sodium sulfate, filtered and concentrated. The residue was purified by chromatatron (hexanes/ethyl acetate=1/1) to give the desired compound in 69% yield (60 mg).

Step D:

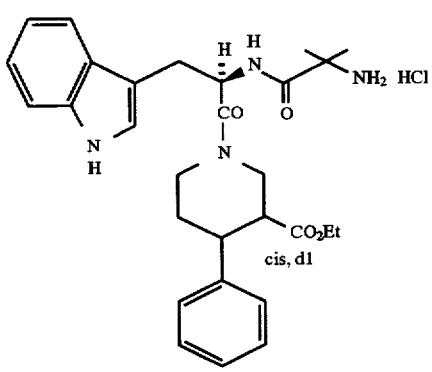

cis, d1

The intermediate obtained from Step C was dissolved in 3 ml of methanol and hydrogenated over Pd(OH)$_2$/C at one atmosphere for an hour (monitored by TLC). The mixture was filtered through Celite and the filtrate concentrated under vacuum. The residue was acidified with HCl in ether to give a whim precipitate (d1, 40 mg).

$^1$H NMR (400 MHz, CD$_3$OD mixture of rotamers): 7.64 (d, 8 Hz, 1/2H), 7.57 (d, 8 Hz, 1/2H), 7.37–7.01 (m, 9H), 5.28 (dd, 8, 5 Hz, 1/2H), 5.18 (t, 7 Hz, 1/2H), 4.76 (m, 1H), 4.30 (m, 1/2H), 4.15 (m, 1/2H), 3.81 (m, 2 1/2H), 3.35 (m, 1/2H), 3.16 (m, 2 1/2H), 3.02 (m, 1 1/2H), 2.98 (m, 1/2H), 2.45 (m, 1H), 2.25 (m, 1/2H), 1.74 (m, 1/2H), 1.63 (m, 1/2H), 1.57 (s, 3/2H), 1.52 (s, 3/2H), 1.49 (s, 3/2H), 1.34 (s, 3/2H), 0.98 (t, 7 Hz, 3/2H), 0.90 (t, 7 Hz, 3/2H). FAB-MS: 505.6 (M+1).

EXAMPLE 13

(cis, d2)

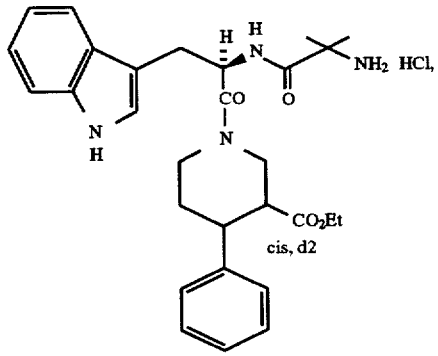

cis, d2

Prepared from the intermediate obtained from the more polar diastereomer of Example 12, Step B (93 mg) by the procedure described in Example 12 Steps C and D to give the desired compound (d2, 56 mg).

$^1$H NMR (400 MHz, CDCl$_3$, mixture of rotamers): 7.57 (m, 1H), 7.35–6.94(m, 9H), 5.37(t, 7 Hz, 2/3H), 5.17 (m, 1/3H), 4.61 (m, 1H), 4.28 (m, 1/3H), 4.06 (m, 2/3H), 3.84–3.53 (m, 2H), 3.28–2.80 (M, 5H), 2.53 (M, 1H), 1.61 (S, 2H), 1.51 (S, 1H), 1.47 (S, 2H), 1.29 (S, 1H), 0.95 (t, 7 Hz, 2H), 0.80 (t, 7 Hz, 1H). FAB-MS: 505.7.

EXAMPLE 14

(trans, d1+d2)

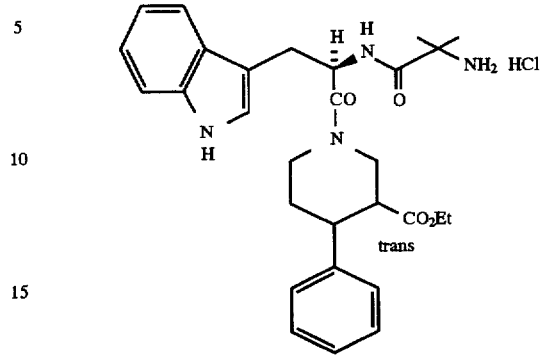

trans

Step A:

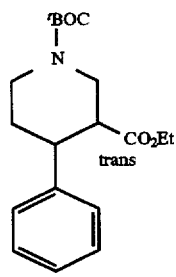

trans

A small piece of sodium was added to 2.5 ml of anhydrous ethanol. When the sodium was dissolved, the intermediate from Example 12, Step A (40 mg) was added to the reaction mixture and placed in an 80° C. oil bath for 2 hours. This mixture was poured into 0.1N HCl and extracted with ether. The organic layer was dried over sodium sulfate, filtered and concentrated. The residue was purified by PLC (hexanes/ethyl acetate=5/1) to give the trans isomer (26 mg).

Step B:

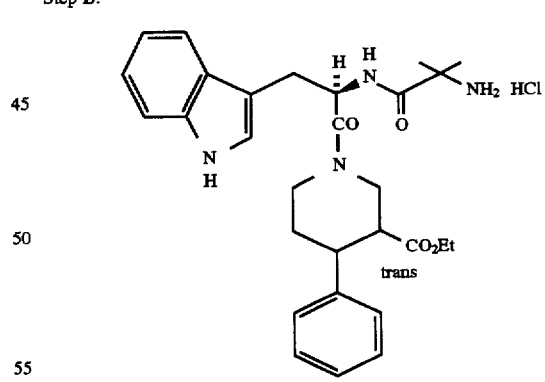

trans

Prepared from the intermediate obtained from Step A (24 mg) and Intermediate 1 according to the procedures described in Example 7, Steps B and C to give 5.4 mg of product as the hydrochloride salt.

$^1$H NMR (400 MHz, CD$_3$OD, mixture of diastereomers and rotamers): 7.63–7.35 (m, 2H), 7.24–6.75 (m, 8H), 5.01 (m, 1H), 4.60 (m, 1H), 4.08–3.68 (m, 3 1/3H), 3.39–2.41 (m, 5 2/3H), 1.78–0.96 (1 1/3H), 1.62 (s, 3H), 1.61 (s, 3H), 0.86 (m, 3H), 0.66 (m, 1/3H), –0.10 (m, 1/3H). FAB-MS: 505.6 (M+1).

EXAMPLE 15

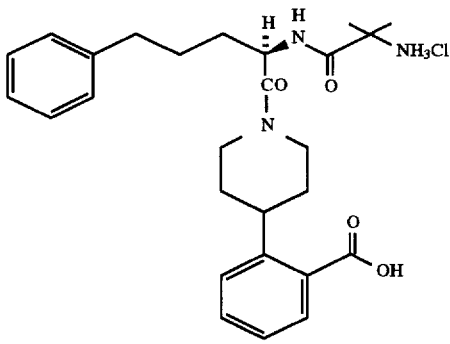

Step A:

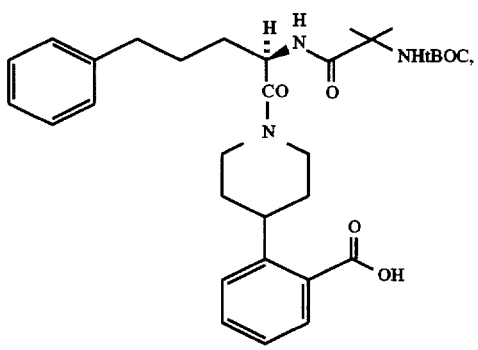

Approximately 0.250 g of the piperidine intermediate prepared in Step A of Example 44 was reacted with 0.39 g of Intermediate 3, 0.152 g of HOBT, 0.17 mL of N-methylmorpholine, and 0.225 g of EDC in 15 mL of chloroform for 18 h. The reaction mixture was washed with 0.50N HCl (10 mL), saturated aqueous $NaHCO_3$ (10 mL), dried over $MgSO_4$ and concentrated. The crude was purified by flash chromatography with hexane-EtOAc (4:1) as the eluent.

To 0.136 g of this material in 10 mL a 1:1 mixture of methanol-water was added 25 mg of lithium hydroxide and stirred overnight. The reaction mixture was diluted with 10 mL of water and washed with water, the aqueous layer was acidified to pH=2 with 0.50N HCl and extracted with ether (3×10 mL). The combined organics were washed with brine, dried over $MgSO_4$ and concentrated to give the desired material as a white solid.

Step B:

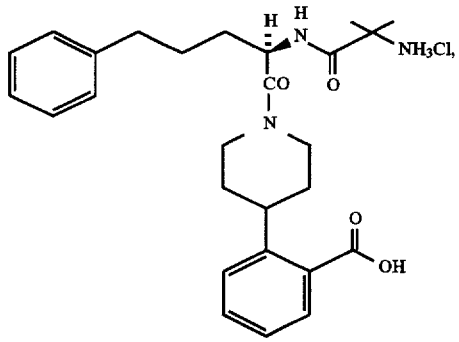

The title compound was prepared from the compound made in Step A by treating it with a saturated solution of HCl(gas) in ethyl acetate for 30 min. at RT. Ether was added and the precipitate was filtered and dried.

$^1$H NMR (400 MHz, $CD_3OD$ mixture of rotamers): 8.10 (t, 1H), 7.78 (dd, 1H), 7.50–7.00 (m, 8H), 4.90 (m, 1H), 4.55 (d, 1H), 3.94 and 3.90 (2doublets, 1H), 3.80–3.60 (m, 1H), 3.05 (dt, 1H), 2.70–2.50 (m, 4H), 1.90–1.50 (m, 6H), 1.55 (s, 3H), 1.50 (s, 3H), 1.40 (m, 1H).

EXAMPLE 16

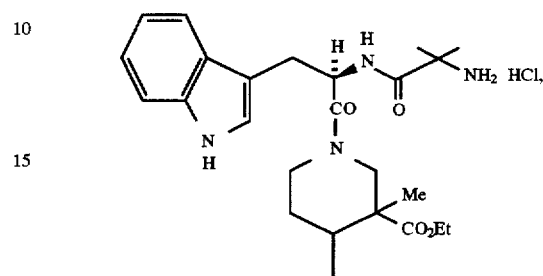

Step A:

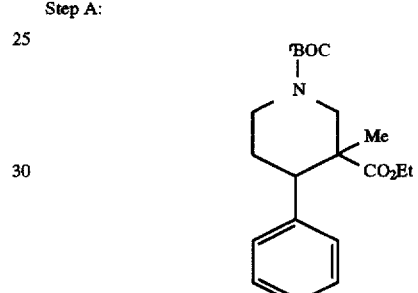

To a solution of the intermediate obtained from Example 12, Step A (89 mg, 0.267 mmole) in 2 ml of THF there was added potassium bis(trimethylsilyl)amide (0.5M, 800 ml, 0.4 mmole) at −78° C. After ½ hour, methyl iodide (22 ml, 0.34 mmole) was added to reaction mixture. This reaction was slowly warmed up to room temperature and stirred for additional 12 hours. The mixture was poured into water and then extracted with ether. The organic layer was dried over sodium sulfate, filtered and concentrated. The residue was purified by a chromatatron (hexanes/ethyl acetate=1/1) to give the desired compound (91 mg, 98%).

Step B:

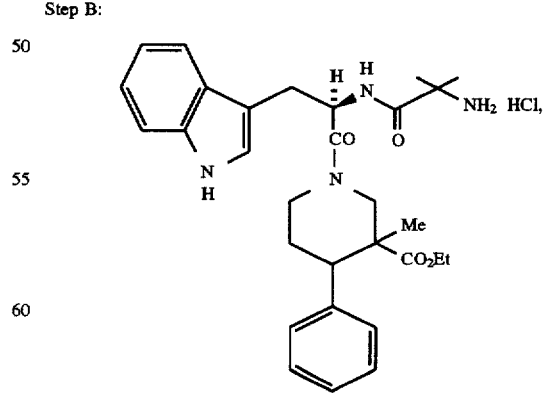

Prepared from the intermediate obtained from Step A (91 mg) by the procedure described in Example 12, Steps B, C, and D to give the desired compound.

$^1$H NMR (400 MHz, CD$_3$OD, mixture of diastereomers and rotamers): 7.58 (m, 1H), 7.37–7.00 (m, 9H), 5.40–5.23 (m, 1H), 4.60 (m, 1H), 4.20–3.73 (m, 3H), 3.40 (m, 1/2H), 3.15 (m, 2H), 2.82 (m, 1H), 2.61–2.30 (m, 2 1/2H), 1.72 (m, 1/2H), 1.63–1.29 (m, 6H), 1.13–0.84 (m, 6H). EI-MS: 518.2 (M).

EXAMPLE 17

(cis, d1+d2)

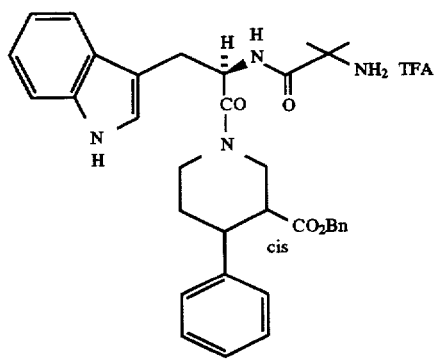

Step A:

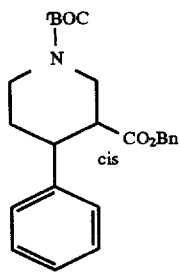

To a stirred solution of the intermediate prepared from Example 12, Step A-1 (1.0 g, 3.02 mmole) in 4 ml of ethanol there was added 4N sodium hydroxide (4 ml). The reaction was stirred at room temperature for 16 hours and evaporated in vacuo. The residue was diluted with water and acidified with 0.5N hydrochloric acid and then exacted with ether. The organic layer was dried over sodium sulfate, filtered and concentrated. The crude residue was dissolved in methanol and hydrogenated over Pd(OH)$_2$ at one atmosphere for 16 hours. The mixture was filtered through Celite and the filtrate concentrated under vacuum. To crude acid in 10 ml of chloroform there was added benzyl alcohol (341 ml), EDC (750 mg) and a catalytic amount of DMAP. After 16 hours, the mixture was diluted with methylene chloride and then washed with water and brine. The organic layer was dried over magnesium sulfate, filtered and concentrated. The residue was purified by MPLC (hexanes/ethyl acetate=5/1) to give the desired compound (459 mg, 38%).

Step B:

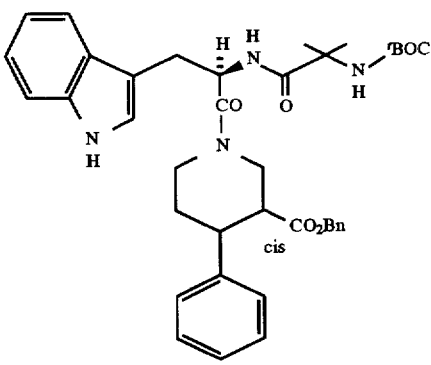

To intermediate prepared from Step A (459 mg, 1.16 mmole) there was added 2 ml of TFA at room temperature. After 10 minutes, the reaction mixture was concentrated and azeotroped with toluene (3×). To the residue in 10 ml of chloroform there was added Intermediate 1 (433 mg), EDC (265 mg), HOBt (172 mg), and triethylamine (194 ml). The reaction was stirred at room temperature for 3 hours and poured into water. The mixture was extracted with methylene chloride, and dried over sodium sulfate. Concentration and purification (MPLC, hexanes/ethyl acetate=1.5/1) gave the coupling product (574 mg) in 76% yield.

Step C:

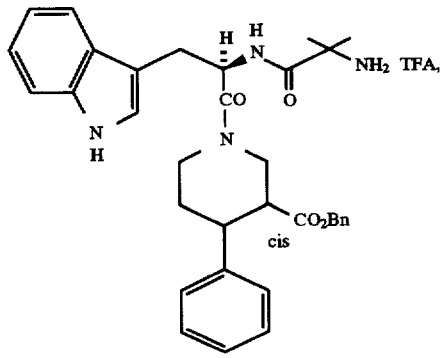

To intermediate (10 mg) obtained from Step B there was added TFA at room temperature. After 10 minutes, the mixture was concentrated to give the desired compound (3 mg).

$^1$H NMR (400 MHz, CD$_3$OD, mixture of diastereomers and rotamers): 7.62 (m, 1H), 7.37–6.81 (m, 14H), 5.42–5.15 (m 1H), 4.79 (m, 2H), 4.65 (m, 1H), 4.32 (m, 1/2H), 4.12 (m, 1/2H), 3.27–2.85 (m, 5 1/2H), 2.55–2.27 (m, 1 1/2H), 1.74 (m, 1H), 1.60–1.29 (m, 6H). FAB-MS: 567.0 (M+1).

EXAMPLE 18

(cis, d1+d2)

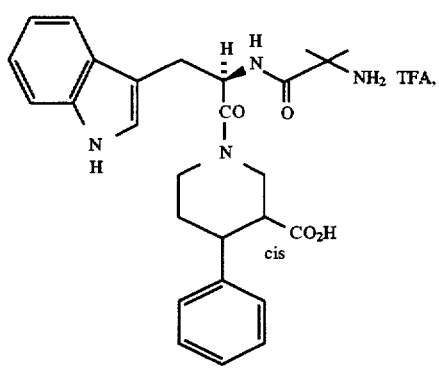

Step A:

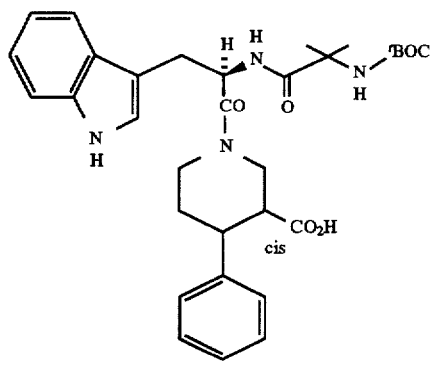

Prepared from the intermediate obtained from Example 17, Step B (20 mg) by the procedure described in Example 8 to give the desired compound.

Step B:

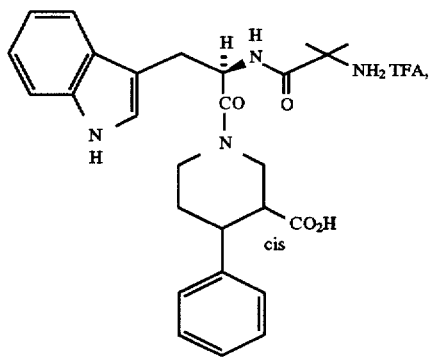

Prepared from the intermediate obtained from Step A by the procedure described in Example 17, Step C to give the desired compound (10 mg).

$^1$H NMR (400 MHz, CD$_3$OD, mixture of diastereomers and rotamers): 7.62 (m, 1H), 7.37–6.98 (m, 9H), 5.36–5.21 (m 1H), 4.69 (m, 1/2H), 4.58 (m, 1/2H), 4.27–3.91 (m, 2H), 3.27–2.75 (m, 5H), 2.51–2.34 (m, 2H), 1.72 (m, 1H), 1.58–1.21 (m, 6H). FAB-MS: 576.9 (M+1).

EXAMPLE 19

(cis, d1+d2)

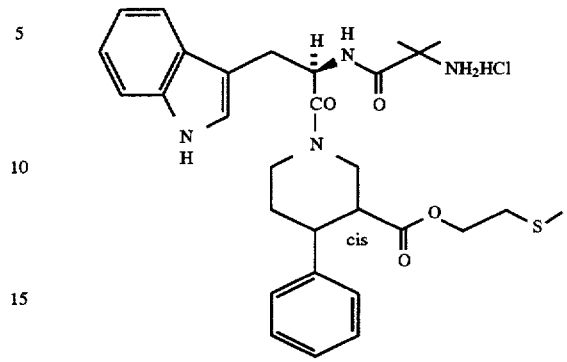

Step A:

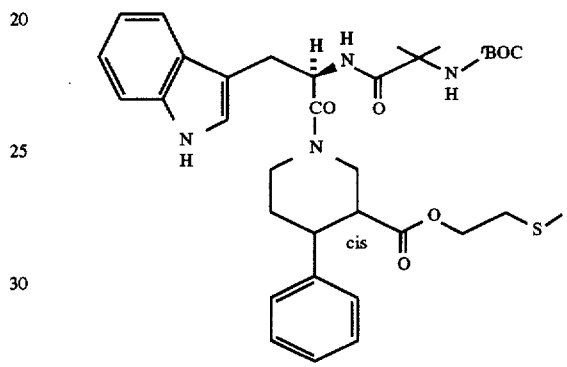

Prepared from the intermediate obtained from Example 18, Step A (142 mg) in 3 ml of methylene chloride to which there was added 2-(methylthio)ethanol (22 ml), EDC (57 mg) and a catalytic amount of DMAP. After 3 hours, the mixture was diluted with methylene chloride and then washed with water and brine. The organic layer was dried over magnesium sulfate, filtered and concentrated. The residue was purified by PLC (hexanes/ethyl acetate=1/1) to give the desired product (69 mg, 43%).

Step B:

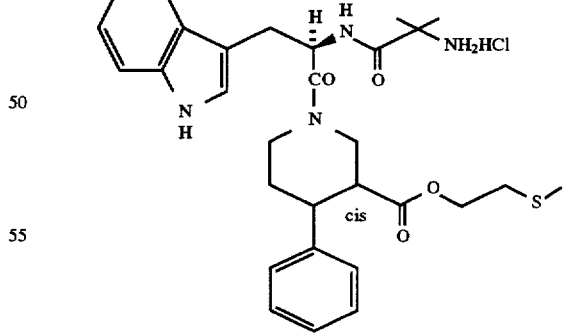

Prepared from the intermediate obtained from Step A (50 mg) in 2 ml of ether into which there was bubbled HCl gas at 0° C. After 30 seconds, the mixture was concentrated to give the white solid (41 mg).

$^1$H NMR (400 MHz, CD$_3$OD, mixture of diastereomers and rotamers): 7.61(m, 1H), 7.37–6.97 (m, 9H), 5.38–5.18 (m 1H), 4.83–4.54 (m, 1H), 4.37–3.77 (m, 3H), 3.57–2.83

(m, 6H), 2.55–2.21 (m, 3H), 2.14–1.84 (m, 3H), 1.72 (m, 1H), 1.61–1.29 (m, 6H). FAB-MS: 551.0 (M+1).

EXAMPLE 20

(cis, d1+d2)

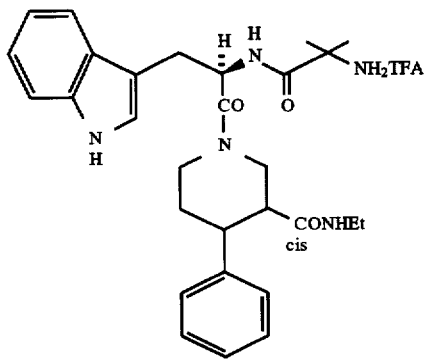

Prepared from the intermediate obtained from Example 18, Step A (52 mg) in 3 ml of methylene chloride to which there was added ethylamine hydrochloride (9 mg), EDC (21 mg), triethylamine (15 ml) and a catalytic amount of DMAP. After 3 hours, the mixture was diluted with methylene chloride and then washed with water and brine. The organic layer was dried over magnesium sulfate, filtered and concentrated. The residue was purified by PLC (methylene chloride/methanol=20/1) to give the coupling product (25 mg). This intermediate by the procedure described in Example 17, Step C gave the desired compound (25 mg).

$^1$H NMR (400 MHz, CD$_3$OD, mixture of diastereomers and rotamers): 7.68–6.93 (m, 10H), 5.34–5.12 (m 1H), 4.75–4.30 (m, 2H), 3.50–2.60 (m, 8H), 1.72–1.17 (m, 8H), 0.83–0.68 (m, 3H). FAB-MS: 504.0 (M+1).

EXAMPLE 21

(cis, d1+d2)

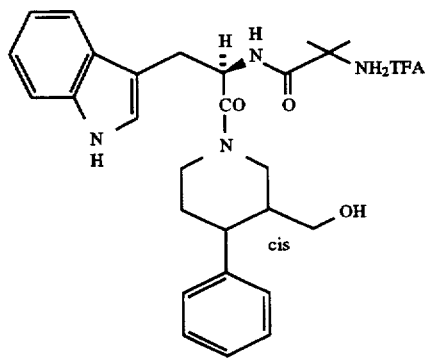

Step A:

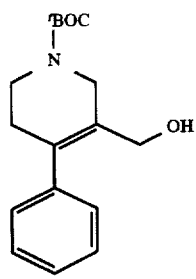

To a solution of the intermediate obtained from Example 12, Step A-1 (950 mg, 2.87 mmole) in 10 ml of THF there was added diisobutylaluminum hydride (1.0N in methylene chloride, 8 ml, 8.0 mmole) at −78° C. The mixture was stirred at 0° C. for 1 hour and then slowly warmed to room temperature. The mixture was quenched with 1N sodium hydroxide, and extracted with ether (3×). The organic layer was dried over sodium sulfate, filtered and concentrated. The residue was purified by MPLC (hexanes/ethyl acetate= 2/1) to give 617 mg of reduction product.

Step B:

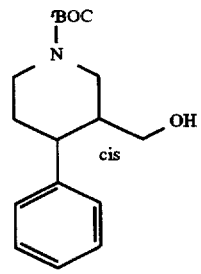

Prepared from the intermediate obtained from Step A (57 mg) by hydrogenation under the conditions described in Example 12, Step A to give the desired compound (13 mg).

Step C:

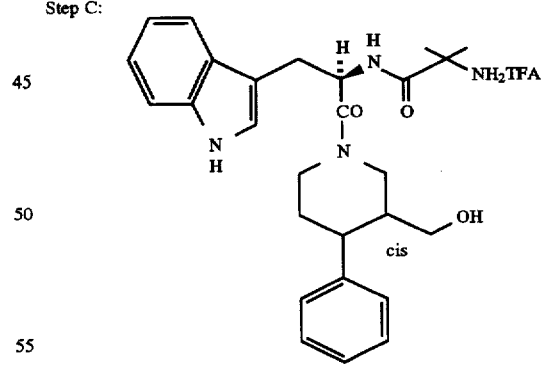

Prepared from the intermediate obtained from Step B (13 mg) by the procedure described in Example 17, Steps B and C to give the desired compound (12 mg).

$^1$H NMR (400 MHz, CD$_3$OD, mixture of diastereomers and rotamers): 7.74–6.80 (m, 10H), 5.55 (m 1/2H), 5.20 (m, 1/2H), 4.66(m, 1H), 4.11 (m, 1/2H), 3.93 (m, 1/2H), 3.20 (m, 3H), 3.00–2.82 (m, 2 1/2H), 2.69–2.45 (m, 2 1/2H), 2.05–1.84 (m, 1H), 1.68 (s, 3/2H), 1.61 (s, 3/2H), 1.60 (s, 3/2H), 1.47 (s, 3/2H), 0.90 (m, 1/2H), 0.17 (m, 1/2H). FAB-MS: 463.0 (M+1).

EXAMPLE 22

(cis, d1+d2)

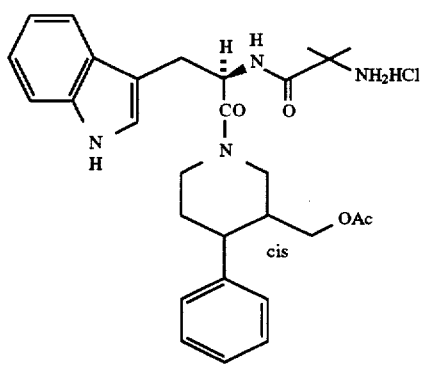

Step A:

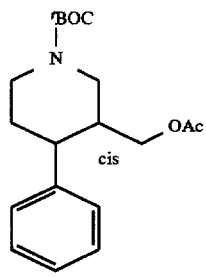

Prepared from the intermediate obtained from Example 21, Step A (330 mg, 1.14 mmole) in 10 ml of methylene chloride to which there was added acetic anhydride (130 ml), triethylamine (240 ml), and a catalytic amount of DMAP at 0° C. After 1 hour, water was added to the mixture and it was stirred an additional 1 hour at room temperature. The mixture was extracted with methylene chloride and then washed sequentially with 1N sodium hydroxide and brine. The organic layer was dried over magnesium sulfate, filtered and concentrated. The residue was hydrogenated under the conditions described in Example 12, Step A to give the desired compound.

Step B:

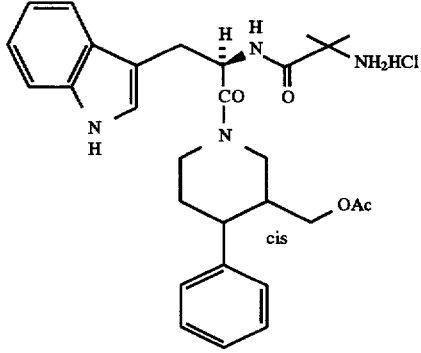

Prepared from the intermediate obtained from Step A (24 mg) by the procedure described in Example 17, Step B and Example 19, Step B to give the desired compound (23 mg).

$^1$H NMR (400 MHz, CD$_3$OD, mixture of diastereomers and rotamers): 7.74–6.87 (m, 10H), 5.55–5.16 (m 1H), 4.65 (m, 1H), 3.96 (m, 1H), 3.81 (m, 1/2H), 3.20 (m, 3H), 2.86 (m, 1H), 2.61 (m, 1H), 2.46 (m, 1/2H), 2.27 (m, 1/2H), 2.13 (m, 1H), 1.98 (s, 1/2H), 1.93 (s, 1H), 1.90 (s, 1H), 1.85 (s, 1/2H), 1.73–1.30 (m, 7 1/2H), 0.85 (m, 1/2H), 0.12(m, 1/2H). FAB-MS: 505.3 (M+1).

EXAMPLE 23

(cis, d1)

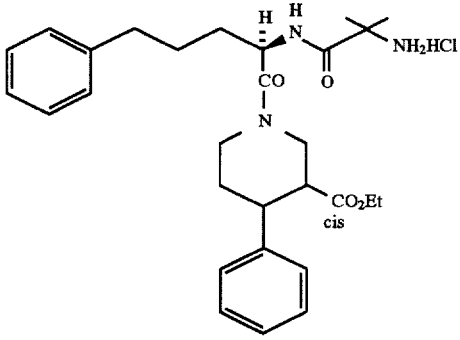

Step A:

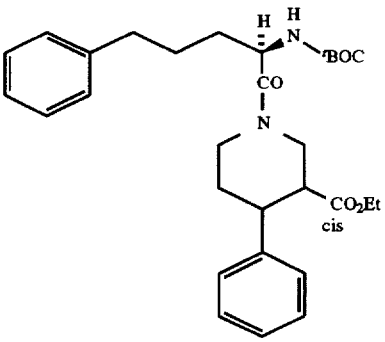

To intermediate prepared from Example 12, Step A (87 mg) there was added 1 ml of TFA. After 10 minutes, the mixture was concentrated and azeotroped with toluene (3×). The residue was dissolved in ethyl acetate and washed with sodium bicarbonate. The organic layer was concentrated. To the residue in 3 ml of methylene chloride there was added N-BOC-(2R)-amino-5-phenylpentanoic acid (70 mg), EDC (55 mg), and HOBt (35 mg). After a couple of hours, the reaction was poured into water and extracted with methylene chloride, dried over sodium sulfate, filtered and concentrated.

Step B:

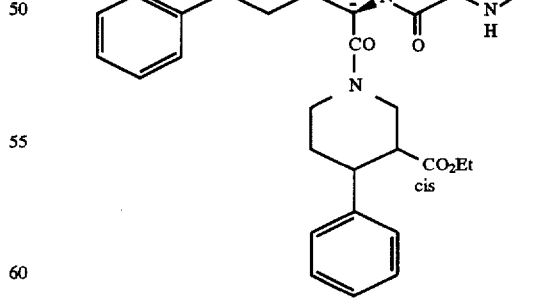

To intermediate prepared from Step A there was added 1 ml of TFA. After 10 minutes, the mixture was concentrated and azeotroped with toluene (3×). To the residue in 3 ml methylene chloride there was added BOC-a-methylalanine, EDC, HOBt, and triethylamine. After a couple of hours, the reaction was poured into water and extracted with methylene chloride, dried over sodium sulfate, filtered and concentrated. The residue was purified by MPLC (hexanes/ethyl acetate=2/1) to give two diastereomers in 75% yield (the less polar diastereomer d1, 54 mg; the more polar diastereomer d2, 53 mg).

Step C:

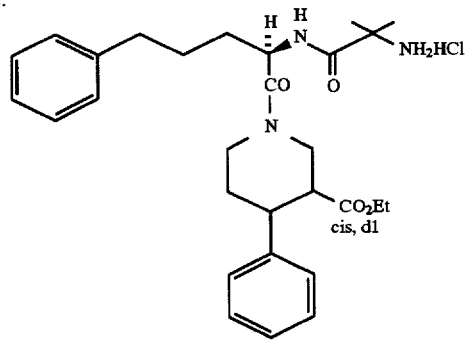

To the less polar diastereomer prepared from Step B (54 mg) was added 1 ml of TFA. After 10 minutes, the mixture was concentrated and azeotroped with toluene (3×). The residue was dissolved in ethyl acetate and washed with sodium bicarbonate. The organic layer was dried over sodium sulfate, filtered and concentrated. The residue was dissolved in ether to which was added HCl in ether to give a white solid (d1, 40 mg).

$^1$H NMR (400 MHz, CD$_3$OD mixture of rotamers): 7.23 (m, 10H), 5.08 (m, 1H), 4.76 (m, 1H), 4.21 (m, 1H), 3.80 (m, 2 1/2H), 3.47 (m, 1/2H), 3.26–2.99 (m, 4H), 2.86 (m, 1/2H), 2.63 (m, 2H), 2.40 (m, 1/2H), 1.75 (m, 4H), 1.63 (s, 2H), 1.60(s, 2H), 1.57 (s, 2H), 0.95 (t, 7 Hz, 2H), 0.87 (t, 7 Hz, 1H). FAB-MS: 494.1 (M+1).

EXAMPLE 24

(cis, d2)

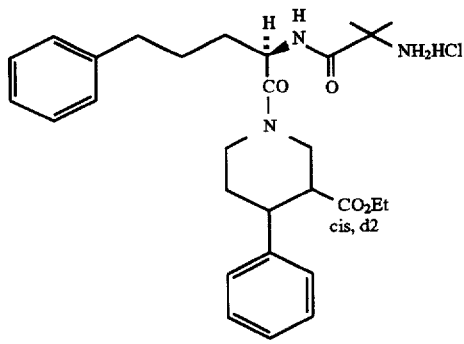

The desired d2 compound (40 mg) was prepared from the more polar diastereomer obtained in Example 23, Step B (53 mg) by the procedure described in Example 23, Step C.

$^1$H NMR (400 MHz, CD$_3$OD mixture of rotamers): 7.23 (m, 10H), 4.91 (m, 1H), 4.75 (m, 1H), 4.03 (m, 1H), 3.81 (m, 2H), 3.45 (m, 1/2H), 3.26–2.96 (m, 4H), 2.71 (m, 2 1/2H), 2.40 (m, 1H), 1.90–1.64 (m, 4H), 1.63 (s, 2H), 1.61 (s, 3H), 1.59 (s, 3H), 0.93 (t, 7 Hz, 3H). FAB-MS: 494.3 (M+1).

EXAMPLE 25

(cis, d1+d2)

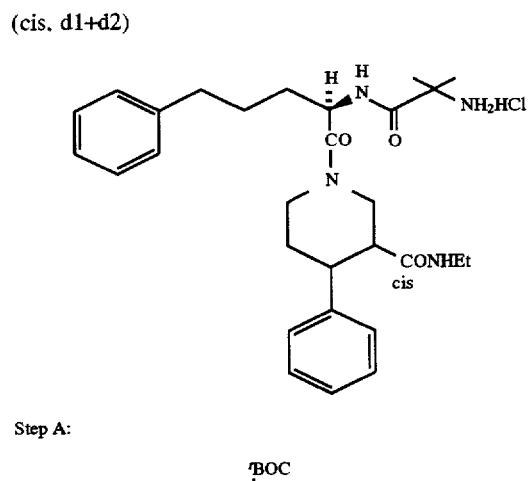

Step A:

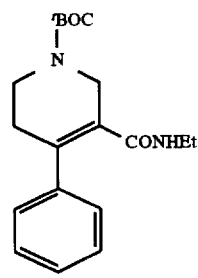

To a stirred solution of the intermediate prepared from Example 12, Step A-1 in 4 ml of ethanol there was added 4N sodium hydroxide (4 ml). The reaction was stirred at room temperature for 16 hours and evaporated in vacuo. The residue was diluted with water and acidified with 0.5N hydrochloric acid and then extracted with ether. The organic layer was dried over sodium sulfate, filtered and concentrated. The residue (100 mg) in 3 ml of methylene chloride there was added ethylamine hydrochloride (74 mg), EDC (115 mg), HOBt (49 mg) and triethylamine (83 ml). After a couple of hours, the reaction was poured into water and extracted with methylene chloride, dried over sodium sulfate, filtered and concentrated. The residue was purified by MPLC (hexanes/ethyl acetate=1/1) to give desired compound (74 mg).

Step B:

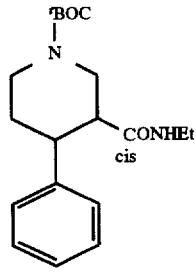

Prepared from the intermediate obtained from Step A (74 mg) by the procedure described in Example 12, Step A to give desired compound (60 mg).

Step C:

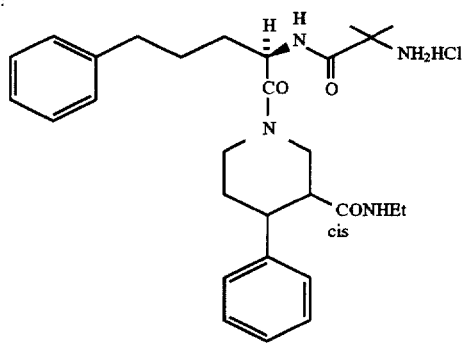

Prepared from the intermediate obtained from Step B (60 mg) by the procedure described in Example 23, Steps A, B, and C to give the desired compound (15 mg).

$^1$H NMR (400 MHz, CD$_3$OD mixture of diastereomers and rotamers): 7.27 (m, 10H), 4.91 (m, 1H), 4.67 (m, 1H), 3.96 (m, 1H), 3.42 (m, 1/2H), 3.26–2.59 (m, 9 1/2H), 1.90–1.64 (m, 4H), 1.64–1.57 (m, 6H), 0.79 (t, 7 Hz, 3/2H), 0.77 (t, 7 Hz, 3/2H). FAB-MS: 493.3 (M+1).

INTERMEDIATE 4

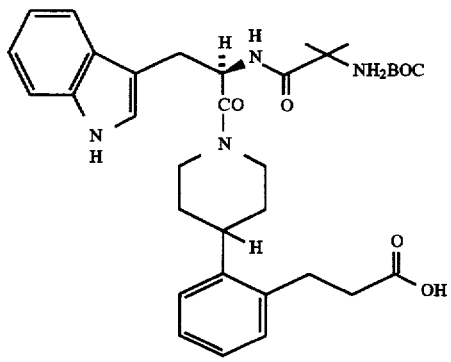

To a solution of 0.80 g of the compound prepared in Step B of Example 7 in 20 mL of ethanol was added 0.080 g of 20% pallium hydroxide/C and hydrogenated at atmospheric pressure for 3 h. The catalyst was filtered through a pad of celite and the filtrate was concentrated to give the title compound.

EXAMPLES 26, 27, 28, 29

The following compounds shown in Table 1 were prepared in two steps from Intermediate 4. The acid intermediate in a methylene chloride solution was coupled with alcohols or amines in the presence of EDC and DMAP at ambient temperature and these intermediates were purified and treated with hydrochloric acid(gas) in ethyl acetate to provide the compounds shown in Table 1.

TABLE 1

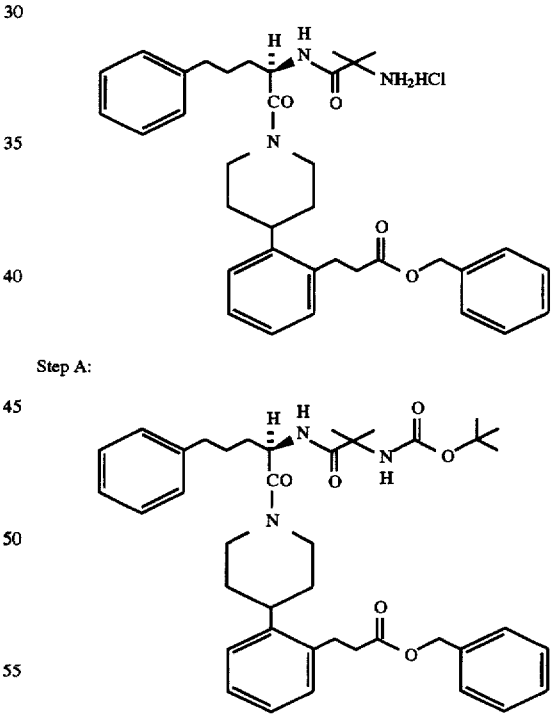

| Example No. | R | molecular formula | FAB MS m/e calc. | m/e found (m + 1) |
|---|---|---|---|---|
| 26 | OCH(CH$_3$)$_2$ | C$_{31}$H$_{42}$N$_4$O$_4$ | 569 | 570.2 |
| 27 | O(CH$_2$)$_3$CH$_3$ | C$_{33}$H$_{44}$N$_4$O$_4$ | 560 | 561.1 |
| 28 | –N(CH$_2$CH$_2$)$_2$O (morpholine) | C$_{33}$H$_{43}$N$_5$O$_4$ | 573.33 | 574.1 |
| 29 | NHCH$_2$CH$_3$ | C$_{31}$H$_{41}$N$_5$O$_3$ | 531 | 532.3 |

EXAMPLE 30

Step A:

To a solution of 1.1 g of the piperidine intermediate prepared in Example 7, Step A in 5 mL of ethyl acetate at room temperature was bubbled in HCl (gas) for 10 seconds and stirred for 30 min. The solvent was removed and the oily residue was basified with aqueous sodium bicarbonate solution and extracted with CH$_2$Cl$_2$. The combined organics were washed with brine, dried over K$_2$CO$_3$, filtered, and concentrated to give 0.90 g of the amine as a thick oil. To a solution of the above intermediate in 20 mL of CH$_2$Cl$_2$ was added 0.97 g of (2R)-N-t-BOC-5-phenylpentanoic acid, 0.45 g of HOBT, and 0.80 g of EDC and stirred at RT overnight. The reaction mixture was poured into saturated aqueous sodium bicarbonate solution and extracted with CH$_2$Cl$_2$. The combined organics were washed with 0.50N hydrochloric acid solution, brine, dried over MgSO$_4$, filtered and concentrated. The residue was purified by flash chromatography with hexane-acetone (5:1) as the eluent to yield about 2.0 g of the coupled product.

The above intermediate was treated with 2 mL of trifluoroacetic acid in 20 mL of CH$_2$Cl$_2$ at room temperature for 1 h. The volatiles were removed on the rotary evaporater and the residue was basified with aqueous NaHCO$_3$ and extracted with CH$_2$Cl$_2$. The combined organics were dried over K$_2$CO$_3$, filtered and concentrated. The residue was dissolved in CH$_2$Cl$_2$ and coupled with 0.60 g of N-t-BOC-a-methylalanine in the presence of 0.40 g of HOBT and 0.70 g of EDC. The reaction was stirred overnight and worked up as described above. The residue was purified by flash chromatography using hexane-acetone (5:1) as the eluent to give the title compound as a colorless foam.

$^1$H NMR (400 MHz, CDCl$_3$ mixture of rotamers): 7.40–6.85 (m, 14H), 5.10 (s, 2H), 5.05–4.88 (m, 2H), 4.70–4.60 (m, 1H), 3.93 (d, 1/2H), 3.85 (d, 1/2H), 3.10–2.85 (m, 4H), 2.70–2.50 (m, 5H), 1.85–1.60 (m, 7H), 1.50 (s, 3H), 1.48 and 1.47 (2s, 3H), 1.42 (s, 9H), 1.40–1.20 (m, 1H).

Step B:

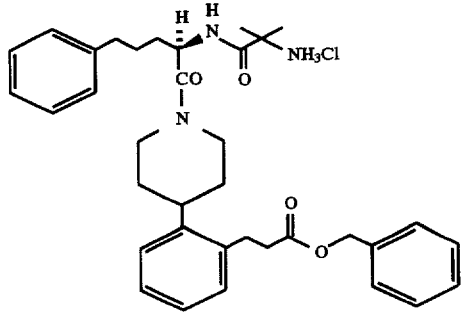

Approximately 0.050 g of the intermediate from Step A was dissolved in 1 mL of ethyl acetate and 1 mL of saturated HCl(gas) in ethyl acetate was added and stirred for at room temperature for 30 min. The reaction mixture was cooled to 0° C. and ether was added and the solvents were evaporated to leave the derired product as a foam.

$^1$H NMR (400 MHz, CD$_3$OD mixture of rotamers): 7.40–7.00 (m, 14H), 5.10 (s, 2H), 4.90 (m, 1H), 4.58 (d, 1H), 3.95 and 3.90 (2 doublets, 1H), 3.20–2.95 (m, 4H), 2.80–2.60 (m, 5H), 1.85–1.60 (m, 9H), 1.62 (s, 3H), 1.60 (s, 1H), 1.40 (m, 1H).

EXAMPLE 31

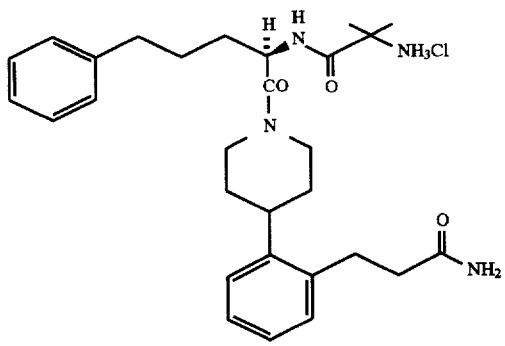

Step A:

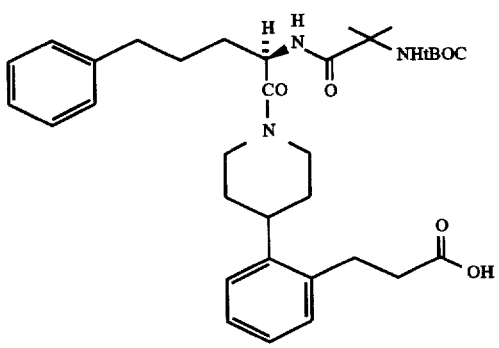

To 0.90 g of the intermediate prepared in Step A Example 30 in 5 mL of methanol was added 0.10 g of 20% palladium hydroxide and hydrogenated at atmospheric pressure overnight. The catalyst was filtered off through a pad of celite and washed with methanol. The filtrate was concentrated and the residue was dried under vacuum to provide the acid as a colorless foam that was used without purification.

Step B:

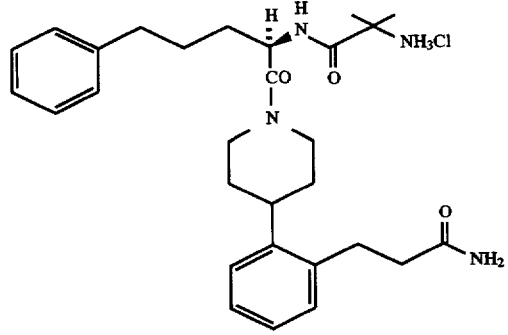

To a solution of 0.30 g of the acid intermediate prepared in Step A in 10 mL of dry THF was added 0.14 mL of triethylamine and 0.07 mL of ethylchloroformate and stirred for 1 h. The reaction was quenched with 2 mL of aqueous ammonium hydroxide solution and extracted with CH$_2$Cl$_2$. The combined organics were washed with 0.50N hydrochloric acid, dried over MgSO$_4$ and concentrated. The residue was purified by flash chromatography with chloroform-methanol (95:5) as the eluent to provide a solid that was deprotected with HCl in ethyl acetate as described above to give the title compound as a white solid.

$^1$H NMR (400 MHz, CD$_3$OD mixture of rotamers): 8.15 (t, 1H), 7.30–7.00 (m, 9H), 4.90 (m, 1H), 4.70 (d, 1H), 4.05 and 3.95 (2 doublets, 1H), 3.30–2.95 (m, 4H), 2.90–2.60 (m, 3H), 2.50 (bs, 2H), 1.90–1.65 (m, 7H), 1.60 (2 singlets, 6H), 1.48 (m, 1H).

EXAMPLES 32–35 AND 49

The compounds described in Table 2 were prepared from intermediate synthesized in Step A of Example 31 by taking advantage of chemistry used to prepare the title compound in Example 5. Other amines as depicted below were used in place of ethanolamine and the final deprotection was carried in ethyl acetate and dry hydrochloric acid. Ether was generally used to precipitate the hydrochloride salt.

TABLE 2

| Example No. | R | molecular formula | FAB MS m/e calc. | m/e found (m + 1) |
|---|---|---|---|---|
| 32 | N(CH₃)₂ | C₃₁H₄₄N₄O₃ | 520 | 521.2 |
| 33 | NHtBu | C₃₃H₄₈N₄O₃ | 548 | 549.2 |
| 34 | ⌒N S⌒ | C₃₃H₄₆N₄O₃S | 578 | 579.2 |
| 49 | NHCH₂CH₃ | C₃₁H₄₄N₄O₃ | 520 | 521.2 |

EXAMPLE 35

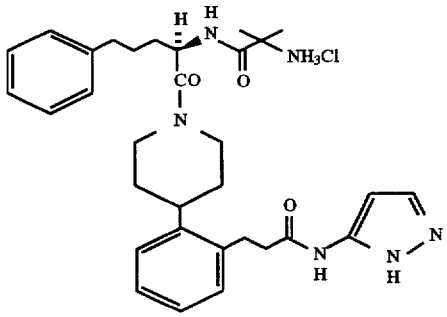

To a solution of 0.50 g of the acid intermediate prepared in Step A of Example 31 in 5 mL of 1,2-dichloroethane was added 0.16 g of carbonyldiimidazole and stirred at 60° C. for 30min. The reaction was cooled to RT, half of it was then treated with 0.12 g of 2-aminopyrazole and heated at 60° C. for 1 h, cooled to RT and stirred for 2 days. The reaction mixture was poured into 0.50N aqueous hydrochloric acid and extracted with CH₂Cl₂. The combined organics were washed with brine, dried over MgSO₄, concentrated and the residue was purified by flash chromatography with hexane-acetone (1:1) as the eluent. The purified material was deprotected with the HCl/EtOAc protocol as described above to give the title compound as a white solid.

FAB MS m/e cacl. (for C₃₂H₄₂N₆O₃) 558; found 559.2 (m+1)

EXAMPLE 36

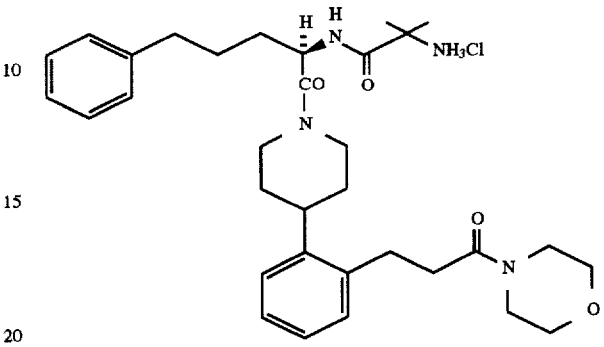

The title compound was prepped as described in Example 5 but morpholine was used in place of ethanolamine.

¹H NMR (400 MHz, CD₃OD mixture of rotamers): 7.30–6.95 (m, 9H), 4.95 (m, 1H), 4.68 (d, 1H), 4.00 and 3.95 (2 doublets, 1H), 3.59 (m, 4H), 3.35 (m, 4H), 3.25–2.90 (m, 4H), 2.80–2.50 (m, 5H), 1.90–1.65 (m, 7H), 1.63 (s, 3H), 1.60 (s, 3H), 1.47 (m, 1H).

EXAMPLE 37

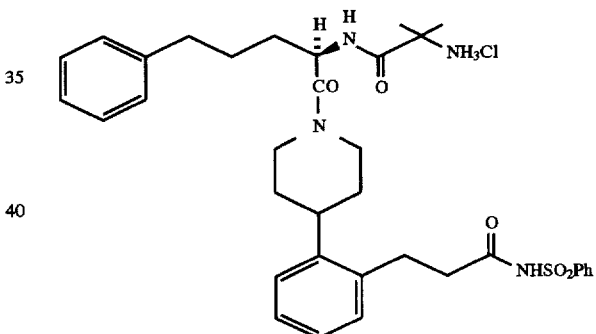

Step A:

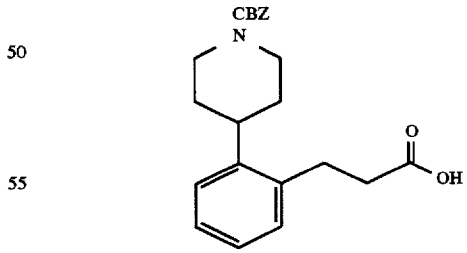

To a stirred solution of 5.0 g of the piperidine intermediate prepared in Example 1 Step B was added 5 mL of triethylamine at 0° C. and 2.8 mL of CBZ-Cl. The reaction was allowed to warm up to Rt and stir overnight. The reaction mixture was poured into aqueous ammonium chloride solution and extracted with CH₂Cl₂. The organic layer was washed with 0.50N HCl solution, dried over MgSO₄ and concentrated. This crude residue was dissolved in 25 mL of methanol-water and 3 eq. of sodium hydroxide was added and stirred for 2 h. The reaction mixture was acidified to pH=2 with 2N HCl and extracted with EtOAc. The combined organics were washed with brine, dried over Na₂SO₄ and concentrated to give the acid as a foam.

Step B:

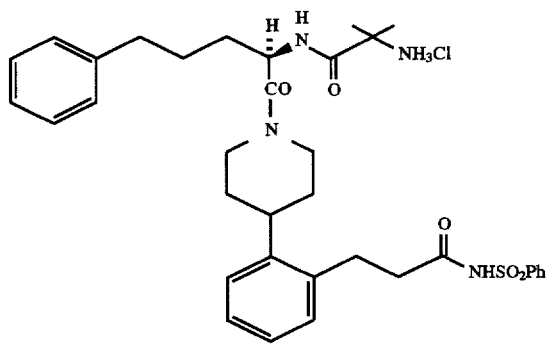

To a solution of 0.225 g of the above acid intermediate in mL of CH₂Cl₂ was added 0.12 g of benzenesulfonamide, 0.093 g of DMAP and 0.164 g of EDC and stirred overnight. The reaction mixture was washed with 0.50N HCl (2×10 mL), dried over Na₂SO₄ and concentrated. The crude residue was dissolved in 10 mL of methanol and 0.10 g of 10% Pd/C and hydrogenated at 40 psi overnight. The catalyst was filtered off through a pad of celite and the filtrate was concentrated to provide the piperidine that was used without purification.

The piperidine intermediate was now coupled to Intermediate 3 and deprotected with HCl/EtOAC as described above to give the title compound as a white solid.

FAB MS m/e cacl. (for C₃₅H₄₄N₄O₅S) 632; found 633.1 (m+1)

EXAMPLE 38

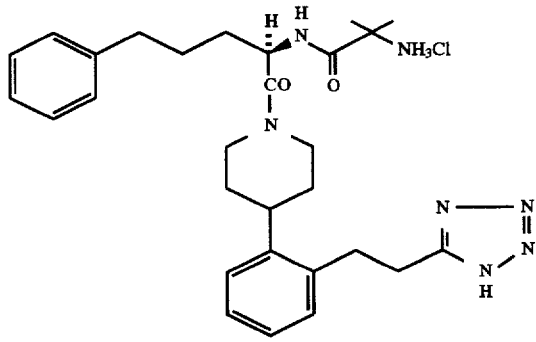

Step A:

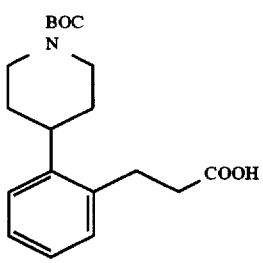

This intermediate was prepared as described in Step A of Example 37 but di-t-butylcarbonate was used in place of CBZ-Cl.

Step B:

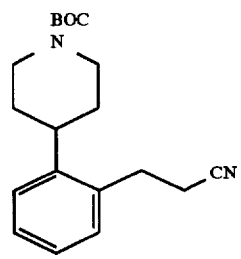

To a stirred solution of 2.90 g of the acid prepared in Step A in 30 mL of dry THF was added 2.5 mL of triethylamine and 1.25 mL of ethylchloroformate and stirred for 30 min. 10 mL of the reaction mixture was removed. The remaining mixture was quenched with 20 mL of aqueous ammonium hydroxide solution, stirred for 30 min., and extracted with EtOAc. The combined organics were washed with 0.50N HCl, brine, dried over Na₂SO₄, filtered and evaporated to give an oily residue. This material was dissolved in 20 mL of CH₂Cl₂ and 20 mL of pyridine at 0° C. and 1.1 mL of POCl₃ was added and stirred for 30 min. The reaction mixture was poured into brine and washed with 0.50N HCl solution, saturated NaHCO₃ solution, brine, dried over Na₂SO₄ and concentrated. Flash chromatography of the residue with hexane-ethyl acetate (5:1) as the eluent gave the desired product.

Step C:

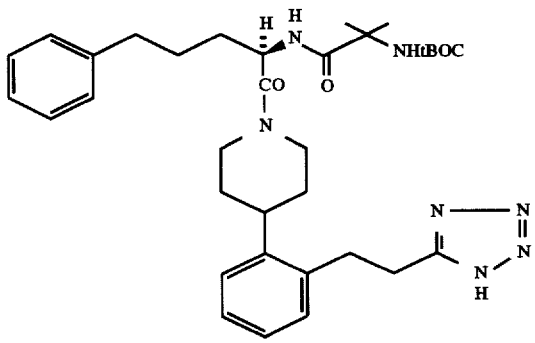

To a solution of 1.0 g of the nitrile intermediate prepared in Step B in 20 mL of toluene was added 1.96 g of trimethyltin azide and heated at reflux for 18 h. The excess azide that participated upon cooling to more temperature was filtered off. The filtrate was concentrated and split in half. To this half was added 10 mL of EtOAc and a trace of methanol and HCl(gas) was bubbled in for 5 minutes and stirred for 1 h. Ether was added and concentrated to give a gummy material that was washed with ether and dried under vacuum to give a brownish solid. 400 MHz NMR (CD$_3$OD) revealed that this was the desired tetrazole intermediate.

To 0.30 g of the piperidine hydrochloride synthesized above in 10 mL of chloroform was added 0.47 g of Intermediate 3, 0.16 g of HOBT, 0.45 mL of N-methylmorpholine, and 0.29 g of EDC and stirred overnight. The reaction mixture was poured into 0.50N HCl solution and extracted with CHCl$_3$. The combined organics were washed with brine, dried over Na$_2$SO$_4$, and concentrated to give a gummy residue that was purified by flash chromatogaphy with CHCl$_3$—MeOH—NH$_4$OH (85:15:1) as the eluent. This provided 0.15 g of the desired product.

Step D:

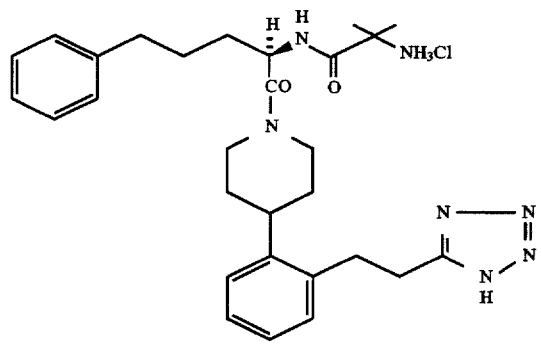

This material was prepared from the intermediate prepared in Step C by the EtOAc/HCl protocol described above.

$^1$H NMR (400 MHz, CD$_3$OD mixture of rotamers): 8.15 (t, 1H), 7.60–7.05 (m, 9H), 4.90 (m, 1H), 4.60 (d, 1H), 4.05 and 3.95 (2 doublets, 1H), 3.30–3.10 (m, 4H), 3.10–2.60 (m, 5H), 1.90–1.65 (m, 9H), 1.60 (s, 6H), 1.50 (m, 1H).

EXAMPLE 39

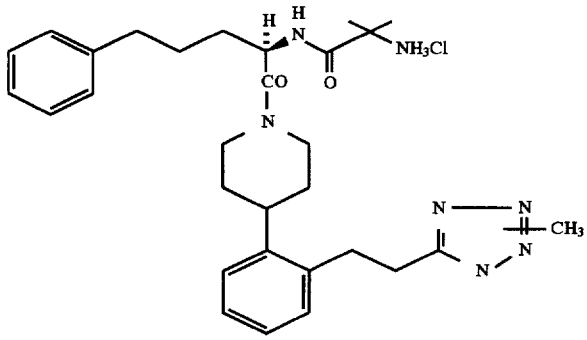

To a solution of 0.030 g of the intermediate prepared in Step C of Example 38 in 2 mL of dry acetone was added 13 mg of powdered potassium carbonate and 0.006 mL of methyl iodide and stirred at RT overnight. The reaction mixture was poured into brine and extracted with CHCl$_3$. The combined organics were washed with brine, dried over Na$_2$SO$_4$, filtered and evaporated to give the alkylated product that was deprotected by the EtOAc/HCl protocol without further purification. This gave 0.006 g of the title compound as a mixture of isomers.

FAB MS m/e cacl. (for C$_{30}$H$_{41}$N$_7$O$_2$) 531; found 532.3 (m+1)

EXAMPLE 40

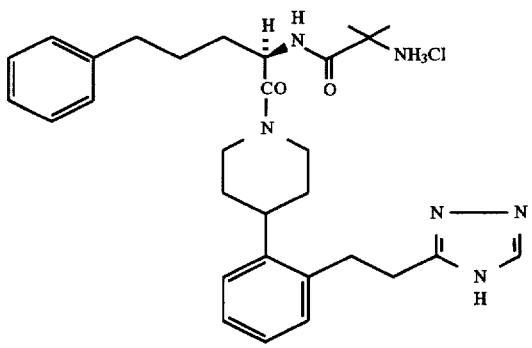

Step A:

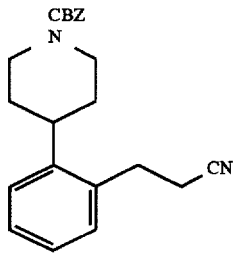

This intermediate was prepared in an analogous manner to the BOC material prepared in Step B of Example 38.

Step B:

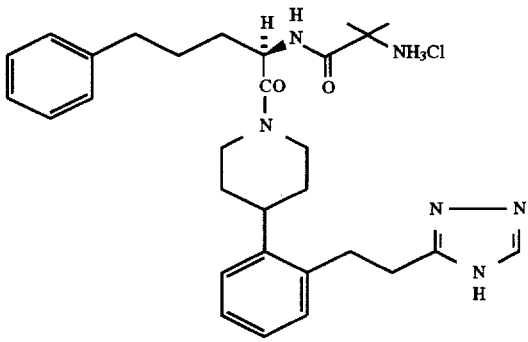

To a stirred solution of 1.0 g of the nitrile from Step A in mL of dry ethanol at 0° C. was bubbled in HCl(gas) for 1 h. The reaction was capped and stored in the freezer overnight. The excess HCl(gas) was removed by bubbling N$_2$ gas for 1 h and ether was added to induce precipitation of the imino-ether intermediate, but only an oily material formed. Hence, the solvents were removed on the rotary evaporator and the gummy residue was dissolved in CH$_2$Cl$_2$ and evaporated twice. Ether was now added and this provided the iminoether hydrochloride as a foam.

To 0.20 g of the above intermediate in 5 mL of dichloroethane was added 0.073 mL of diisopropylethylamine and 0.030 g of formylhydrazine and stirred at room temperature overnight. The reaction mixture was poured into water and extracted with CH$_2$Cl$_2$. The combined organics were washed with brine, dried over Na$_2$SO$_4$ and concentrated. The residue thereby obtained was dissolved in 5 mL of xylenes and heated at reflux for several hours. The reaction mixture was cooled to room temperature and the xylenes were evaporated. The residue was hydrogenated for 2 h in 2 mL of methanol and 40mg of 20% palladium hydroxide catalyst. The piperidine thereby obtained was coupled with Intermediate 3 under the standard EDC/HOBT conditions described earlier. The crude product was purified by flash chromatography with CH$_2$Cl$_2$—MeOH—NH$_4$OH (95:5:1) as the eluent. Removal of the BOC protecting group under the EtOAc/HCl conditions gave the title compound as a white solid.

1H NMR (400 MHz, CD$_3$OD mixture of rotamers): 9.15 (s, 1H), 8.16 (bs, 1H), 7.30–7.00 (m, 9H), 4.90 (m, 1H), 4.60 (bs, 1H), 4.10 and 3.95 (2 doublets, 1H), 3.30–3.00 (m, 4H), 3.00–2.60 (m, 5H), 1.90–1.60 (m, 9H), 1.62 (s, 3H), 1.60 (s, 3H), 1.40 (m, 1H).

EXAMPLE 41

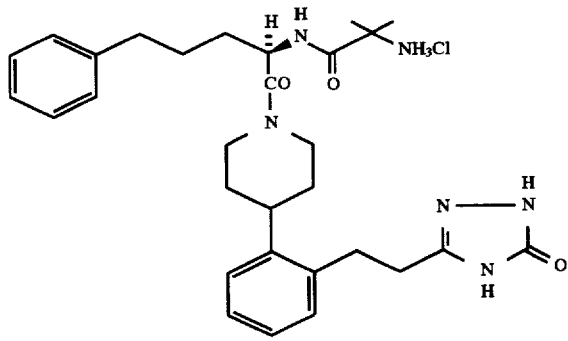

The title compound was prepared in an analogous manner to Example 40 but N-carbomethoxyhydrazine was used in place of N-formylhydrazine.

$^1$H NMR (400 MHz, CD$_3$OD mixture of rotamers): 7.30–7.02 (m, 9H), 4.90 (m, 1H), 4.60 (d, 1H), 4.05 and 3.95 (2 doublets, 1H), 3.30–2.95 (m, 5H), 2.80–2.60 (m, 4H), 1.90–1.70 (m, 9H), 1.60 (s, 3H), 1.59 (s, 3H), 1.39 (m, 1H).

EXAMPLE 42

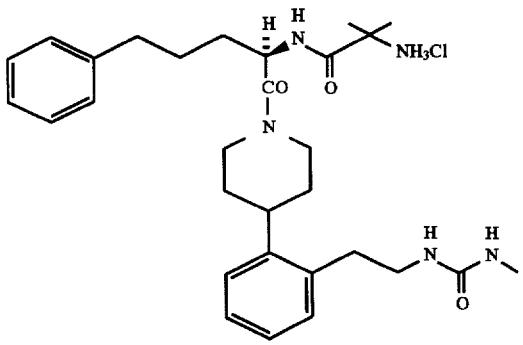

Step A:

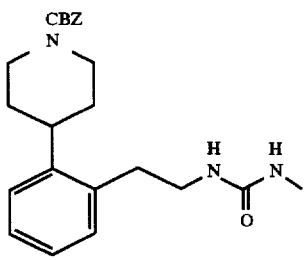

To a solution of 3.0 g of the acid intermediate prepared in Step A of Example 37 in 50 mL of benzene was added 0.70 mL of oxalyl chloride and 3 drops of DMF and stirred at RT for 2 h. The benzene was evaporated off and the residue was dissolved in acetone at 0° C. A solution of 1.59 g of sodium azide in 5 mL of water was added at stirred at 0° C. for 1 h. The reaction was diluted with ether and water and the organic layer was separated. The organics were washed with brine, dried over Na$_2$SO$_4$ and concentrated to give an oily residue. This material was dissolved in dry toluene and heated at reflux for 4 h. The reaction mixture was concentrated and the isocyanate thereby obtained was storred in the refrigerator.

To 0.40 g of the isocyanate in toluene was added 0.80 mL of triethylamine and 0.20 g of methylamine hydrochloride and stirred for overnight. The reaction mixture was poured into aqueous NaHCO$_3$ solution and extracted with EtOAc. The combined organics were washed with brine, dried over MgSO$_4$ and concentrated to give the methylurea that was used without purification.

Step B:

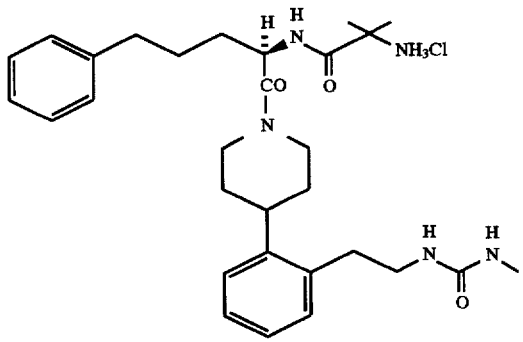

The piperidine intermediate prepared in Step A was hydrogenated with Pd(OH)$_2$ in methanol to remove the CBZ protecting group, coupled with Intermediate 3, purified and deprotected with the EtOAc/HCl protocol as described above to give the title compound.

$^1$H NMR (400 MHz, CD$_3$OD mixture of rotamers): 8.10 (m, 1H), 7.40–7.00 (m, 9H), 4.95 (m, 1H), 4.63 (d, 1H), 4.10 and 4.00 (2 doublets, 1H), 3.40–3.10 (m, 4H), 2.85–2.90 (m, 2H), 2.70 (s, 3H), 2.80–2.60 (m, 3H), 1.90–1.62 (m, 7H), 1.63 (s, 3H), 1.60 (s, 3H), 1.40(m, 1H).

EXAMPLE 43

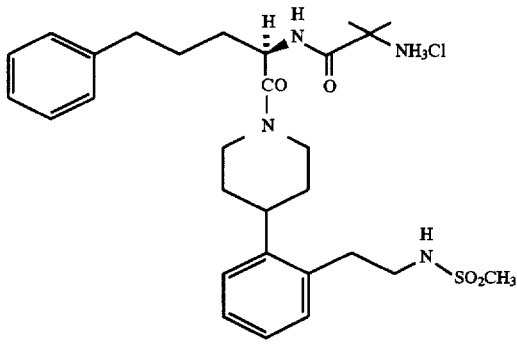

The isocyanate intermediate prepared (0.20 g) in Step A of Example 42 was refluxed in 5 mL of 6N aqueous HCl overnight. The reaction mixture was washed with ether and the ether layer was discarded. The aqueous layer was basified to pH=10 with aqueous potassium carbonate solution and extracted with $CH_2Cl_2$. The combined organics were washed with brine, dried over $K_2CO_3$ and concentrated. This crude amine was converted to the methanesulfonamide by treating it with methanesulfonyl chloride and triethylamine in dichloromethane. After standard workup the CBZ group was removed by hydrogenation and elaborated to the title compound as discussed previously.

$^1$H NMR (400 MHz, $CD_3OD$ mixture of rotamers): 7.30–7.00 (m, 9H), 4.85 (m, 1H), 4.55 (d, 1H), 4.00 and 3.90 (2 doublets, 1H), 3.30–3.10 (m, 4H), 2.95–2.83 (m, 2H), 2.80 (2 s, 3H), 2.80–2.60, (m, 3H), 1.90–1.65 (m, 9H), 1.60 (s, 3H), 1.56 (s, 3H), 1.55 (m, 1H).

EXAMPLE 44

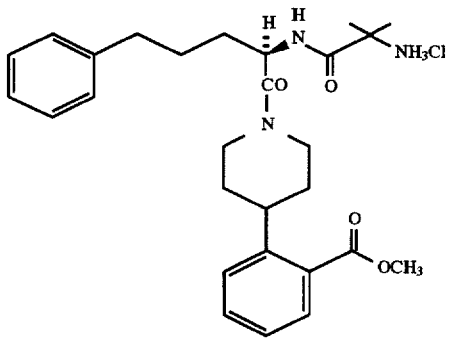

Step A:

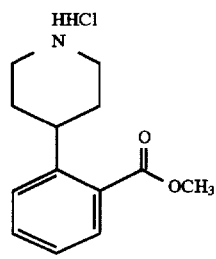

To a solution of 5.0 g of the pyridine aldehyde intermediate prepared in Step A of Example 1 in 100 mL of methanol was added 4.0 g of sodium cyanide, 5 mL of glacial acetic acid and 20 g of manganese dioxide and stirred for 2 h. The solids were filtered off through a pad of celite and the filtrate was concentrated. The residue was taken up in 100 mL of saturated sodium bicarbonate solution and extracted with 3×100 mL of ethyl acetate. The combined organics were washed with brine, dried over $Na_2SO_4$ and concentrated to provide the pyridine methyl ester. This material was dissolved in methanol and 5 mL of saturated HCl in ethyl acetate was added and concentrated to give the hydrochloride salt.

To 2 g of the above pyridine hydrochloride salt in 15 mL of methanol was added 0.225 g of platinum oxide and hydrogenated at 50 psi on the Parr shaker for 2 h. The catalyst was filtered off through a pad of celite and washed with methanol. The filtrate was concentrated to give 2.17 of the piperidine hydrochloride as a foam.

Step B:

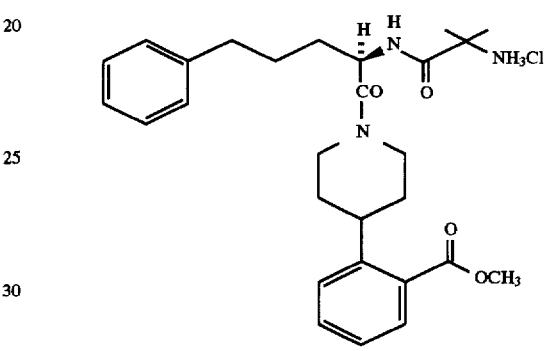

The title compound was prepared from the compound made in Step A and Intermediate 3 as described previously. $^1$H NMR (400 MHz, $CD_3OD$ mixture of rotamers): 8.10 (t, 1H), 7.78 (dd, 1H), 7.50–7.00 (m, 8H), 4.90 (m, 1H), 4.55 (d, 1H), 3.94 and 3.90 (2 doublets, 1H), 3.85 (s, 3H), 3.80–3.60 (m, 1H), 3.05 (dt, 1H), 2.70–2.50 (m, 4H), 1.90–1.50 (m, 6H), 1.55 (s, 3H), 1.50 9s, 3H), 1.40 (m, 1H).

EXAMPLE 45

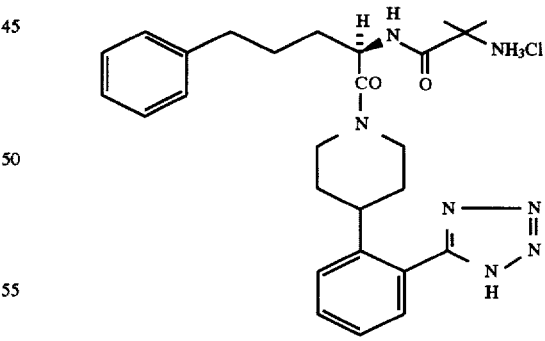

The title compound was prepared from the ester intermediate prepared in Step A of Example 44 in an analogous manner to the tetrazole compound prepared in Example 38.

$^1$H NMR (400 MHz, $CD_3OD$ mixture of rotamers): 7.60–7.45 (m, 2H), 7.45–7.38 (m, 2H), 7.30–7.10 (m, 5H), 4.90 (m, 1H), 3.95 and 3.90 (2 doublets, 1H), 3.30–3.00 (m, 2H), 2.80–2.55 (m, 4H), 1.90–1.63 (m, 7H), 1.65–1.50 (4 singlets, 6H), 1.40 (m, 1H).

EXAMPLE 46

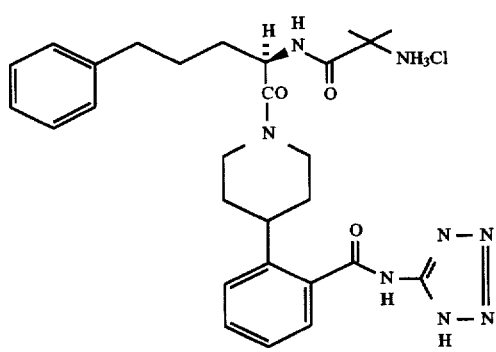

Step A:

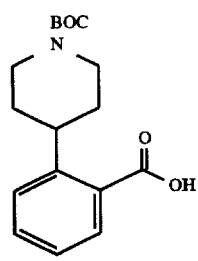

This compound was prepared in an analogous manner to the protected piperidine acid compound synthesized in Step A of Example 37.

Step B:

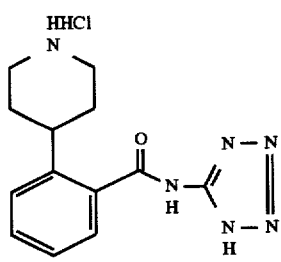

This intermediate was prepared from the compound synthesized in Step A by using the carbonyldiimidazole method descibed in Example 35. but amino-tetrazole was used in place of aminopyrazole.

Step C:

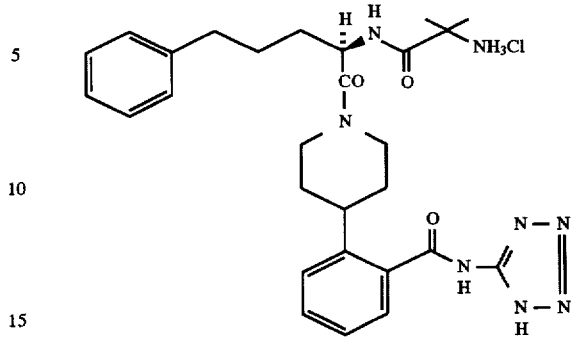

This compound was synthesized from the piperidine intermediate made in Step B and Intermediate 3 by using chemistry presented above.

FAB MS m/e cacl. (for $C_{28}H_{36}N_8O_3$) 532; found 533.1 (m+1)

EXAMPLE 47

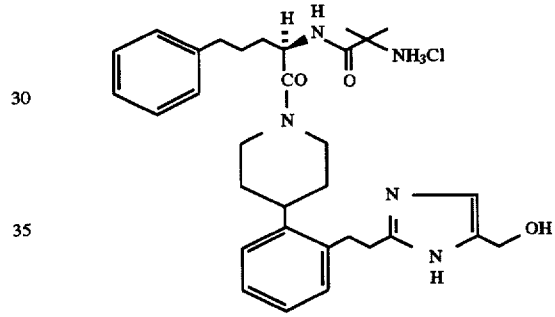

Step A:

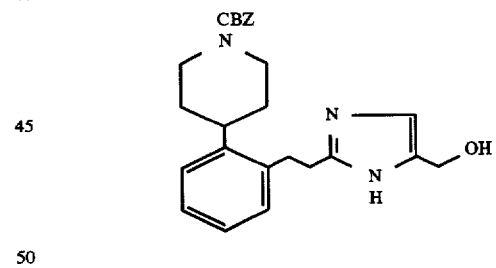

To a solution of 0.30 g of the imino-ether intermediate prepared in Step B of Example 40 in 10 mL of ethanol was added 0.124 g of dihydroxyacetone and heated at 60° C. under an ammonia atmosphere in a bomb for 16 h. The reaction was cooled to room temperature and the solvent was evaporated. The residue was purified by flash chromatography to give 0.129 g of the desired product that was still contaminated with other impurities.

Step B:

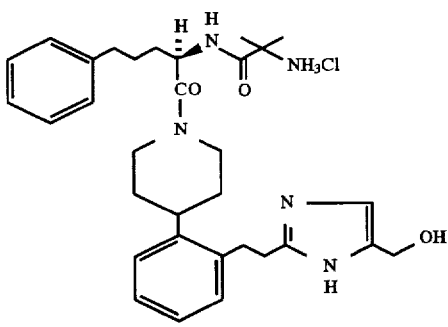

The intermediate prepared in Step A was elaborated to the title compound after removal of the CBZ protecting group, coupling with Intermediate 3, purification, and a final deprotection with the EtOAc/HCl protocol described earlier. $^1$H NMR (400 MHz, CD$_3$OD mixture of rotamers): 8.18 (2 triplets, 1H), 7.30 (s, 1H), 7.30–7.00 (m, 9H), 4.90 (m, 1H), 4.56–4.55 (singlet overlapping a doublet, 3H), 4.05–3.95 (2 doublets, 1H), 3.30–2.95 (m, 4H), 2.95–2.60 (m, 5H), 1.90–1.65 (m, 7H), 1.63 (s, 3H), 1.60 (s, 3H), 1.45 (m, 1H).

EXAMPLE 48

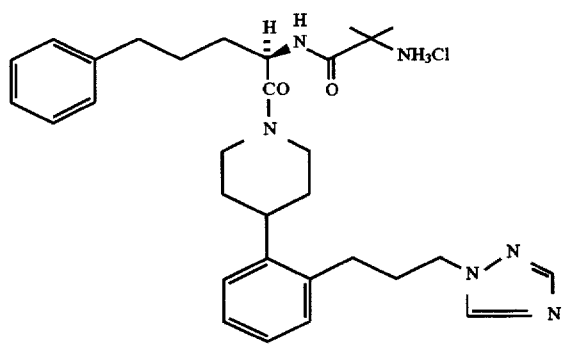

Step A:

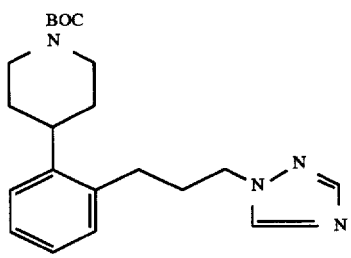

To a solution of 1.0 g of the ester prepared in Step B of Example 1 in 50 mL of dry THF at 0° C. was added 0.20 g of lithium aluminum hydride and stirred at room temperature overnight. The reaction was quenched at 0° C. with 10 mL of water and 10 mL of 30% aqueous sodium hydroxide solution. The precipitate was filtered and washed with EtOAc. The ethyl acetate extracts were washed with brine, dried over Na$_2$SO$_4$ and concentrated. The crude alcohol was dissolved in 30 mL of CH$_2$Cl$_2$ and 1.3 mL of triethylamine and 1.4 g of di-t-butylcarbonate was added at 0° C. and then stirred at RT for 2 h. The reaction was poured into saturated NaHCO$_3$ solution and extracted with CH$_2$Cl$_2$. The combined organics were washed with 0.50N HCl, brine, dried over Na$_2$SO$_4$ and concentrated. This material was purified by flash chromatography with hexane-acetone (5:1) as the eluent.

The alcohol obtained above was dissolved in 10 mL of CH$_2$Cl$_2$ at 0° C. and 0.45 mL of triethylamine and 0.14 mL of methanesulfonyl chloride were added and stirred for 1 h. The reaction was diluted with water and extracted with CH$_2$Cl$_2$. The combined organics were washed with 0.50N HCl, brine, dried over Na$_2$SO$_4$ and concentrated. The crude mesylate was heated at 60° C. with 0.20 g of the sodium salt of 1,2,4-triazole in 10 mL of dry DMF for 3 h. The reaction was cooled to RT and quenched with aqueous ammonium chloride solution. The reaction mixture was extracted with ether (3×15 mL). The combined organics were washed with brine, dried over Na$_2$SO$_4$, filtered and concentrated. This gave the triazole product that was used without purification.

Step B:

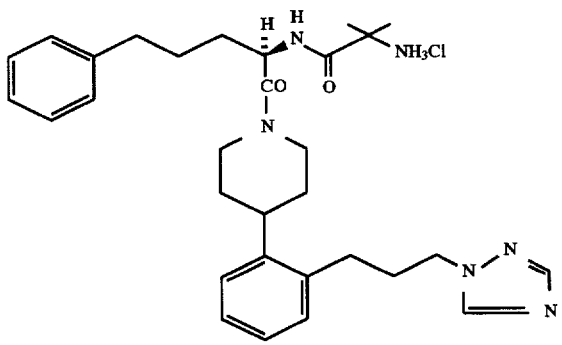

The BOC protecting from the piperidine synthesized in Step A was removed with the TFA procedure as described previously and elaborated to the title compound by coupling with Intermediate 3, purification and a final deprotection with the EtOAc/HCl protocol. FAB MS m/e cacl. (for C$_{31}$H$_{42}$N$_6$O$_2$) 530; found 531.4 (m+1)

EXAMPLE 50

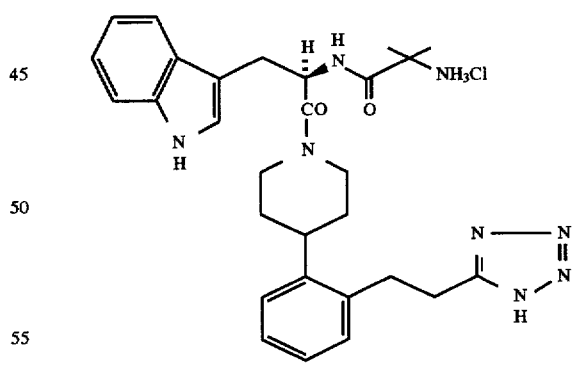

Prepared as described in Example 40 Step B but Intermediate 1 was used in place of Intermediate 3.

$^1$H NMR (400 MHz, CD$_3$OD mixture of rotamers): 832 and 8.20 (2 doublets, 1H), 7.65 and 7.58 (2 doublets, 1H), 740 and 735 (2 doublets, 1H), 7.25–7.00 (m, 6H), 6.50 (d, 1H), 530–5.20 (m, 1H), 4.58 and 4.55 (2 doublets, 1H), 4.10 and 3.95 (2 doublet, 1/2H), 3.90 (d, 1/2H), 3.40–3.00 (m, 7H), 2.70–2.45 (m, 3H), 2.80–2.50 (m, 2H), 1.60 (s, 6H), 134 (d, 1H), 0.95 (d, 1/2H), 0.70 (dt, 1/2H).

EXAMPLE 50A

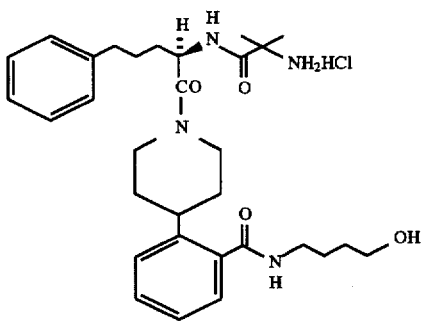

To a solution of 0.330 g of the acid intermediate prepared in Step A of Example 15 in 3.3 mL of dry THF was added 0.196 g of carbonyldiiimidazole and heated to 60° C. for 2 h. A small aliquot of the reaction mixture was removed and to the remaining solution was added 0.10 mL of 4-aminobutanol and heated for 2 h. The reaction mixture was concentrated, taken up in chloroform, washed twice with water, once with 1M $K_2HPO_4$, brine, dried over $MgSO_4$, filtered and concentrated to provide a residue that was separated by prep TLC (1 mm plate) with $CHCl_3$—MeOH—$NH_4OH$ (90:10:1) as the eluent to give the desired intermediate.

To a solution of 0.20 g of the above material in 2 mL of anisole was added 3–4 mL of TFA and allowed to stand at rt for 30 min. The volatiles were removed under reduced pressure and the residue was partitioned between chloroform and 1M K2HPO4 and basified to pH>9 with NaOH. The organic phase was separated and the aqueous phase was extracted with chloroform. The combined organics were washed with brine, dried over MgSO4, filtered and concentrated to provide a gum that was separated by prep TLC (1 mm plate) with $CHCl_3$—MeOH—$NH_4OH$ (90:10:1) as the eluent to give the desired product.

$^1$H NMR (200 MHz; $CDCl_3$ mixture of rotamers): 8.24 (d, J=8); 7.42–7.07 (m); 6.16 ("dd", J=12, 4); 4.97–4.8 (m); 4.69 (bd, J=13); 3.93 ("bt", J~10); 3.75–3.64 (m); 3.54–3.4 (m); 3.35–3.16 (m); 3.07 (quart., J=13); 2.77–2.5 (m); 1.97–1.42 (m); 1.34 (s). .FAB MS Calc. for $C_{31}H_{44}N_4O_4$: MW=536.34; found m/e=(m+1) 537.1.

A solution of 0.150 g of the above free base was lyophillized from 0.50 mL of acetic acid and 0.030 mL of conc. HCl to give title compound.

EXAMPLE 50B

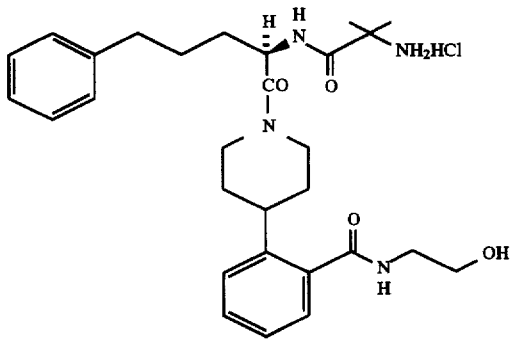

Prepared in an analogous manner to the compound prepared in Example 50A but ethanolamine was used in place of 4-aminobutanol.

$^1$H NMR (200 MHz; $CDCl_3$ mixture of rotamers): 8.22 (d, J=8); 7.45–7.05 (m); 6.58 (dt, J=16, 5); 4.88 (bs); 4.64 (bd, J=12); 3.90 (t, J=11); 3.79 (bs); 3.65–3.50 (m); 3.25–3.15 (m); 3.05 (quart., J=12); 2.8–2.5 (m); 2.32 (vbs); 2.0–1.77 (m); 1.77–1.45 (m); 1.35 (s). FAB MS Calc. for $C_{29}H_{40}N_4O_4$: MW=508.30; found m/e=(m+1) 509.2.

A solution of 0.029 g of the above free base was lyophillized from 0.50 mL of acetic acid and 0.010 mL of conc. HCl to give title compound.

EXAMPLE 50C

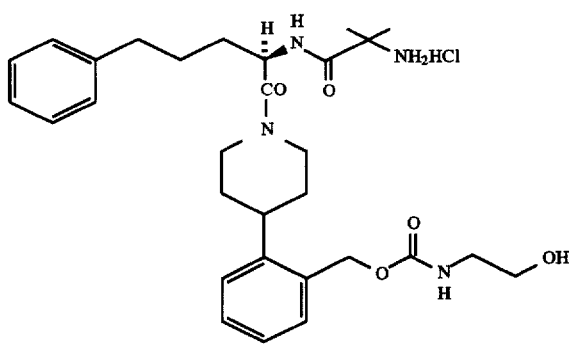

Step A:

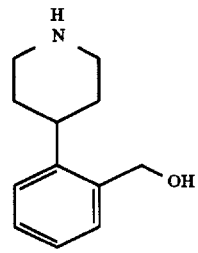

To a solution of 0.379 g of the free base (prepared by basification to pH>9 with NaOH and extraction with $CHCl_3$) of the intermediate prepared in Step A of Example 44 in 20 mL of dry THF was added 5.5 mL of 1M solution of lithium aluminum hydride in THF and stirred overnight. The reaction was quenched with 10 mL of 30% aqueous NaOH, the organic phase was decanted, and the paste was extracted with ethyl acetate. The combined organics were dried over MgSO4 and concentrated. Purification of the residue by prep TLC (1 mm plate) gave the desired amino alcohol. $^1$H NMR (200 MHz; $CDCl_3$ mixture of rotamers): 7.38–7.13 (m); 4.75 (s); 3.22 (bd, J=12 Hz); 3.1–2.92 (m); 2.81 (td, J=10, 4 Hz); 2.13 (bs); 1.85–1.6 (m).

Step B:

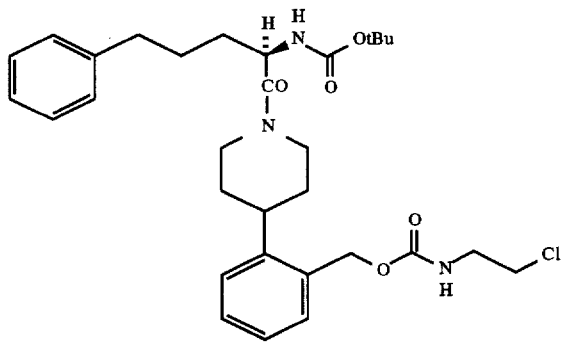

The intermediate prepared in Step A was coupled with (2R)-N-t-BOC-5-phenyl pentanoic acid under the standard EDC/HOBT protocol as described above and purified by prep TLC (1 mm plate).

To a solution of 0.145 g of the above coupled product in 2 mL of $CDCl_3$ was added 0.50 mL of 2-chloroethylisocyanate and was heated at 60° C. for 6 h and allowed to stand at RT overnight. Prep TLC of this mixture with hexane-EtOAc (1:1) as the eluent gave 0.11 g of the desired carbamate.

$^1$H NMR (200 MHz; $CDCl_3$ mixture of rotamers): 7.45–7.05 (m); 5.50 (bd, J=6); 5.19 (s); 5.14 (bs); 4.86–4.45 (bdd?); 4.11 (bd, J=7); 3.93 (bt, J=12); 3.72–3.42 bm); 3.2–2.88 (m); 2.8–2.5 (bm); 1.95–1.55 (m); 1.44 (s).

Step C:

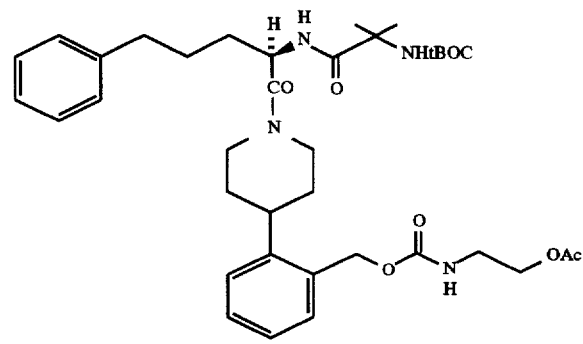

The intermediate prepared in Step B was deprotected with EtOAc/HCl and the hydrochloride salt thereby obtained was coupled with N-t-BOC-α-methylalanine under standard EDC/HOBT conditions. This material was purified by prep TLC (1 mm plate) with hexane-EtOAc (1:1) as the eluent. $^1$H NMR (200 MHz; $CDCl_3$ mixture of rotamers): 7.40–7.04 (m); 5.19 (s); 5.17 (bs); 4.98 (s); 4.92 (bs); 4.72 (bd, J=13); 4.54 (bd, J=13); 4.18–4.04 (m); 3.95 (bt, J=13); 3.68–3.45 (m); 3.2–2.85 (m); 2.78–2.47 (m); 2.0–1.6 (m); 1.6–1.4 (m); 1.44 (s).

Approximately 85 mg (0.13 mmoles) of the above product was taken up in 1.0 mL of DMSO-$d_6$ to which was added 38 mg (0.37 mmoles) of LiOAc.2$H_2$O, and 30 mg (0.2 moles) of NaI; the solution was heated in an 80° C. oil bath over night. The reaction mixture was then taken to a gum under a nitrogen stream. It was then partitioned in a mixture of $CHCl_3$ and water, the organic phase separated, dried with anhydrous $MgSO_4$, filtered, and after concentration to a gum under reduced pressure, purified by preparative tlc on one 8"×8"×1,000 m plate in 1:1 EtOAc: hexane to give 85 mg of the title compound.

$^1$H NMR (200 MHz; $CDCl_3$ mixture of rotamers) :7.40–7.04 (m); 5.19 (s); 5.17 (bs); 4.98 (s); 4.92 (bs); 4.72 (bd, J=13); 4.54 (bd, J=13); 4.18–4.04 (m); 3.95 (bt, J=13); 3.68–3.45 (m); 3.2–2.85 (m); 2.78–2.47 (m); 2.0–1.6 (m); 1.6–1.4 (m); 1.44 (s).: 7.4–7.0 (m); 7.88–7.69 (bm); 5.4 (s); 5.14 (s); 4.95–4.74 (m); 4.67 (bd, J=12); 4.38 (bd, J=13); 4.15–4.02 (m); 3.93 (bt, J=14); 3.50–3.30 (m); 3.18–2.8 (m); 2.75–2.35 (bm); 2.01 (s); 1.9–1.7 (bm); 1.5–1.3 (m); 1.40 (s).

Step D:

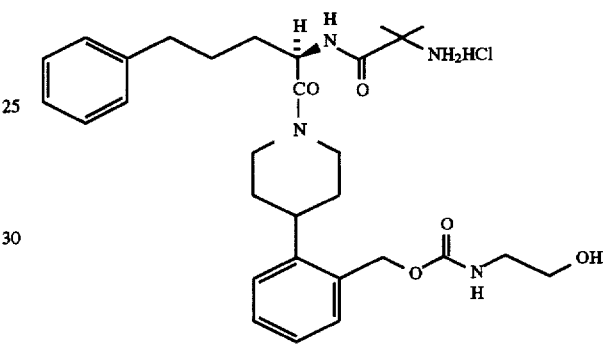

To 49 mg of the intermediate from Step D in 0.5 mL of methanol was added 1–2 mL of conc. $H_2SO_4$. After standing over night a 1M solution of $K_2HPO_4$ was added and the reaction mixture was taken to dryness under a stream of nitrogen and the residue was partitioned between $CHCl_3$ and 1M $K_2HPO_4$, adjusted to pH>9 with NaOH. The organic phase was removed and the aqueous phase extracted several more times with $CHCl_3$. The combined organic phases were dried with anhydrous $MgSO_4$, filtered, and concentrated under reduced pressure. The resultant gum was subjected to preparative tlc on one 8"×8"×1,000 m silica gel GF plate using 1:10:90 (conc. $NH_4OH$:MeOH:$CHCl_3$); two major bands were observed. Isolation of the faster band afforded the title compound. $^1$H NMR (200 MHz; $CDCl_3$ mixture of rotamers): 7.4–7.05 (m); 5.44–5.12 (m); 5.18 (s); 5.12–4.8 (m); 5.05 (s); 4.69 (bd, J=12); 4.52 (bd, J=12); 4.12 (bs); 3.93 (bt, J=12); 3.78–3.63 (m); 3.44–3.24 (bm); 3.24–2.83 (m); 2.83–2.5 (m); 2.01–1.6 (m); 1.6–1.35 (m); 1.45 (s). FAB MS Calc. for $C_{35}H_{50}N_4O_7$: MW=638.37; found m/e= (m+1) 639.3.

A solution of 23 mg (0.042 mmoles) of the above free base in 0.5 mL of acetic acid in a vial was treated with 0.005 mL (0.06 mmoles) of conc. HCl, shell frozen, and lyophylized overnight to give the title compound.

EXAMPLE 51

(cis, $d_1$)

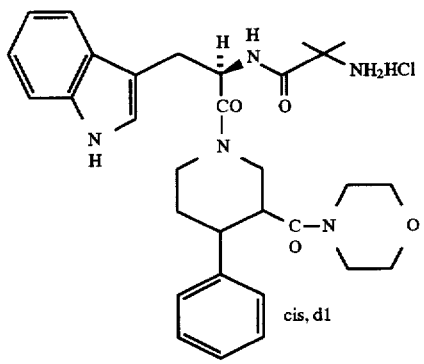

cis, d1

Step A:

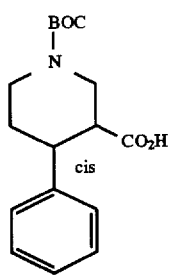

To a solution of 4.1 g of the intermediate prepared in Example 12 Step A-1 in 25 ml of ethanol was added 25 ml of 6N NaOH and stirred 12 hours. The mixture was diluted with water and extracted with ether. The organic layer was discarded. The aqueous layer was cooled to 0° C. and acidified with conc. HCl and then extracted with ether. The organic layer was dried over sodium sulfate, filtered and concentrated to give 2.57 g of the crude acid. The crude acid (438 mg) was dissolved in methanol and hydrogenated over Pd(OH)$_2$ at one atmosphere for 16 hours. The mixture was filtered though Celite and the filtrate was concentrated under vacuum to give the desired compound (370 mg).

Step B:

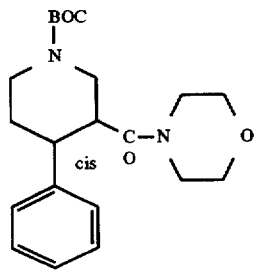

To the intermediate prepared in Step A (100 mg) chloroform was added morpholine (0.35 ml, EDC (95 mg), and HOBt (49 mg). The reaction was stirred for 12 hours at room temperature and was diluted with methylene chloride and then washed with water and brine. The organic layer was dried over sodium sulfate, filtered and concentrated. The residue was purified by prep TLC (hexanes/ethyl acetate= 1/1) to give the desired product (71 mg).

Step C:

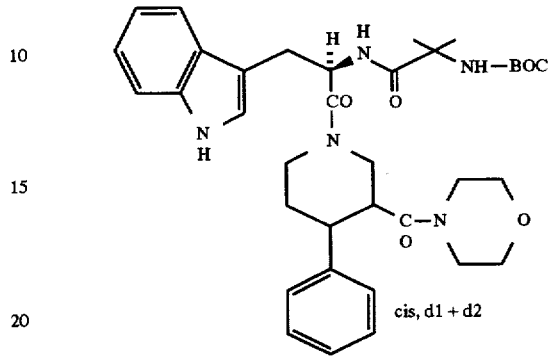

cis, d1 + d2

To the intermediate prepared in Step B (71 mg) in ethyl acetate was bubbled in HCl (g) at 0° C. for 15 seconds. The mixture was allowed to stand at room temperature for 30 min., concentrated to give a solid (64 mg). To this crude material (32 mg) in 2 ml of chloroform was added Intermediate 1 (43 mg), EDC (29 mg), HOBt (15 mg) and triethylamine (21 mL). The reaction was stirred at room temperature for 3 hours and poured into water and extracted with methylene chloride, dried over sodium sulfate and concentrated. Purification (prep TLC, methylene chloride/methanol=20/1) gave two diastereomers ($d_1$, the less polar diastereomer, 14 mg; $d_2$, the more polar diastereomer, 16 mg).

Step D:

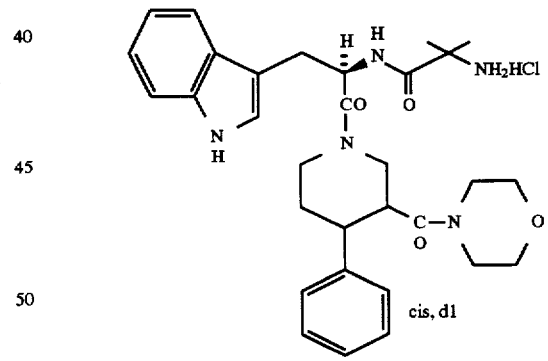

cis, d1

The less polar diastereomer ($d_1$, 14 mg) prepared in Step C was dissolved in ethyl acetate and treated with HCl$_{(g)}$ at 0° C. for 15 seconds. After 30 minutes at room temperature the mixture was concentrated to give the desked product (10 mg).

FAB-MS: 546.3 (M+1)

EXAMPLE 52

(cis, d₂)

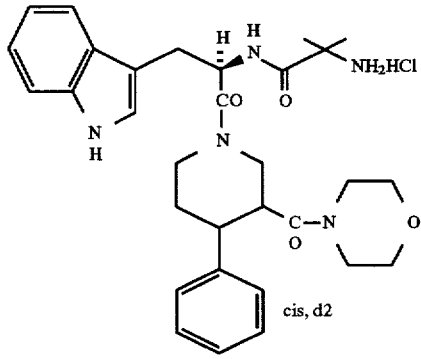

cis, d2

The title compound (12 mg) was prepared from the more polar diastereomer (d₂, 16 mg) obtained in Example 51, Step C by the procedure described in Example 51, Step D.

FAB-MS: 546.3 (M+1)

The compounds 1–7 shown in Table 3 were prepared according to the procedures reported above (using different amines in the coupling step). Details are available in Example 51 Steps B, C and D.

TABLE 3

| | R | | FAB-MS (M + 1) |
|---|---|---|---|
| 1 | d₁ + d₂ | thiomorpholine | 562.2 |
| 2 | d₁ + d₂ | pyrrolidine | 530.2 |
| 3 | d₁ + d₂ | N-methylpiperazine | 559.3 |
| 4 | d₁ + d₂ | piperidine | 544.3 |
| 5 | d₁ + d₂ | ethanolamine | 520.2 |
| 6 | d₁ + d₂ | dimethylamine | 504.3 |
| 7 | d₁ + d₂ | glycine ethyl ester | 562.3 |

EXAMPLE 53

(cis, d₁)

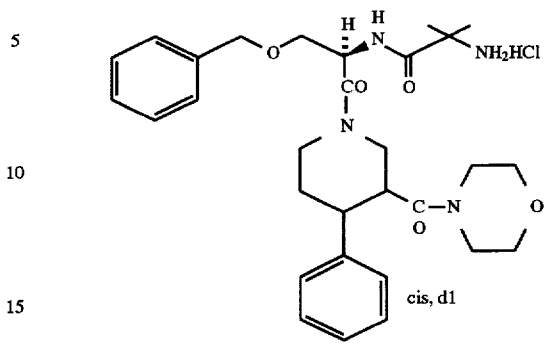

cis, d1

Step A:

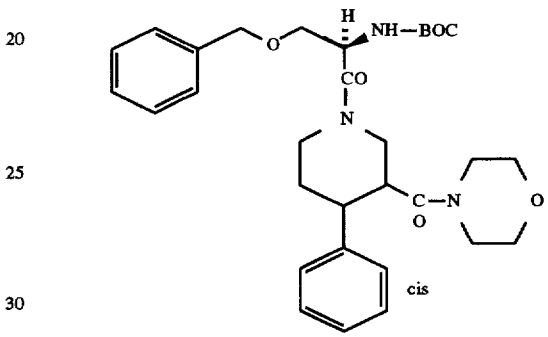

cis

The intermediate prepared from Example 51, Step B in ethyl acetate was treated with HCl$_{(g)}$ at 0° C. for 15 seconds and allowed to stand at room temperature for 30 min. The mixture was concentrated to dryness to give the crude material. To this crude material (99 mg) in 3 ml of chloroform was added N-t-BOC-O-benzyl-D-serine (107 mg), EDC (92 mg), HOBt (47 mg) and triethylamine (67 ml) and stirred at room temperature for 3 hours and poured into water. The mixture was extracted with methylene chloride and dried over sodium sulfate, and concentrated. Purification of the residue by RPLC (chromatatron, methylene chloride/methanol=20/1) gave the desired product (97 mg).

Step B:

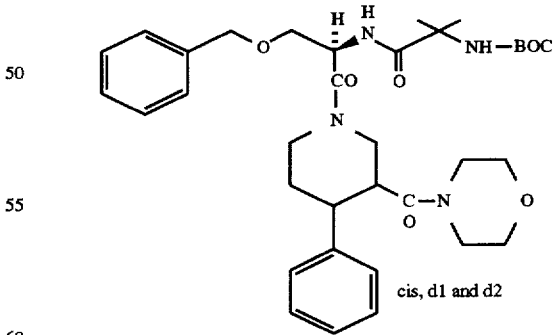

cis, d1 and d2

The intermediate prepared from Step B (97 mg) in ethyl acetate was treated with HCl$_{(g)}$ at 0° C. for 15 seconds and allowed to stand at room temperaturte for 30 minutes. The reaction mixture was concentrated to give a residue that was dissolved in 2 ml of chloroform and reacted with N-t-BOC-α-methylalanine (52 mg) in the presence of EDC (62 mg).

HOBt (36 mg) and triethylamine (40 ml). After 64 hours at room temperature the reaction mixture was poured into water and extracted with methylene chloride. The combined extracts were dried over sodium sulfate, filtered and concentrated to give a residue that was purified by RPLC (chromatatron, methylene chloride/methanol=20/1) to give two diastereomers ($d_1$, the less polar diastereomer, 65 mg; $d_2$, the more polar diastereomer, 23 mg).

Step C:

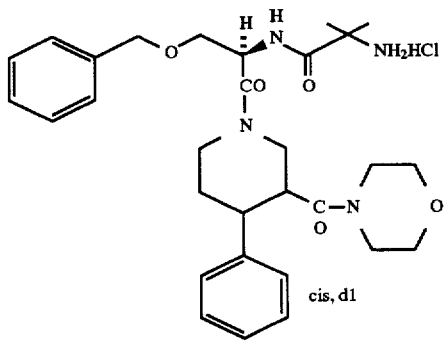

cis, d1

The less polar diastereomer ($d_1$, 65 mg) prepared from Step B in ethyl acetate was treated with $HCl_{(g)}$ at 0° C. for 15 seconds. After standing at room temperature for 30 minutes, the mixture was concentrated to give the disired product (58 mg).

FAB-MS: 537.4 (M+1)

EXAMPLE 54

(cis, $d_2$)

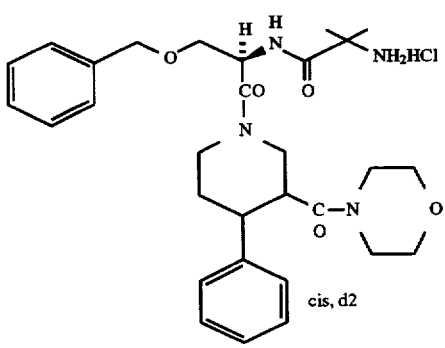

cis, d2

The title compound (20 mg) was prepared from the more polar diastereomer ($d_2$, 23 mg) obtained in Example 53, Step C by the procedure described in Example 51, Step D.

FAB-MS: 537.3 (M+1).

The compounds 1–6 shown in Table 4 were prepared as described above (with different amines). The details of the syntheses are available in Example 51, Step B and Example 53, Steps A, B and C.

TABLE 4

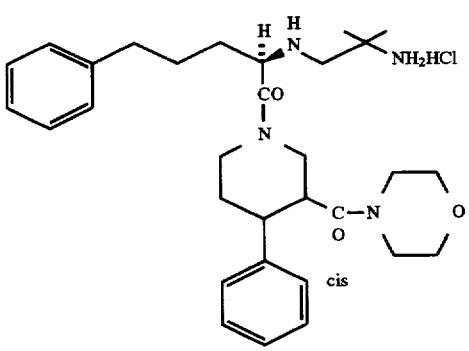

cis

| | R | | FAB-MS (M + 1) |
|---|---|---|---|
| 1 | $d_1 + d_2$ | thiomorpholine | 553.3 |
| 2 | $d_1 + d_2$ | pyrrolidine | 521.3 |
| 3 | $d_1$ | N-methylpiperazine | 550.4 |
| 4 | $d_2$ | N-methylpiperazine | 550.4 |
| 5 | $d_1 + d_2$ | piperidine | 535.4 |
| 6 | $d_1 + d_2$ | dimethylamine | 495.2 |

EXAMPLE 55

(cis, $d_1+d_2$)

The intermediate prepared from Example 51, Step B in ethyl acetate was treated with $HCl_{(g)}$ at 0° C. for 15 seconds. The reaction mixture was allowed to stand at room temperature for 30 minutes and concentrated to give the crude product. To this material (209 mg) in 10 ml of chloroform was added Intermediate 3 (295 mg), EDC (202 mg), HOBt (105 mg) and triethylamine (147 ml) and stirred at room temperature for 16 hours and poured into water. The mixture was extracted with methylene chloride and dried over sodium sulfate, concentrated and the residue was purified by RPLC (chromatatron, methylene chloride/methanol=20/1) to give the desired product (387 mg). This mixture of diastereomers in ethyl acetate was treated with $HCl_{(g)}$ at 0° C. for 15 seconds and allowed to stand at room temperature for 30 minutes. The reaction mixture was concentrated to give the desired product (330 mg).

FAB-MS: 535.3

The compounds shown in Table 5 were prepared according to established procedures (with ethanolamine instead of morpholine) as exemplified in Example 51, Step B and Example 53, Steps A, B and C using Intermediate 3.

TABLE 5

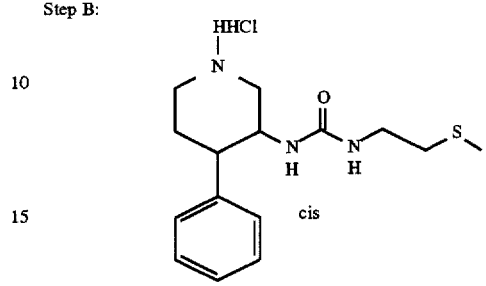

| | | R | FAB-MS (M + 1) |
|---|---|---|---|
| 1 | d₁ | ethanolamine | 509.1 |
| 2 | d₂ | ethanolamine | 509.2 |

EXAMPLE 56

(cis, d₁+d₂)

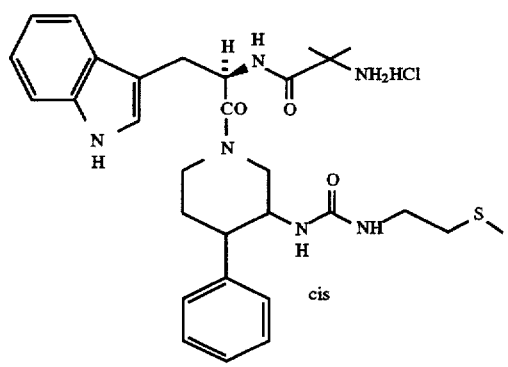

Step A:

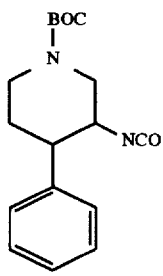

To the intermediate prepared in Example 51, Step A (1.15 g) in benzene (80 ml) was added oxalyl chloride (365 ml) and DMF (2 drops) at 0° C. and stirred at 0° C. for 10 minutes and room temperature for 2 hours and concentrated to give the acyl chloride. To a solution of acyl chloride at 0° C. in acetone (10 ml) was added sodium azide (741 mg) in water (3 ml) and stirred at room temperature for 45 minutes. The mixture was extracted with ether, washed with water, brine, dried over MgSO₄, filtered and evaporated to give the acyl azide which was dissolved in toluene (35 ml) and was refluxed 12 hours to give the isocyanate (1.02 g).

Step B:

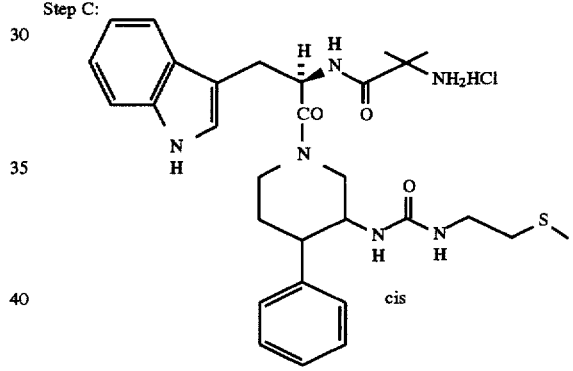

A solution of the intermediate prepared in Step A (55 mg) and 2-(methylthio)ethylamine (147 mg) in toluene (5 ml) was refluxed for one hour. The reaction was quenched with 1N HCl and extracted with ether and then dried over sodium sulfate. Concentration and purification (chromatatron, methylene chloride/methanol=20/1) gave the desired urea. Deprotection of the BOC protecting group under conditions described above gave the desired product (40 mg).

Step C:

To the intermediate prepared in Step B (20 mg) in 2 ml of chloroform was added Intermediate 1 (28 mg), EDC (19 mg), HOBt (10 mg) and triethylamine (14 ml). The reaction was stirred at room temperature for 16 hours and poured into water. The mixture was extracted with methylene chloride and dried over sodium sulfate. Concentration and purification (chromatatron, methylene chloride/methanol=20/1) gave desired product The mixture was treated with HCl in EtOAc to give the final product (6 mg).

FAB-MS: 565.3 (M+1)

The compounds shown in Table 6 were prepared according to established procedures (with different amines or alcohol).

TABLE 6

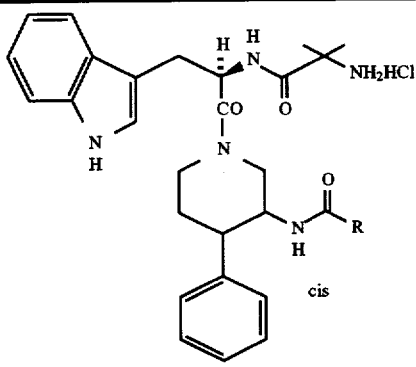

| | R | | FAB-MS (M + 1) |
|---|---|---|---|
| 1 | d1 + d2 | ethanol | 520.3 |
| 2 | d1 + d2 | morpholine | 561.4 |
| 3 | d1 + d2 | ethanolamine | 535.3 |
| 4 | d1 + d2 | ethylamine | 519.2 |

TABLE 7

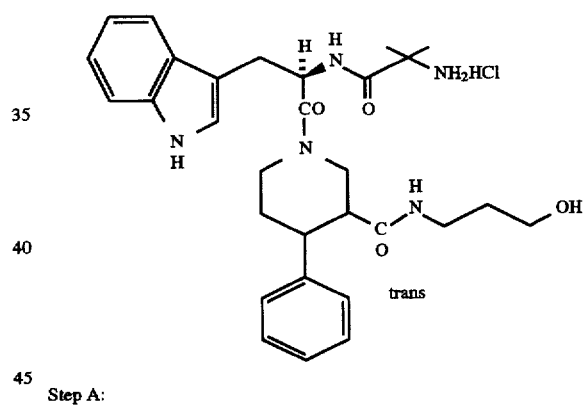

| | R | | FAB-MS (M + 1) |
|---|---|---|---|
| 1 | d1 + d2 | ethanol | 509.3 |
| 2 | d1 + d2 | morpholine | 550.4 |
| 3 | d1 + d2 | ethanolamine | 524.3 |
| 4 | d1 + d2 | thiomorpholine | 566.2 |

EXAMPLE 57

(cis, d1+d2)

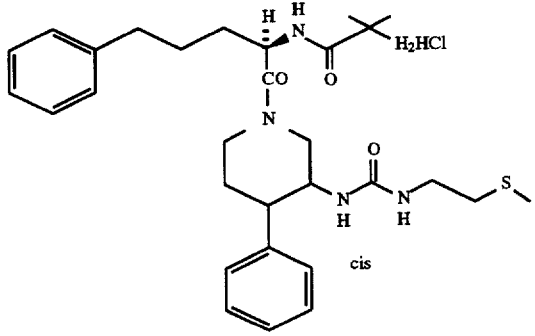

To a solution of the intermediate prepared from Example 56, Step B (20 mg) in 1 ml of chloroform was added Intermediate 3 (28 mg), EDC (19 mg), HOBt (10 mg) and triethylamine (14 ml). The reaction was stirred at room temperature for 16 hours and poured into water. The mixture was extracted with methylene chloride and dried over sodium sulfate. Concentration and purification (chromatatron, methylene chloride/methanol=20/1) gave the desired product Deprotection of this diastereomeric mixture with HCl/EtOAc gave the final product (8 mg).

FAB-MS: 554.4 (M+1)

The compounds shown in Table 7 were prepared according the above-described procedures (with ethanol and different amines).

EXAMPLE 58

(trans, d1+d2)

Step A:

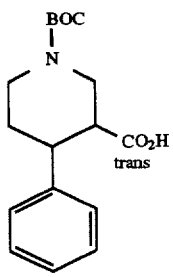

To a solution of the intermediate prepared from Example 14, Step A (2.52 g) in ethanol was added 6N NaOH. The mixture was refluxed for 3 hours and then concentrated. The residue was diluted with water and acidified with 0.5N hydrochloric acid and extracted with ether. The organic layer was dried over sodium sulfate, filtered and concentrated to give the desired product (2.12 g).

Step B:

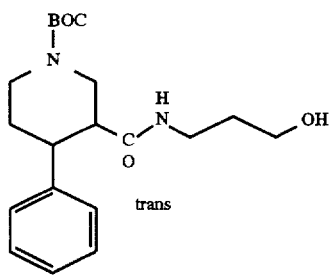

To a solution of the intermediate prepared from Step A (15 mg) in 1 ml of chloroform was added 4-amino-1-butanol (9 ml), EDC (19 mg), and HOBt (7.5 mg). The reaction was stirred at room temperature for 2 hours and poured into water. The mixture was extracted with methylene chloride and dried over sodium sulfate. Concentration and purification (chromatatron, methylene chloride/methanol=20/1) gave the desired product.

Step C:

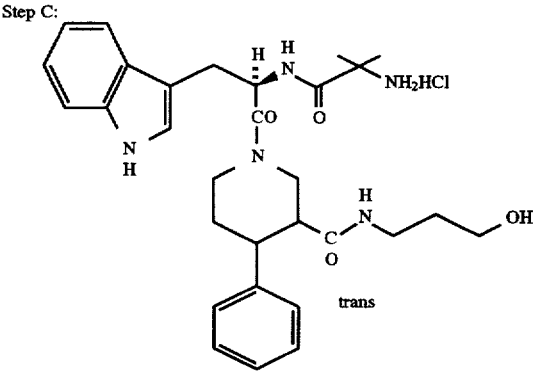

The intermediate prepared from Step B was deprotected with the HCl/EtOAc protocol. To this crude material in 1 ml of chloroform was added Intermediate 1 (18 mg), EDC (19 mg), HOBt (7.5 mg) and triethylamine (20 ml). The reaction was stirred at room temperature for 4 hours and poured into water. The mixture was extracted with methylene chloride and dried over sodium sulfate. Concentration and purification (PLC, methylene chloride/methanol=10/1) gave the desired product (20 mg, unseparable diastereomer mixture) that was treated with HCl (gas) in EtOAc to give the desired product (18 mg).

$^1$H NMR (400 MHz, CD$_3$OD, mixture of diastereomers and rotamers): 7.73 (d, 8 Hz, 1/2H), 7.65 (d, 8 Hz, 1/2H), 7.54–6.98 (m, 7 1/2H), 6.78 (t, 7 Hz, 1 1/2 Hz), 5.25 (m, 1H), 4.53 (m, 1H), 3.89 (m, 1H), 3.39–2.37 (m, 10H), 1.71–0.93 (m, 5H), 1.61 (s, 3/2H), 1.60 (s, 3H), 1.58 (s, 3/2H), 0.41 (m, 1/2H), 0.11 (m, 1/2H).

FAB-MS: 548.2 (M+1).

The compounds shown in Table 8 were prepared according to the above procedures (with different amines).

TABLE 8

| | | R | FAB-MA (M + 1) |
|---|---|---|---|
| 1 | d1 + d2 | ethylamine | 504.3 |
| 2 | d1 + d2 | morpholine | 546.3 |
| 3 | d1 + d2 | ethanolamine | 520.2 |
| 4 | d1 | (imidazolylmethylamine) | 556.1 |
| 5 | d2 | (imidazolylmethylamine) | 556.1 |

EXAMPLE 59

(trans, d2)

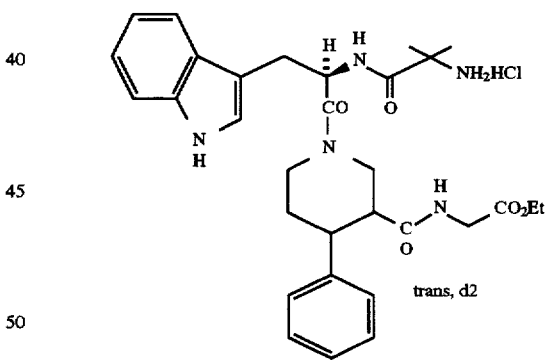

Step A:

To a solution of the intermediate prepared from Example 58, Step A (915 mg) in chloroform was added (1R, 2R)-N- methyl pseudoephedrine (590 ml), EDC (1.14 g), and a catalytic amount of DMAP. The reaction was stirred at room temperature for 12 hours and poured into water. The mixture was extracted with methylene chloride and dried over sodium sulfate. Concentration and purification (MPLC, hexanes/ethyl acetate=3/1) gave two diastereomers (d1, the less polar diastereomer, 316 mg; d2, the more polar diastereomer, 138 mg).

Step B:

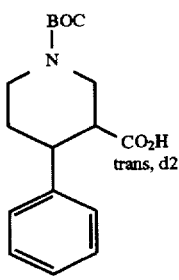

A solution of the more polar intermediate prepared in Step A (138 mg) in methanol was hydrogenated with Pd(OH)$_2$/C at one atmosphere for a couple of hours. The mixture was filtered through Celite and the filtrate was concentrated. The residue was redissolved in ether and washed with 1N hydrochloric acid. The aqueous layer was discarded. The organic layer was dried over sodium sulfate, filtrated and concentrated to give the desired product (84 mg).

Step C:

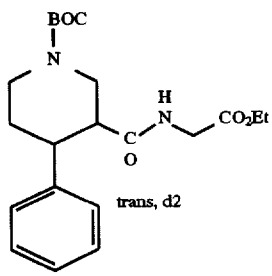

To the intermediate prepared from Step B (16 mg) in chloroform was added glycine ethyl ester hydrochloride salt (21 mg), EDC (19 mg), HOBt (13 mg) and triethylamine (35 ml). After 3 hours at room temperature the mixture was diluted with methylene chloride and then washed with water and brine. The organic layer was dried over sodium sulfate, filtered and concentrated. The residue was purified by prep TLC (hexanes/ethyl acetate=1/1) to give the desired product (16 mg).

Step D:

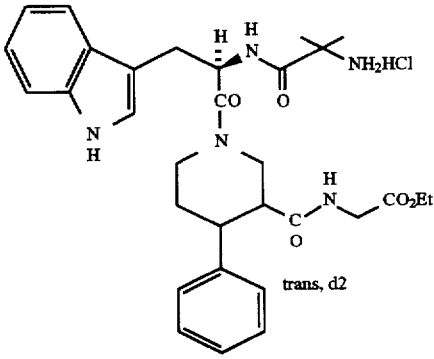

The intermediate prepared in Step C (8 mg) was treated with HCl (gas) in EtOAc to give a crude hydrochloride. To this crude material in 1 ml of chloroform was added intermediate 1 (8 mg), EDC (8 mg), HOBt (5 mg) and triethylamine (8 ml). The reaction was stirred at room temperature for 12 hours and poured into water. The mixture was extracted with methylene chloride and dried over sodium sulfate. Concentration and purification (PLC, hexanes/ethyl acetate=1/2) gave the desired product which was deblocked with the HCl/EtOAc protocol to give the desired product (11 mg).

$^1$H NMR (400 MHz, CD$_3$OD, mixture of rotamers): 7.73 (d, 8 Hz, 1/2H), 7.54 (d, 8 Hz, 1/2H), 7.38–6.99 (m, 8H), 6.84 (d, 7 Hz, 1H), 5.28–5.05 (m, 2H), 4.80–4.52 (m, 1H), 4.09 (m, 3H), 3.59 (m, 1 1/2H), 3.34 (m, 1 1/2H), 3.24 (m, 1H), 2.98 (m, 1H), 2.70–2.48 (m, 2 1/2H), 1.70–1.55 (m, 1 1/2H), 1.61 (s, 3H), 1.60 (s, 3H), 1.22 (t, 7 Hz, 3H), 1.00 (m, 1/2H), 0.57 (m, 1/2H).

FAB-MS: 562.3 (M+1)

The compounds shown in Table 9 were prepared according to the above procedure shown in Example 59.

TABLE 9

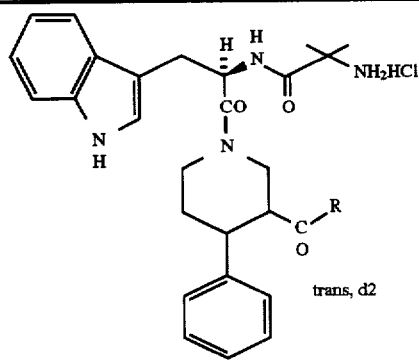

| | | R | FAB-MS (M + 1) |
|---|---|---|---|
| 1 | d2 | β-alanine ethyl ester | 576.3 |
| 2 | d2 | L-alanine methyl ester | 562.3 |

EXAMPLE 60

(trans, d2)

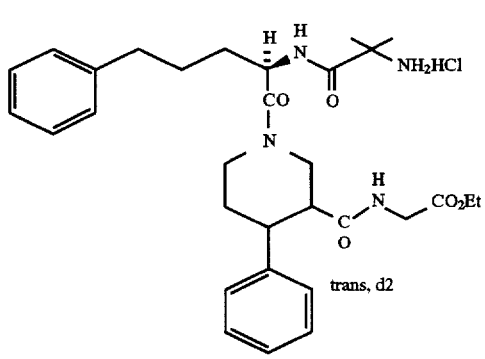

trans, d2

The intermediate prepared in Example 59, Step C (8 mg) in ethyl acetate was treated with $HCl_{(g)}$ at 0° C. for 15 seconds and maintained at room temperature for 30 minutes, concentrated to dryness to give the crude material. To this crude material in 1 ml of chloroform was added intermediate 3 (8 mg), EDC (8 mg), HOBt (5 mg) and triethylamine (8 mg). The reaction was stirred at room temperature for 12 hours and poured into water. The mixture was extracted with methylene chloride and dried over sodium sulfate. Concentration and purification (PLC, hexanes/ethyl acetate=1/2) gave the desired product which was treated with HCl(gas) in EtOAc to provide the title compound (11 mg).

FAB-MS: 551.4 (M+1)

The compounds shown in Table 10 were prepared according to the above procedure (coupled with different amino acids).

TABLE 10

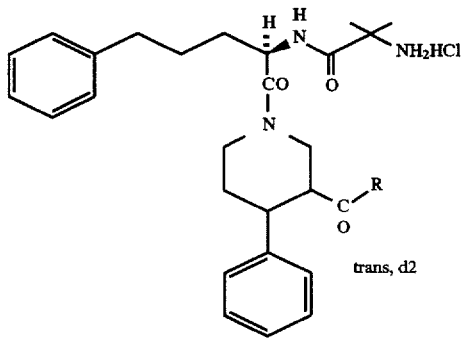

trans, d2

| | | R | FAB-MS (M + 1) |
|---|---|---|---|
| 1 | d2 | β-alanine ethyl ester | 565.4 |
| 2 | d2 | L-alanine methyl ester | 551.4 |

EXAMPLE 61

(trans, d1+d2)

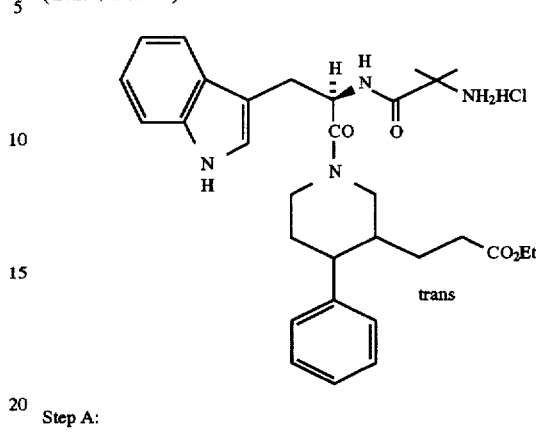

trans

Step A:

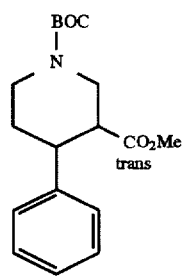

To a solution of the intermediate prepared in Example 12, Step A (200 mg) in methanol was added a catalytic amount of sodium methoxide in methanol and refluxed for a couple of hours. The mixture was poured into 0.1N hydrochloric acid and extracted with ether. The organic layer was dried over sodium sulfate, filtered and concentrated to give the desired product (190 mg).

Step B:

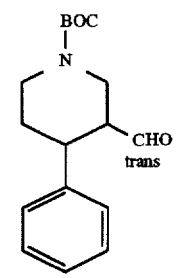

To a solution of the intermediate from Step A (120 mg) in 2 ml of toluene was added diisobutylaluminum hydride (1N in hexanes, 0.49 ml) at −78° C. After the reaction was stirred at −78° C. for 1 hour it was quenched with methanol and then poured into 0.5N hydrochloric acid solution. The mixture was extracted with ether. The organic layer was dried over sodium sulfate, filtered and concentrated. The residue was purified by PLC (hexanes/ethyl acetate=3/1) to give the desired product (60 mg).

Step C:

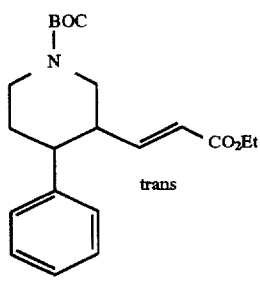

To a solution of triethyl phosphonoacetate in THF (5 ml) was added potassium bis(trimethylsilyl)amide (0.5N in toluene, 1.45 ml) at 0° C. After 1 hour at room temperature the intermediate from Step B (42 mg) in THF (1 ml) was added to the phosphorane solution and refluxed for an hour. This mixture was concentrated and the residue was purified by PLC (hexanes/ethyl acetate=4/1) to give the desired product (50 mg).

Step D:

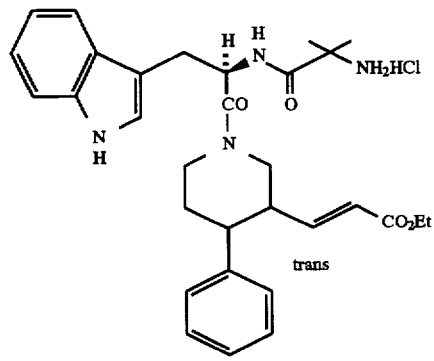

To the intermediate prepared in Step C (50 mg) was added 0.5 ml of TFA at room temperature. After 10 minutes, the mixture was concentrated and azeotroped with toluene (3×). To a solution of the residue in 1 ml of chloroform was added Intermediate 1 (62 mg), EDC (53 mg), HOBt(23 mg) and triethylamine (58 ml). The mixture was stirred at room temperature for 3 hours and poured into water. The mixture was extracted with methylene chloride, and dried over sodium sulfate. Purification (PLC, hexanes/ethyl acetate=1/1) of the residue gave the coupled product (65 mg).

Step E:

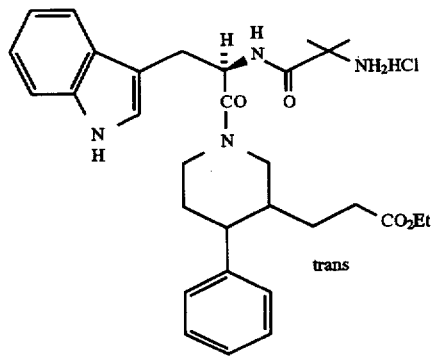

A solution of the intermediate prepared from Step D (50 mg) in methanol was hydrogenated with Pd(OH)$_2$/C at one atmosphere for a couple of hours. The mixture was filtered through Celite and the filtrate was concentrated. The residue was treated with HCl(gas) in EtOAc to give the desired product (36 mg).

FAB-MS: 533.3 (M+1)

EXAMPLE 62

(cis, d1)

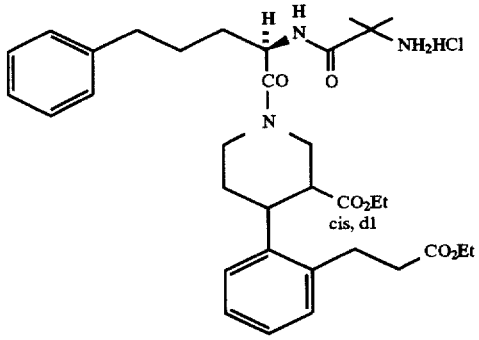

Ethyl chloroformate (12.9 ml) was added to a stirred suspension of cuprous chloride (1.35 g) in THF (200 ml). At 0° C., a solution of ethyl nicotinate was added slowly followed by the addition of Grignard reagent (prepared from 2-bromobenzaldehyde (25 g), 1,3-propandiol (20 ml), and magnesium (4.9 g) by the procedure described in *J. Org. Chem.* 1986, 51, 3490) The reaction was stirred for an hour and poured into a saturated ammonium chloride/ammonia solution (1/1) and extracted with ethyl acetate. The organic layer was washed with 1N hydrochloric acid and brine and dried over sodium sulfate. Evaporation of the solvent gave the desired product. Crystallization of this material from ethyl acetate gave 25 g of the desired material.

Step B:

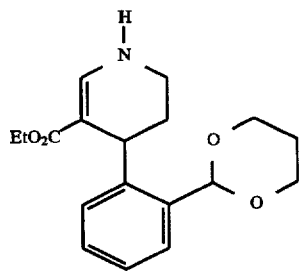

The intermediate prepared in Step A (25 g) was dissolved in hot ethyl acetate (500 ml) and then cooled down to room temperature. This organic solution was hydrogenated with PtO$_2$ at one atmosphere for a couple of hours (monitored by TLC). The mixture was filtered through Celite and the filtrate concentrated under vacuum. The residue was dissolved in hot ethanol (150 ml) was treated with 6N NaOH (75 ml) at reflux for 10 minutes. The mixture was concentrated under vacuum and to the residue was added water and stirred at room temperature for 10 minutes. The pale white solid was collected by filtration. The filtrate was extracted with methylene chloride and washed with brine and dried over sodium sulfate. The solvent was concentrated and combined with pale white solid to give 13.6 g of desired product.

Step C:

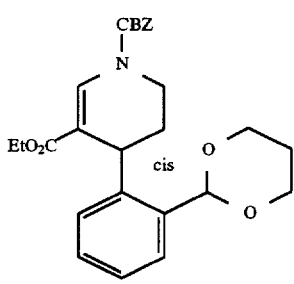

To a solution of the intermediate prepared in Step B (10.1 g) in THF (300 ml) at 0° C. was added a catalytic amount of indicator (bromocresol green) and NaCNBH₃ (64 mmole). To this reaction mixture was added 1N hydrochloric acid till a yellow color persisted (pH=4.0). After an hour, the mixture was poured into 1N NaOH and extracted with chloroform. The organic layer was washed with brine dried over sodium sulfate and concentrated. The residue was purified by filtration through silica gel with methylene chloride/methanol=10/1 to remove very polar material. The material obtained after concentration of the filtrate was dissolved in chloroform and to this mixture was added triethylamine (6 ml) and CBZ-Cl (4.6 ml) at 0° C. After stirring for 15 minutes, the reaction was poured into water and extracted with methylene chloride. The organic layer was washed with brine, dried over sodium sulfate. Concentration and purification (MPLC, hexanes/ethyl acetate=5/1) gave the desired product (6.4 g).

Step D:

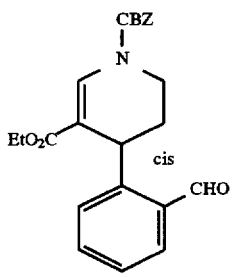

To a solution of the intermediate prepared from Step C (2.17 g) in methanol (30 ml) was added 1N hydrochloric acid (5 ml) and stirred for an hour. The mixture was poured into 1N NaOH solution and extracted with ether. The organic layer was washed with brine and dried over magnesium sulfate. Purification of the residue (chromatatron, hexanes/ethyl acetate=5/1) gave the desired product (1.56 g).

Step E:

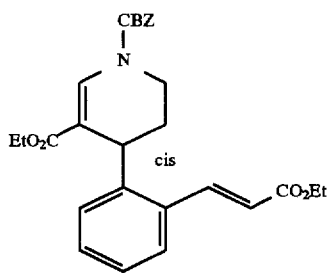

To a solution of triethyl phosphonoacetate in THF (25 ml) was added potassium bis(trimethylsilyl)amide (0.5N in toluene, 4.56 ml) at 0° C. After stirring an hour at room temperature the intermediate from Step D (860 mg) in THF (10 ml) was added to the phosphorane solution at room temperature. The mixture was stirred at room temperature for an hour and then quenched with 1N hydrochloric acid. This mixture was extracted with ether, washed with brine, and dried over magnesium sulfate. Purification of the residue (chromatatron, hexanes/ethyl acetate=5/1) gave the desired product (873 mg).

Step F:

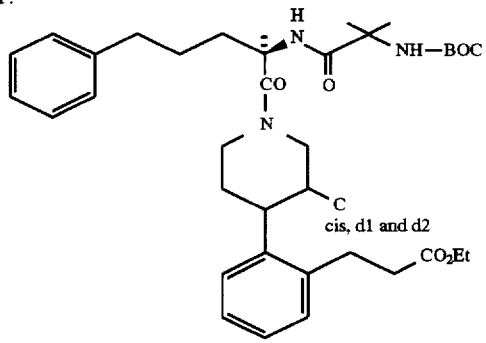

The intermediate prepared in Step E (870 mg) was dissolved in methanol and hydrogenated with Pd(OH)₂/C at one atmosphere for one and one-half hours. The mixture was filtered through Celite and the filtrate was concentrated under vacuum. To the residue in chloroform was added intermediate 3 (749 mg), EDC (714 mg) and HOBt (276 mg) and stirred for 2 h. The mixture was concentrated and purified (chromatatron, hexanes/ethyl acetate=2/1) to give two diastereomers (545 mg, the less polar diastereomer, d1; 500 mg the more polar diastereomer, d2).

Step G:

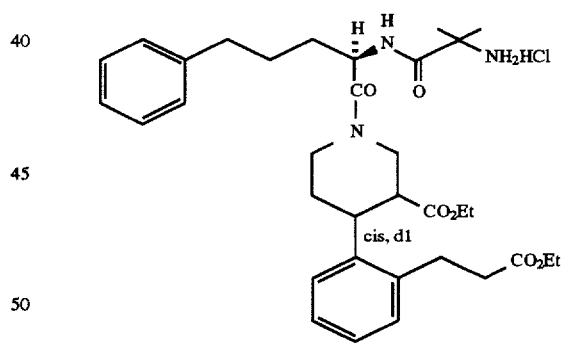

To a solution of the less polar diastereomer prepared in Step F (200 mg) in ethyl acetate was bubbled in HCl$_{(g)}$ at 0° C. for 15 seconds. After standing for 30 minutes at room temperature the mixture was concentrated and purified (LH-20, 100% methanol) to give the cis, d1 product as a white solid (100 mg).

¹H NMR (400 MHz, CD₃OD, mixture rotamers): 7.28–7.06 (m, 9H), 5.09 (m, 1/2H), 4.85–4.55 (m, 1 1/2H), 4.17 (m, 1H), 4.10 (q, 7 Hz, 2 H), 3.77 (m, 2H), 3.46 (m, 1 1/2H), 3.25 (m, 1/2H), 3.15–2.39 (m, 9H), 1.89–1.60 (m, 5H), 1.65 (s, 2H), 1.62 (s, 2H), 1.57 (s, 2H), 1.21 (t, 7 Hz, 3H), 0.91 (t, 7 Hz, 3/2H), 0.85 (t, 7 Hz, 3/2H).

FAB-MS: 594.3 (M+1)

EXAMPLE 63

(cis, d2)

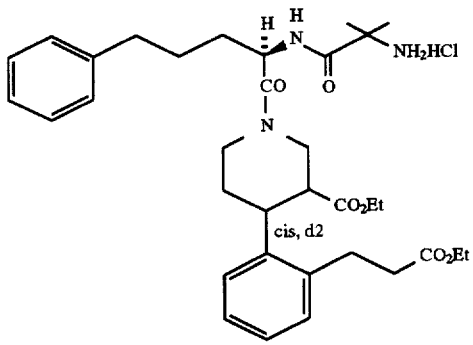

The desired cis, d2 product (3.3 mg) was obtained from the more polar diastereomer obtained in Example 62, Step F by the procedure described in Example 62, Step G.

$^1$H NMR (400 MHz, CD$_3$OD, mixture rotamers): 7.90–7.03 (m, 9H), 4.92–4.61 (m, 2H), 4.10 (q, 7 Hz, 2H), 4.07 (m, 1H), 3.79 (m, 2H), 3.45 (m, 1 1/2H), 3.25 (m, 1/2H), 3.07–2.38 (m, 9H), 1.94–1.69 (m, 4H), 1.63 (s, 3/2H), 1.61 (s, 3/2H), 1.60 (s, 3/2H), 1.59 (s, 3/2H), 1.20 (t, 7 Hz, 3 H), 0.91 (t, 7 Hz, 3H).

FAB-MS: 594.3 (M+1).

EXAMPLE 64

(cis, d1)

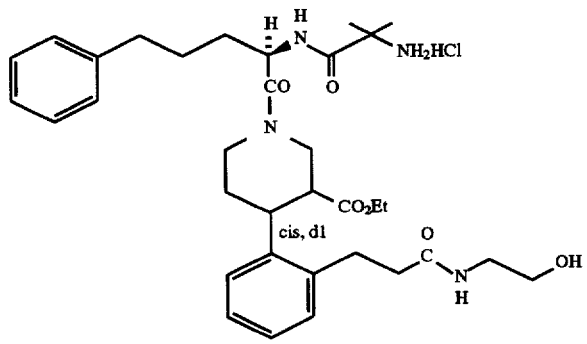

Step A:

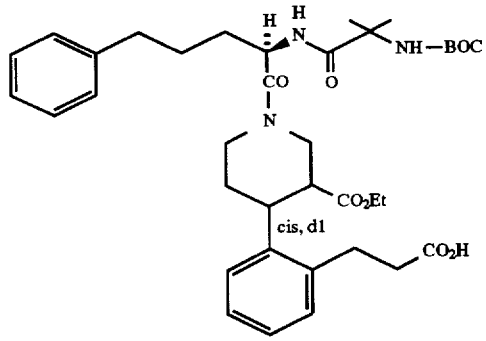

To the less polar diastereomer prepared in Example 62, Step F (30 mg) in ethanol (1 ml) was added 6N NaOH (30 ml) at room temperature. After stirring for an hour the mixture was concentrated. To the residue was added 1N hydrochloric acid and extracted with ethyl acetate. The organic layer was washed with brine, dried over sodium sulfate and concentrated to give the desired product (20 mg).

Step B:

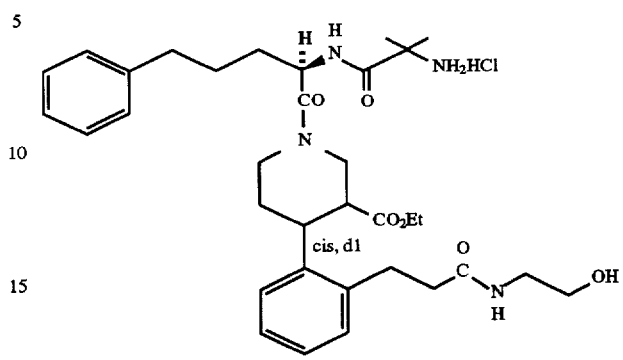

To a solution of the intermediate prepared in Step A (6 mg) in 0.5 ml of chloroform was added ethanolamine (0.8 ml), EDC (3.5 mg), and HOBt (1.8 mg). The reaction was stirred at room temperature for a couple of hours and poured into water. The mixture was extracted with methylene chloride and dried over sodium sulfate. Concentration and purification (PLC, methylene chloride/methanol=20/1) provided the coupled product. This material was deprotected with HCl in EtOAc to give the desired cis, d1 product (1.6 mg).

$^1$H NMR (400 MHz, CD$_3$OD, mixture rotamers): 7.28–7.07 (m, 9H), 5.09 (m, 1/2H), 4.85–4.62 (m, 1 1/2H), 4.19 (m, 1H), 3.75 (m, 2H), 3.55 (t, 6 Hz, 2H), 3.45 (m, 1H), 3.34–2.84 (m, 6 1/2H), 2.73–2.45 (m, 5 1/2H), 1.85–1.57 (m, 5H), 1.65 (s, 3/2H), 1.62 (s, 3/2H), 1.57 (s, 3/2 H), 1.56 (s, 3/2H), 0.92 (t, 7 Hz, 3/2H), 0.85 (t, 7 Hz, 3/2H).

FAB-MS: 609.2 (M+1)

EXAMPLE 65

(cis, d1)

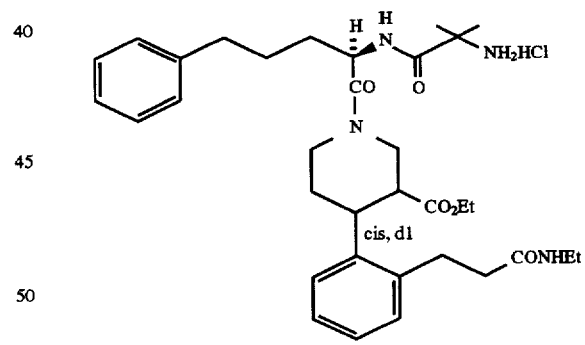

To a solution of the intermediate prepared in Example 64 Step A (6 mg) in 0.5 ml of chloroform was added ethylamine hydrochloride salt (1 mg), EDC (3.5 mg), triethylamine (4 ml) and HOBt (1.8 mg). The reaction was stirred at room temperature for a couple of hours and poured into water, and extracted with methylene chloride and dried over sodium sulfate. Purification of the residue (PLC, methylene chloride/methanol=20/1) gave the coupled product. This material was treated with HCl in EtOAc to yield the desired cis, d1 product (1.5 mg).

$^1$H NMR (400 MHz, CD$_3$OD, mixture rotamers): 7.28–7.07 (m, 9H), 5.09 (m, 1/2H), 4.83–4.62 (m, 1 1/2H), 4.17 (m, 1H), 3.75 (m, 2H), 3.50 (m, 1 1/2H), 3.25–2.84 (m, 6 1/2H), 2.72–2.39 (m, 5H), 1.89–1.58 (m, 5H), 1.65 (s, 3/2H), 1.61 (s, 3/2H), 1.57 (s, 3/2H), 1.56 (s, 3/2H), 1.06 (t, 7 Hz, 3H), 0.91 (t, 7 Hz, 3/2H), 0.85 (t, 7 Hz, 3/2H).

FAB-MS: 593.3 (M+1)

EXAMPLE 66

(cis, d1)

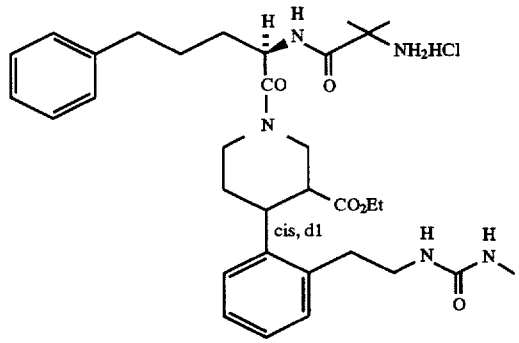

To a solution of the intermediate prepared from Example 64, Step A (8 mg) in methylene chloride (1 ml) was added ethyl chloroformate (2.3 ml) and triethylamine (5 ml) at 0° C. The reaction mixture was stirred at 0° C. for 10 minutes and room temperature for an hour. The mixture was poured into saturated sodium bicarbonate and extracted with methylene chloride. The organic layer was washed with brine and dried over sodium sulfate, and concentrated. To the residue in acetone (0.5 ml) was added sodium azide (2.3 mg) in water (0.2 ml) at 0° C. After stirring at room temperature for an hour the mixture was extracted with ether, washed with water and brine, and dried over $MgSO_4$. Filtration and evaporation gave acyl azide which was dissolved in toluene (1 ml) and refluxed for 3 hours to give the isocyanate. The toluene solution was cooled down to room temperature and methylamine (40% in water, 9 ml) was added. After stirring for 12 hours in room temperature, the reaction was quenched with 1N HCl and extracted with methylene chloride and then dried over sodium sulfate and concentrated. Purification of the residue (PLC, methylene chloride/methanol=20/1) gave desired urea which was deprotected with HCl in EtOAc to yield the desired product (3.5 mg).

FAB-MS: 594.3 (M+1).

EXAMPLE 67

(cis, d1+d2)

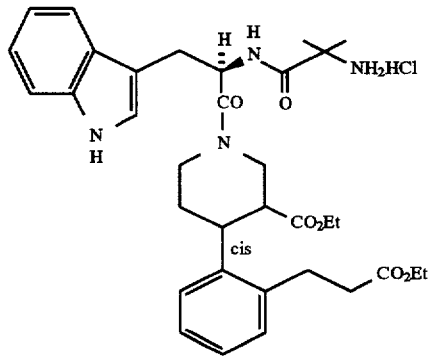

The intermediate prepared in Example 62, Step E (17 mg) was dissolved in methanol and hydrogenated with $Pd(OH)_2/C$ at one atmosphere for one and half hours. The mixture was filtered through Celite and the filtrate was concentrated under vacuum to give the free amine (11 mg). To this free amine (5.5 mg) in chloroform was added Intermediate 1 (7 mg), EDC (6 mg) and HOBt (4 mg). After 12 hours, the mixture was concentrated and purified (chromatatron, hexanes/ethyl acetate=2/1) to give an inseparable mixture of diastereomers. This diastereomeric mixture in ethyl acetate was treated with $HCl_{(g)}$ at 0° C. for 15 seconds. After standing for 30 minutes at room temperature, the mixture was concentrated to give a white solid (8 mg).

FAB-MS: 605.3 (M+1)

EXAMPLE 68

(cis, d1)

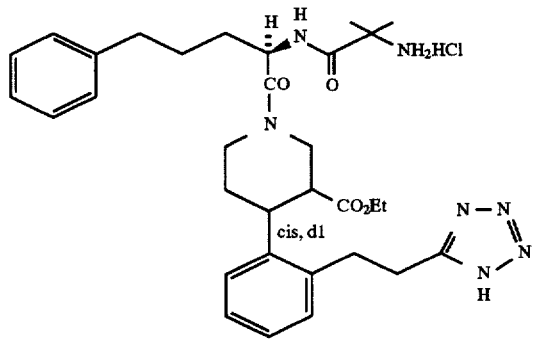

Step A:

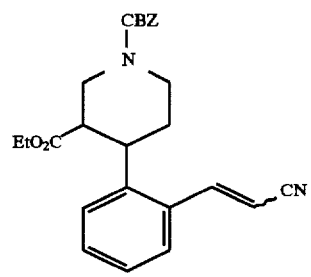

To a solution of diethyl cyanomethyl phosphonate in THF (25 ml) was added potassium bis(trimethylsilyl)amide (0.5N in toluene, 3.44 ml) at 0° C. After stirring an hour at room temperature the intermediate from Example 62, Step D (650 mg) in THF (10 ml) was added to the phosphorane solution at room temperature. The mixture was stirred at room temperature for an hour and then quenched with 1N hydrochloric acid. This mixture was extracted with ether and washed with brine, and dried over magnesium sulfate and concentrated. Purification (chromatatron, hexanes/ethyl acetate=5/1) gave the α, β-unsaturated nitrile (trans, 466 mg; cis, 124 mg).

Step B:

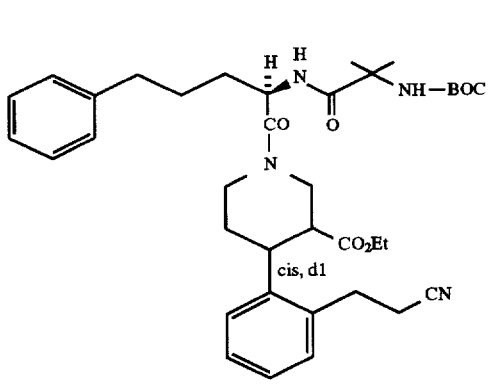

The intermediate prepared in Step A (590 mg) was dissolved in methanol and hydrogenated with Pd(OH)$_2$/C at one atmosphere for one and half hours. The mixture was filtered through Celite and the filtrate was concentrated under vacuum. To the residue in chloroform was added intermediate 3 (560 mg), EDC (560 mg) and HOBt (208 mg). After a couple of hours, the mixture was concentrated and purified (chromatatron, hexanes/ethyl acetate=1/1) to give two diastereomers (220 mg, the less polar diastereomer, d1; 260 mg the more polar diastereomer, d2).

Step C:

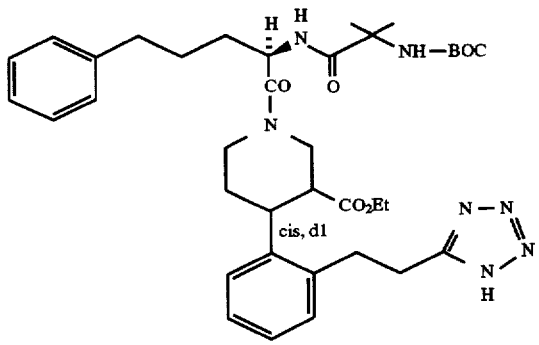

To the less polar diastereomer prepared in Step B (220 mg) in toluene (5 ml) was added trimethyltin azide (206 mg) and refluxed for 6½ hours. The solvent was removed under vacuum. The residue was redissolved in methylene chloride/methanol/acetic acid=20/1/0.1 (20 ml) and allowed to stand at room temperature for 12 hours and the solvent was removed under vacuum. The residue was purified by PLC (methylene chloride/methanol/acetic acid=20/1/0.1) to give the desired product (120 mg).

Step D:

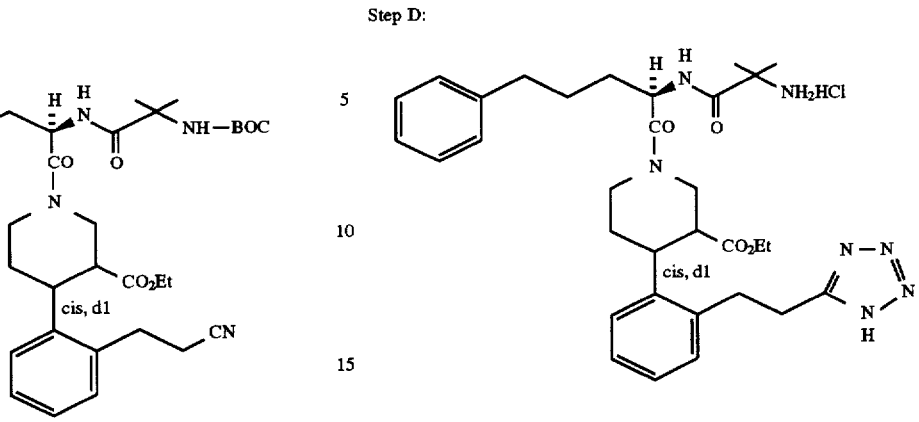

The intermediate in Step C (120 mg) was treated with HCl in EtOAc to give the desired cis, d1 product as a white solid (98 mg).

$^1$H NMR (400 MHz, CD$_3$OD, mixture of rotamers): 7.28–7.08 (m, 9H), 5.08 (m, 1/2H), 4.84–4.53 (m, 1 1/2H), 4.18 (m, 1H), 3.78 (m, 3H), 3.27–3.03 (m, 6H), 2.85–2.30 (m, 4H), 1.90–1.38 (m, 5H), 1.65 (s, 3/2 H), 1.61 (s, 3/2H), 1.57 (s, 3/2H), 1.56 (s, 3/2H), 0.90 (t, 7 Hz, 3/2H), 0.85 (t, 7 Hz, 3/2H).

FAB-MS: 590.2 (M+1).

EXAMPLE 69

(cis, d2)

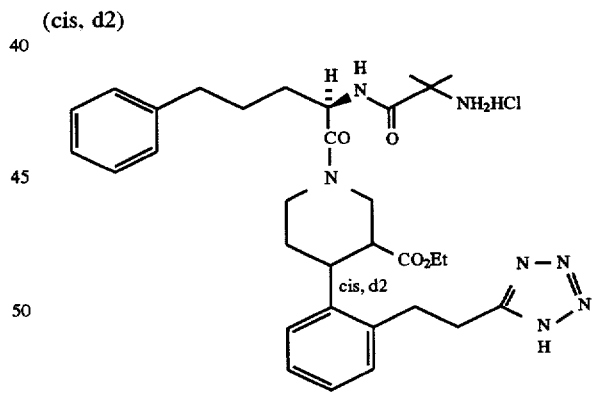

The desired product (2 mg) was prepared from the more polar diastereomer (6.8 mg) obtained in Example 68, Step B by the procedure described in Example 68, Step C and D.

FAB-MS: 590.4 (M+1).

EXAMPLE 70

(cis, d1)

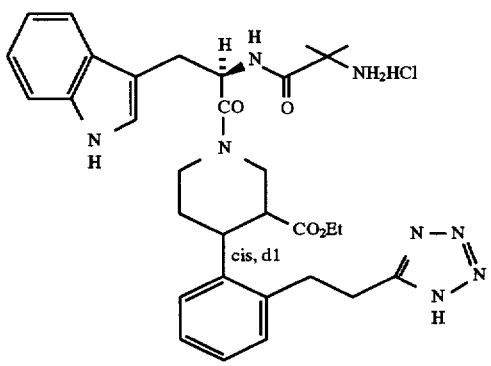

Step A:

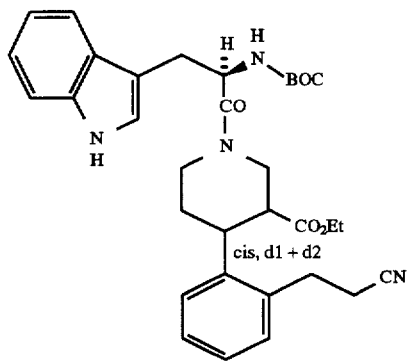

The intermediate prepared in Example 68, Step A (782 mg) was dissolved in methanol and hydrogenated with Pd(OH)$_2$/C at one atmosphere for one and one-half hours. The mixture was filtered through Celite and the filtrate was concentrated under vacuum. To the residue in chloroform was added Boc-D-Tryptophan (468 mg), EDC (534 mg) and HOBt (207 mg). After a couple of hours, the mixture was concentrated and purified (MPLC, hexanes/ethyl acetate=1/1) to give two diastereomers (316 mg, the less polar diastereomer, d1; 300 mg the more polar diastereomer, d2).

Step B:

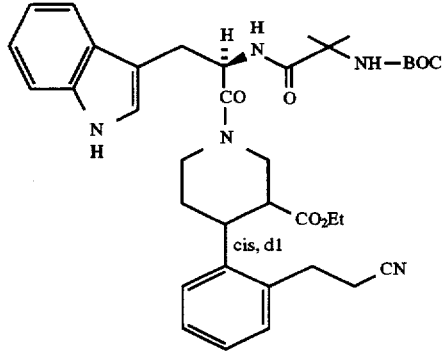

The less polar diastereomer from Step A (316 mg) in ethyl acetate was treated with HCl$_{(g)}$ at 0° C. for 15 seconds. After standing 30 minutes at room temperature, the mixture was concentrated to dried to give crude material. To the residue in 5 ml of chloroform was added N-Boc-a-methylalanine (158 mg), EDC (149 mg), triethylamine (217 ml) and HOBt (77 mg) and stirred for 12 hours at room temperature. The mixture was poured into water and extracted with methylene chloride and washed with brine. The organic layer was dried over sodium sulfate, filtered and concentrated. The residue was purified by chromatatron (hexanes/ethyl acetate=1/2) to give the desired compound (287 mg).

Step C:

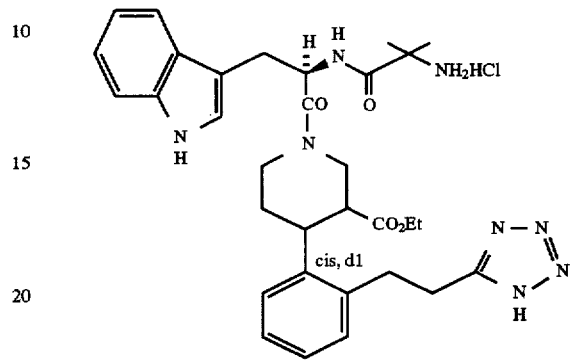

The desired cis, d1 product (135 mg) was prepared from above intermediate (287 mg) prepared in Example 70, Step B by the procedure described in Example 68, Steps C and D.

$^1$H NMR (400 MHz, CD$_3$OD, mixture rotamers): 8.09 (d, 8 Hz, 1/2H), 7.80 (d, 8 Hz, 1/2H), 7.64 (d, 8 Hz, 1/2H), 7.57 (d, 8 Hz, 1/2H), 7.35 (d, 7 Hz, 1H), 7.22–7.00 (m, 7H), 5.31–5.20 (m, 1H), 4.71 (d, 12 Hz, 1/2 H), 4.41 (d, 12 Hz, 1/2H), 4.15 (m, 1/2H), 3.92–3.67 (m, 2 1/2H), 3.43–3.03 (m, 8 1/2H), 2.80 (m, 1H), 2.52–2.25 (m, 1 1/2H), 1.59 (s, 3/2H), 1.54 (s, 3/2H), 1.50 (s, 3/2H), 1.35 (3/2H), 1.43 (m, 1H), 0.93 (t, 7 Hz, 3/2H), 0.84 (t, 7 Hz, 3/2H).

FAB-MS: 601.1 (M+1).

EXAMPLE 71

(cis, d2)

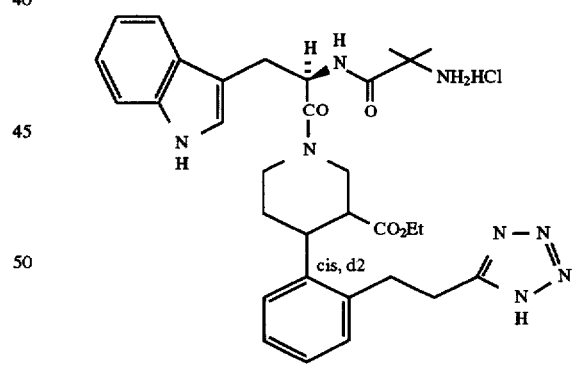

The title product (125 mg) was prepared from the more polar diastereomer (300 mg) prepared in Example 70, Step A by the procedure described in Example 70, Step B and Example 68, Steps C and D.

$^1$H NMR (400 MHz, CD$_3$OD, mixture rotamers): 8.24 (d, 8 Hz, 1/2H), 8.09 (d, 8 Hz, 1/2H), 7.59 (d, 8 Hz, 1/2H), 7.54 (d, 8 Hz, 1/2H), 7.34–6.92 (m, 8H), 5.40 (m, 1/2H), 5.15 (m, 1/2H), 4.64 (d, 13 Hz, 1/2H), 4.55 (d, 13 Hz, 1/2H), 4.22 (m, 1/2H), 4.09 (m, 1/2H), 3.81–3.58 (m, 2 1/2H), 3.40–2.84 (m, 9 1/2H), 2.71–2.32 (m, 1 1/2H), 1.63 (s, 3/2H), 1.52 (s, 3/2H), 1.48 (s, 3/2H), 1.29 (3/2H), 1.53 (m, 1/2H), 1.32 (m, 1/2H), 0.90 (t, 7 Hz, 3/2H), 0.79 (t, 7 Hz, 3/2H).

FAB-MS: 601.2 (M+1).

EXAMPLE 72

(cis, d1+d2)

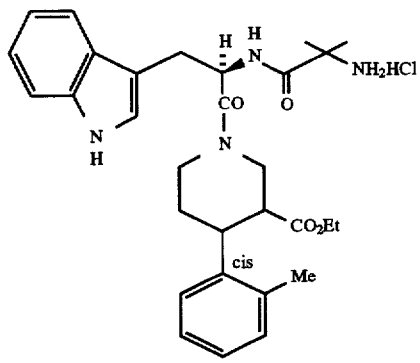

Step A:

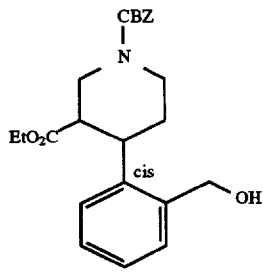

To a solution of the intermediate prepared in Example 62, Step C (235 mg) in methanol (3 ml) was added 1N hydrochloric acid (0.5 ml) and stirred for an hour. To the resulting mixture was added NaCNBH₃ (1.0N in THF, 0.7 ml) and after 5 minutes the reaction mixture was poured into 1N hydrochloric acid and extracted with ether. The organic layer was washed with brine, dried over sodium sulfate and concentrated. The residue was purified (chromatatron, hexanes/ethyl acetate=1/1) to give the desired product (142 mg).

Step B:

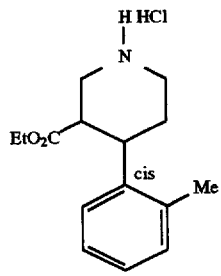

To a solution of the intermediate prepared in Step A (142 mg) in methanol was added HCl in ether and Pd(OH)₂ and stirred under an hydrogen atmosphere for 12 hours. The mixture was filtered through Celite and the filtrate was concentrated to give the desired product (105 mg).

Step C:

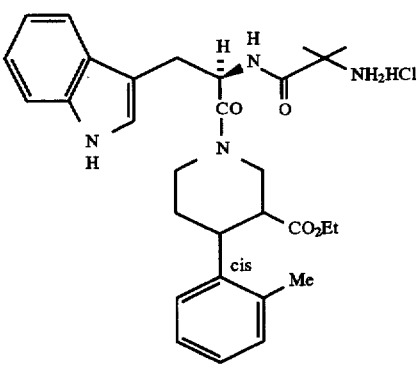

To the intermediate (105 mg) prepared in Step B in 2 ml of chloroform was added Intermediate 1 (81 mg), EDC (54 mg), HOBt (28 mg) and triethylamine (53 ml) and the reaction was stirred at room temperature for 12 hours and poured into water. The mixture was extracted with methylene chloride, dried over sodium sulfate and concentrated. Purification of the residue (chromatatron, hexanes/ethyl acetate=1/1) gave the desired product which was treated with HCl in EtOAc to give the desired product (56 mg).

FAB-MS: 519.2 (M+1)

EXAMPLE 73

(cis, d1+d2)

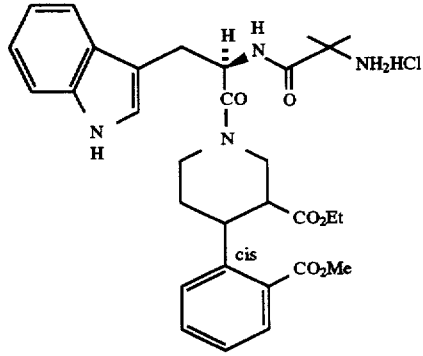

Step A:

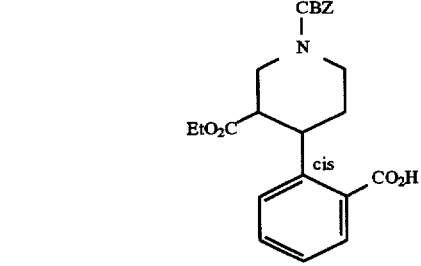

To the intermediate prepared in Example 72, Step A (100 mg) at 0° C. in acetone was added Jones reagent (4N, 0.2 ml). After stirring for 16 hours in room temperature the mixture was quenched with isopropanol, filtered through celite. The filtrate was extracted with ethyl acetate. The organics were washed with brine and dried over sodium Step B:

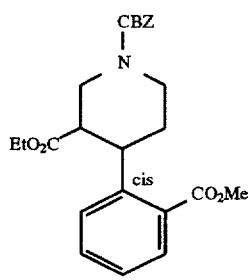

To the intermediate prepared in Step A (50 mg) in ether at 0° C. was added diazomethane (Blatt, Org. Syn. Collective Vol. 4, p225). The mixture was slowly warmed up to room temperature and stirred for hours. Concentration and purification of the residue (PLC, hexanes/ethyl acetate=3/1) gave the desired product (50 mg).

Step C:

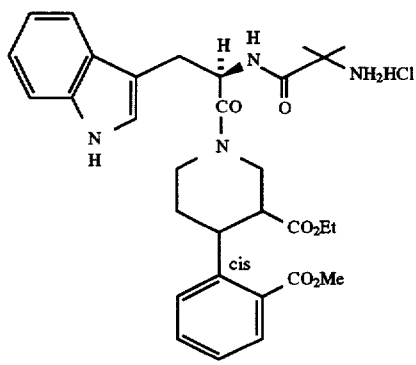

The intermediate prepared in Step B (50 mg) was dissolved in methanol and hydrogenated over Pd(OH)$_2$/C at one atmosphere for one and half hours. The mixture was filtered through Celite and the filtrate was concentrated under vacuum. To the residue in chloroform was added intermediate 1 (48 mg), EDC (45 mg) and HOBt (24 mg). After a couple of hours, the mixture was concentrated and purified (chromatatron, hexanes/ethyl acetate=1/1) to give the coupled product. Deprotection of this material by the HClEtOAc protocol gave the desired product (47

FAB-MS: 563.1 (M+1)

EXAMPLE 74

(cis, d1+d2)

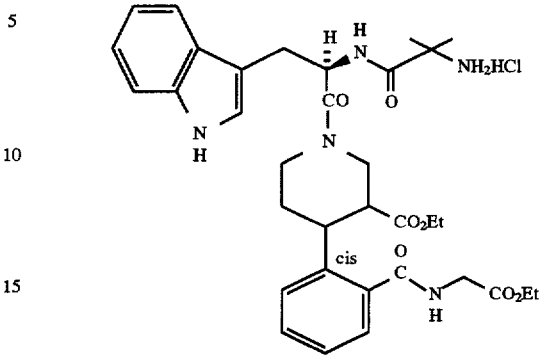

Step A:

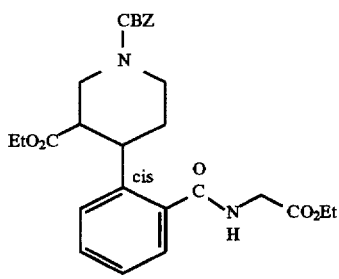

To the intermediate prepared in Example 73, Step A (50 mg) in chloroform was added glycine ethyl ester HCl salt (51 mg), EDC (46 mg) triethylamine (84 ml), and HOBt (32 mg). The reaction was stirred at room temperature for 12 hours and poured into water. The mixture was extracted with methylene chloride and dried over sodium sulfate, concentrated and purified (PLC, hexanes/ethyl acetate=1/1) to give the coupled product (45 mg).

Step B:

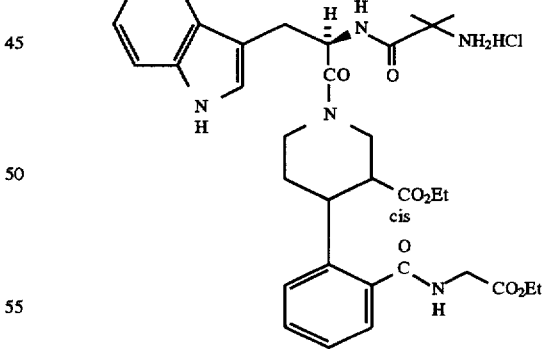

The title product (43 mg) was prepared from the intermediate (45 mg) obtained in Step A by the procedure desired in Example 73, Step C.

FAB-MS: 634.2 (M+1).

EXAMPLE 75

(cis, d1+d2)

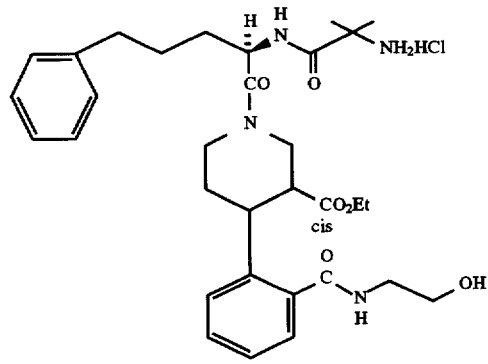

Step A:

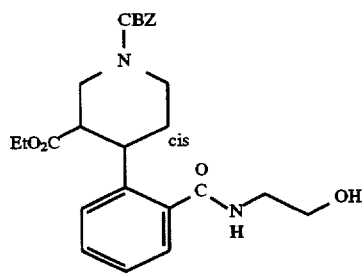

To intermediate prepared in Example 73, Step A (53 mg) in chloroform was added ethanolamine (12 ml), EDC (37 mg) and HOBt (19 mg) and stirred at room temperature for 12 hours and poured into water. The mixture was extracted with methylene chloride and dried over sodium sulfate and concentrated. The residue was purified (chromatatron, methylene chloride/methanol=20/1) to give the coupled product (29 mg).

Step B:

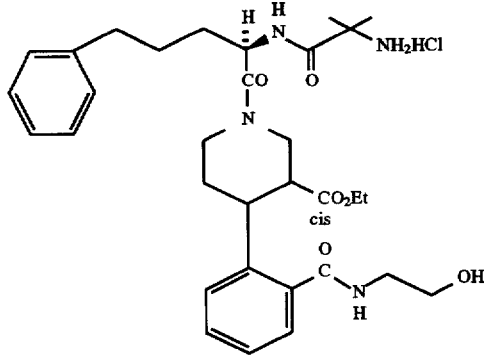

The desired product (16.8 mg) was prepared from the above intermediate (29 mg) by the procedure described in Example 62, Steps F and G.

FAB-MS: 581.2 (M+1).

EXAMPLE 76

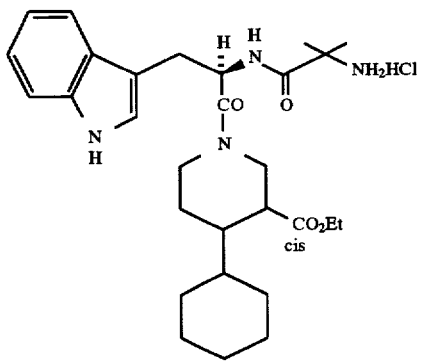

To a solution of the intermediate prepared in Example 12, Step A-1 (100 mg) in acetic acid was added $PtO_2$ and hydrogenated at one atmosphere for 24 hours (monitored by TLC). The mixture was filtered through Celite, the filtrate was concentrated and the residue was azeotroped with toluene. The residue was dissolved in TFA and stirred for 20 minutes at room temperature. The reaction mixture was concentrated and the residue was dissolved in methylene chloride (0.5 ml) and was reacted with intermediate 1 (15 mg), EDC (15 mg), HOBt (6 mg) and triethylamine (11 ml). The mixture was stirred at room temperature for 3 hours and poured into water. The mixture was extracted with methylene chloride, dried over sodium sulfate and concentrated. Purification of the residue (PLC, hexanes/ethyl acetate=1/1) gave the coupled product which was treated with HCl in EtOAc to yield the desired product (8 mg).

FAB-MS: 511.1 (M+1)

EXAMPLE 77

(cis, d1+d2)

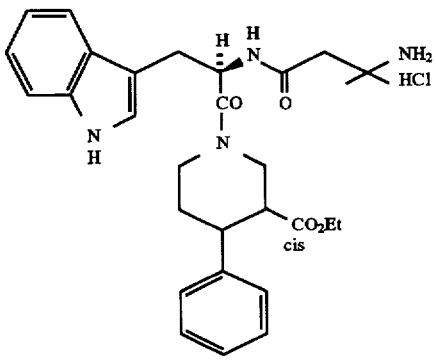

The intermediate prepared in Example 12, Step B was dissolved in methanol and hydrogenated over Pd(OH)2 at one atmosphere for a couple of hours. The mixture was filtered though celite and the filtrate was concentrated under vacuum. To the residue (88 mg) in chloroform (1 ml) was added N-Boc-β,β-dimethyl-β-alanine (48 mg, W. R. Schoen etc., *J. Med. Chem.* 1994,37,897), EDC (48 mg), and HOBt (30 mg), stirred for 12 hours and the mixture was poured into water. The mixture was extracted with methylene chloride, dried over sodium sulfate and concentrated. Purification of the residue (chromatatron, hexanes/ethyl acetate=1/1) gave the coupled product that was deblocked with HCl in EtOAc to give the desired product (58 mg).

FAB-MS: 519.2 (M+1)

EXAMPLE 78

(cis, d1+d2)

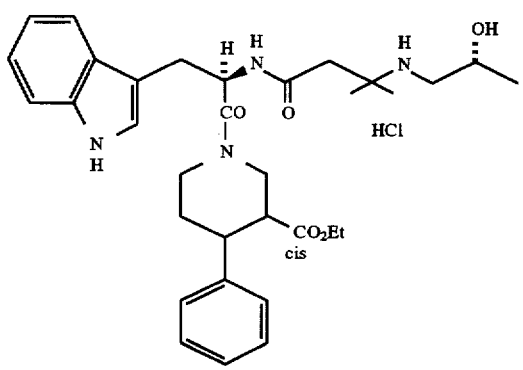

Step A:

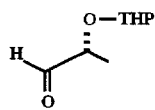

To a solution of methyl (R)-lactate (1 ml) in dihydropyran (5 ml) was added one drop of concentrated hydrochloric acid at room temperature. The reaction was stirred for an hour, concentrated and purified by chromatatron (hexanes/ethyl acetate=3/1) to give the desired product (1.49 g). To the THP protected lactate (500 mg) in toluene (10 ml) was added diisobutylaluminum hydride (1N in cyclohexane, 3.45 ml) at −78° C. and after one and half hours, the reaction was quenched with methanol at low temperature. The mixture was poured into 5% aqueous citric acid and extracted with ether. The organic layer was washed with brine, dried over sodium sulfate and concentrated to give the protected aldehyde.

Step B

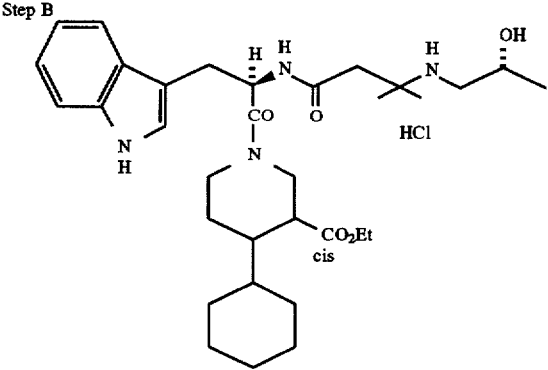

To a solution of the product (25 mg) prepared in Example 77 in methanol (0.5 ml) was added the intermediate (36 mg) prepared in Step A and sodium acetate (18 mg) and stirred at room temperature for an hour. To the mixture was added NaCNBH$_3$ (1N in THF, 90 ml) slowly and stirred for 16 hours and concentrated. The residue was purified by chromatatron (methylene chloride/methanol/ammonium hydroxide=10/1/0.1) to give the desired product which was dissolved in methanol (0.5 ml) and was treated with 9N hydrochloric acid (0.2 ml). After stirring for 2 hours, the mixture was concentrated and dried to give the desired product (10.5 mg). FAB-MS: 577.4 (M+1).

EXAMPLE 79

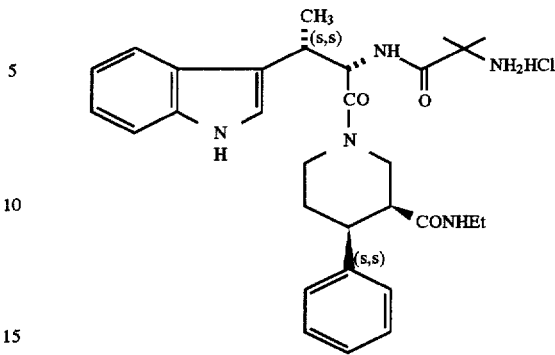

Step A:

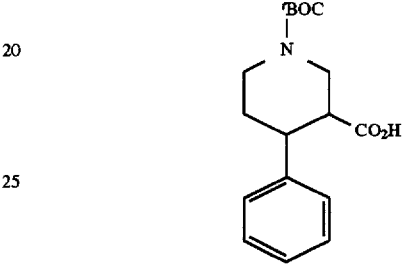

To a solution of 3-ethoxycarbonyl-4-piperidone hydrochloride (25 g, 120 mmole) and 3-methoxycarbonyl-4-piperidone hydrochloride (25.3 g, 130 mmole) in 70 ml of 6N aqueous sodium hydroxide was added di-t-butyl-dicarbonate (55 g, 255 mmole) in 200 ml of dioxane at 0° C. After stirring ½ hour at 0° C. and 3 hours at room temperature, the mixture was diluted with ethyl acetate and washed with 0.5N hydrochloric acid and brine. The organic layer was dried over magnesium sulfate, filtered and concentrated. To crude residue in 800 ml of methylene chloride there was added diisopropylethylamine (65 ml, 375 mmole) and triflic anhydride (46 ml, 275 mmole) at −78° C. After ½ hour, the mixture was poured into saturated sodium bicarbonate solution and extracted with methylene chloride. The organic layer was washed with 1N hydrochloride, brine and dried over magnesium sulfate. The organic layer was concentrated to give the vinyl triflate. To a solution of the vinyl triflate in 700 ml of THF was added K$_2$CO$_3$ (51.7, 375 mmole), phenylboronic acid (25 g, 205 mmole) and Pd(PPh$_3$)$_4$ (3.7 g, 3.2 mmole) at room temperature. The reaction mixture was refluxed for 16 hours and then poured into water and extracted with ether (3×). The organic layers were washed with water (3×), brine and dried over magnesium sulfate. The solution was then concentrated to dry. To the resulting residue in 100 ml of ethanol there was added 6N NaOH (100 ml) and the solution was heated at reflux for 3 hours. The mixture was concentrated to dryness. The residue was dissolved in water and extracted with methylene chloride. The organic layer was discarded. The aqueous layer was cooled in an ice bath and was acidified with 6N HCl to pH=2.0. The aqueous layer was extracted with ether (3×), brine, dried over sodium sulfate. After concentration, the desired acid was isolated (68.3 g).

Step B:

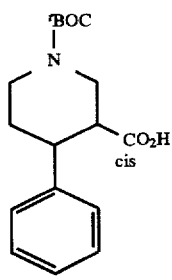

The title compound was prepared from the intermediate obtained in Step A (68.3 g, 225 mmole) which was dissolved in 300 ml of methanol, hydrogenated over Pd(OH)$_2$ (3.7 g) at 40 psi for 6 hours and then one atmosphere for 16 hours. The mixture was filtered through Celite to remove Pd catalyst. The filtrate was concentrated under vacuum to give the cis acid (68.9 g).

Step C:

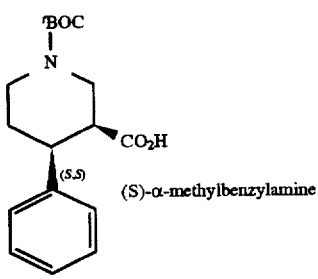

The title compound was prepared from the intermediate obtained in Step B (68.9 g) and (S)-a-methylbenzylamine (28.9 ml, 225 mmole) which were dissolved in methanol with heating. The solution was left in refrigerator for 16 hours and the crystals which were formed were filtered off (25 g). Recrystallization in 1500 ml of ethyl acetate/methanol (5/1) after cooling in a refrigerator gave the desired amine salt (19 g). The stereochemistry of this compound was determined by X-ray crystallographic analysis.

Step D:

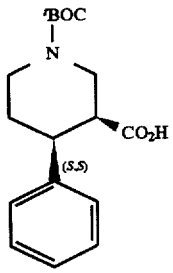

The intermediate from Step C (19 g) was suspended in 1N HCl and was extracted with ether. The extracts were combined, dried over sodium sulfate, and evaporated to give a white solid. (13.6 g).

Step E:

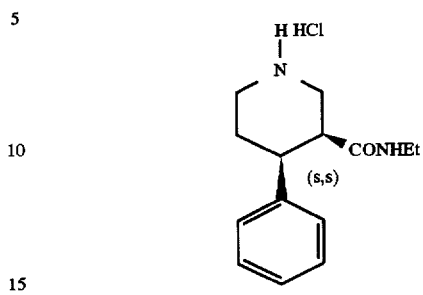

The title compound was prepared from the intermediate obtained from Step D (1.05 g) in chloroform to which was added ethylamine hydrochloride (697 mg), EDC (1.3 g), N-methylmorpholine (1.0 ml) and a small amount of DMF. After 12 hours, the mixture was diluted with methylene chloride and then washed with 1N HCl, water and brine. The organic layer was dried over magnesium sulfate, filtered and concentrated. The residue was purified by chromatatron (hexanes/ethyl acetate=1/1) to give the coupling product. To this coupling product in ethyl acetate at 0° C. was bubbled HCl gas until it was saturated. The mixture was stirred at room temperature for 10 minutes and was evaporated to dryness to give a desired product (990 mg).

Step F:

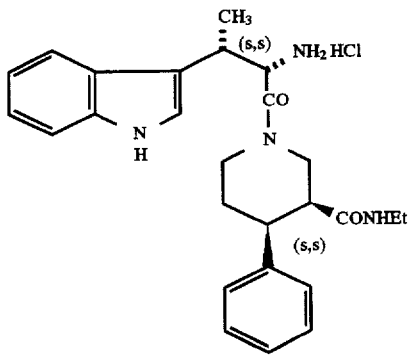

To the intermediate prepared from Step E (149 mg) in chloroform was added N-BOC-β-(S)-methyl-(L)-trp (147 mg), EDC (176 mg), HOBt (75 mg) and triethylamine (0.17 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/3) to give coupling product. To this coupling product in ethyl acetate at 0° C. was bubbled HCl gas until it was saturated. The mixture was stirred at room temperature for 10 minutes and was evaporated to give a desired product (170 mg).

Step G:

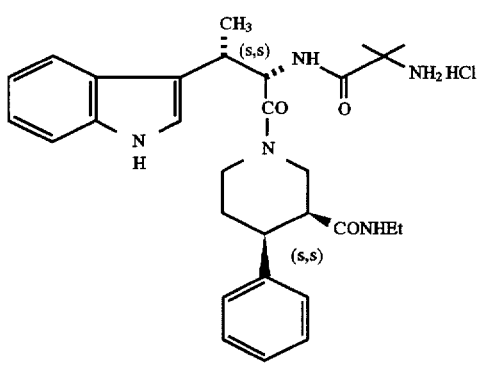

To the intermediate prepared from Step F (36 mg) in chloroform was added N-BOC-α-methyl-Ala (15 mg), EDC (29 mg), HOBt (12 mg) and triethylamine (0.035 ml). After 12 hours stirring at room temperature, the mixture was poured into 1N HCl and extracted with methylene chloride, dried over sodium sulfate, filtered and concentrated. The residue was purified by PLC (hexanes/ethyl acetate=1/2) to give coupling product. To this coupling product in ethyl acetate at 0° C. was bubbled HCl gas until it was saturated. The mixture was stirred at room temperature for 10 minutes and was evaporated to dryness to give a desired product (25 mg). $^1$H NMR (400 MHz, CD3OD, mixture of rotamers): 7.68 (d, 8 Hz, 1H), 7.33–7.01 (m, 9H), 5.36 (d, 9 Hz, 1H), 4.82 (m, 1H), 4.42 (m, 1H), 3.68 (m, 1H), 3.21 (m, 1H), 3.10 (m, 2H), 2.90–2.73 (m, 4H), 1.64 (m, 1H), 1.50 (s, 3H), 1.36 (d, 7 Hz, 3 H), 0.91 (s, 3H), 0.80 (t, 7 Hz, 3H). FAB-MS: 518.4 (M+1).

EXAMPLE 80

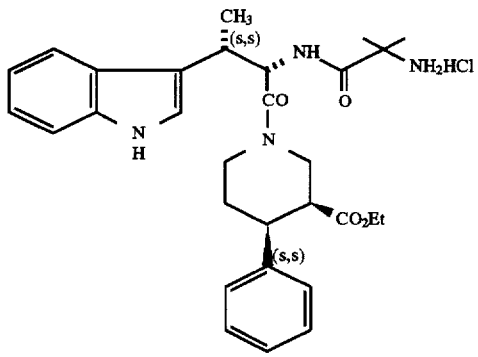

Step A:

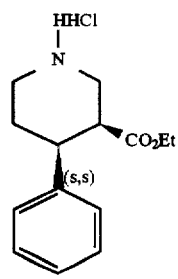

To the intermediate from Example 79, Step D (1.11 g) in ethanol was added thionyl chloride (457 mg) and this solution was refluxed for 48 hours. The mixture was concentrated to dry to give the desired product as a white solid. (960 mg).

Step B:

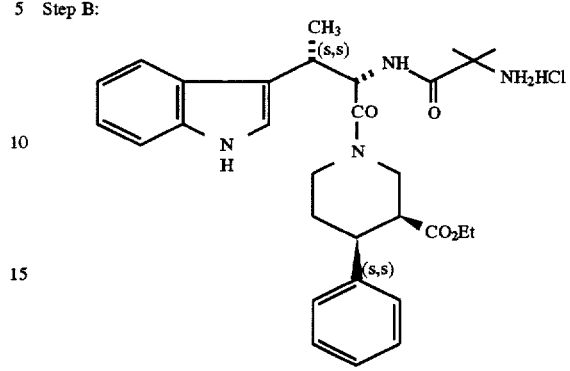

The title compound was prepared from the intermediate obtained from Step A by the procedure described in Example 79, Step F and G to give the desired compound. FAB-MS: 519.5 (M+1).

EXAMPLE 81

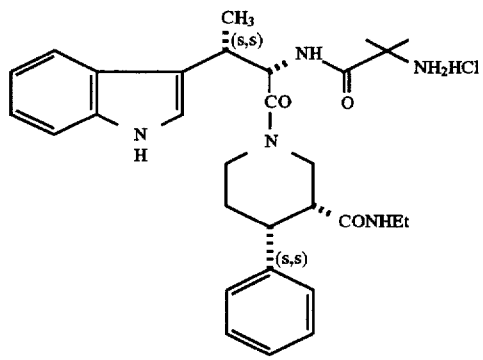

Step A:

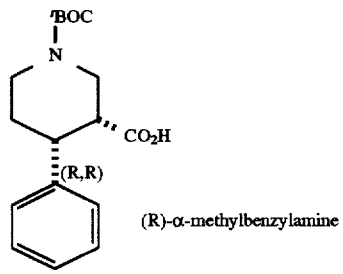

(R)-α-methylbenzylamine

The mother liquid left from Example 79, Step C was concentrated to give off white solid (68 g), which was dissolved in 1N NaOH and was extracted with methylene chloride. The organic layer was discarded. The aqueous layer was acidified with conc. HCl at 0° C. to pH=1.0 to form a white crystalline precipitate. After stirring at 0° C. for 10 minutes, the mixture was filtrated and the solid was collected. The white solid was dried under nitrogen to give 28 g of acid, which was dissolved in hot methanol and (R)-α-methylbenzylamine (11.12 g) was added. The solution was left in the refrigerator for 16 hours and the crystals which were formed were filtered off (15 g).

Step B:

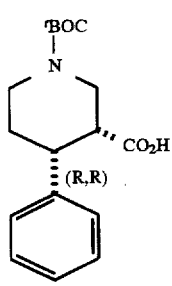

The intermediate from Step A (4.3 g) was suspended in 1N HCl and was extracted with ether. The extracts were combined, dried over sodium sulfate, and evaporated to give a white solid. (3.0 g).

Step C:

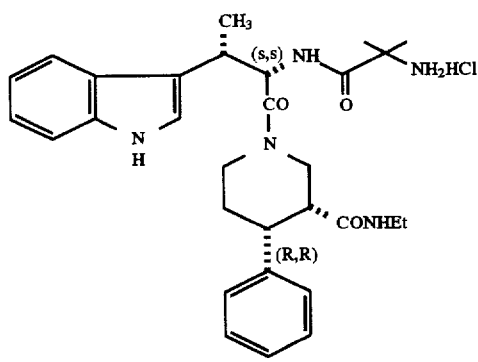

The title compound was prepared from the intermediate obtained from Step B by the procedure described in Example 79, Steps E, F and G to give the desired compound. FAB-MS: 518.4 (M+1).

EXAMPLE 82

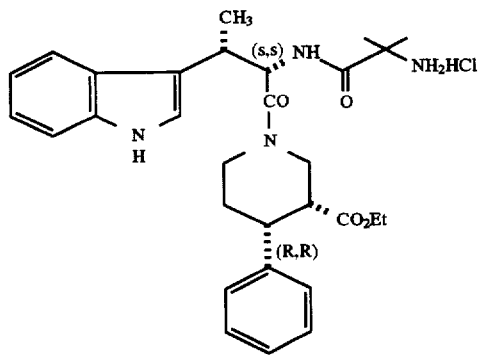

The title compound was prepared from the intermediate obtained from Example 81, Step B by the procedure described in Example 80, Steps A and Example 79, Steps F, and G to give the desired compound. FAB-MS: 519.5 (M+1).

EXAMPLE 83

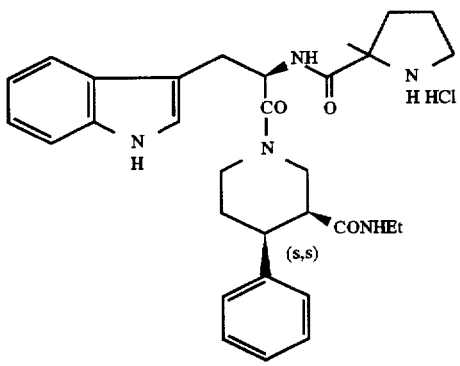

The title compound was prepared from the intermediate obtained from Example 79, Step E by the procedure described in Example 79, Step F (using N-Boc-(D)-Trp instead of N-BOC-β(S)-methyl-(L)-Trp) and G (using N-Boc-α-methyl-Pro instead of N-BOC-α-methyl-Ala) to give the desired compound. FAB-MS: 530.3 (M+1).

EXAMPLE 84

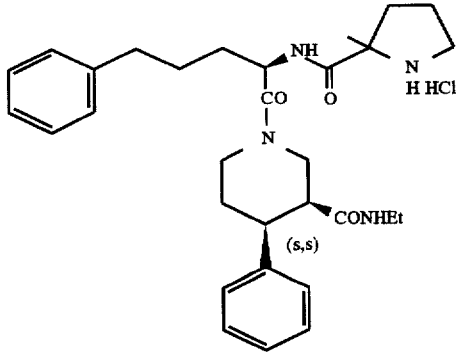

The title compound was prepared from the intermediate obtained from Example 79, Step E by the procedure described in Example 79, Step F (using (D)-N-Boc-2-amino-5-phenylpentanoic acid instead of N-BOC-β-(S)-methyl-(L)-Trp) and G (using N-Boc-α-methyl-Pro instead of N-BOC-α-methyl-Ala) to give the desired compound. FAB-MS: 519.4 (M+1).

EXAMPLE 85

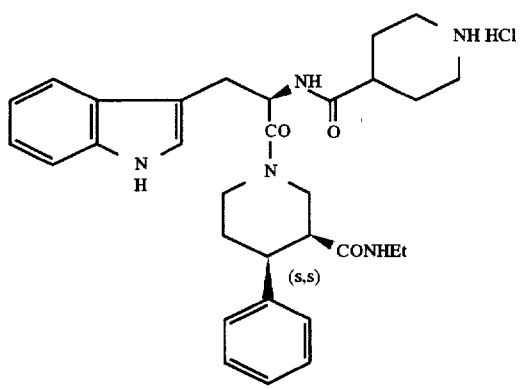

The title compound was prepared from the intermediate obtained from Example 79, Step E by the procedure described in Example 79, Step F (using N-Boc-(D)-Trp instead of N-BOC-β-S-methyl-(L)-Trp) and G (using N-Boc-isonipecotic acid instead of N-BOC-α-methyl-Ala) to give the desired compound. FAB-MS: 530.5 (M+1).

EXAMPLE 86

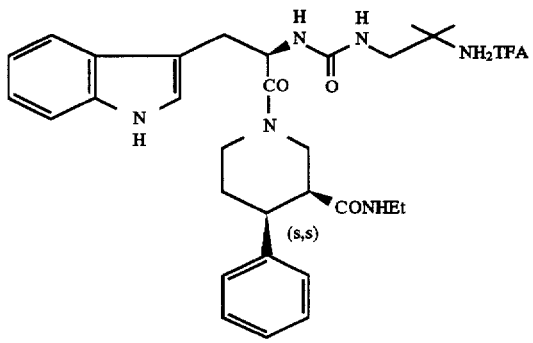

Step A:

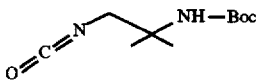

To a solution of 3-t-butyloxycarbonylamino-3-methylbutanoic acid (753 mg) in chloroform was added triethylamine (0.97 ml), and ethyl chloroformate (0.37 ml) at 0° C. After ½ hour stirring, the mixture was poured into 1N HCl and extracted with methylene chloride, dried over sodium sulfate, filtrated and concentrated. To this residue in acetone (7 ml) was added sodium azide (1.1 g) in water (7 ml) at room temperature. After stirring for 45 minutes the reaction mixture was poured into ether and washed with water and brine. The organic layer was dried over magnesium sulfate, filtered and concentrated. The residue was dissolved in 10 mL of toluene which was refluxed for ½ hour and then concentrated to give the isocyanate (727 mg).

Step B:

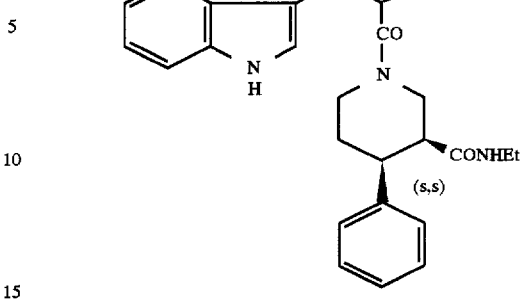

To the intermediate prepared from Example 79, Step E (253 mg) in chloroform was added N-BOC-(D)-trp (343 mg), EDC (359 mg), HOBt (153 mg) and triethylamine (0.29 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/3) to give coupling product (460 mg). To this coupling product in ethyl acetate at 0° C. was bubbled HCl gas until it was saturated. The mixture was stirred at room temperature for 10 minutes and was evaporated to give the desired product (349 mg). To the amine HCl salt in water there was added 1N NaOH and extracted with chloroform and washed with brine. The organic layer was dried over sodium sulfate, filtered and concentrated to give the desired product.

Step C:

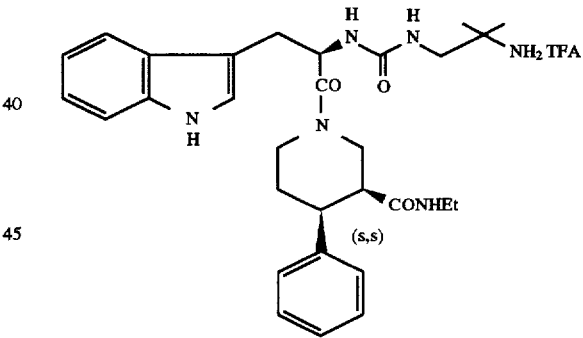

To the intermediate prepared from Step B (29 mg) in toluene there was added the intermediate prepared from Step A (45 mg). This solution was refluxed for 4 hours and the mixture was concentrated. The residue was purified by PLC (methylene chloride/methanol=20/1) to give desired product to which was added TFA at room temperature and stirred for 10 minutes. The mixture was concentrated and azeotroped with toluene (3×) to give the desired product as a off white solid (36 mg). $^1$H NMR (400 Hz, $CD_3OD$, mixture of rotamers): 7.66 (d, 8 Hz, 1/3H), 7.54 (d, 8 Hz, 2/3H), 7.35–6.97 (m, 9H), 5.07 (m, 1/3H), 4.73 (m, 2/3H), 4.58 (m, 2/3H), 4.25 (m, 1/3H), 3.73 (m, 1/3H), 3.45–2.47 (m, 10H), 2.31 (m, 2/3H), 1.77 (m, 1/3H), 1.57 (m, 2/3H), 1.32 (s, 6H), 1.22 (m, 1H), 0.89 (t, 7 Hz, 3/3H), 0.81 (t, 7 Hz, 6/3H), 0.72 (t, 7 Hz, 3/3H).

FAB-MS: 533.5 (M+1).

EXAMPLE 87

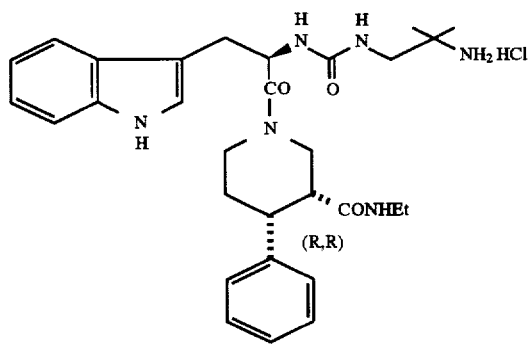

The title compound was prepared from the intermediate obtained from Example 81, Step B by the procedure described in Example 79, Step E and Example 86, Steps B and C to give the desired product. FAB-MS: 535.5 (M+1).

EXAMPLE 88

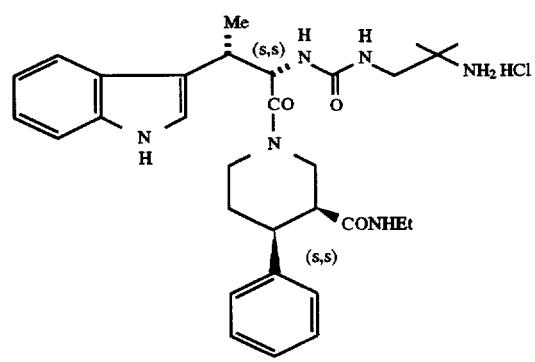

The title compound was prepared from the intermediate obtained from Example 79, Step E by the procedure described in Example 86, Step B (using N-BOC-β-(S)-methyl-(L)-Trp instead of N-BOC-(D)-Trp) and Step C to give the desired product. FAB-MS: 547.5 (M+1).

EXAMPLE 89

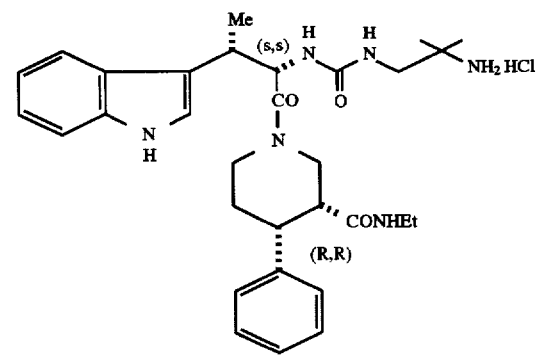

The title compound was prepared from the intermediate obtained from Example 81, Step B by the procedure described in Example 79, Step E and Example 86, Step B (using N-BOC-β-(S)-methyl-(L)-Trp instead of N-BOC-(D)-Trp) and Step C to give the desired product. FAB-MS: 547.5 (M+1).

EXAMPLE 90

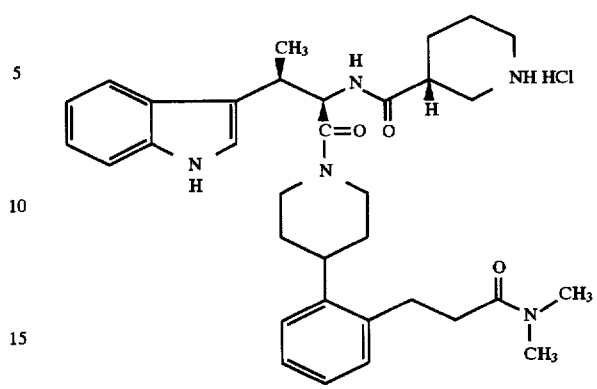

Step A:

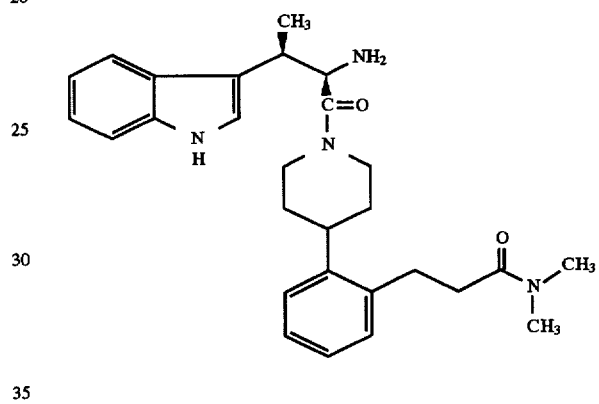

To a solution of 1.0 g of (2R) β-methyl (D)-tryptophan in 20 mL of dichloromethane was added 1.05 g of the piperidine intermediate prepared in Example 1 Step B, 0.80 mL of N-methylmorpholine, 0.57 g of HOBT and 0.84 g of EDC and stirred at room temperature for 18 h. The reaction mixture was diluted with 50 mL of dichloromethane and washed with 10% aqueous citric acid (25 mL), 25 mL of saturated NaHCO$_3$ solution, dried over MgSO$_4$ and concentrated. This ester intermediate was dissolved in 15 mL of dioxane and 5 mL of water at 0° C. and treated with 0.40 g of lithium hydroxide for 4 h. The reaction mixture was acidified to pH=2 with 10% aqueous citric acid and extracted with dichloromethane (2×20 mL). The combined organics were washed with 25 mL of brine, dried over MgSO$_4$ and concentrated. This acid intermediate was coupled with dimethylamine using the peptide-type coupling method described above. The BOC protecting group was removed by treating the dimethylamide intermediate with 20 mL of trifluoroacetic acid and 3 mL of dichloromethane for 1h. The volatiles were removed under reduced pressure and the residue was taken up in 50 mL of dichloromethane and washed with saturated sodium carbonate solution till pH of the aqueous layer was about 8.00. The organic phase was dried over K$_2$CO$_3$ and concentrated to give 1.47 g of the title compound as a pale yellow solid.

Step B:

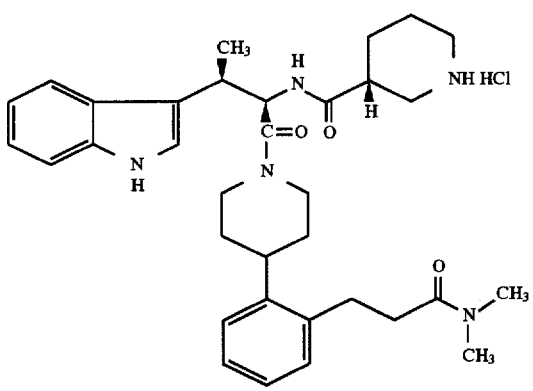

To a solution of 25 mg of the intermediate from Step A was added 15 mg of (R)-N-tBoc-nipecotic acid, 15 mg of HOBT and 25 mg of EDC and stirred for 18 h. The reaction was worked-up as described in Step A and the residue was purified by flash chromatography (10 g of silica gel) with CH$_2$Cl$_2$-acetone (5:1) as the eluent to give 28 mg of the coupled product. This material was dissolved in 2 mL of ethyl acetate and HCl(gas) was bubbled into the solution for 1 min. After 30 min ether was added and the precipitate was collected by filtration under nitrogen. The desired material is a colorless solid. Key resonances in 1H NMR (CD$_3$OD; mixture of rotamers) 8.23 and 8.20 (2d, 1H), 7.80 and 7.65 (2d, 1H), 7.38 (d, 1H), 7.23–7.00 (m, 7H), 5.40 and 5.20 (2t, 1H), 4.73–4.60 (m, 2H), 2.90, 2.88, 2.86, 2.85 (4s, 6H), 1.50 and 1.40 (2d, 3H).

EXAMPLE 91

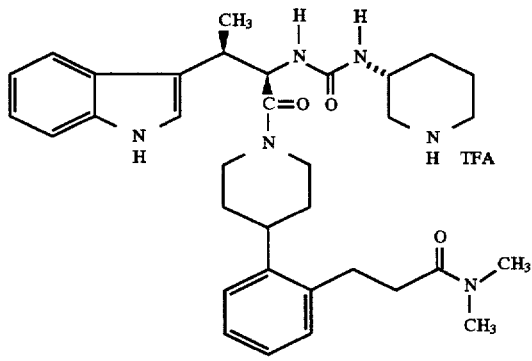

To a solution of 0.10 g of the intermediate synthesized in Step A of Example 90 in 5 mL of dichloromethane was added 1 mL of a 0.3M solution of (R)-[2-N-tBoc-piperidinyl]isocyanate and stirred at room temperature for 18 h. The reaction mixture was diluted with 10 mL of dichloromethane and washed with 0.1N aqueous HCl solution, saturated NaHCO$_3$ solution, brine, dried over MgSO$_4$ and concentrated. The residue was purified by flash chromatography with hexane-acetone (2:1) as the eluent to give the urea compound as a colorless foam. Deprotection of N-tBoc group was carried out under the standard TFA-dichloromethane conditions to give the title compound as a pale yellow. Key resonances in $^1$H NMR (CD$_3$OD; mixture of rotamers) 7.80 (d, 1H), 7.55 (d, 1H), 7.38 (d, 2H), 7.25–6.90 (m, 5H), 5.30 and 5.10 (2d, 1H), 4.60–4.50 (m, 2H), 4.00 (bd, 1H), 3.90–3.70 (m, 2H), 3.60–3.50 (m, 2H), 3.00 and 2.98(2s, 3H), 1.48 and 1.40 (d, 3H). FAB MS calcd. for C34H46N6O3 586; found 587.4(m+1)

EXAMPLE 92

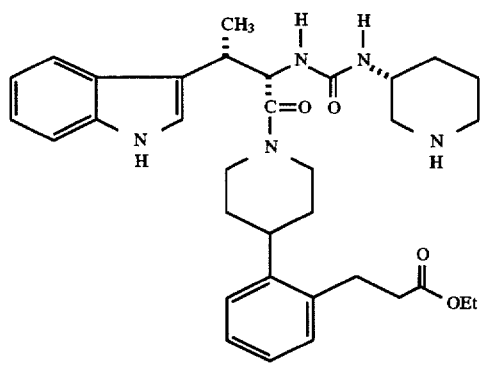

Step A:

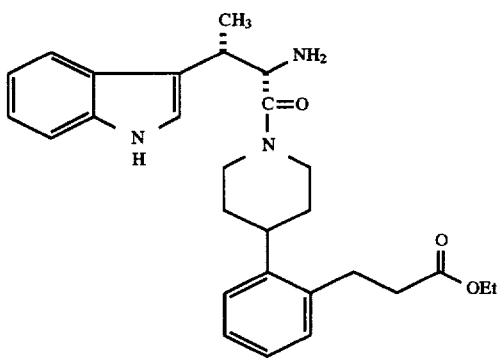

The above intermediate was prepared essentially as described in Step A of Example 90.

Step B:

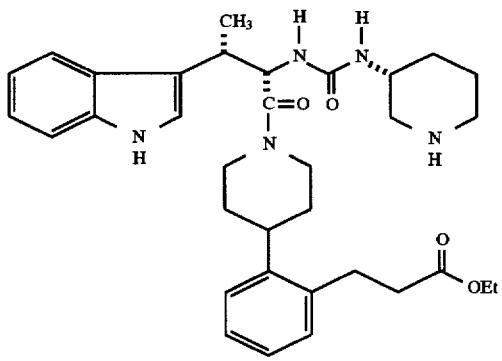

The title compound was synthesized essentially as described in Example 91. Key resonances in $^1$H NMR (CD$_3$OD; mixture of rotamers) 7.80 and 7.65 (2d, 1H), 7.32 (d, 1H), 7.30–7.00 (m, 7H), 5.50 and 5.35 (2d, 1H), 4.80–4.65 (bt, 2H), 4.18–4.00 (2q, 2H), 3.1–2.90 (m, 2H), 2.65–2.50 (m, 2H), 1.49 and 1.40 (2 d, 3H), 1.30–1.10 (2t, 3H).

FAB MS calcd. for C34H47N6O3 587; found 588.7(m+1)

EXAMPLE 93

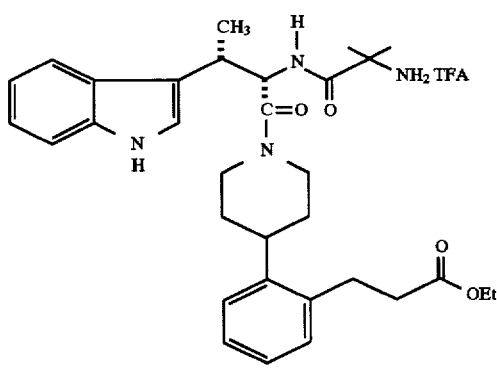

The title compound was prepared by coupling the amine intermediate synthesized in Step A of Example 92 with N-tBoc-amino isobutyric acid (N-tBoc AIB) under standard peptide-type coupling conditions and then deprotecting the Boc group with HCl(gas) in ethyl acetate. Key resonances in $^1$H NMR (CD$_3$OD; mixture of rotamers) 7.80 and 7.65 (2d, 1H), 7.32 (d, 1H), 7.30–7.00 (m, 7H), 5.50 and 5.35 (2d, 1H), 4.80–4.65 (bt, 2H), 4.18–4.00 (2q, 2H), 3.1–2.90 (m, 2H), 2.65–2.50 (m, 2H), 1.49 and 1.40 (2 d, 3H), 1.48 (2s, 6H), 1.30–1.10 (2t, 3H).

FAB MS calcd. for C32H42N4O4 546; found 547.3(m+1)

EXAMPLE 94

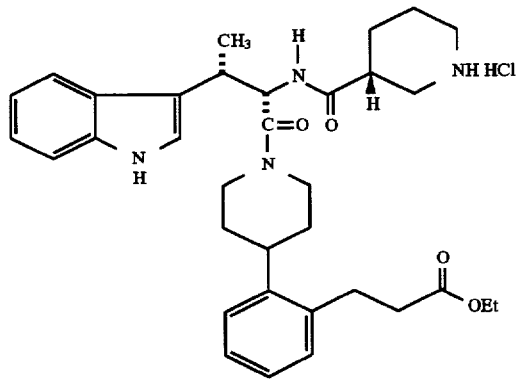

The title compound was prepared from the intermediate synthesized in Step A of Example 92 by using methodology described in Example 90. The BOC protecting was removed by the HCl/ethyl acetate method. Key resonances in $^1$H NMR (CD$_3$OD; mixture of rotamers) 7.80 and 7.65 (2d, 1H), 7.45 (d, 1H), 7.30–7.00 (m, 7H), 5.45 and 5.35 (2d, 1H), 4.80–4.65 (bt, 2H), 4.45–4.00 (m, 4H), 3.1–2.90 (m, 2H), 2.65–2.50 (m, 2H), 1.49 and 1.40 (2 d, 3H), 1.30–1.10 (2t, 3H). FAB MS calcd. for C34H44N4O4 572; found 573.3(m+1)

EXAMPLE 95

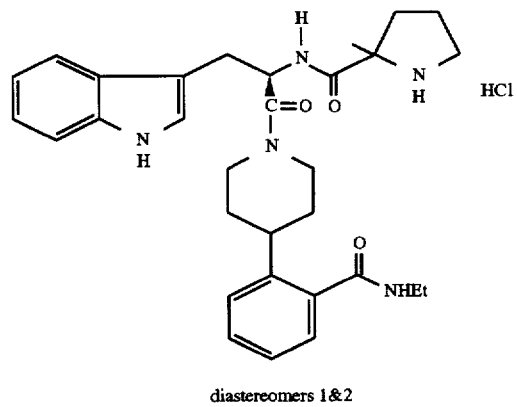

diastereomers 1&2

Step A:

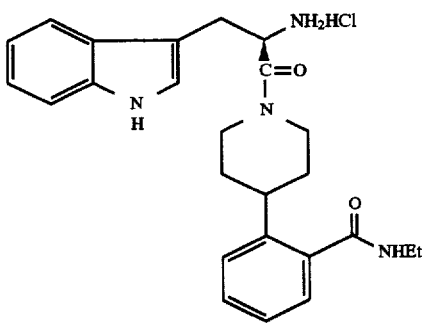

The above intermediate was synthesized by coupling N-tBOC-(D)-Trp with 4-[(2-carboxamidoethyl)phenyl]piperidine hydrochloride under standard peptide-type coupling conditions and then deprotecting the BOC group by the HCl/ethyl acetate procedure.

Step B:

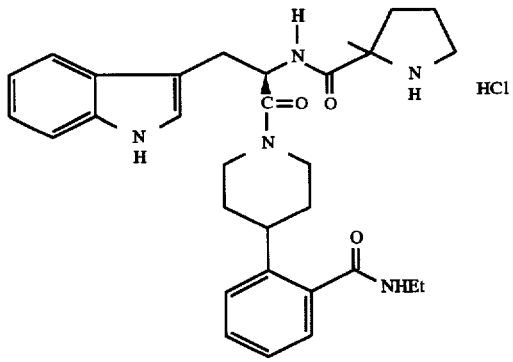

diastereomers 1 & 2

To a solution of 0.20 g of the intermediate from StepA in 5 mL of chloroform was added 0.10 g of N-tBOC-(DL-)-α-methylproline, 0.10 mL of N-methylmorpholine, 0.11 g of EDC and 0.06 g of HOBT and stirred at room temperature for 4 h. The reaction mixture was washed with 0.50N HCl, NaHCO$_3$ solution, brine, dried over MgSO$_4$ and concentrated. The residue was purified by flash chromatography (hexane-acetone 3:1 as the eluent) to give the two separated diastereomers designated as d1 and d2. These compounds was treated with HCl in ethyl acetate separately to provide the individual diastereomers of the title compound. Diastereomer d1: Key resonances in $^1$H NMR (CD$_3$OD; mixture of rotamers) 7.60 and 7.50 (2d, 1H), 7.40–7.00 (m, 7H), 6.65 (d, 1H), 5.25–5.20 (m, 1H), 4.55 and 4.45 (2d, 1H), 3.90 and 3.85 (2d, 1H), 3.40–3.28 (m, 5H), 3.22 (dd, 1H), 1.70 and 1.60 (2s, 3H), 1.15 (2t, 3H), 0.70 and −0.10 (2dq, 1H). Diastereomer d2: FAB MS calcd. for C31H39N5O3 529; found 530.4 (m+1).

EXAMPLE 96

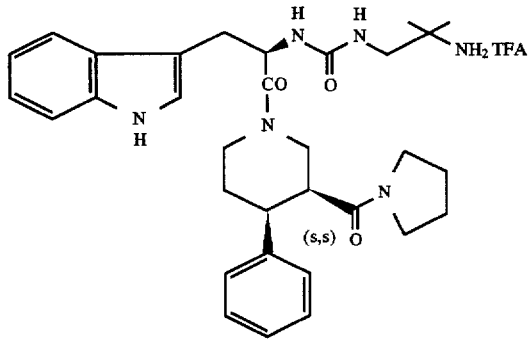

Step A:

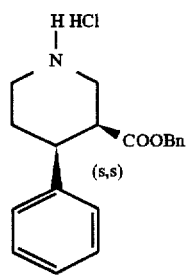

The title compound was prepared from the intermediate obtained from Example 79, Step D (2.0 g) in chloroform to which was added benzyl alcohol (0.69 ml), EDC (1.5 g) and DMAP (80 mg). After 12 hours, the mixture was diluted with methylene chloride and then washed with 1N HCl, water and brine. The organic layer was dried over magnesium sulfate, filtered and concentrated. The residue was purified by chromatatron (hexanes/ethyl acetate=10/1) to give the coupling product. To this coupling product in ethyl acetate at 0° C. was bubbled HCl until it was saturated. The mixture was stirred at room temperature for 10 minutes and was evaporated to dryness to give a desired product (2.03 g).

Step B:

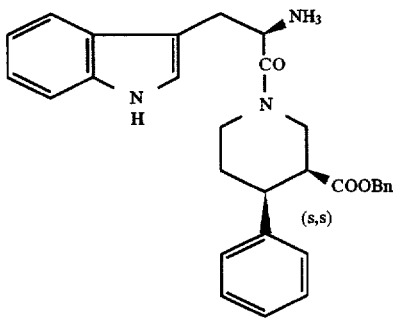

To the intermediate prepared from Step A (942 mg) in chloroform was added N-BOC-(D)-Trp (1.03 g), EDC (1.08 g), HOBt (460 mg) and triethylamine (1.2 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/1) to give coupling product. To this coupling product in ethyl acetate at 0° C. was bubbled HCl gas until it was saturated. The mixture was stirred at room temperature for 10 minutes and was evaporated. The residue was diluted with 1N NaOH and extracted with methylene chloride. The organic layer was dried over sodium sulfate, filtered and concentrated to give a desired product (1.2 g).

Step C:

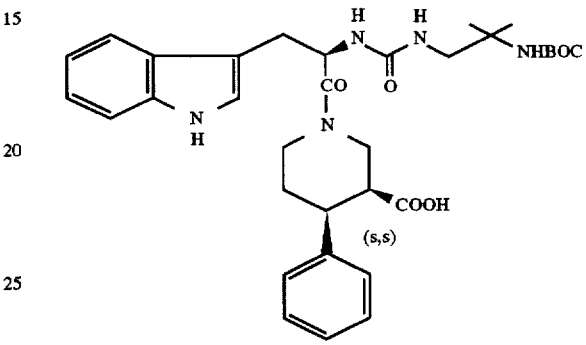

To the intermediate prepared from Step B (1.2 g) in toluene there was added the intermediate prepared from Example 86, Step A (1.07 g). This solution was refluxed for 4 hours and the mixture was concentrated. The residue was purified by chromatatron (hexanes/ethyl acetate=1/3) to give the desired product to which was dissolved in methanol, and hydrogenated over Pd(OH)$_2$ at one atmosphere for ½ hours. The mixture was filtered through Celite to remove Pd catalyst. The filtrate was concentrated and purified by chromatatron (hexanes/ethyl acetate/acetic acid=2/1/0.2) to give the title compound (430 mg).

Step D:

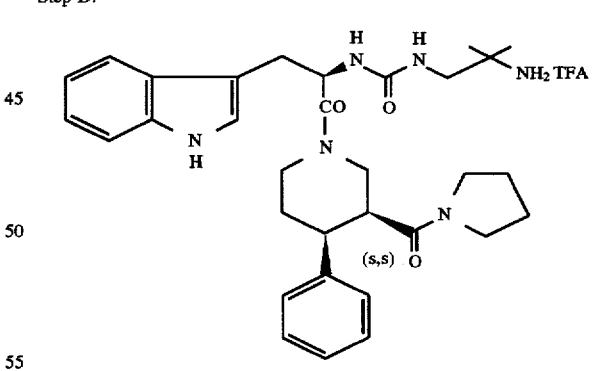

The title compound was prepared from the intermediate obtained from Step C (40 mg) in chloroform to which was added pyrrolidine(0.017 ml), EDC (38 mg) and DMAP (0.8 mg). After ½ hours, the mixture was diluted with methylene chloride and then washed with 1N HCl, water and brine. The organic layer was dried over magnesium sulfate, filtered and concentrated. The residue was purified by PLC (hexanes/ethyl acetate=1/5) to give the desired product to which was added TFA at room temperature and stirred for 10 minutes. The mixture was concentrated and azeotroped with toluene (3×) to give the desired as a off white solid (15 mg). $^1$H NMR (400 Hz, CD3OD, mixture of rotamers): 7.65 (d, 8 Hz, 1/3H), 7.57 (d, 8 Hz, 2/3H), 7.36–6.99 (m, 9H), 5.07 (m, 1/3H), 4.73 (m, 2/3H), 4.55 (m, 2/3H), 4.30 (m, 1/3H), 3.70 (m, 1/3H), 3.50–2.47 (m, 12H), 2.27 (m, 2/3H), 1.75–1.40 (m, 5H), 1.31 (s, 6H). FAB-MS: 559.4 (M+1).

The compounds shown in Table 11 were prepared according to the above procedures employing the appropriate amine.

TABLE 11

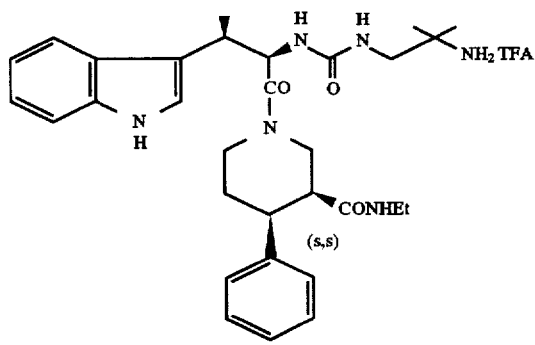

| R | FAB-MS (M + 1) |
|---|---|
| Me | 519.3 |
| n-Pro | 547.5 |
| i-Bu | 562.5 |

EXAMPLE 97

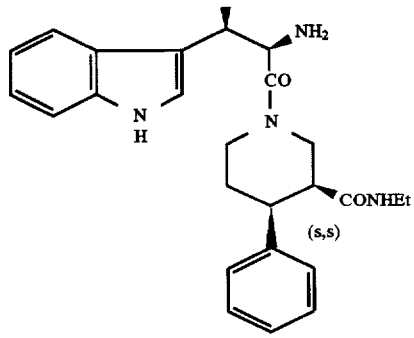

Step A:

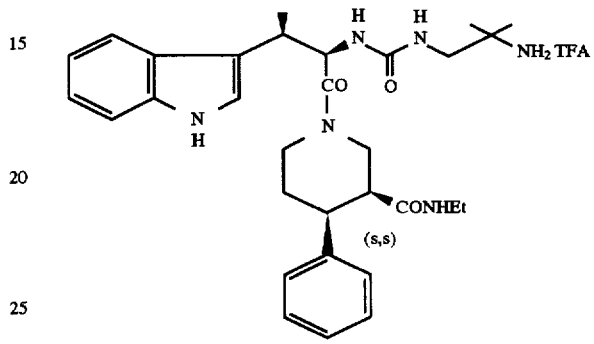

To the intermediate prepared from Example 79, Step E (460 mg) in chloroform was added N-BOC-β-(R)-methyl-(D)-Trp (648 mg), EDC (654 mg), HOBt (275 mg) and triethylamine (0.7 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/3) to give coupling product. To this coupling product in ethyl acetate at 0° C. was bubbled HCl gas until it was saturated. The mixture was stirred at room temperature for 10 minutes and was evaporated to give the desired product (752 mg). To amine HCl salt (640 mg) in water was added 1N NaOH and extracted with chloroform and washed with brine. The organic layer there was dried over sodium sulfate, filtered and concentrated to give the desired product (410 mg).

Step B:

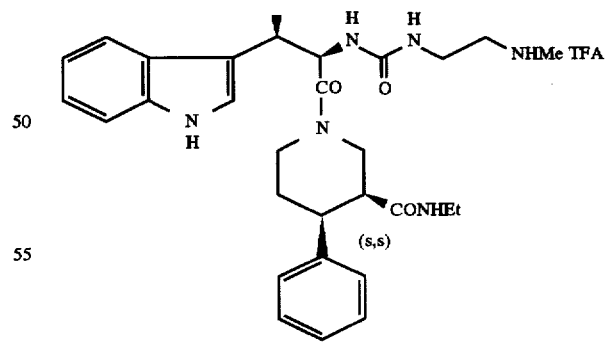

To the intermediate prepared from Step A (94 mg) in toluene there was added the intermediate prepared from Example 86, Step A (70 mg). This solution was refluxed for 4 hours and the mixture was concentrated. The residue was purified by PLC (methylene chloride/methanol=20/1) to give desired product to which was added TFA at room temperature and stirred for 10 minutes. The mixture was concentrated and azeotroped with toluene (3×) to give the desired product as a off white solid (72 mg). $^1$H NMR (400 Hz, CD$_3$OD, mixture of rotamers): 7.76 (m, 1H), 7.34–6.98 (m, 9H), 5.05 (m, 2/3H), 4.70 (m, 1/3H), 4.60 (m, 2/3H), 4.03 (m, 1/3H), 3.55–2.67 (m, 10 1/3H), 2.55 (m, 1H), 2.31 (m, 2/3H), 1.57 (m, 1H), 1.55 (d, 7 Hz, 3/3H), 1.36 (d, 7 Hz, 6/3H), 1.31 (s, 6/2H), 1.30 (s, 6/2H), 0.89 (t, 7 Hz, 3/3H), 0.82 (t, 7 Hz, 3/3H), 0.72 (t, 7 Hz, 6/3H). FAB-MS: 547.5 (M+1).

EXAMPLE 98

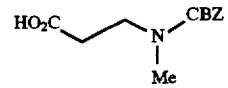

Step A:

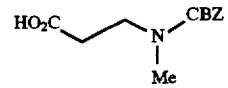

To a suspension solution of oil free NaH (144 mg) in THF (20 ml) was added CBZ-β-Ala-OMe (1.19 g) in THF (10 ml)

slowly at room temperature. After 30 minutes stirring, the mixture was added MeI (0.37 ml) and then stirred for another 30 minutes. The mixture was poured into water and extracted with ether, dried over sodium sulfate, filtered and concentrated. The mixture was purified by chromatatron (hexanes/ethyl acetate=6/1). To this residue in methanol was added 6N NaOH and stirred for 30 minutes. The mixture was poured into water and extracted with ether. The organic layer was discarded. The aqueous layer was acidified with 6N HCl to pH=1.0 and extracted with ether. The organic layer was washed with brine, dried over sodium sulfate, filtered and concentrated to give the desired product (603 mg).

Step B:

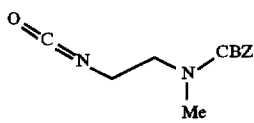

To the intermediate prepared from Step A (603 mg) in methylene chloride was added triethylamine (0.7 ml), and ethyl chloroformate (0.29 ml) at 0° C. After 1 hour stirring, the mixture was poured into 1N HCl and extracted with methylene chloride, dried over sodium sulfate, filtered and concentrated. To this residue in acetone (7 ml) was added sodium azide (812 mg) in water (7 ml) at room temperature. After 10 minutes, this mixture was poured into ether and washed with water and brine. The organic layer was dried over magnesium sulfate, filtered and concentrated. The residue was dissolved in 10 ml of toluene which was refluxed for 1 hour to give the isocyanate (0.25N in toluene).

Step C:

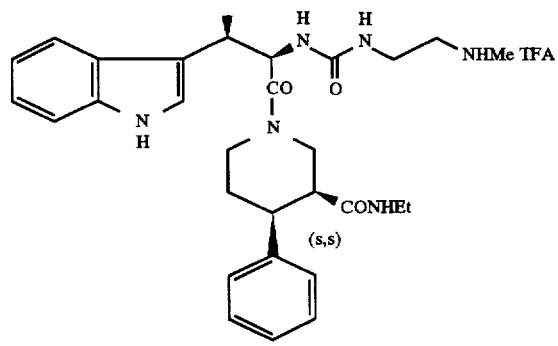

To the intermediate prepared from Example 97, Step B (43 mg) in toluene there was added the intermediate prepared from Step B (0.8 ml). This solution was stirred for 60 hours at room temperature and the mixture was concentrated. The residue was purified by PLC (100% ethyl acetate) to give desired product. The resulting material was dissolved in methanol and hydrogenated over Pd(OH)$_2$ at one atmosphere for 15 minutes. The mixture was filtered through Celite to remove Pd catalyst. The filtrate was concentrated and re-dissolved in methylene chloride to which was added TFA at room temperature. The mixture was concentrated and azeotroped with toluene (3×) to give the desired product as a off white solid (40 mg). $^1$H NMR (400 Hz, CD$_3$OD, mixture of rotamers): 7.74 (m, 1H), 7.34–6.98 (m, 9H), 5.05 (m, 2/3H), 4.70 (m, 1/3H), 4.55 (m, 2/3H), 4.03 (m, 1/3H), 3.55–2.47 (m, 12 1/3H), 2.68 (s, 3H), 2.27 (m, 2/3H), 1.57 (m, 1H), 1.55 (d, 7 Hz, 3/3H), 1.36 (d, 7 Hz, 6/3H), 0.89 (t, 7 Hz, 3/3H), 0.82 (t, 7 Hz, 3/3H), 0.75 (t, 7 Hz, 6/3H).

FAB-MS: 533.4 (M+1).

EXAMPLE 99

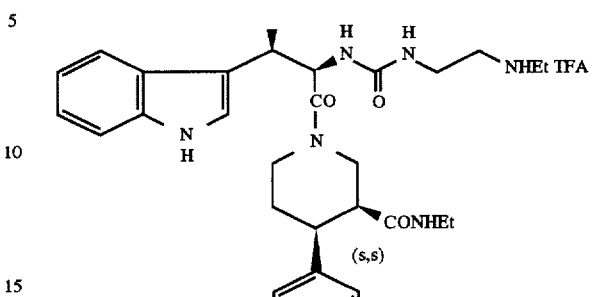

Step A:

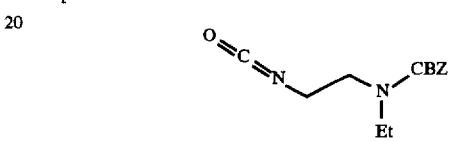

To a solution of CBZ-β-Ala-OMe (1.19 g) in THF (20 ml) was added potassium bis(trimethylsilyl)amide (0.5N in toluene) slowly at −78° C. After 30 minutes stirring, the mixture was added EtI (1.2 ml) and then heated the reaction for 12 hours. The mixture was poured into water and extracted with ether, dried over sodium sulfate, filtered and concentrated. The mixture was purified by chromatatron (hexanes/ethyl acetate=6/1). To this residue in methanol was added 6N NaOH and stirred for 60 minutes. The mixture was poured into water and extracted with ether. The organic layer was discarded. The aqueous layer was acidified with 6N HCl to pH=1.0 and extracted with ether. The organic layer was washed with brine, dried over sodium sulfate, filtered and concentrated to give the acid (560 mg). This acid was converted to corresponding isocyanate by the procedure described in Example 98, Step B.

Step B:

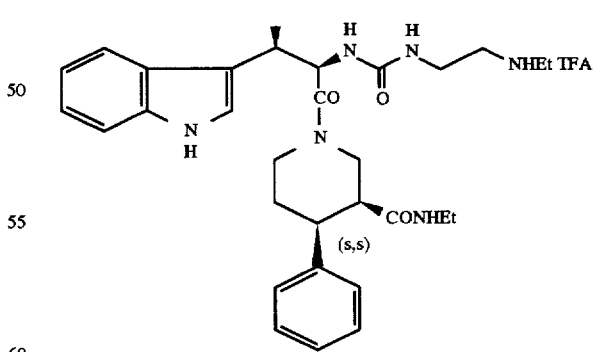

The title compound was prepared from the intermediate obtained from Example 97, Step B (74 mg) and the isocyanate obtained from Step A, by the procedure described in Example 98, Step C to give the desired product (29 mg). FAB-MS: 547.4 (M+1).

EXAMPLE 100

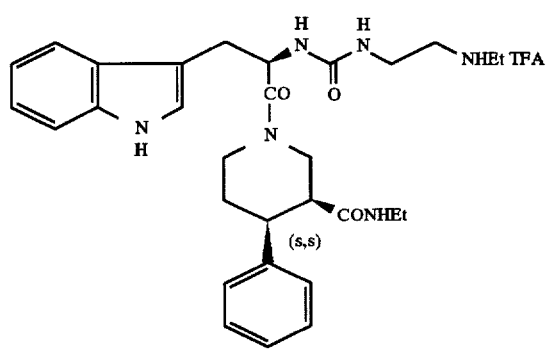

The title compound was prepared from the intermediate obtained from Example 86, Step B (71 mg) and the isocyanate obtained from Example 99, Step A, by the procedure described in Example 98, Step C to give the desired product (62 mg). FAB-MS: 533.4 (M+1).

EXAMPLE 101

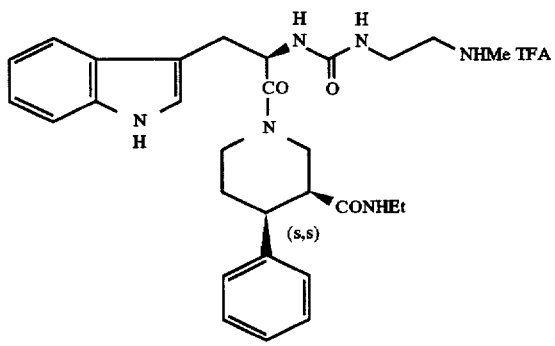

The title compound was prepared from the intermediate obtained from Example 86, Step B (43 mg) and the isocyanate obtained from Example 98, Step B, by the procedure described in Example 98, Step C to give the desired product (26 mg). FAB-MS: 519.4 (M+1).

EXAMPLE 102

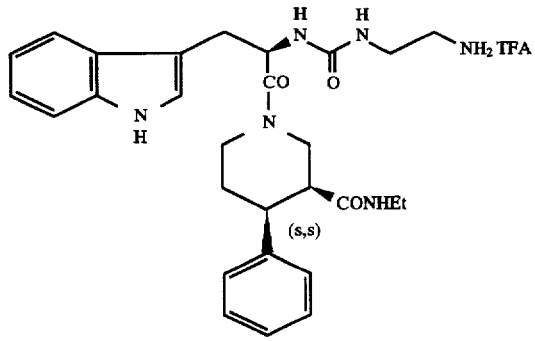

Step A:

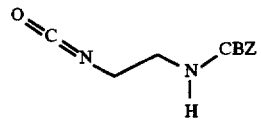

CBZ-β-Ala-OH was converted to the corresponding isocyanate by the procedure described in Example 98, Step B.

Step B:

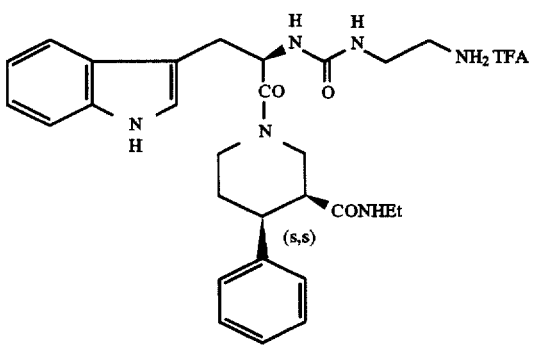

The title compound was prepared from the intermediate obtained from Example 86, Step B (43 mg) and the isocyanate obtained from Step A, by the procedure described in Example 98, Step C to give the desired product (48 mg). FAB-MS: 519.4 (M+1).

EXAMPLE 103

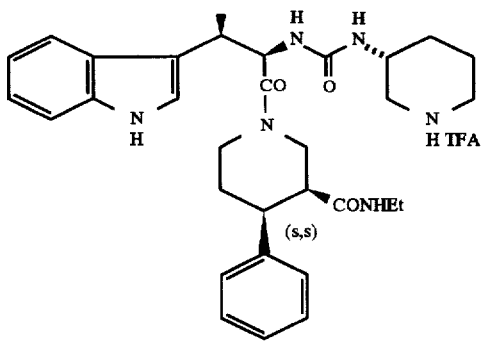

To the intermediate prepared from Example 86, Step A (43 mg) in toluene there was added (R)-[2-N-BOC-piperidinyl] isocyanate. This solution was heated to 60° C. for 1 hour and the mixture was concentrated. The residue was purified by PLC (100% ethyl acetate) to give desired product to which was added TFA at room temperature and stirred for 10 minutes. The mixture was concentrated and azeotroped with toluene (3×) to give the desired product (47 mg).

FAB-MS: 559.4 (M+1).

EXAMPLE 104

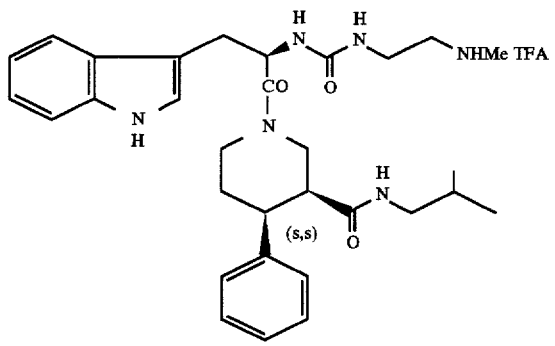

Step A:

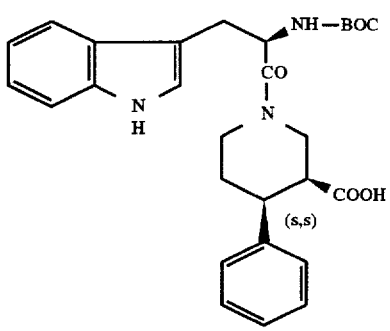

To the intermediate prepared from Example 96, Step A (960 mg) in chloroform was added N-BOC-(D)-Trp (1.06 g), EDC (1.1 g), HOBt (469 mg) and triethylamine (1.2 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/1) to give coupling product. To this coupling product in methanol was hydrogenated over Pd(OH)$_2$ at one atmosphere for 30 minutes. The mixture was filtered through Celite to remove Pd catalyst. The filtrate was concentrated under vacuum to give the desired product (1.42 g).

Step B:

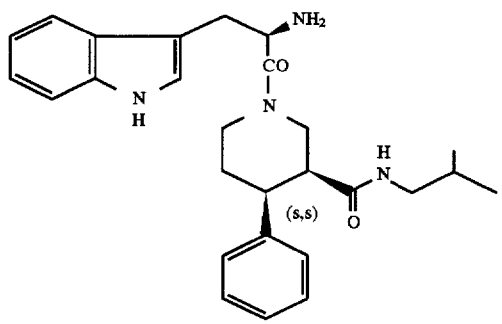

To the intermediate prepared from Step A (356 mg) in chloroform was added isobutylamine (0.15 ml), EDC (276 mg), DMAP (7 mg). After 12 hours stirring at room temperature, the mixture was poured into 1N HCl and extracted with methylene chloride, dried over sodium sulfate, filtered and concentrated. Purification of the residue (chromatatron, hexanes/ethyl acetate=1/2) gave the desired product. To this coupling product in ethyl acetate at 0° C. was bubbled HCl gas until it was saturated. The mixture was stirred at room temperature for 10 minutes and was evaporated. The residue was diluted with 1N NaOH and extracted with methylene chloride. The organic layer was dried over sodium sulfate, filtered and concentrated to give a desired product (155 mg).

Step C:

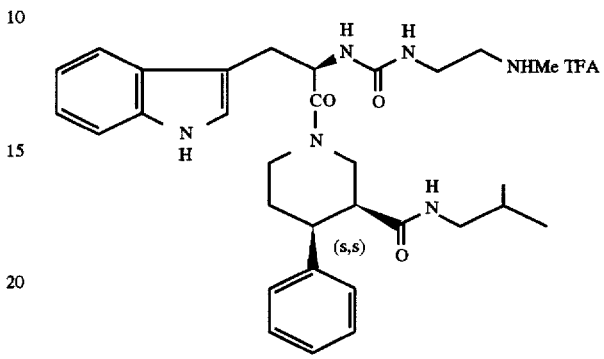

The title compound was prepared from the intermediate obtained from Step B (45 mg) and the isocyanate obtained from Example 98, Step B, by the procedure described in Example 98, Step C to give the desired product (20 mg). FAB-MS: 547.4 (M+1).

EXAMPLE 105

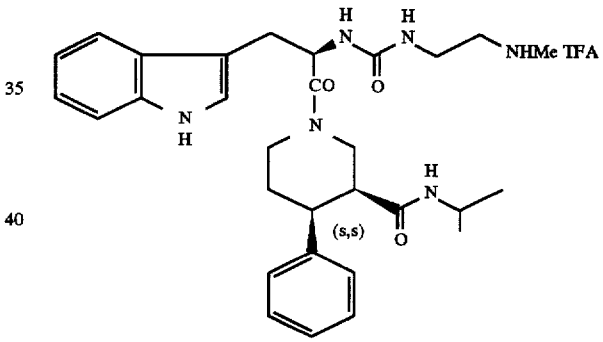

Step A:

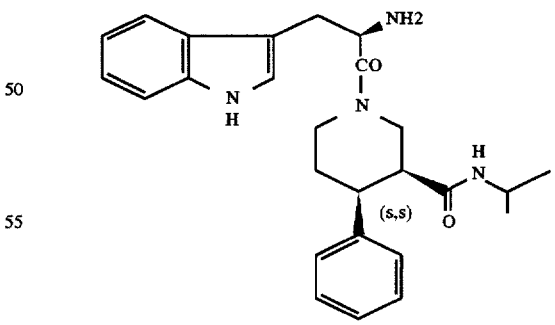

To the intermediate prepared from Step A (350 mg) in chloroform was added isopropylamine (0.15 ml), EDC (280 mg), DMAP (7 mg). After 12 hours stirring at room temperature, the mixture was poured into 1N HCl and extracted with methylene chloride, dried over sodium sulfate, filtered and concentrated. Purification of the residue (chromatatron, hexanes/ethyl acetate=1/2) gave the desired product. To this coupling product in ethyl acetate at 0° C. was bubbled HCl gas until it was saturated. The mixture was stirred at room temperature for 10 minutes and was evaporated. The residue was diluted with 1N NaOH and extracted with methylene chloride. The organic layer was dried over sodium sulfate, filtered and concentrated to give a desired product (150 mg).

Step B:

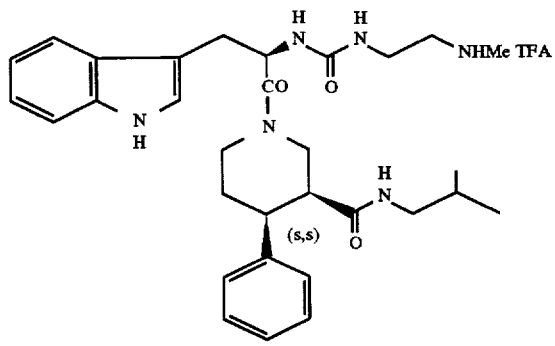

The title compound was prepared from the intermediate obtained from Step A (29 mg) and the isocyanate obtained from Example 98, Step B, by the procedure described in Example 98, Step C to give the desired product (17 mg). FAB-MS: 533.3 (M+1).

EXAMPLE 106

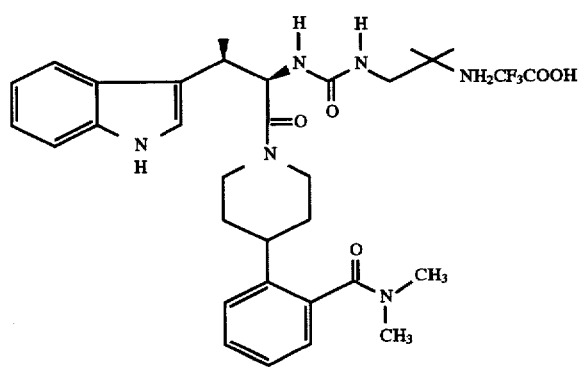

Step A:

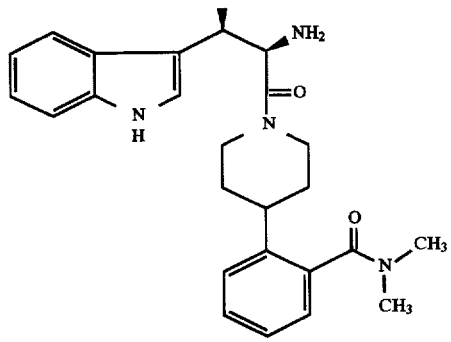

To a solution of 3.0 g of N-t-BOC-threo-(2R, 3R)-β-methyltryptophan (prepared as described in Example A7) in 50 mL of dichloromethane was added 2.8 g of the piperidine hydrochloride (prepared as described in Example 44 Step A) was added 2.5 mL of N-methylmorpholine, 1.5 g of HOBT and 2.2 g of EDC and stirred at room temperature for 18 h. The reaction mixture was washed with 0.5N hydrochloric acid (20 mL), saturated aqueous sodium bicarbonate solution (25 mL) dried over sodium sulfate and concentrated to give give 5 g of the coupled product. To 5.0 g of the ester from above in 30 mL of dioxane-water (4:1) was added 1.0 g of lithium hydroxide and stirred for 18 h. No hydrolysis was observed. Sodium hydroxide (3 eq) was added and stirred at room temperature. After 48 h the reaction mixture was diluted with water and extracted with ether. The aqueous layer was acidified with 0.5N HCl and extracted with ethyl acetate. The combined organics were washed with brine, dried over sodium sulfate, filtered and concentrated to give 3.0 g of the acid that was coupled with dimethylamine under standard peptide-type coupling conditions to give the dimethylamide. The BOC protecting group was removed by treatment with dry HCl(gas) in ethyl acetate to give the amine hydrochloride as a pale yellow solid.

Step B:

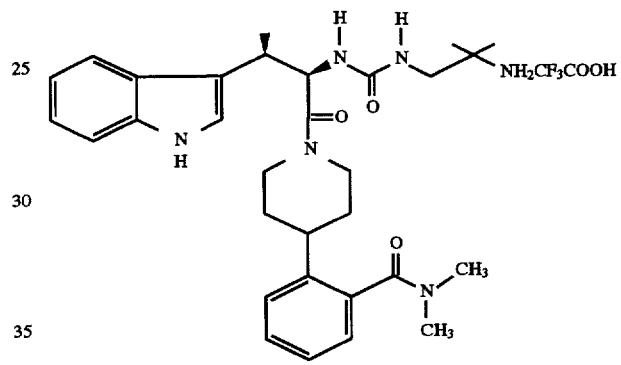

The title compound was prepared by the 2-step protocol as described in Example 91 by using the isocyanate synthesized in Step A of Example 86. ESI MS m/e Cacld for $C_{31}H_{42}N_6O_3$ 546; found 547.4

EXAMPLE 107

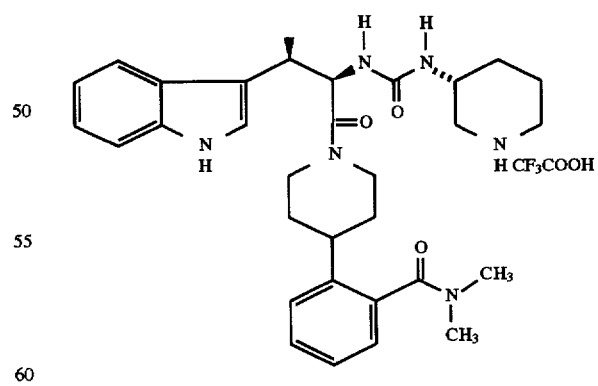

Prepared from the intermediate prepared in Step A of Example 106 by using chemistry as described in Example 91.

ESI MS m/e Cacld for $C_{32}H_{42}N_6O_3$ 558; found 559.3

EXAMPLE 108

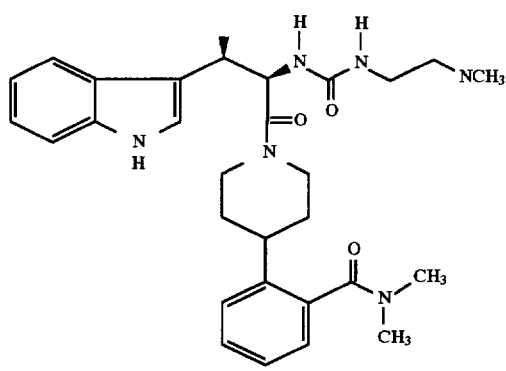

Prepared by a 2 step protocol from the intermediate synthesized in Step A of Example 106 by reacting it with the isocyanate prepared in Step B of Example 96 and then hydrogenatting the CBZ compound with Pd(OH)$_2$ in methanol. Characteristic $^1$H NMR resonances (400 MHz, CD3OD; mixture of rotamers) 9.80 and 9.75 (2bs, 1H), 7.80–6.90 (m, 9H), 5.20–5.10 (m, 1H), 4.60–4.40 (m, 1H), 4.30–4.05 (m, 1H), 2.30 (s, 3H), 1.48 and 1.39 (2d, 3H).

EXAMPLE 109

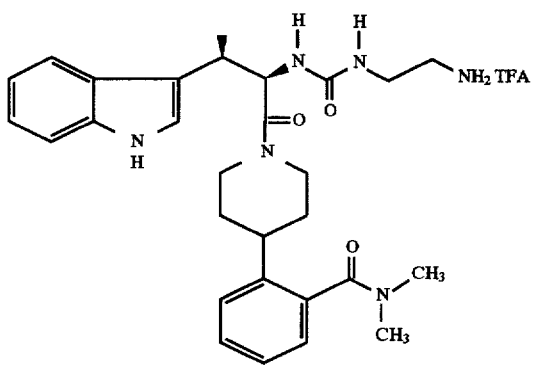

To a solution of the amine prepared in Step A of Example 106 in 3 mL of dry tetrahydrofuran was added 0.10 mL of diisopropylethylamine and stirred at room temperature for 30 min. Mono-N-BOC ethylenediamine (0.10 g) in 1 mL of THF was added and stirred overnight. The reaction mixture was diluted with 20 mL of chloroform and washed with 5 mL of 1N aqueous sodium hydroxide solution, 10 mL of 10% aqueous citric acid solution, dried over over anhydrous magnesium sulfate, filtered and concentrated. Flash chromatography of the residue with 10 g of silica gel with chloroform-acetone 1:1 to 1:2 as the eluent gave 0.12 g of the coupled product. This material was treated with 1:1 mixture of trifluoroacetic and dichloromethane for 30 min. The volatiles were removed on the rotary evaporator and the residue was triturated with ether to give the title compound as a pink solid. Characteristic $^1$H NMR resonances (400 MHz, CD3OD; mixture of rotamers) 9.80 and 9.75 (2 bs, 1H), 7.80–6.90 (m, 9H), 5.20–5.10 (m, 1H), 4.60–4.40 (m, 1H), 4.30–4.05 (m, 1H), 1.48 and 1.39 (2d, 3H).

EXAMPLE 110

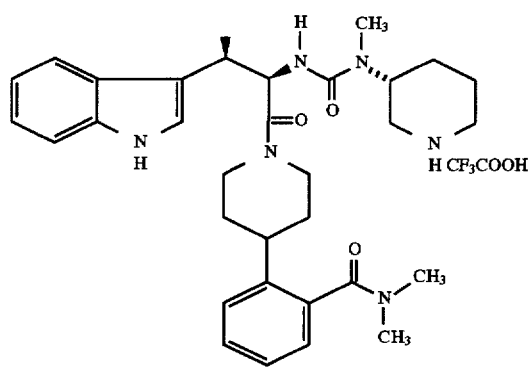

Step A:

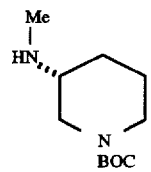

The isocyanate prepared in Step A of Example 86 was trapped with benzyl alcohol to give a CBZ compound that was first alkylated with methyl iodide with use of potassium bis(trimethylsilyl)amide in THF and the CBZ protecting group was removed by hydrogenolysis over 10% Pd/C in methanol.

Step B:

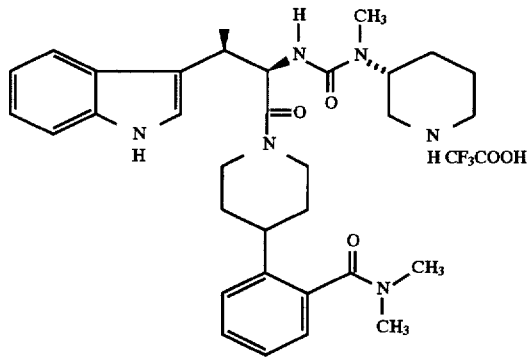

To a stirred solution of 0.16 g of the amine intermediate prepared in Step A of Example 106 in 10 mL of dichloromethane at −78° C. was added 0.16 mL of N-methylmorpholine and 0.19 mL of a 10% solution of phosgene in toluene. The reaction was warmed to 0° C. over 45 min. and then a solution of the amine prepared in Step A in dichloromethane was added and stirred at room temperature for 4 h. The reaction mixture was washed with 0.5N hydrochloric acid solution, brine, dried over anhydrous sodium sulfate, filtered and concentrated to give an oily residue that was purified by flash chromatography with hexane-acetone (1.5:1) as the eluent. The BOC protecting was deblocked with the TFA/CH2Cl2 procedure to give the title compound. ESI MS m/e Cacld for $C_{33}H_{44}N_6O_3$ 572; found 573.5

EXAMPLE 111

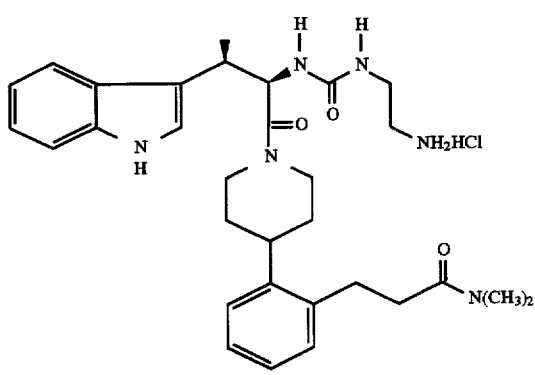

Prepared from the intermediate prepared in Step A of Example 90 as described in the experimental of Example 109. The TFA salt was basified with 1N NaOH and extracted with dichloromethane. The combined organics were washed with brine, dried over anhydrous magnesium sulfate and concentrated. To a solution of this residue in ethyl acetate was added a saturated solution of HCl(gas) in ethyl acetate, the solid thereby generated was filtered and dried to give the title compound as a pink solid. Characteristic $^1$H NMR resonances (400 MHz, CD$_3$OD; mixture of rotamers) 7.80 and 7.59 (2d, 1H), 7.33 (d, 1H), 7.25–7.00 (m, 7H), 5.30 and 5.11 (2d, 1H), 4.60 (bt, 1H), 2.97, 2.95, 2.90, and 2.88 (4s, 6H), 1.50 and 1.40 (2d, 3H).

EXAMPLE 112

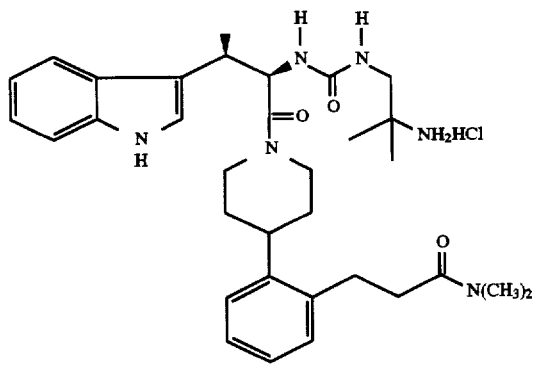

Prepared from the intermediate prepared in Step A of Example 90 as described in the experimental of Example 106. The TFA salt was basified with 1N NaOH and extracted with dichloromethane. The combined organics were washed with brine, dried over anhydrous magnesium sulfate and concentrated. To a solution of this residue in ethyl acetate was added a saturated solution of HCl(gas) in ethyl acetate, the solid thereby generated was filtered and dried to give the title compound as a white solid. Characteristic $^1$H NMR resonances (400 MHz, CD$_3$OD; mixture of rotamers) 7.80 and 7.59 (2d, 1H), 7.33 (d, 1H), 7.25–7.00 (m, 7H), 5.30 and 5.11 (2d, 1H), 4.60 (bt, 1H), 2.97, 2.95, 2.90, and 2.88 (4s, 6H), 1.50 and 1.40 (2d, 3H), 1.30, 1.28, 1.23, and 1.21 (4s, 6H).

EXAMPLE 113

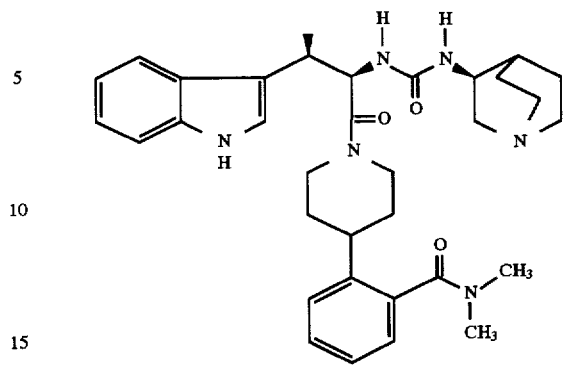

Prepared from the intermediate synthesized in Step A of Example 90 by using chemistry to form ureas as described in Example 109. (S)-Aminoquinuclidine was used in the coupling protocol with acetonitrile as the solvent. ESI MS m/e Cacld for C$_{34}$H$_{45}$N$_6$O$_3$ 585; found 586.5

EXAMPLE 114

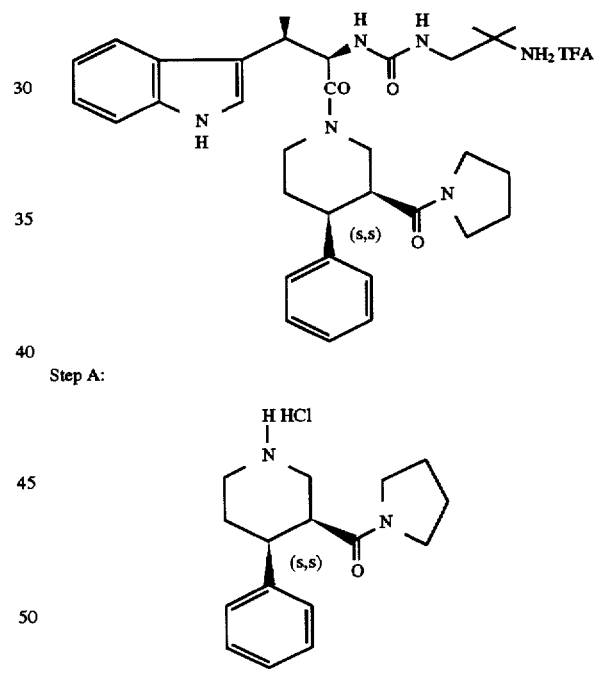

Step A:

The title compound was prepared from the intermediate obtained from Example 79, tep D (620 mg) in chloroform to which was added pyrrolidine (0.42 ml), EDC (764 mg) and HOBt (324 mg). After hours, the mixture was diluted with methylene chloride and then washed with 1N HCl, water and brine. The organic layer was dried over magnesium sulfate, filtered and concentrated. The residue was purified by chromatatron (hexanes/ethyl acetate=2/1) to give the coupling product (575 mg). To this coupling product in ethyl acetate at 0° C. was bubbled HCl until it was saturated. The mixture was stirred at room temperature for 10 minutes and was evaporated to dryness to give a desired product.

173

Step B:

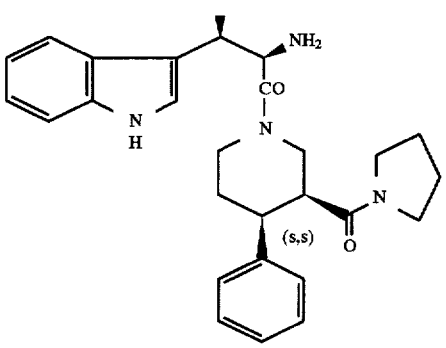

To the intermediate prepared from Step A in chloroform was added N-BOC-β-(R)-Me-(D)-Trp (606 mg), EDC (607 mg), HOBt (257 mg) and triethylamine (0.66 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/1) to give coupling product (860 mg). To this coupling product in ethyl acetate at 0° C. was bubbled HCl gas until it was saturated. The mixture was stirred at room temperature for 10 minutes and was evaporated (850 mg). The residue was diluted with 1N NaOH and extracted with methylene chloride. The organic layer was dried over sodium sulfate, filtered and concentrated to give a desired product.

Step C:

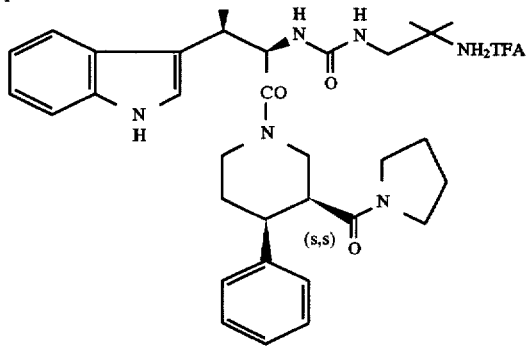

To the intermediate prepared from Step B (160 mg) in toluene there was added the intermediate prepared from Example 86, Step A (110 mg). This solution was refluxed for 4 hours and the mixture was concentrated. The residue was purified by chromatatron (hexanes/ethyl acetate=1/3) to give the desired product to which was added TFA at room temperature and stirred for 10 minutes. The mixture was concentrated and azeotroped with toluene (3×) to give the desired as a off white solid (62 mg). ¹H NMR (400 Hz, CD3OD, mixture of rotamers): 7.79 (m, 1H), 7.35–6.95 (m, 9H), 5.00 (m, 1/3H), 4.70 (m, 1/3H), 4.59 (m, 1H), 4.25 (m, 1/3H), 3.53–2.57 (m, 11 1/3H), 2.37 (m, 2/3H), 1.80–1.42 (m, 5 H), 1.35 (d, 7 Hz, 3H), 1.31 (s, 6H). FAB-MS: 573.4 (M+1).

174

EXAMPLE 115

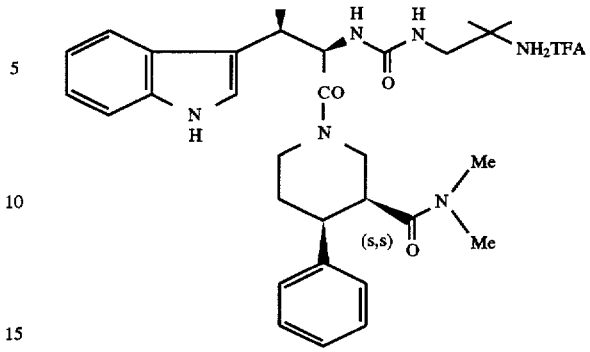

Step A:

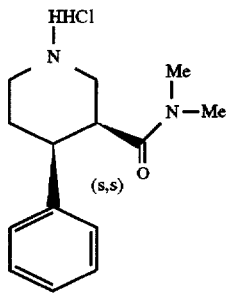

The title compound was prepared from the intermediate obtained from Example 79, step D (540 mg) in chloroform to which was added dimethylamine HCl (480 mg), EDC (688 mg), HOBt (316 mg), triethyl amine (0.75 ml) and a small amount of DMF. After 12 hours, the mixture was diluted with methylene chloride and then washed with 1N HCl, water and brine. The organic layer was dried over magnesium sulfate, filtered and concentrated. The residue was purified by chromatatron (hexanes/ethyl acetate=2/1) to give the coupling product (520 mg). To this coupling product in ethyl acetate at 0° C. was bubbled HCl until it was saturated. The mixture was stirred at room temperature for 10 minutes and was evaporated to dryness to give a desired product.

Step B:

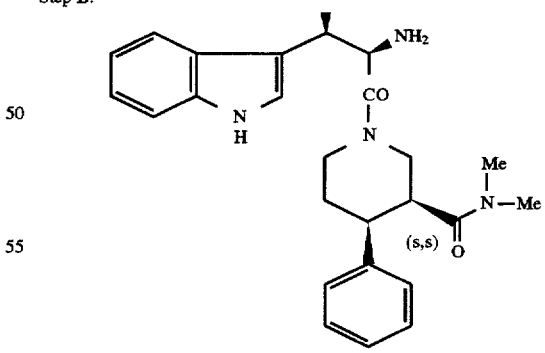

To the intermediate prepared from Step A in chloroform was added N-BOC-D-(R)-Me-(D)-Trp (590 mg), EDC (598 mg), HOBt (253 mg) and triethylamine (0.65 ml). After 12 hours stirring at room temperature, the mixture was poured into 1N HCl and extracted with methylene chloride, dried over sodium sulfate, filtered and concentrated. The residue was purified by chromatatron (hexanes/ethyl acetate=1/1) to give coupling product. To this coupling product in ethyl acetate at 0° C. was bubbled HCl gas until it was saturated. The mixture was stirred at room temperature for 10 minutes and was evaporated. The residue was diluted with 1N NaOH and extracted with methylene chloride. The organic layer was dried over sodium sulfate, filtered and concentrated to give a desired product (600 mg).

Step C:

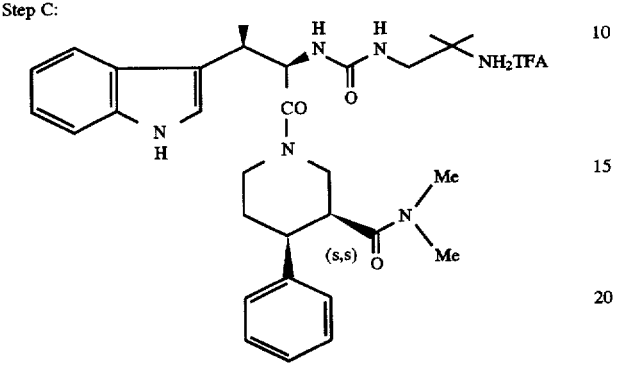

To the intermediate prepared from Step B (180 mg) in toluene there was added the intermediate prepared from Example 86, Step A (110 mg). This solution was refluxed for 4 hours and the mixture was concentrated. The residue was purified by chromatatron (hexanes/ethyl acetate=1/3) to give the desired product to which was added TFA at room temperature and stirred for 10 minutes. The mixture was concentrated and azeotroped with toluene (3×) to give the desired as a off white solid (180 mg). $^1$H NMR (400 Hz, CD3OD, mixture of rotamers): 7.79 (m,1H), 7.35–6.95 (m, 9H), 5.00 (m, 1/3H), 4.58 (m, 1 1/3H), 4.05 (m, 1/3 H), 3.53–2.48 (m, 9H), 2.56 (s, 3H), 2.22 (s, 3H), 1.53 (m, 1H), 1.37 (d, 7 Hz, 3H), 1.30 (s, 3H), 1.29 (s, 3H). FAB-MS: 547.5 (M+1).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

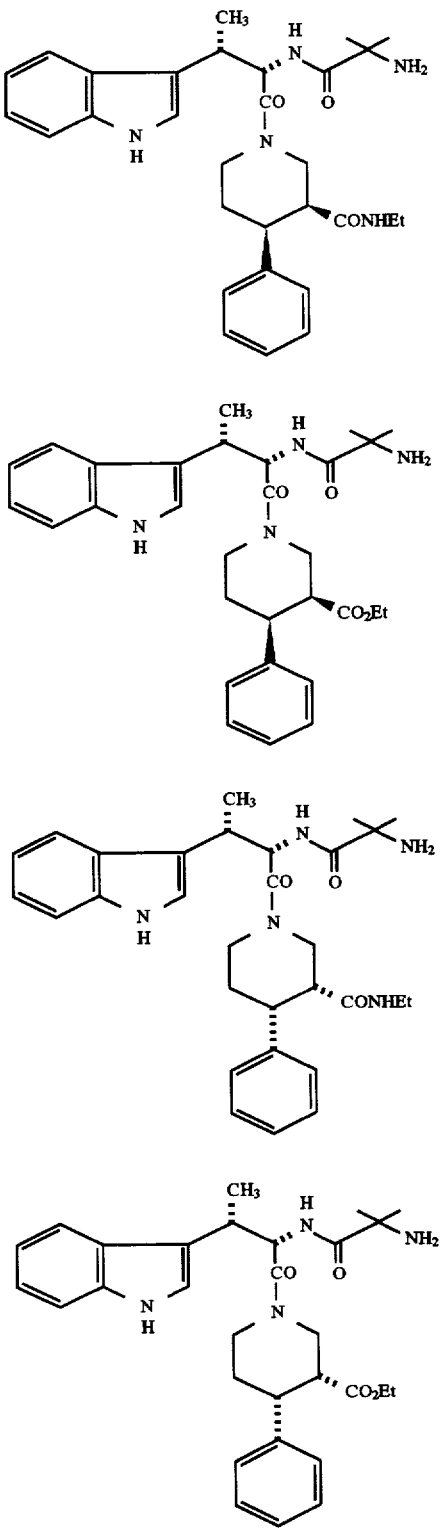

177
-continued
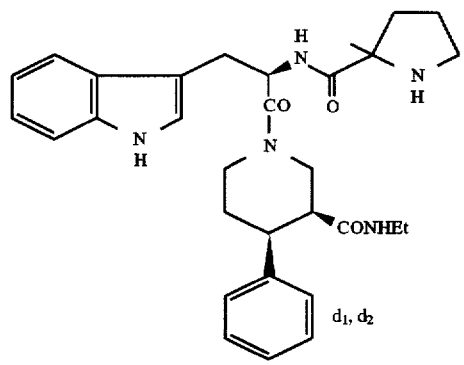
d₁, d₂
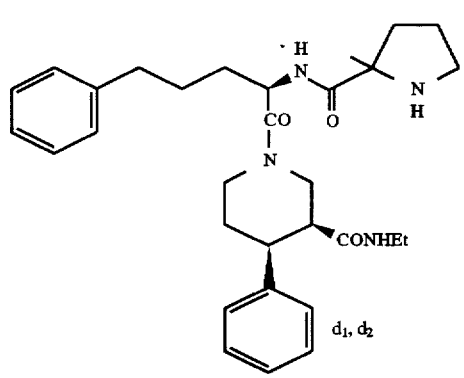
d₁, d₂
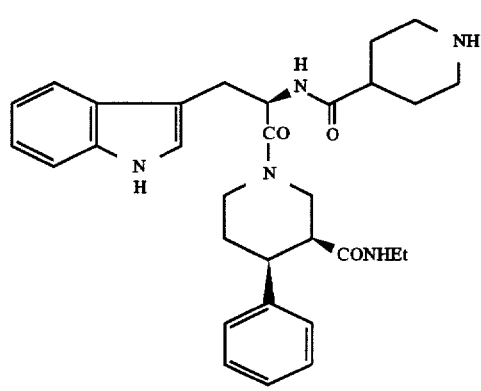
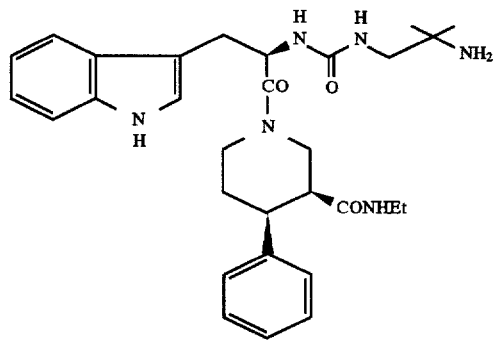
178
-continued
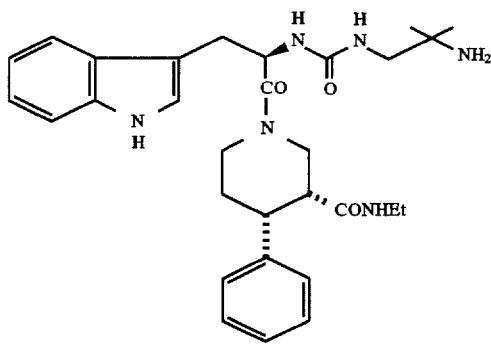
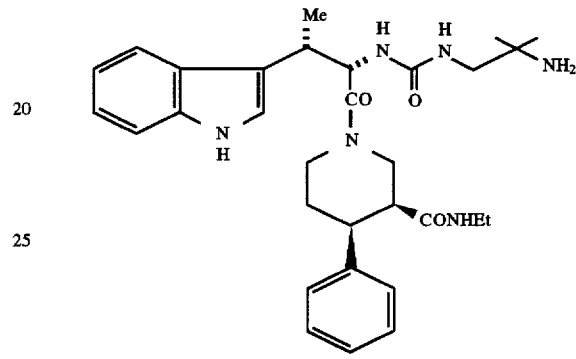
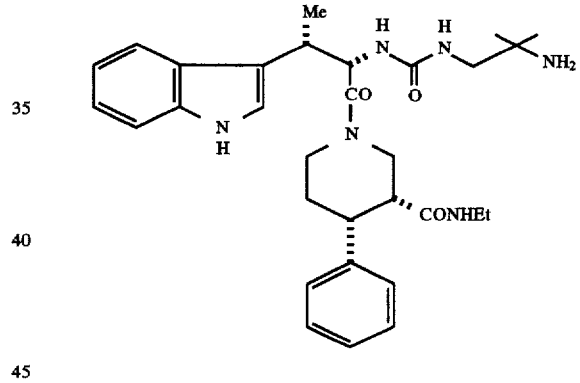

179
-continued
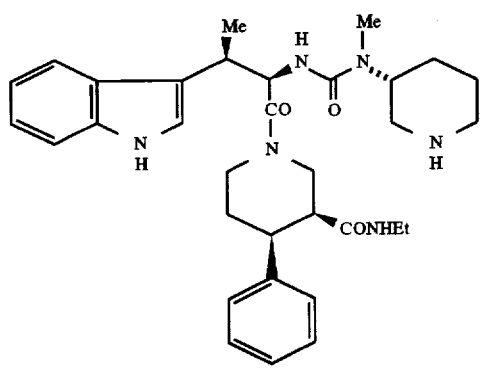
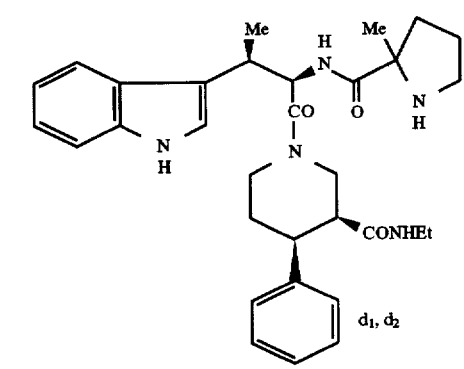
d₁, d₂
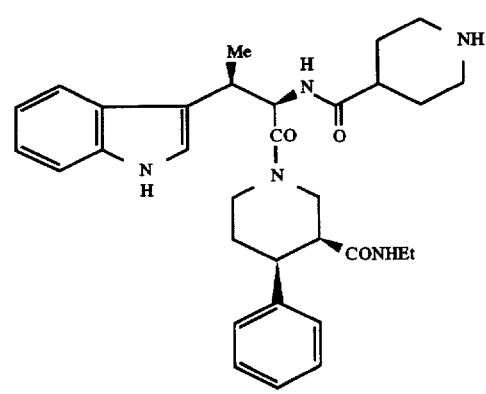
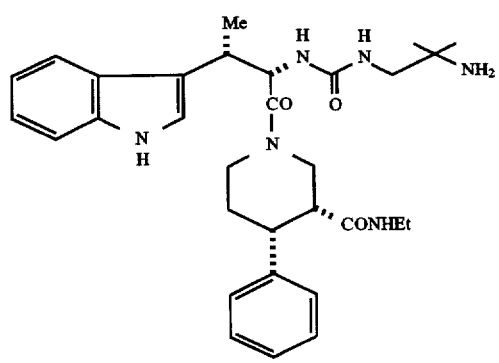
180
-continued
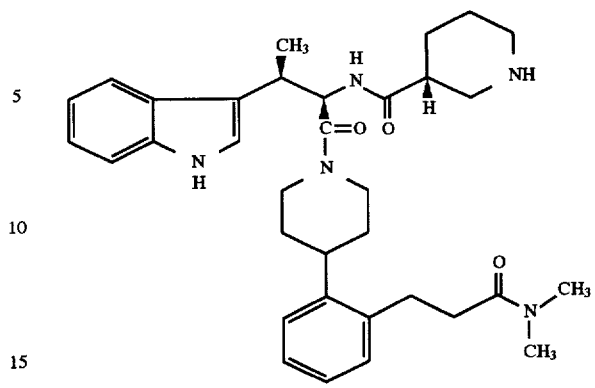
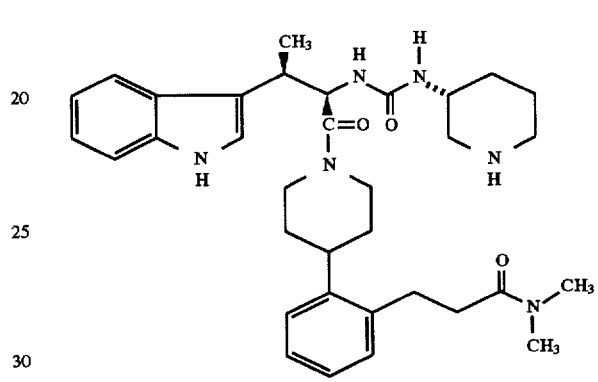
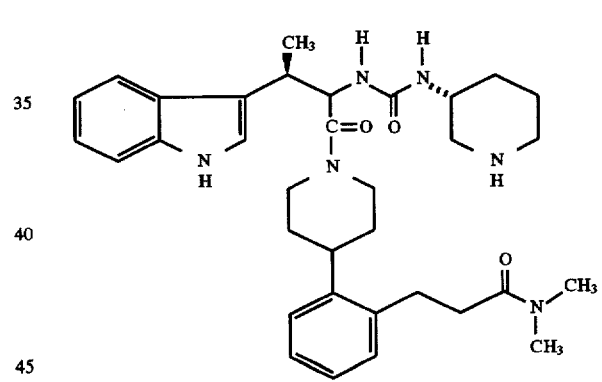
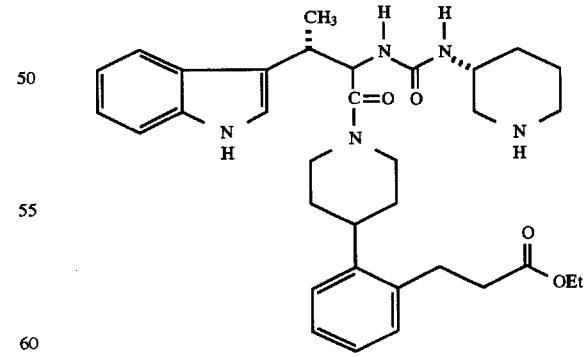

181
-continued
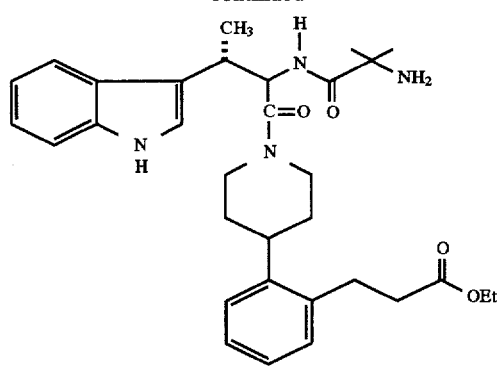
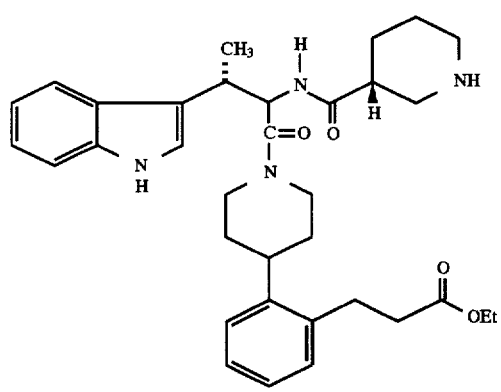
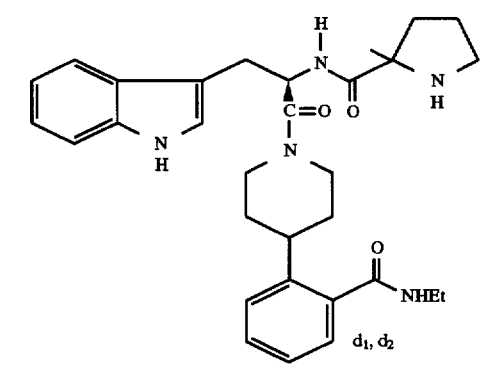
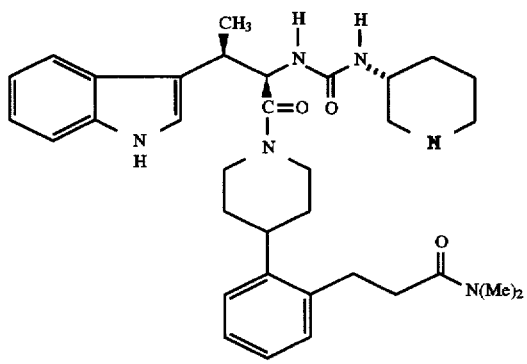
182
-continued
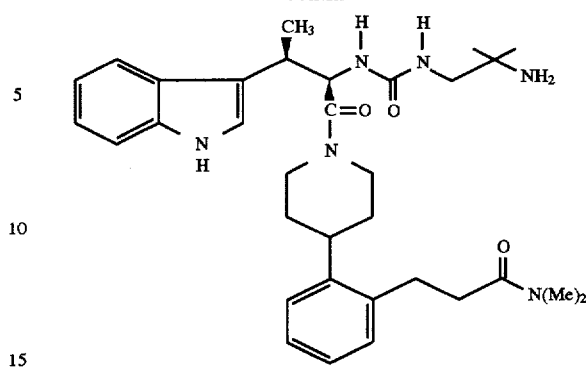
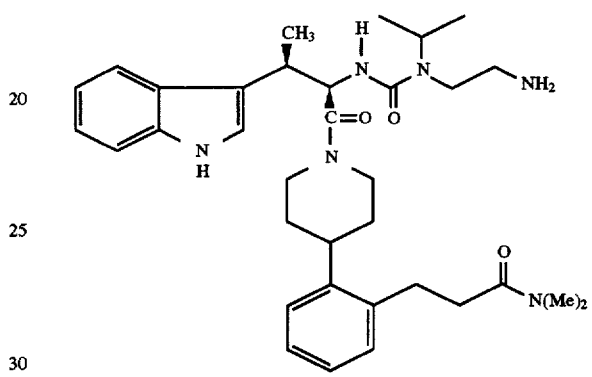
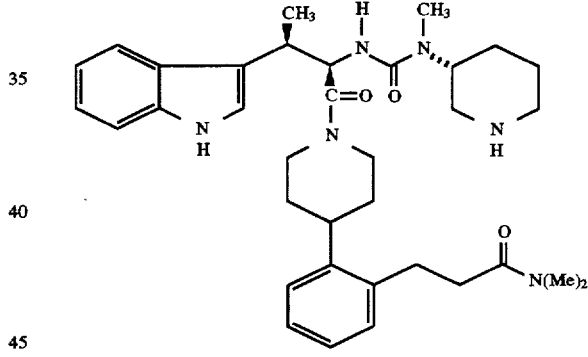
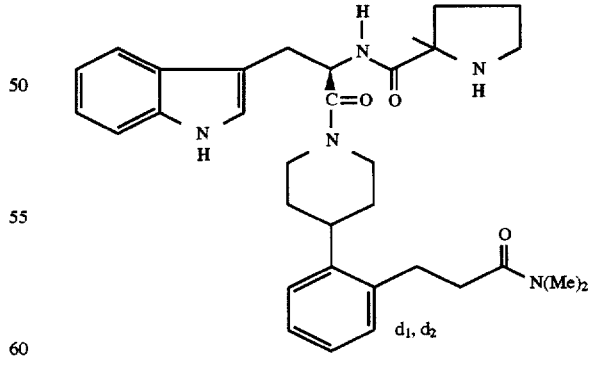

183
-continued
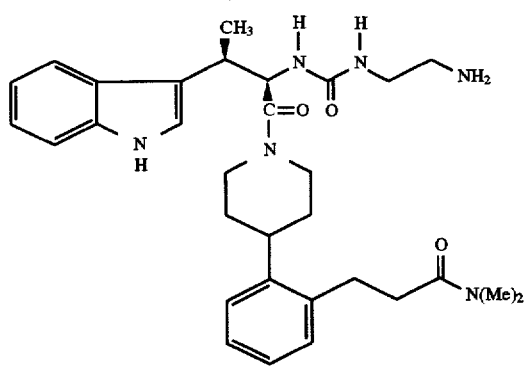
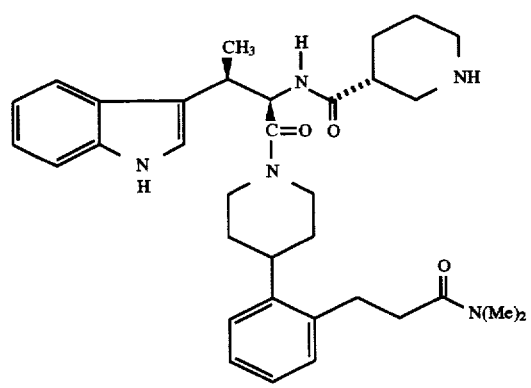
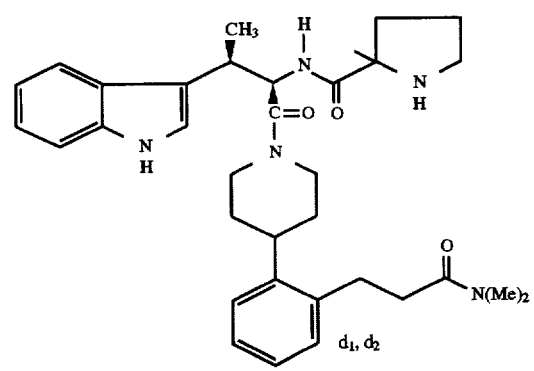
d₁, d₂
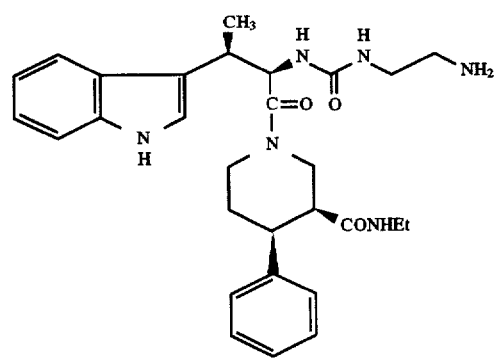
184
-continued
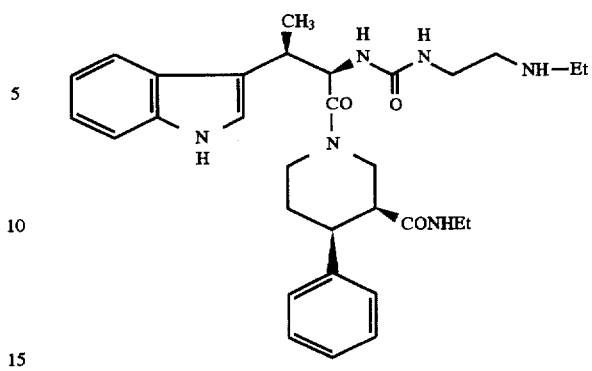
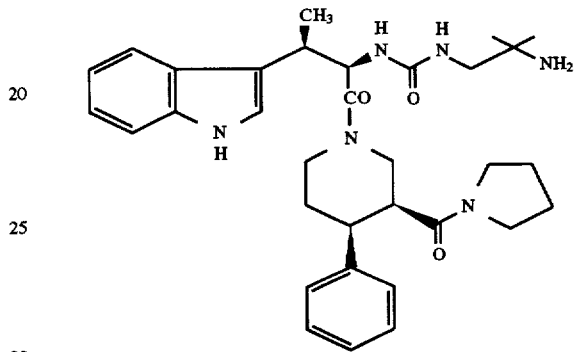
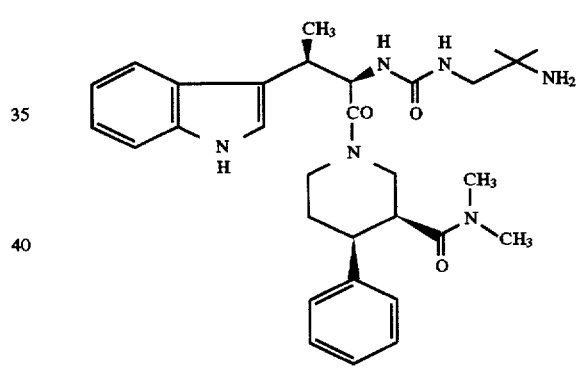
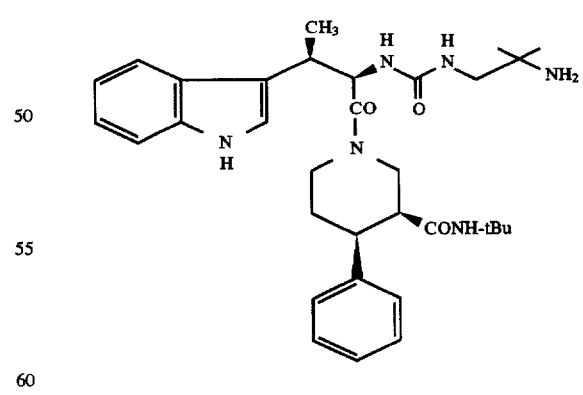

185
-continued
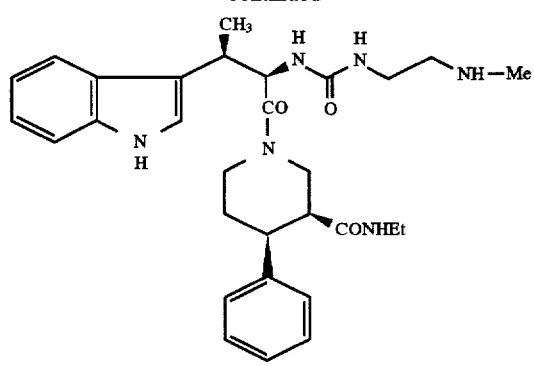
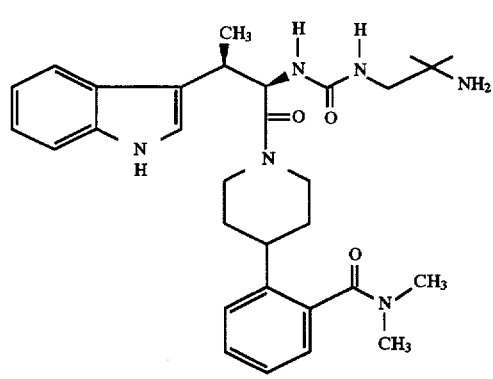
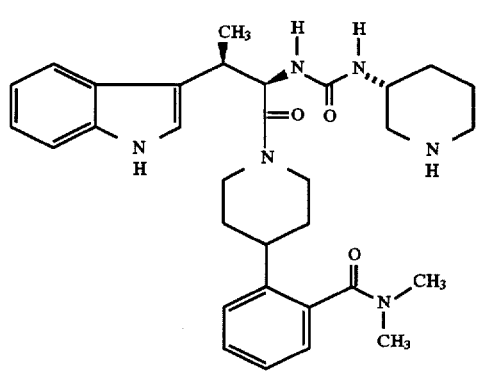
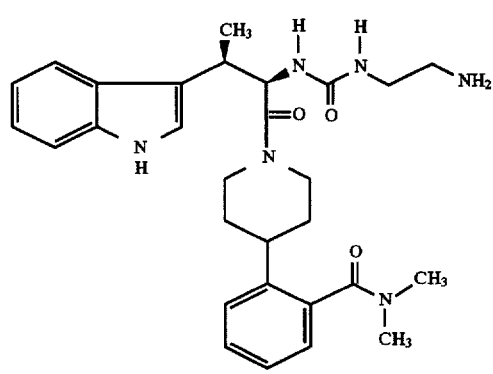
186
-continued
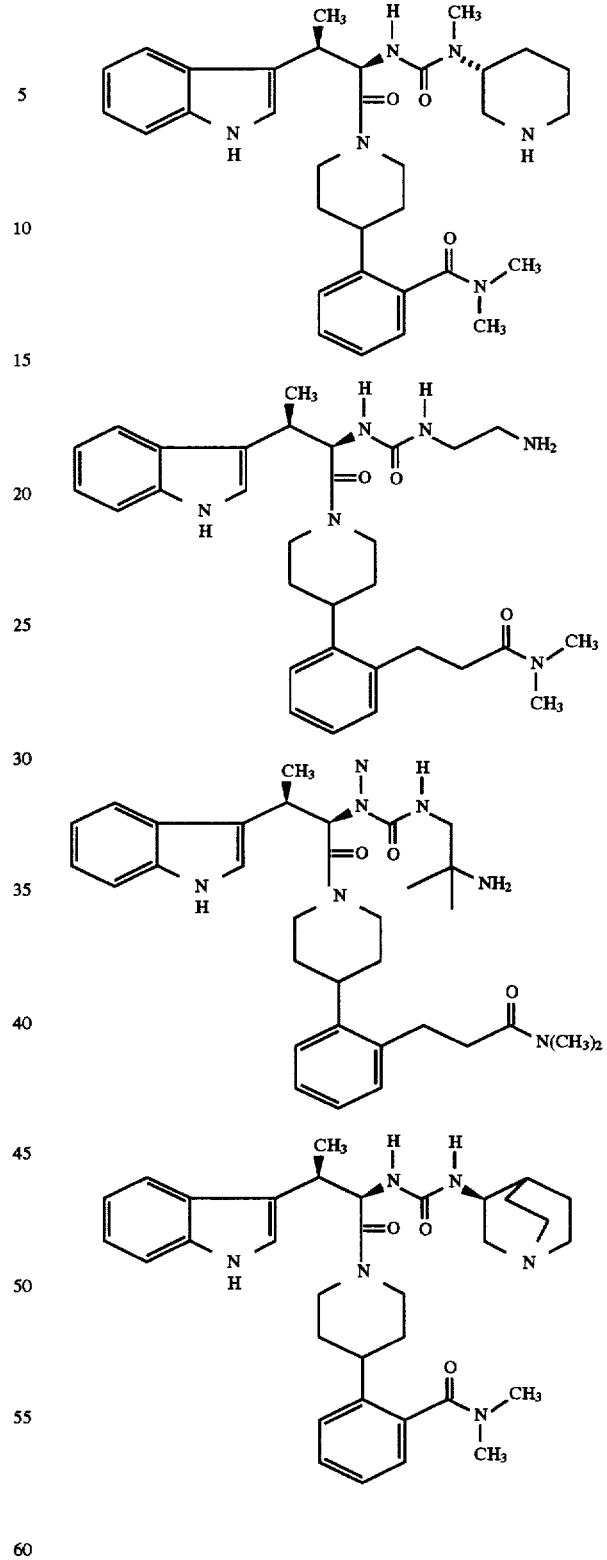
and pharmaceutically acceptable salts and individual diastereomers thereof where not otherwise specified.

2. A pharmaceutical composition which comprises a pharmaceutically acceptable carrier and a compound of claim 1.

3. A method for increasing levels of endogenous growth hormone in a human or an animal which comprises administering to such human or animal an effective amount of a compound of claim 1.

* * * * *